United States Patent
Young et al.

(10) Patent No.: US 10,265,458 B2
(45) Date of Patent: *Apr. 23, 2019

(54) VASCULAR ACCESS PORTS AND RELATED METHODS

(71) Applicant: Advent Access Pte. Ltd., Singapore (SG)

(72) Inventors: Nathaniel P. Young, Salt Lake City, UT (US); Mark A. Crawford, Sandy, UT (US)

(73) Assignee: ADVENT ACCESS PTE. LTD., Singapore (SG)

(*) Notice: Subject to any disclaimer, the term of this patent is extended or adjusted under 35 U.S.C. 154(b) by 334 days.

This patent is subject to a terminal disclaimer.

(21) Appl. No.: 14/936,567

(22) Filed: Nov. 9, 2015

(65) Prior Publication Data

US 2016/0199564 A1  Jul. 14, 2016

Related U.S. Application Data

(63) Continuation of application No. 13/018,277, filed on Jan. 31, 2011, now Pat. No. 9,179,901, which is a
(Continued)

(51) Int. Cl.
*A61M 1/36* (2006.01)
*A61B 17/00* (2006.01)
(Continued)

(52) U.S. Cl.
CPC ....... *A61M 1/3661* (2014.02); *A61B 17/0057* (2013.01); *A61B 17/3423* (2013.01);
(Continued)

(58) Field of Classification Search
CPC ............ A61B 17/0057; A61B 17/3423; A61B 2017/3425; A61M 1/3653; A61M 1/3659;
(Continued)

(56) References Cited

U.S. PATENT DOCUMENTS

| | | | |
|---|---|---|---|
| 3,998,222 A | 12/1976 | Shihata | |
| 4,164,221 A | 8/1979 | Bentley et al. | |

(Continued)

FOREIGN PATENT DOCUMENTS

| | | | |
|---|---|---|---|
| JP | 5395592 U | 8/1978 | |
| JP | 08501008 A | 2/1996 | |

(Continued)

OTHER PUBLICATIONS

Notice of Allowance dated Jul. 11, 2017 for U.S. Appl. No. 14/792,486.
(Continued)

*Primary Examiner* — Imani Hayman
(74) *Attorney, Agent, or Firm* — Pillsbury Winthrop Shaw Pittman LLP

(57) ABSTRACT

A vascular access port can include a base that can be attached to a vessel and a body extending away from the base in at least a vertical direction. A height of the body in the vertical direction can be sufficiently small such that the entire port can be implanted subcutaneously in a patient. The port can include a guidance passageway that is at least partially defined by the body and can direct an access device into a vessel of a patient when the port is attached to the vessel. In some arrangements, the guidance passageway includes a funnel region that decreases in size from a proximal end of the guidance passageway toward a distal end of the guidance passageway that defines an opening through the bottom surface of the port.

20 Claims, 91 Drawing Sheets

Related U.S. Application Data continuation-in-part of application No. 12/697,167, filed on Jan. 29, 2010, now Pat. No. 8,337,464, which is a continuation-in-part of application No. 12/697,192, filed on Jan. 29, 2010, now Pat. No. 9,072,880.

(60) Provisional application No. 61/148,372, filed on Jan. 29, 2009, provisional application No. 61/229,023, filed on Jul. 28, 2009.

(51) Int. Cl.
*A61B 17/34* (2006.01)
*A61M 39/02* (2006.01)

(52) U.S. Cl.
CPC ........ *A61M 1/3653* (2013.01); *A61M 1/3659* (2014.02); *A61M 39/0208* (2013.01); *A61B 2017/3425* (2013.01); *A61M 2205/04* (2013.01)

(58) Field of Classification Search
CPC ............ A61M 1/3661; A61M 2205/04; A61M 39/0208
See application file for complete search history.

(56) References Cited

U.S. PATENT DOCUMENTS

| | | |
|---|---|---|
| 4,318,401 A | 3/1982 | Zimmerman |
| 4,405,319 A | 9/1983 | Cosentino |
| 4,423,730 A | 1/1984 | Gabbay |
| 4,484,912 A | 11/1984 | Raible |
| 4,559,033 A | 12/1985 | Stephen et al. |
| 4,667,673 A | 5/1987 | Li et al. |
| 4,781,695 A | 11/1988 | Dalton |
| 4,822,341 A | 4/1989 | Colone |
| 5,092,849 A | 3/1992 | Sampson |
| 5,127,412 A | 7/1992 | Cosmetto et al. |
| 5,222,963 A | 6/1993 | Brinkerhoff et al. |
| 5,222,974 A | 6/1993 | Kensey et al. |
| 5,263,930 A | 11/1993 | Ensminger |
| 5,275,322 A | 1/1994 | Brinkerhoff et al. |
| 5,281,199 A | 1/1994 | Ensminger et al. |
| 5,282,827 A | 2/1994 | Kensey et al. |
| 5,306,254 A | 4/1994 | Nash et al. |
| 5,334,217 A | 8/1994 | Das |
| 5,350,360 A | 9/1994 | Ensminger et al. |
| 5,356,381 A | 10/1994 | Ensminger et al. |
| 5,441,517 A | 8/1995 | Kensey et al. |
| 5,527,277 A | 6/1996 | Ensminger et al. |
| 5,540,715 A | 7/1996 | Katsaros et al. |
| 5,662,616 A | 9/1997 | Bousquet |
| 5,676,689 A | 10/1997 | Kensey et al. |
| 5,707,393 A | 1/1998 | Kensey et al. |
| 5,741,228 A | 4/1998 | Lambrecht et al. |
| 5,792,104 A | 8/1998 | Speckman et al. |
| 5,817,113 A | 10/1998 | Gifford et al. |
| 5,848,989 A | 12/1998 | Villani |
| 5,861,004 A | 1/1999 | Kensey et al. |
| 5,882,341 A | 3/1999 | Bousquet |
| 5,989,213 A | 11/1999 | Maginot |
| 6,004,301 A | 12/1999 | Carter |
| 6,004,341 A | 12/1999 | Zhu et al. |
| 6,007,563 A | 12/1999 | Nash et al. |
| 6,007,576 A * | 12/1999 | McClellan ............ A61F 2/064 623/23.64 |
| 6,090,130 A | 7/2000 | Nash et al. |
| 6,099,508 A | 8/2000 | Bousquet |
| 6,156,016 A | 12/2000 | Maginot |
| 6,190,371 B1 | 2/2001 | Maginot et al. |
| 6,213,973 B1 | 4/2001 | Eliasen |
| 6,261,255 B1 | 7/2001 | Mullis et al. |
| 6,261,257 B1 | 7/2001 | Ulfacker et al. |
| 6,287,322 B1 | 9/2001 | Zhu et al. |
| 6,355,020 B1 | 3/2002 | Bousquet |
| 6,425,901 B1 | 7/2002 | Zhu et al. |
| 6,475,207 B1 | 11/2002 | Maginot et al. |
| 6,508,790 B1 | 1/2003 | Lawrence |
| 6,524,326 B1 | 2/2003 | Zhu et al. |
| 6,527,754 B1 | 3/2003 | Tallarida |
| 6,544,206 B1 | 4/2003 | Johnston |
| 6,585,705 B1 | 7/2003 | Maginot et al. |
| 6,595,941 B1 | 7/2003 | Blatter |
| 6,626,921 B2 | 9/2003 | Blatter et al. |
| 6,656,151 B1 | 12/2003 | Blatter |
| 6,682,489 B2 | 1/2004 | Tenerz et al. |
| 6,723,084 B1 | 4/2004 | Maginot et al. |
| 6,726,704 B1 | 4/2004 | Loshakove et al. |
| 6,743,218 B2 | 6/2004 | Maginot et al. |
| 6,764,500 B1 | 7/2004 | Muijs Van De Moer et al. |
| 6,726,711 B1 | 8/2004 | Langenbach et al. |
| 6,913,609 B2 | 7/2005 | Yencho et al. |
| 6,960,185 B2 | 11/2005 | Adaniya et al. |
| 6,964,675 B2 | 11/2005 | Zhu et al. |
| 6,979,338 B1 | 12/2005 | Loshakove et al. |
| 6,997,914 B2 | 2/2006 | Smith et al. |
| 7,008,412 B2 | 3/2006 | Maginot |
| 7,022,131 B1 | 4/2006 | Derowe et al. |
| 7,044,916 B2 | 5/2006 | Tenerz et al. |
| 7,060,084 B1 | 6/2006 | Loshakove et al. |
| 7,063,711 B1 | 6/2006 | Loshakove et al. |
| 7,073,509 B2 | 7/2006 | Tenerz et al. |
| 7,118,546 B2 | 10/2006 | Blatter |
| 7,128,734 B1 | 10/2006 | Wilson et al. |
| 7,261,705 B2 | 8/2007 | Edoga et al. |
| 7,285,097 B2 | 10/2007 | Tenerz et al. |
| 7,331,981 B2 | 2/2008 | Cates et al. |
| 7,396,359 B1 | 7/2008 | Derowe et al. |
| 7,708,722 B2 | 5/2010 | Glenn |
| 7,828,781 B2 | 11/2010 | Edoga et al. |
| 7,909,804 B2 | 3/2011 | Stats |
| 8,034,064 B2 | 10/2011 | Blatter |
| 8,337,464 B2 | 12/2012 | Young et al. |
| 8,337,465 B2 | 12/2012 | Young et al. |
| 8,343,028 B2 | 1/2013 | Gregoric et al. |
| 8,409,228 B2 | 4/2013 | Blatter et al. |
| 8,574,204 B2 | 11/2013 | Bourne et al. |
| 8,585,663 B2 | 11/2013 | Powers et al. |
| 8,668,706 B2 | 3/2014 | Blatter et al. |
| 8,690,816 B2 | 4/2014 | Dakin et al. |
| 9,033,931 B2 | 5/2015 | Young et al. |
| 9,039,717 B2 | 5/2015 | Blatter et al. |
| 2001/0007931 A1 | 7/2001 | Blatter |
| 2001/0037094 A1 | 11/2001 | Adaniya |
| 2001/0056266 A1 | 12/2001 | Tallarida et al. |
| 2002/0087127 A1 | 7/2002 | Finch et al. |
| 2003/0004520 A1 | 1/2003 | Haarala et al. |
| 2003/0023208 A1 | 1/2003 | Osypka et al. |
| 2003/0078597 A1 | 4/2003 | Blatter et al. |
| 2003/0089757 A1 | 5/2003 | Whitman et al. |
| 2004/0097994 A1 | 5/2004 | Blatter |
| 2004/0133173 A1 | 7/2004 | Edoga et al. |
| 2004/0254537 A1 | 12/2004 | Conlon et al. |
| 2004/0260333 A1 | 12/2004 | Dubrul et al. |
| 2005/0125060 A1 | 6/2005 | Perry et al. |
| 2005/0171565 A1 | 8/2005 | Yencho et al. |
| 2005/0177176 A1 | 8/2005 | Gerbi et al. |
| 2005/0283188 A1 | 12/2005 | Loshakove et al. |
| 2006/0247605 A1 | 11/2006 | Edoga et al. |
| 2007/0083156 A1 | 4/2007 | Muto et al. |
| 2007/0123811 A1 | 5/2007 | Squitieri |
| 2007/0265584 A1 | 11/2007 | Hickman et al. |
| 2008/0051811 A1 | 2/2008 | Blatter et al. |
| 2008/0086075 A1 | 4/2008 | Isik et al. |
| 2008/0086100 A1 | 4/2008 | Isaacson et al. |
| 2008/0147114 A1 | 6/2008 | Derowe et al. |
| 2008/0195124 A1* | 8/2008 | Borghi ............ A61B 17/11 606/153 |
| 2008/0243080 A1 | 10/2008 | Chang |
| 2008/0249509 A1 | 10/2008 | Glenn |
| 2009/0076466 A1 | 3/2009 | Quebbemann et al. |
| 2009/0118683 A1 | 5/2009 | Hanson et al. |
| 2009/0192473 A1 | 7/2009 | Crocker et al. |
| 2009/0209918 A1 | 8/2009 | Berglund |

(56) References Cited

U.S. PATENT DOCUMENTS

| | | | |
|---|---|---|---|
| 2010/0121358 A1 | 5/2010 | Blatter et al. |
| 2010/0152640 A1 | 6/2010 | Golding et al. |
| 2010/0152658 A1 | 6/2010 | Hanson et al. |
| 2010/0191166 A1 | 7/2010 | Phillips et al. |
| 2010/0191179 A1 | 7/2010 | Young et al. |
| 2010/0191191 A1 | 7/2010 | Young et al. |
| 2010/0274223 A1 | 10/2010 | Teitelbaum et al. |
| 2010/0318016 A1 | 12/2010 | Nugent et al. |
| 2011/0184347 A1 | 7/2011 | Mason |
| 2011/0213309 A1 | 9/2011 | Young et al. |
| 2012/0245536 A1 | 9/2012 | Gerber et al. |
| 2013/0060200 A1 | 3/2013 | Dalton et al. |
| 2013/0066282 A1 | 3/2013 | Dalton et al. |
| 2013/0184725 A1 | 7/2013 | Blatter et al. |
| 2013/0245550 A1 | 9/2013 | Young et al. |
| 2013/0245572 A1 | 9/2013 | Young et al. |
| 2014/0163588 A1 | 6/2014 | Blatter et al. |
| 2014/0207086 A1 | 7/2014 | Stats et al. |

FOREIGN PATENT DOCUMENTS

| | | | |
|---|---|---|---|
| WO | 199818506 A1 | 5/1998 |
| WO | 2006092724 A2 | 9/2006 |
| WO | 2007109164 A | 9/2007 |
| WO | 2009149474 A1 | 12/2009 |
| WO | 2010088532 A1 | 8/2010 |
| WO | 2010088541 A1 | 8/2010 |
| WO | 2011094712 A1 | 8/2011 |

OTHER PUBLICATIONS

Office Action dated Aug. 9, 2017 for U.S. Appl. No. 14/715,553.
10736487.9, et al., Extended European Search Report, dated Mar. 4, 2015 ,6 pages.
U.S. Appl. No. 12/480,678, et al., Non-Final Office Action, dated Feb. 1, 2012 ,31 pages.
U.S. Appl. No. 12/480,678, et al., Notice of Allowance ,dated Nov. 29, 2012 ,8 pages.
U.S. Appl. No. 12/697,167, et al., Non-Final Office Action, dated Jul. 3, 2012 ,24 pages.
U.S. Appl. No. 12/697,167, et al., Notice of Allowance, dated Nov. 19, 2012 ,7 pages.
U.S. Appl. No. 12/697,190, et al., Notice of Allowance, dated Jul. 12, 2012 ,11 pages.
U.S. Appl. No. 12/697,190, et al., Notice of Allowance, dated Nov. 2, 2012 ,10 pages.
U.S. Appl. No. 12/697,190, et al., Non-Final Office Action, dated Sep. 13, 2011 ,23 pages.
U.S. Appl. No. 12/697,192, et al., Non-Final Office Action, dated Aug. 29, 2013 ,22 pages.
U.S. Appl. No. 12/697,192, et al., Final Office Action, dated Feb. 26, 2013 ,19 pages.
U.S. Appl. No. 12/697,192, et al., Notice of Allowance, dated Mar. 2, 2015 ,24 pages.
U.S. Appl. No. 12/697,192, et al., Final Office Action, dated Mar. 28, 2014 ,20 pages.
U.S. Appl. No. 12/697,192, et al., Notice of Allowance, dated Nov. 13, 2014 ,19 pages.
U.S. Appl. No. 12/697,192, et al., Non-Final Office Action, dated Oct. 9, 2012 ,27 pages.
U.S. Appl. No. 13/018,277, et al., Non-Final Office Action, dated Aug. 7, 2013 ,19 pages.
U.S. Appl. No. 13/018,277, et al., Notice of Allowance, dated Feb. 4, 2015 ,26 pages.
U.S. Appl. No. 13/018,277, et al., Notice of Allowance, dated Jul. 1, 2015 ,8 pages.
U.S. Appl. No. 13/018,277, et al., Notice of Allowance, dated Jun. 3, 2014 ,12 pages.
U.S. Appl. No. 13/018,277, et al., Notice of Allowance, dated Sep. 18, 2014 ,12 pages.
U.S. Appl. No. 13/723,763, et al., Final Office Action, dated Dec. 16, 2015 ,25 pages.
U.S. Appl. No. 13/723,763, et al., Notice of Allowance, dated Jul. 21, 2016 ,18 pages.
U.S. Appl. No. 13/725,529, et al., Notice of Allowance, dated Apr. 1, 2014 ,19 pages.
U.S. Appl. No. 13/725,529, et al., Notice of Allowance, dated Feb. 20, 2015 ,2 pages.
U.S. Appl. No. 13/725,529, et al., Notice of Allowance, dated Jan. 14, 2015 ,5 pages.
U.S. Appl. No. 13/725,529, et al., Non-Final Office Action, dated Nov. 21, 2013 ,9 pages.
U.S. Appl. No. 13/725,529, et al., Notice of Allowance, dated Oct. 7, 2014 ,5 pages.
U.S. Appl. No. 13/781,575, et al., Notice of Allowance, dated May 10, 2013 ,32 pages.
U.S. Appl. No. 13/781,575, et al., Notice of Allowance, dated Oct. 7, 2013 ,36 pages.
U.S. Appl. No. 14/181,401, et al., Notice of Allowance, dated Jan. 21, 2015 ,7 pages.
U.S. Appl. No. 14/181,401, et al., Non-Final Office Action, dated Jun. 26, 2014 ,36 pages.
U.S. Appl. No. 14/720,969, et al., Non-Final Office Action, dated Dec. 8, 2015 ,22 pages.
U.S. Appl. No. 14/792,486, et al., Non-Final Office Action, dated May 25, 2016 ,19 pages.
Brunette, et al.,Titanium in Medicine: Material Science, Surface Science, Engineering, Biological Responses and Medical Applications, Berlin: Springer, ISBN 3-540-66936-1 ,2001 ,p. 727.
PCT/US2009/046664, et al., International Preliminary Report on Patentability, dated Dec. 6, 2010 ,7 pages.
PCT/US2009/046664, et al., International Search Report and Written Opinion, dated Jul. 31, 2009 ,8 pages.
PCT/US2010/022607, et al., International Search Report and Written Opinion, dated Apr. 8, 2010 ,9 pages.
PCT/US2010/022607, et al., International Preliminary Report on Patentability, dated Aug. 2, 2011 ,8 pages.
PCT/US2010/022622, et al., International Search Report and Written Opinion, dated Apr. 8, 2010 ,11 pages.
PCT/US2010/022622, et al., International Preliminary Report on Patentability, dated Aug. 2, 2011 ,10 pages.
PCT/US2011/023228, et al., International Preliminary Report on Patentability, dated Jul. 31, 2012 ,6 pages.
PCT/US2011/023228, et al., International Search Report and Written Opinion, dated Mar. 25, 2011 ,8 pages.
Office Action dated Apr. 19, 2018 for U.S. Appl. No. 14/715,553.
Vascular Access 2006, American Journal of Kidney Diseases, vol. 48 No. 1 ,Jul. 2006 ,S180-S182.

\* cited by examiner

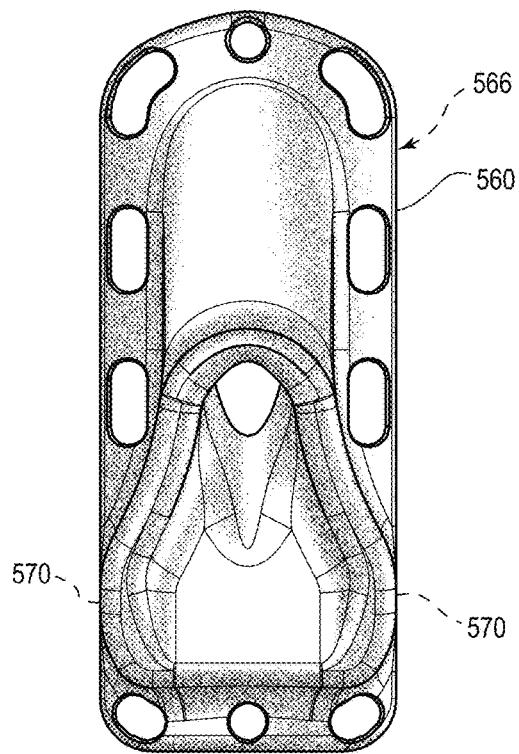
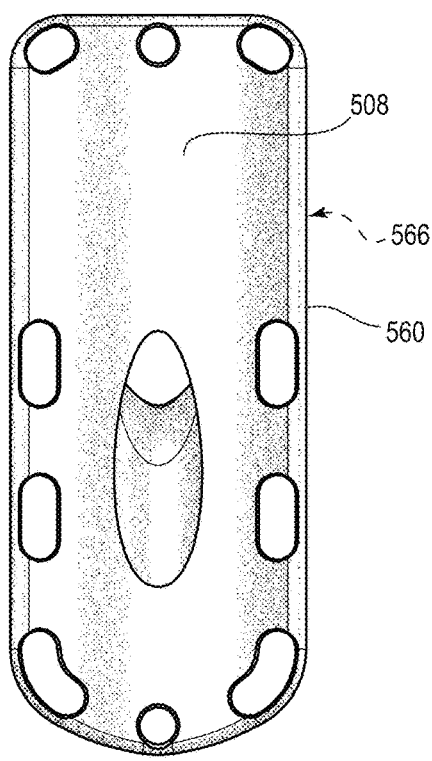
FIG. 16D    FIG. 16E
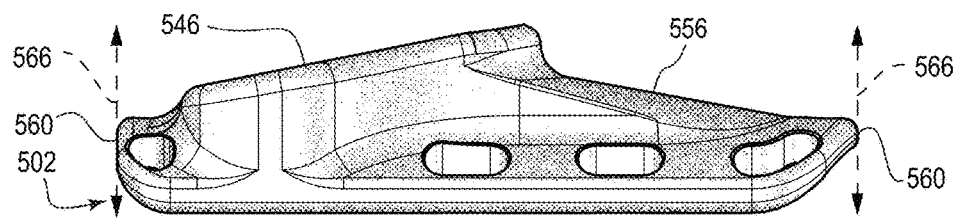
FIG. 16F
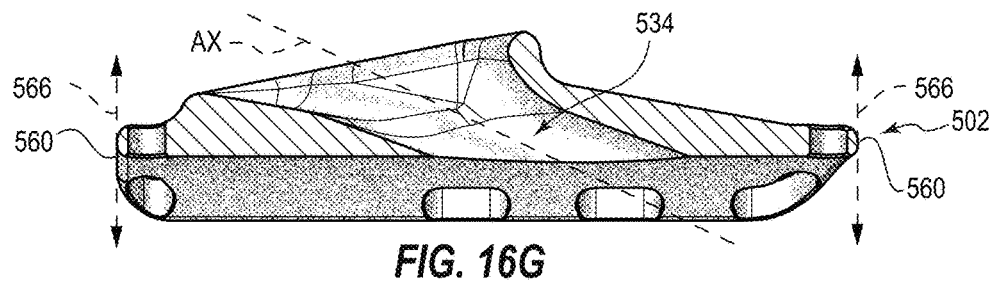
FIG. 16G

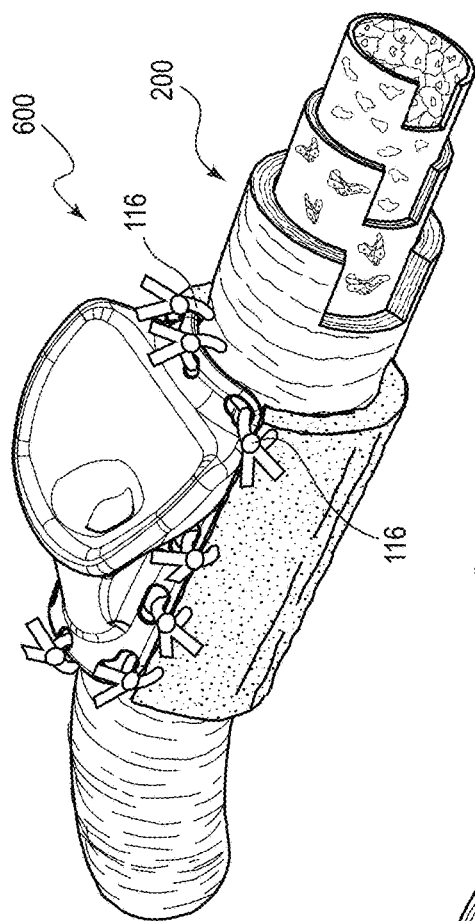
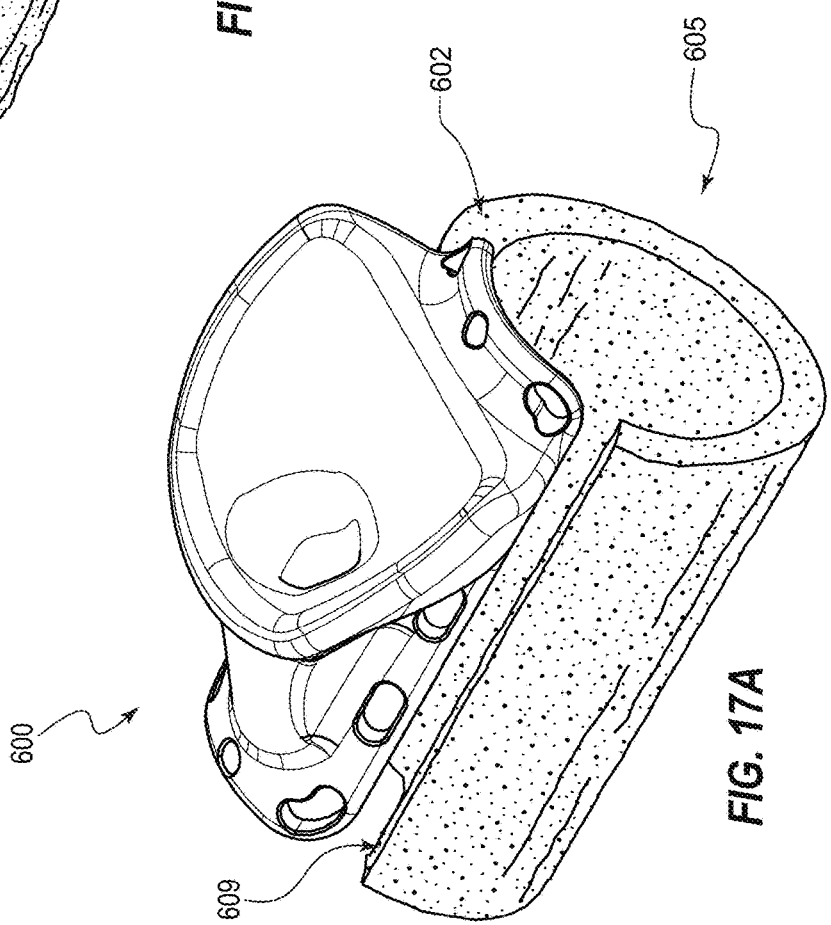
FIG. 17B
FIG. 17A

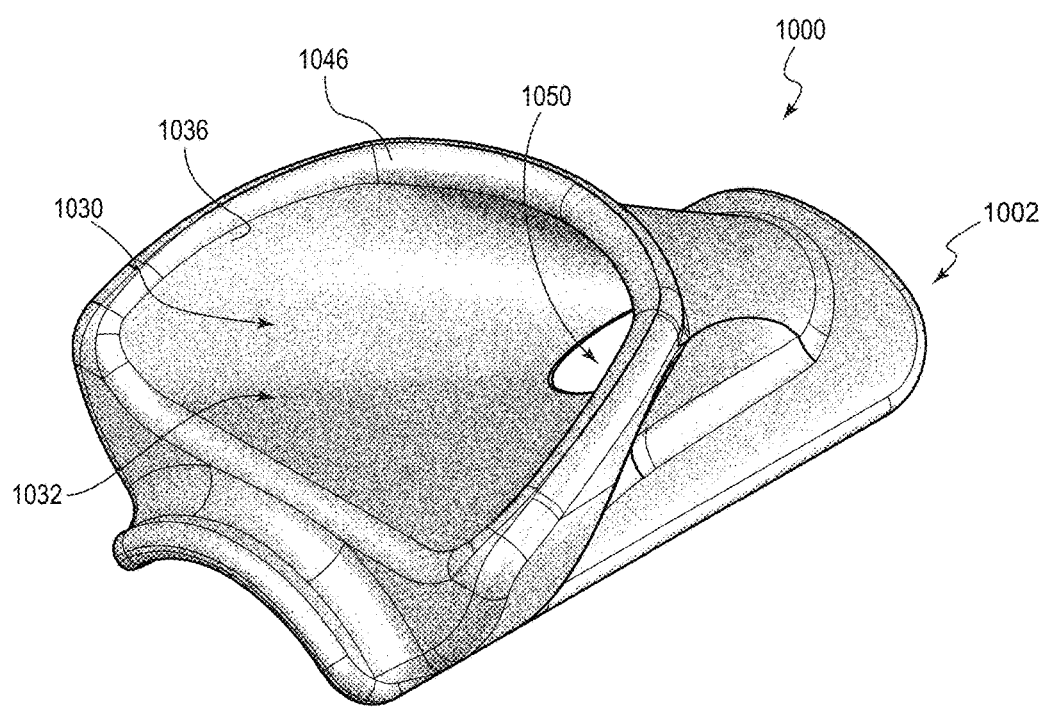
FIG. 21A
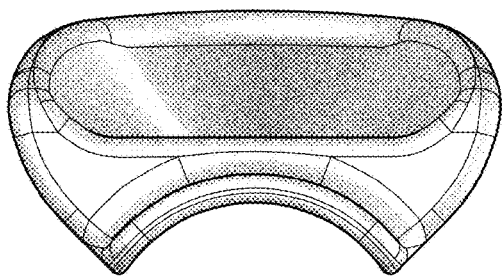  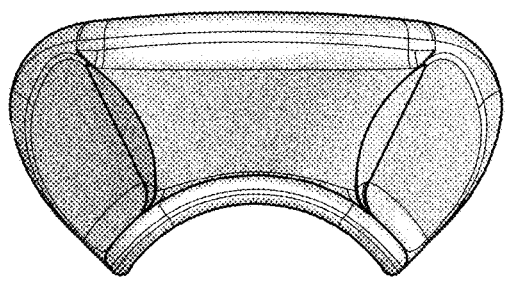
FIG. 21B          FIG. 21C

VASCULAR ACCESS PORTS AND RELATED METHODS

CROSS-REFERENCE TO RELATED APPLICATIONS

This application is a continuation of prior U.S. patent application Ser. No. 13/018,277, filed Jan. 31, 2011, which is a continuation-in-part of prior U.S. patent application Ser. No. 12/697,167, filed Jan. 29, 2010, titled VASCULAR ACCESS PORTS AND RELATED METHODS, now U.S. Pat. No. 8,337,464, and which is also a continuation-in-part of prior U.S. patent application Ser. No. 12/697,192, filed Jan. 29, 2010, titled SUBCUTANEOUS VASCULAR ACCESS PORTS AND RELATED SYSTEMS AND METHODS, now U.S. Pat. No. 9,072,880; each of the U.S. patent application Ser. Nos. 12/697,167 and 12/697,192 claims the benefit under 35 U.S.C. § 119(e) of U.S. Provisional Patent Application No. 61/148,372, titled VASCULAR ACCESS METHODS, APPARATUS AND SYSTEMS, filed on Jan. 29, 2009, and of U.S. Provisional Patent Application No. 61/229,023, titled SURGICALLY IMPLANTED DIRECT VASCULAR ACCESS PORT METHOD AND APPARATUS, filed on Jul. 28, 2009. The entire contents of each of the foregoing applications are hereby incorporated by reference herein.

STATEMENT REGARDING FEDERALLY SPONSORED RESEARCH OR DEVELOPMENT

The invention was made with support from the U.S. Government under Grant No. SBIR R44 CA 139608, which was awarded by the National Institutes of Health. The U.S. Government has certain rights in the invention.

TECHNICAL FIELD

The present disclosure relates to subcutaneous vascular access ports and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 16D is a top plan view thereof;
FIG. 16E is a bottom plan view thereof;
FIG. 16F is a right side elevation view thereof, wherein a left side elevation view thereof is a mirror image of the right side elevation view;
FIG. 16G is a cross-sectional view thereof;
FIG. 17A is a perspective view of another embodiment of a vascular access port;
FIG. 17B is a perspective view of the vascular access port of FIG. 17A coupled to a vessel;
FIG. 21A is a perspective view of another embodiment of a vascular access port;
FIG. 21B is a rear elevation view thereof;
FIG. 21C is a front elevation view thereof.

DETAILED DESCRIPTION

Figure 1:
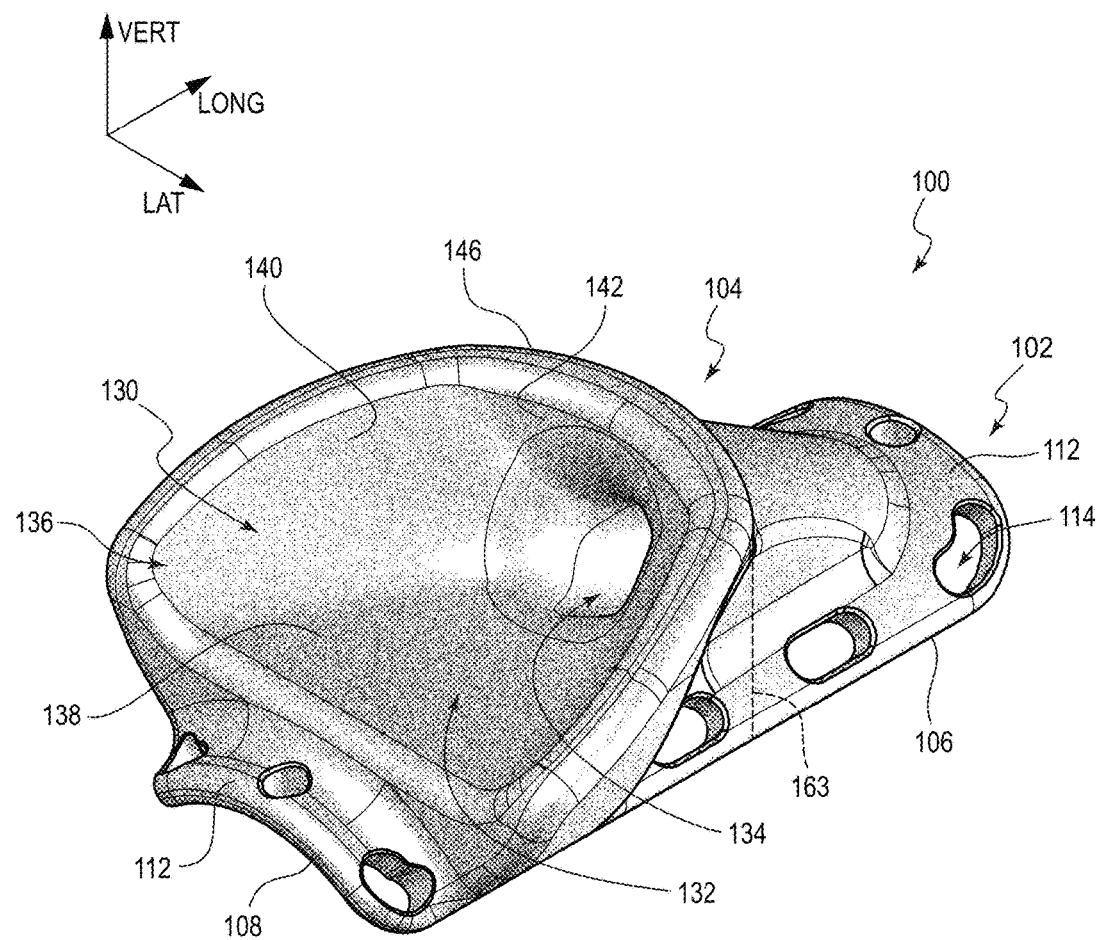
FIG. 1 is a perspective view of an embodiment of a vascular access port.

Certain embodiments of vascular access ports described herein are configured to be implanted subcutaneously in a patient for relatively long or indefinite periods. The vascular access ports can be implanted in any suitable manner and can be substantially fixed relative to a vessel wall once implanted. For example, in some implantation methods, a bottom surface of a vascular access port placed in contact with the tunica adventitia of a vessel and the port is secured to the vessel via one or more sutures that extend through at least a portion of every layer of the vessel. In further embodiments, a portion of the tunica adventitia is separated or removed from a blood vessel such that the bottom surface of a port is relatively close to the tunica media layer of the blood vessel, and the port is secured to the vessel via one or more sutures that extend through at least a portion of the tunica adventitia layer and substantially entirely through the media and the tunica intima layers. In some embodiments, the surface of the port that contacts the vessel wall can comprise an opening through which an access device, such as a needle, can be inserted into a lumen of the blood vessel. The vascular access ports can be well-suited for buttonhole cannulation techniques in which buttonhole access sites are created in vessel walls and/or are used to access the vessels. The term "buttonhole" is used herein in its ordinary sense in the field of vascular access (e.g., in the field of hemodialysis), particularly in the context of cannulation techniques, and the term can include single-site cannulation holes that are approximately the same size as access devices that are inserted therethrough (e.g., needles or other cannulation devices), and that can permit relatively easy insertion of the access devices as compared with other areas along a vessel wall. Similarly, the ports can be well-suited for the creation and/or use of tracts through the skin of a patient through which the buttonholes can be repeatedly accessed. These and other features and advantages of various embodiments of vascular access ports, of systems that employ the ports, and of methods of implanting and using the ports will be apparent from the disclosure herein.

FIGS. 1-7 illustrate an embodiment of a vascular access port 100. The vascular access port 100 includes a base 102 and a body 104. In the illustrated embodiment, the base 102 and the body 104 are integrally formed as a unitary piece, and the body 104 extends away from the base 102. The base 102 is elongated in a longitudinal direction LONG. In particular, the illustrated base 102 defines a substantially rectangular perimeter 106 that extends a greater distance in the longitudinal direction LONG than it does in a transverse or lateral direction LAT (see, e.g., FIG. 5). The edges and corners of the rectangular perimeter 106 can be rounded, or radiused, which can prevent trauma to surrounding tissue when the vascular access port 100 is implanted.

In the drawings, the longitudinal and lateral directions LONG, LAT are represented by perpendicular axes. A vertical direction VERT is represented by a third axis that is perpendicular to each of the longitudinal and lateral axes. In the illustrated embodiment, the longitudinal direction LONG corresponds with a direction in which a longitudinal axis of a vessel extends when the port 100 is attached to the vessel (see FIG. 8). The three sets of mutually perpendicular axes are provided for illustration, and are not intended to limit the potential orientations of the port 100. For example, although the term "vertical" is used with respect to the vertical direction, this term does not imply any preferred gravitational orientation of the port 100. By way of illustration, in some embodiments, the port 100 may be fixedly attached to a vessel in an arm or a leg of a patient such that the vertical direction VERT relative to the port may assume any orientation relative to a true or gravitationally-based vertical direction depending on the position of the arm or the leg.

Figure 2:
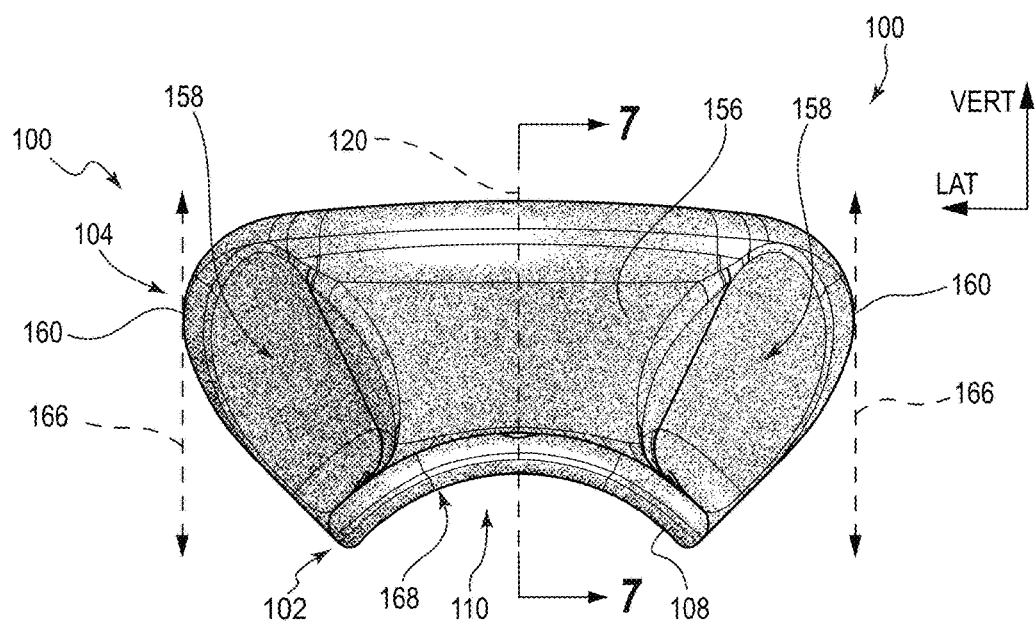
FIG. 2 is a front elevation view thereof.
Figure 3:
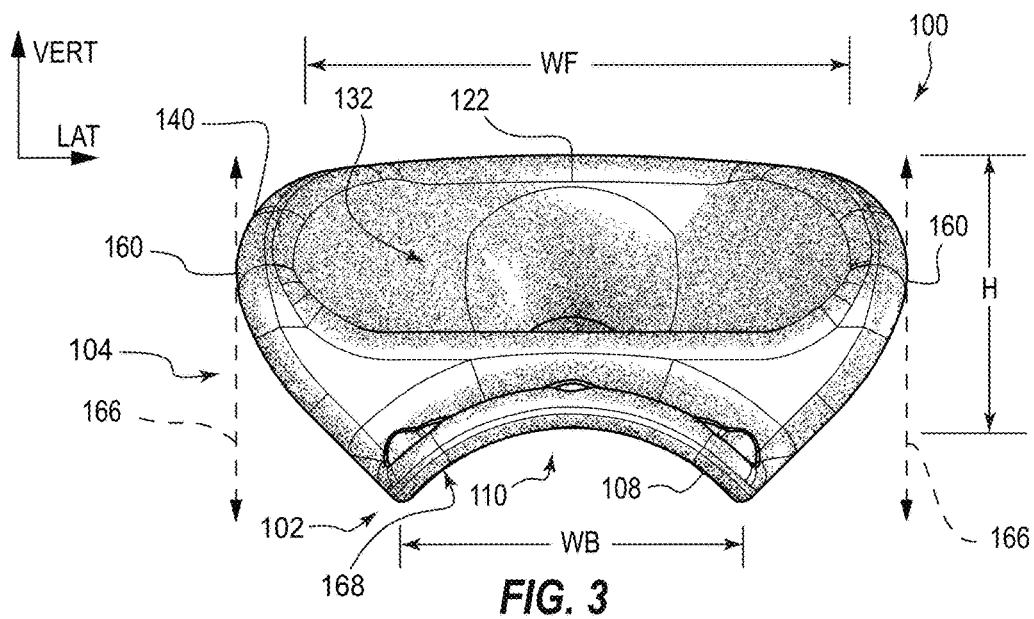
FIG. 3 is a rear elevation view thereof.

The base 102 can include a base surface or bottom surface 108 that is configured to face a vessel when the vascular access port 100 is coupled to the vessel. The bottom surface 108 can be configured to conform to a contour of a wall of the vessel. For example, the bottom surface 108 of the base 102 can be bowed in the lateral direction and can have a radius of curvature that is substantially the same as a radius of curvature of an outer surface of a vessel to which the vascular access port 100 is to be attached. Stated otherwise, as shown in FIGS. 2 and 3, the base 102 can extend from a central position both outwardly in the lateral direction and downwardly in the vertical direction so as to define a bowed or arched shape such that the bottom surface 108 of the base 102 can conform to an outer surface of a vessel. The bowed bottom surface 108 can define a cavity 110 into which at least a portion of a circumference of a vessel can be received. In the illustrated embodiment, the width and the curvature of the bottom surface 108 are such that the cavity 110 is sized to receive a substantial portion of the circumference of a vessel therein. Such a configuration can permit the bottom surface 108 to form a stable contact with the vessel. Other suitable arrangements are also possible, as discussed below.

The base 102 can include one or more connection flanges 112 that extend about a least a portion of a periphery of the base 102. In the illustrated embodiment, a first connection flange 112 extends about a front end of the base 102 and a second connection flange 112 is at a back end of the base 102. One or more attachment channels or attachment passages 114 can extend through the connection flanges 112. The attachment passages 114 can be configured to permit one or more ties or attachment devices 116 to extend therethrough so as to attach the vascular access port 100 to a vessel (see, e.g., FIGS. 8, 9C, 10F, 11A, and 12), as discussed further below. Any suitable attachment devices 116 may be used, such as one or more sutures, pinch rings, hooks, or wires. Accordingly, in some embodiments, one or more of the attachment passages 114 may be referred to as suture holes. As further discussed below, in the illustrated embodiment, the base 102 includes a centrally situated attachment passage 114 at each of the front and rearward ends thereof.

Figure 4:
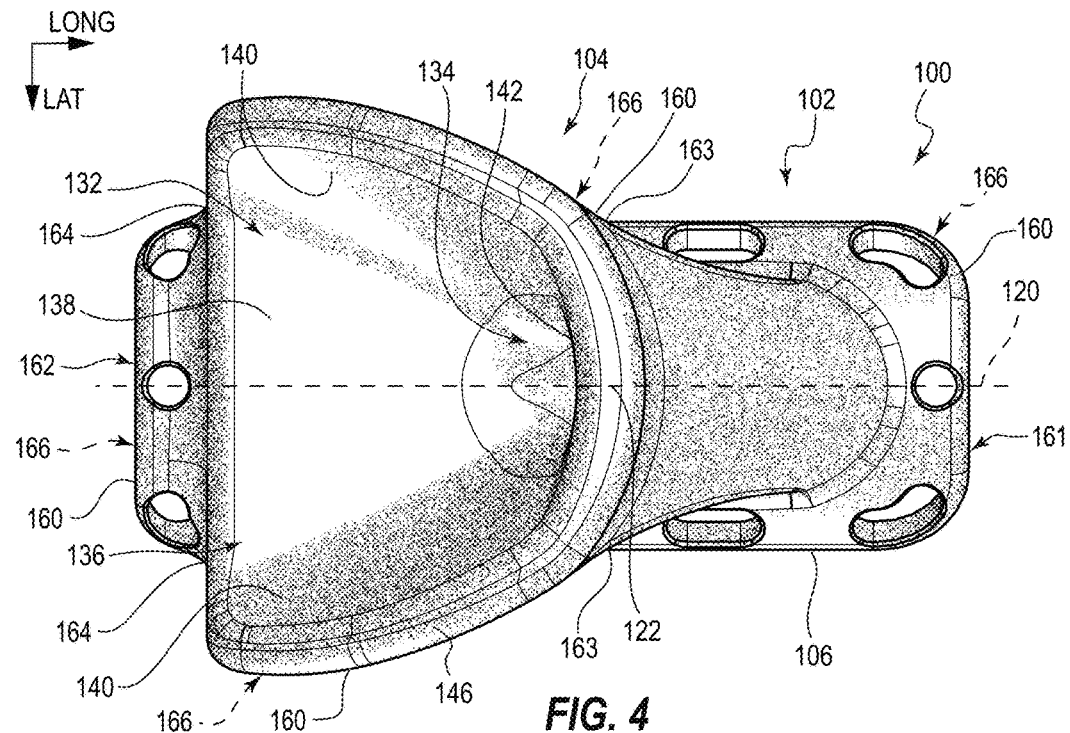
FIG. 4 is a top plan view thereof.
Figure 6:
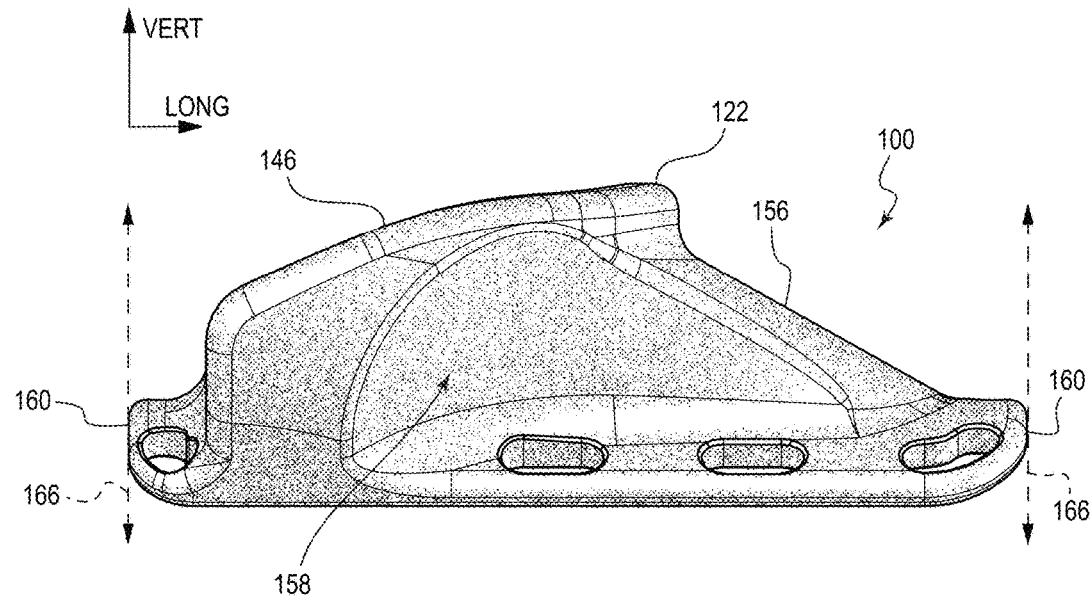
FIG. 6 is a right side elevation view of the vascular access port of FIG. 1, wherein a left side elevation view is a mirror image of the right side elevation view.

The body 104 can extend vertically upward from the base 102. In the illustrated embodiment, the body 104 rises upwardly along a central vertical-longitudinal plane 120 (see FIGS. 2 and 4) of the vascular access port 100. With reference to FIG. 4, the body 104 can expand laterally outward from the central vertical-longitudinal plane 120 and can widen in a rearward direction. Additionally, as shown in FIGS. 3, 4, and 6, a pinnacle region 122 of the body 104 can be positioned along the central vertical-longitudinal plane 120 and at approximately a longitudinal center of the body 104. As previously mentioned, in the illustrated embodiment, the body 104 is integrally formed with the base 102. The port 100 thus may seamlessly or smoothly transition from the base 102 to the body 104. In other embodiments, the base 102 and the body 104 may comprise separate pieces that are attached to each other.

It is noted that directional terms, such as bottom, front, and rearward, are used relative to the orientation of the vascular access port 100 shown in FIG. 1. Such directional terms are not intended to limit the possible orientations of the vascular access port 100 within a patient. For example, in some embodiments, the front end of the vascular access port 100 may be oriented downstream from the rearward end thereof when the port 100 is coupled to a vessel (e.g., may be used for antegrade access to the vessel), whereas in other embodiments, the front end may be oriented upstream from the rearward end (e.g., may be used for retrograde access to the vessel).

Figure 5:
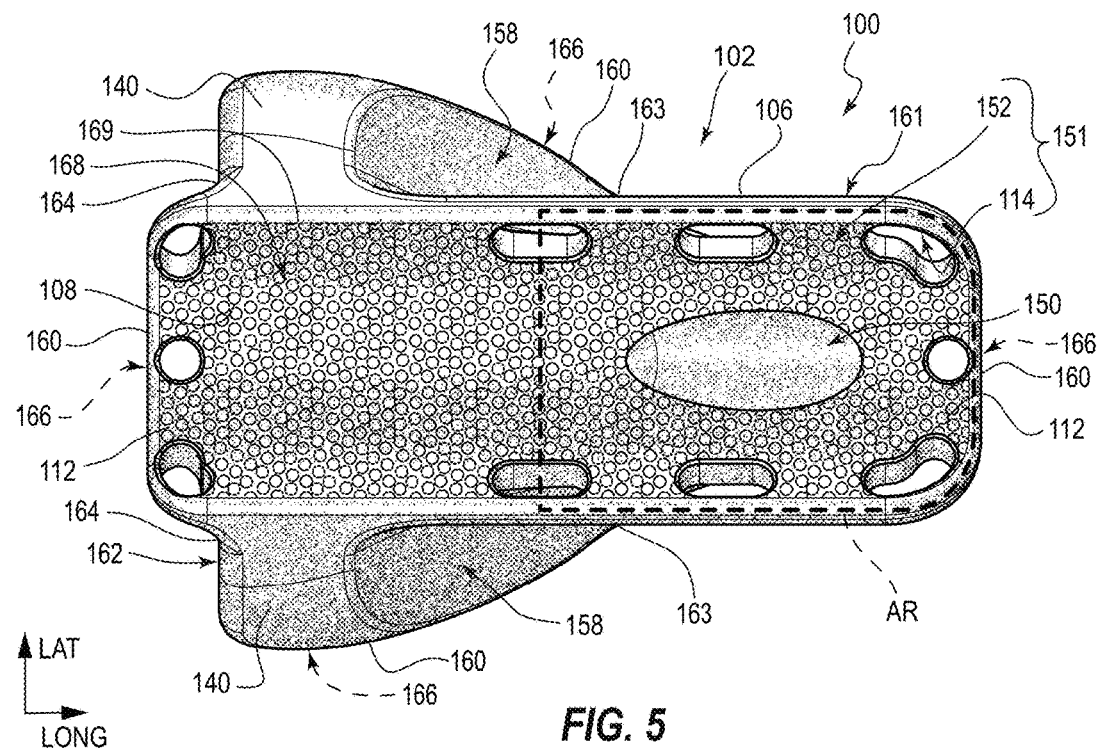
FIG. 5 is a bottom plan view thereof.
Figure 7:
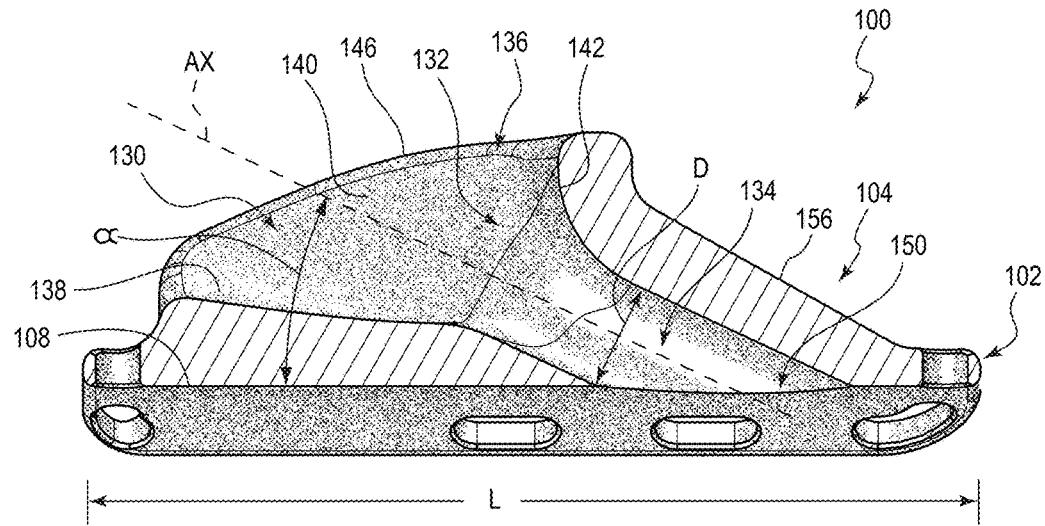
FIG. 7 is a cross-sectional view of the vascular access port of FIG. 1 taken along the view line 7-7 in FIG. 2.

A guidance passageway 130 can extend through the body 104. In the illustrated embodiment, the guidance passageway 130 includes a funnel region 132 and a channel 134. The funnel region 132 defines a relatively large entry mouth 136, which extends about or circumscribes the proximal end or proximal opening thereof, and the funnel region 132 narrows from the entry mouth 136 in a forward and downward direction. In the illustrated embodiment, a forward end of the funnel region 132 transitions into the channel 134. The funnel region 132 can include a base surface 138 that projects rearwardly from the channel 134 and that flares outwardly in the rearward direction. As shown in FIG. 7, the base surface 138 of the funnel region 132 can be angled upwardly (in a rearward direction) relative to the bottom surface 108 of the base 102. The body 104 can further include wings 140 that each curve upwardly and outwardly from the base surface 138 of the funnel region 132 and that are each joined to a backstop portion 142 at a forward end thereof. As shown in FIGS. 4 and 5, the wings 140 can extend outwardly past the perimeter 106 of the base 102 so as to provide for a wide entry mouth 136 of the funnel region 132. The backstop portion 142 can rise upwardly from an upper surface of the channel 134 and may include a surface that is directed substantially vertically. The backstop portion 142 can span the channel 134, and at least a portion thereof can be positioned directly above the channel 134.

The funnel region 132 can fully encompass an entrance end of the channel 134 and can encourage a tip of an access device 144, such as a needle (see FIG. 11B), to enter the channel 134. The funnel region 132 thus can serve as an enlarged target area that can assist in directing an access device 144 to a desired portion of a vessel, as discussed further below. The funnel region 132 can comprise a material that can prevent or discourage a tip of an access device 144 from embedding therein or removing a portion thereof as the tip moves toward the channel 134. For example, in various embodiments, the funnel region 132 can comprise titanium, stainless steel, ceramic, rigid plastic, and/or similar materials.

At least a portion of the entry mouth 136 of the funnel region 132 can include a palpation projection 146, such as a palpation ridge. In the illustrated embodiment, the palpation projection 146 is substantially U-shaped and extends over the wings 140 and the backstop portion 142 of the funnel region 132, and the pinnacle region 122 of the body 104 is located at a forward end of the palpation projection 146. The palpation projection 146 can be rounded or radiused so as to be free from sharp edges that could lead to tissue erosion. As further discussed below, the palpation projection 146 can be used to locate the vascular access port 100 and/or confirm an orientation thereof when the port 100 is positioned subcutaneously in a patient.

The entry mouth 136 of the funnel region 132 may be used to assist in achieving hemostasis after removal of an access device 144 from the vascular access port 100. To this end, the palpation projection 146 may substantially define a plane, in some embodiments. As shown in FIG. 6, the palpation projection 146 of the illustrated embodiment is nearly or substantially planar, as it is not perfectly planar due to a slight curvature in the longitudinal direction. The palpation projection 146 also exhibits a slight curvature in the transverse direction, as can be seen in FIG. 3. Moreover, in the illustrated embodiment, a rearward edge of the entry mouth 136 smoothly transitions into the palpation projection 146 at either end thereof and is only slightly below the substantially planar region defined by the palpation projection 146. Accordingly, as further discussed below, a seal can readily be formed about a periphery of the entry mouth 136 of an implanted vascular access port 100 by pressing tissue that surrounds the port 100 against at least one of the palpation projection 146 and the entry mouth 136. In some instances, the pressure may be applied in a single direction so as to achieve the seal. The smooth transitions can prevent trauma to tissue that is pressed against the palpation projection 146 and/or the entry mouth 136 and, due to the substantially planar orientation thereof, can be particularly well-suited for sealing when pressure is applied in a direction that is generally normal to the plane. Orientations other than substantially planar may also permit effective sealing of the entry mouth 136, as discussed further below.

In some embodiments, the palpation projection 146 can include one or more bumps or other features which may cause the palpation projection 146 to deviate from a substantially planar orientation. Such features may provide additional information regarding the port 100, such as its position, orientation, etc. In other or further embodiments, the palpation projections 146, which comprise bumps or other protrusions, may be located at positions that are spaced from a border of the entry mouth 136. For example, one or more palpation projections 146 may be positioned on the body 104 at positions that are forward of the entry mouth 136.

With reference to FIG. 7, the channel 134 can extend through the base 102, and a bottom end of the channel 134 can define an opening 150 in the bottom surface 108 of the base 102. The opening 150 may be referred to as a distal opening 150 of the guidance passageway 130. The channel 134 can be configured to constrain movement of one or more access devices 144 inserted individually therethrough along a predetermined and/or repeatable path toward the opening 150. Accordingly, when the vascular access device 100 is fixed relative to a vessel, the channel 134 and the opening 150 can cause the one or more access devices 144 to cannulate or pass through the same portion of the vessel. In certain embodiments, the channel 134 defines a substantially constant inner diameter D along a length thereof, which can constrain the movement of an access device 144 that has an outer diameter that is slightly smaller than the diameter D. For example, in the illustrated embodiment, the channel 134 is substantially cylindrical and can constrain movement of a substantially cylindrical access device 144 (e.g., a fistula needle) that has an outer diameter slightly smaller than the diameter D (see FIG. 11B) along a path that is coaxial with the channel 134. The diameter D and/or the length of the channel 134 can be selected to achieve a desired degree of alignment for a given access device 144.

With continued reference to FIG. 7, the channel 134 can define a central axis AX, which can define an angle α relative to the bottom surface 108. For example, in the illustrated embodiment, the axis AX and a longitudinal line along the bottom surface 108 form the angle α. The angle α can be acute relative to the longitudinal line, or more generally, can be nonparallel and/or non-perpendicular thereto. In FIG. 7, the longitudinal line is represented in FIG. 7 by a line L that defines a longitudinal length of the base 10. When the vascular access port 100 is connected to a vessel, the longitudinal line L can be substantially parallel to a longitudinal axis of a lumen of the vessel (see FIG. 11A). Accordingly, in the illustrated embodiment, the channel 134 can constrain movement of an access device 144 along a path that is both nonparallel and non-orthogonal to the lumen of the vessel. In particular, the channel 134 can constrain movement of the access device 144 along a path that is at or is approximately at the angle α relative to the lumen of the vessel. In various embodiments, the angle α can have a value that is no greater than about 15, 20, 25, 30, 35, 45, or 60 degrees; can have a value that is no less than about 10, 15, 20, 25, 30, 35, 45, or 60 degrees; or can have a value that is within a range of from about 30 degrees to about 60 degrees, from about 15 degrees to about 45 degrees, or from about 20 degrees to about 35 degrees. As further discussed below, some protocols for the creation and use of buttonhole cannulation sites can require introduction of a needle into a vessel at a designated acute angle. Accordingly, certain embodiments of the vascular access port 100 can be configured for use with such protocols, and the angle α can be selected to correspond with the angle designated by the protocol.

As previously discussed, the diameter D defined by the channel 134 can be larger than a diameter of an access device 144 that is inserted through the channel 134. In some embodiments, the channel 134 is larger than the access device 144 by a sufficient amount to allow the access device 144 to pass through it easily or with little or no resistance. Reduction or elimination of insertion and removal forces between an access device 144 and the channel 134 can assist in maintaining a secure attachment between the vascular access port 100 and a vessel over the course of multiple insertion and removal events. Moreover, in the illustrated embodiment, the channel 134 is open, unobstructed, clear, free, or vacant. Stated otherwise, the channel 134 is devoid of closure apparatus, such as, for example, septums, valves, flaps, obturators, etc., which could be used to selectively open the channel 134 prior to or during insertion of an access device 144 therein, or which could be used to selectively close the channel 134 during or after removal of an access device 144 therefrom. The term "closure apparatus," as used herein, is directed to mechanical, electromechanical, or other synthetic, foreign, or non-native devices or systems that may be manufactured outside of a patient and introduced into a patient, but does not include natural or patient-generated materials that may close the channel 134, such as, for example, clotted blood, tissue ingrowth, or vascular structures, such as a neointima or a pseudo vessel wall.

In certain embodiments, a configuration of the channel 134, or more generally, the guidance passageway 130, can remain unchanged upon insertion of an access device 144 therein or removal of an access device 144 therefrom, which may result, at least in part, from an absence of closure apparatus within the channel 134 or the guidance passageway 130. The channel 134 and/or the guidance passageway 130 may be substantially rigid or non-deformable. For example, a surface defining at least a portion of the guidance passageway 130 (e.g., a portion of the guidance passageway 130 that is immediately adjacent to the opening 150) can be non-deformable. More generally, a configuration of the guidance passageway 130 can remain unchanged upon insertion of an access device 144 therein or removal of an access device 144 therefrom. In other or further embodiments, a configuration of the port 100 can remain unchanged upon insertion of an access device 144 therein or removal of an access device 144 therefrom. Stated otherwise, in certain embodiments, no portion of one or more of the channel 134, the full guidance passageway 130, and the vascular access port 100 in its entirety may be deformed, rotated, translated, pivoted, expanded, contracted, reshaped, resized, or otherwise moved relative to remaining portions of one or more of the channel 134, the guidance passageway 130, and the vascular access port 100, respectively. Any resistive forces to the insertion or removal of an access device 144 that might be provided by closure apparatus thus are absent during use of such embodiments of the vascular access port 100. Methods by which hemostasis may be achieved via embodiments of the vascular access port 100 that are devoid of closure apparatus are discussed below.

Manufacture of embodiments of the vascular access port 100 can be facilitated by their lack of closure apparatus. For example, in the illustrated embodiment, the vascular access port 100 comprises a unitary piece and/or comprises a single material, and it is devoid of moving parts. Likewise, in the illustrated embodiment, the guidance passageway 130 is defined by a single unitary piece and/or by a single material, and it is devoid of moving parts. Other or further embodiments may comprise multiple parts that are fixedly attached to each other in a non-separable fashion. Embodiments of the vascular access port 100 can be manufactured via any suitable method, such as machining, die casting, injection molding, etc., and may comprise any suitable biocompatible material, such as, for example, titanium, stainless steel, rigid plastic, ceramic, etc. In some embodiments, the vascular access port 100 comprises a resorbable material. For example, in various embodiments, the vascular access port 100 can comprise one or more of caprilactone and glycolide (e.g., Panacryl, in proportions of about 90% and 10%, respectively); ε-caprolactone; cellulose; ethylene oxide with propylene oxide (e.g., Pleuronic F-108); ethylene oxide with block polymer (e.g., DynaGraft proloxamer); glycolide, dioxanone, and trimethylene carbonate (e.g., Biosyn, in proportions of about 60%, 14%, and 26%, respectively); glycolide and ε-caprolactone (e.g., Monocryl); hyaluronic acid ester (e.g., Hyaff); poly(butylene-terephthalate)-co-(polyethyleneglycol) (e.g., Poly-active, Osteo-active); polydioxanon (e.g., PDS); polyethyleenoxyde, polyglactin (e.g. Vicryl, Vicryl Rapide, Vicryl Plus, Polysorb); poly-glecapron (e.g., Monocryl); polyglycolic acid (e.g., Dexon); polyglyconate (e.g., Maxon); polyglyceride (e.g., Trilucent); polylactic acid (e.g., PLLA); poly L-lactic acid (PLLA) and polyglycolic acid (PGA) (e.g., in proportions of about 82% and 18%, respectively); poly L-lactic acid (PLLA) and copolymer (e.g., Lactosorb); poly-L-lactide, poly-D-lactide, and poly-glycolide; polyvinylalcohol (e.g., Bioinblue); polysaccharide; and propylene oxide.

In other embodiments, the vascular access port 100 can be formed of a combination of materials. For example, as discussed further below, in some embodiments, the guidance passageway 130 can be formed of a material that remains rigid indefinitely, or for a relatively long period, such as titanium, stainless steel, or a first type of resorbable material, and other portions of the vascular access port 100 can comprise a resorbable material, such as, for example, a second type of resorbable material that is resorbed within the body of a patient much quicker than is the first type of resorbable material.

With reference to FIG. 5, the base 102 can include one or more ingrowth-inducing features 151 of any suitable variety that can facilitate integration or ingrowth of tissue in order to provide or enhance an attachment between a vessel and the vascular access port 100. The ingrowth-inducing features 151 can comprise the material or materials of which the base is formed, one or more structural features, and/or one or more coverings. For example, in some embodiments, the base 102 may comprise a material such as hydroxyapatite, which is configured to promote tissue ingrowth or tissue attachment thereto. In such embodiments, the composition of the base 102 can constitute an ingrowth-inducing feature 151 thereof. In the illustrated embodiment, the attachment passages 114 can promote tissue ingrowth in or through the base 102, and thus are identified in FIG. 5 as an ingrowth-inducing feature 151 of the base 102. Other structural features can include, for example, a dovetail groove.

In some embodiments, such as that illustrated in FIG. 5, an ingrowth-inducing feature 151 can comprise an ingrowth-inducing covering 152 that comprises a porous or roughened texture, which can be formed in any suitable manner. For example, in some embodiments, the texture is provided by compaction and sintering of metallic beads or powders, such as titanium beads, onto the base 102. In some embodiments, the beads may have a diameter of about 5 thousandths of an inch (i.e., approximately 0.13 millimeters) or smaller. In various embodiments, the ingrowth-inducing covering 152 can comprise a spherical bead porous coating, a coating of asymmetrical powder, and/or a coating of irregular particles such as those that are available from Orchid Bio-Coat of Southfield, Mich. In other or further embodiments, the ingrowth-inducing covering 152 can be formed by machining, sandblasting, laser etching, or injection molding of the base 102, or by attaching to the base 102 a fabric, such as polyester, Dacron®, or e-PTFE. Stated otherwise, the ingrowth-inducing covering 152 can be integrated into the base 102 or can be applied to the base 102, and in either case, the ingrowth-inducing covering 152 can be positioned at the bottom surface 108 of the base 102.

In other embodiments, the ingrowth-inducing covering 152 can comprise a a porous material, such as a porous metal or plastic. For example, in some embodiments, the covering 152 comprises a plate that is formed of porous titanium, such as, for example, Trabeculite™, which is available from Tecomet of Wilmington, Mass. Other suitable porous materials include Trabecular Metal™, which is available from Zimmer of Warsaw, Ind.

The ingrowth-inducing covering 152 can extend over the entire bottom surface 108 of the base 102, as shown in the illustrated embodiment, or over a significant portion thereof. In some embodiments, it can be desirable for the ingrowth-inducing covering 152 to cover a region that is forward of and/or that encompasses at least a portion of the opening 150 so as to provide a secure attachment between a vessel and the base 102 in this region, which can assist in ensuring that access devices 144 inserted through the opening 150 are consistently and repeatedly directed to the same portion of the vessel. For example, an attachment area AR may be defined over which it is desirable to provide a secure attachment to a vessel. The attachment area AR may be encompassed by a series of attachment passages 114 through which one or more attachment devices 116 may be advanced through the sidewall of a vessel into the lumen of a vessel to couple the vascular access device 100 to a vessel. The attachment area AR likewise may be covered by the ingrowth-inducing covering 152 which can provide a further connection between the vascular access port 100 and an outer layer of the vessel (e.g., the adventitia or media). The attachment area AR can surround the opening 150, as shown. In the illustrated embodiment, a rearward end of the attachment area AR is shown approximately at a middle region of the base 102. In other or further embodiments, the attachment area AR can extend to any suitable position up to a rearward end of the base 102.

In some embodiments, the base 102 can be provided with an adhesive (not shown) or other suitable coating in addition to or instead of the ingrowth-inducing features 151 to provide a secure attachment between the base 102 and a vessel. For example, in some embodiments, the adhesive can comprise cyanoacrylate or fibrin glue.

It can be desirable for the vascular access port 100 to be configured for sufficiently secure attachment to a vessel such that the port 100 remains fixed relative to the vessel when it is influenced by forces from a needle or other access device 144. For example, attachment devices 116 coupled to the attachment passages 114, tissue attached to the ingrowth-inducing covering 152, and/or a bond provided by adhesives can resist relative longitudinal movement between the vascular access port 100 and the vessel when a tip of the access device 144 is urged forwardly along the funnel region 132 or forwardly within the channel 134. Similarly, such attachment features can resist relative rotational movement between the vascular access port 100 and the vessel when a tip of the access device 144 presses downwardly on either of the wings 140.

In some embodiments, it can be desirable to constrain the ingrowth-inducing covering 152 to the bottom surface 108 of the base 102, such as when it is desired to discourage, inhibit, or prevent the body 104 from attaching to surrounding tissue when the vascular access port 100 is implanted in a patient. For example, vessels can be somewhat mobile relative to surrounding tissue, and it may be more desirable for the vascular access port 100 to remain fixed relative to a vessel rather than relative to the tissue that surrounds the vessel. Accordingly, in some embodiments, the body 104 is relatively smooth. In other embodiments, at least a portion of the body 104 can comprise an ingrowth-inducing covering 152.

Figure 5A:
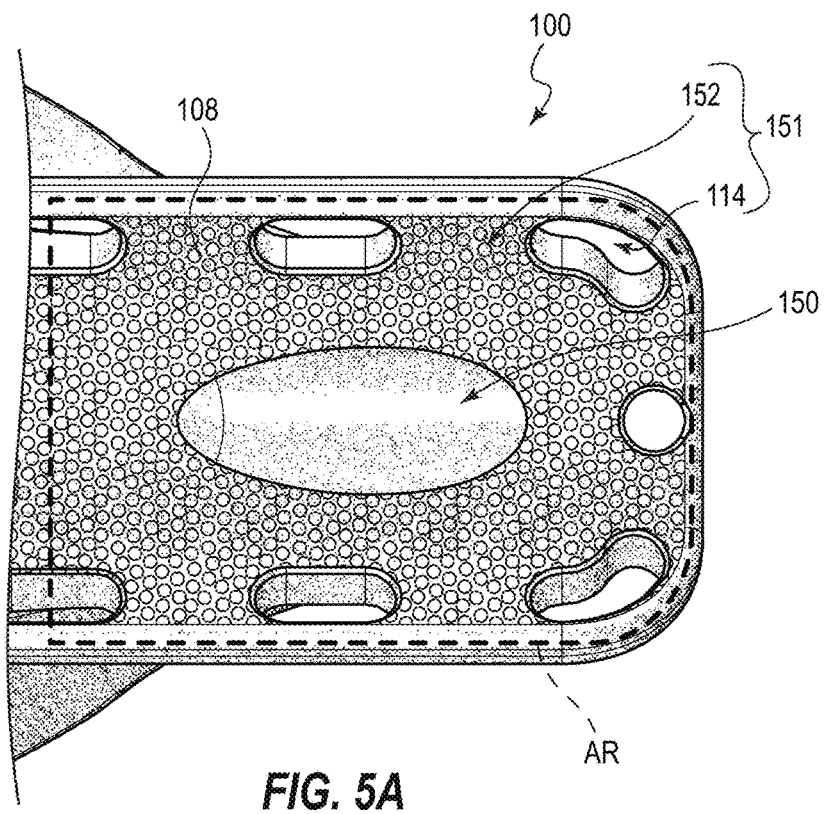
FIG. 5A is a partial bottom plan view thereof.

As discussed further below, the ingrowth-inducing features 151 can provide a seal about at least a portion of the opening 150. With reference to FIG. 5A, the illustrated embodiment includes multiple attachment passages 114 that extend about the opening 150. Sutures or other suitable attachment devices 116 (see FIG. 8) can be advanced through the attachment passages 114 so as to connect the port 100 to a vessel wall. The attachment devices 116 can be sufficiently tight to cause the bottom surface 108 to form seal with the vessel wall in a region that extends about at least a portion of the opening 150. The seal can prevent blood that has exited from a vessel to which the port 100 is attached from moving between the bottom surface 108 of the port 100 and the vessel wall. The seal thus formed via the attachment devices 116 may be acute, and in further instances, the seal may be long-term. For example, in some embodiments the attachment devices 116 may be resorbable, such that the seal is primarily acute (e.g., may be present only during the first several access events through the port 100), whereas in other embodiments, the attachment devices 116 may be more permanent, such that the acute seal formed thereby may persist for a longer period. A long-term seal that encompasses at least a portion of the opening 150 can also be formed by the ingrowth of tissue in or through the attachment passages 114.

Other ingrowth-inducing features 151 may be configured for the creation of a long-term seal that extends about at least a portion of the opening 150. In the illustrated embodiment, the ingrowth-inducing covering 152 extends about a full periphery of the opening 150. Over time, tissue can integrate with or grow into the ingrowth-inducing covering 152. Such ingrowth can provide a seal that prevents blood from passing thereby. Accordingly, in some embodiments, a long-term seal that may take time to form (and thus may not necessarily be considered as an acute seal) can be provided wherever the ingrowth-inducing covering 152 is located. Accordingly, in the illustrated embodiment, a seal can form about the full periphery of the opening 150 and can fully encompass the opening 150.

Figure 5B:
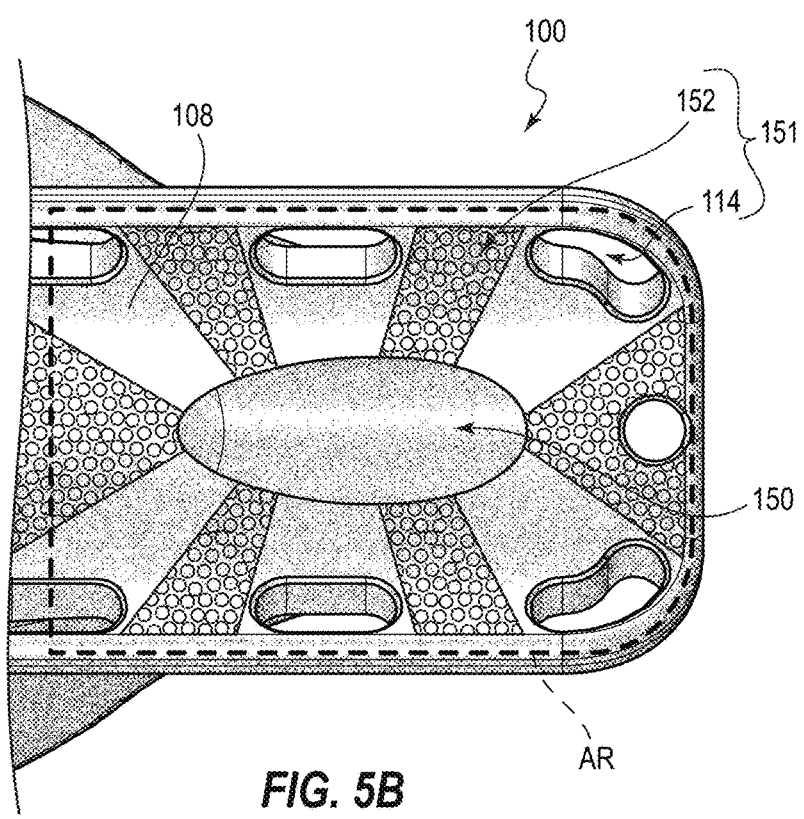
FIG. 5B is a partial bottom plan view of another embodiment of a vascular access port.
Figure 5C:
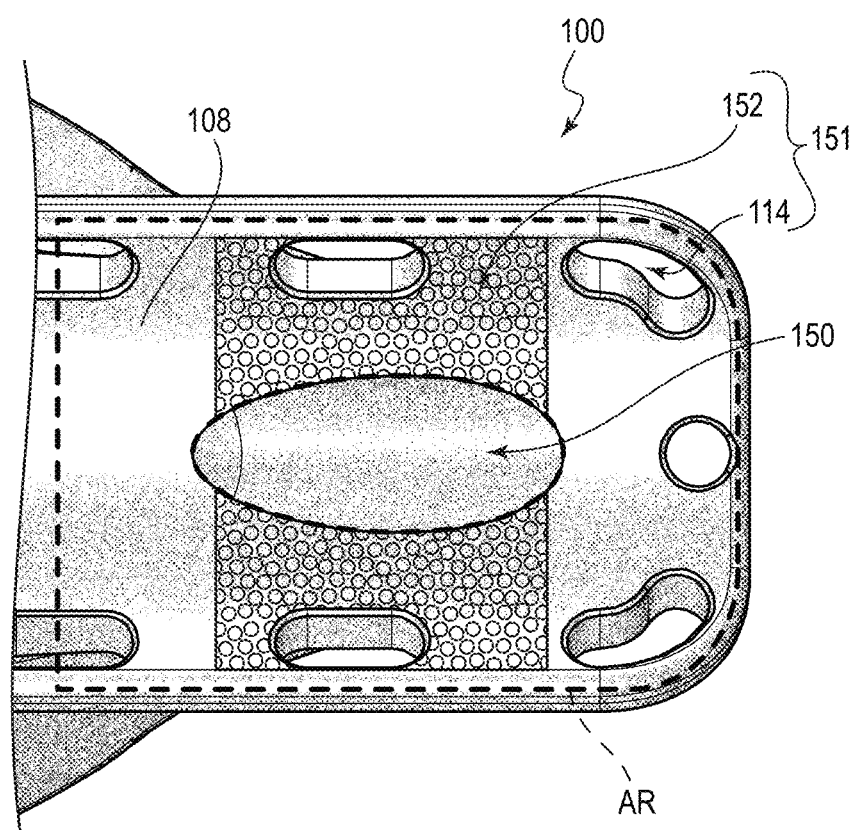
FIG. 5C is a partial bottom plan view of yet another embodiment of a vascular access port.

Additional illustrative arrangements of the ingrowth-inducing covering 152 are shown in FIGS. 5B and 5C. In each illustrated embodiment, the attachment area AR includes attachment passages 114 that are arranged in the same manner as those shown in FIG. 5A. The attachment passages 114 thus can be used to form acute and/or long-term seals in manners such as described above. In FIG. 5B, multiple swaths of an ingrowth-inducing covering 152 extend outwardly from the opening 150. The ingrowth-inducing covering 152 thus partially or incompletely encompasses or encircles the opening 150. When tissue integrates with or grows into the ingrowth-inducing covering 152, it can create a seal about a portion of the opening 150. In the illustrated embodiment, the long-term seal formed by the ingrowth-inducing covering 152 can be complementary to a long-term seal that can form when tissue grows through the attachment passages 114. Accordingly, in the illustrated embodiment, the separate varieties of ingrowth-inducing features 151—namely, the attachment passages 114 and the ingrowth-inducing covering 152—can fully encompass the opening 150 so as to promote the creation of a seal about the entirety of the opening 150, even though each tissue-ingrowth feature 151 individually extends about only a portion of the opening 150.

FIG. 5C illustrates another arrangement of the ingrowth-inducing covering 152 that only partially encompasses the opening 150 in a manner that is not complementary to the attachment passages 114. In such an embodiment, the ingrowth-inducing features 151, both collectively as well as individually, only partially encompass or encircle the opening 150.

It is to be appreciated that arrangements of the ingrowth-inducing features 151 other than those illustrated in FIGS. 5A-5C are also possible. Moreover, while only the attachment passages 114 and the ingrowth-inducing covering 152 are illustrated in these drawings, it is to be understood that any other suitable arrangement or combination of ingrowth-inducing features is possible.

With reference more generally to FIGS. 1-7, in some embodiments, at least a portion of the vascular access port 100 can include a covering (not shown), such as a coating and/or an embedded portion, that comprises one or more materials or agents that provide antiseptic, antimicrobial, antibiotic, antiviral, antifungal, anti-infection, or other desirable properties to the vascular access port 100, such as the ability to inhibit, decrease, or eliminate the growth of microorganisms at or near a surface of the port. For example, in various embodiments, the vascular access port 100 can comprise one or more of silver, platinum, gold, zinc, iodine, phosphorus, bismuth, alexidine, 5-flurouracil, chlorhexidine, sulfadiazine, benzalkonium chloride, heparin, complexed heparin, benzalkonoium chloride, 2,3 dimercaptopropanol, ciprofloxacin, cosmocil, cyclodextrin, dicloxacillin, EDTA, EGTA, myeloperoxidase, eosinophil peroxidase, fusidic acid, hexyl bromide, triclosan, polymyxin B, isopropanol, minocycline rifampin, minocycline EDTA, octenidine, orthophenyl phenol, triclocarban, triclosan, cephazolin, clindamycin, dicloxacillin, fusidic acid, oxacillin, rifampin, antibodies, peptides, polypeptides, free fatty acids, and oxidative enzymes. In some embodiments, the coating and/or the embedded material may be separate or independent from (e.g., non-coextensive with) the ingrowth-inducing covering 152. For example, in some embodiments, the ingrowth-inducing covering 152 is constrained to the base 102 of the vascular access port 100, whereas an antimicrobial covering is constrained to the body 104 of the vascular access port 100.

In the illustrated embodiment, a forward face 156 of the body 104 rises smoothly from the base 102 and is angled rearwardly. As shown in FIG. 7, in some embodiments, the forward face 156 may generally follow a contour of the channel 134 and may be substantially parallel thereto. For example, the forward face 156 can be convexly rounded in a manner similar to the channel 134. The body 104 can smoothly transition from the forward face 156 into depressions 158 at either side thereof, which can provide for a relatively smaller surface area of the body to which tissue might attach. The depressions 158 can reduce the material costs associated with manufacture of the vascular access port 100.

Various parameters of the vascular access port 100 can be adjusted or selected to achieve a desired performance. For example, with reference to FIG. 3, a maximum width WF of the funnel region 132 can be greater than a maximum width WB of the base 102. Such an arrangement may be desirable where the vascular access port 100 is configured to be coupled with a relatively small vessel, or where a relatively large target area otherwise is desired. In various embodiments, the width WF is no less than about 1.0, 1.25, 1.50, 1.75, or 2.0 times the value of the width WB.

In some embodiments, the width WB of the base 102 can be approximately the same as or smaller than a width of a vessel to which the vascular access port 100 is configured to be attached. In various embodiments, the width WB of the base 102 can be no less than about 6, 7, 8, 9, 10, 11 or 12 millimeters, or can be no more than about 6, 7, 8, 9, 10, 11, or 12 millimeters.

In some embodiments, a height H of the vascular access port 100 can be adjusted or selected depending on the depth at which the port 100 is to be implanted within the patient. For example, some embodiments of the vascular access port 100 may be well-suited for use with a shallow vessel, such as a vein associated with an arteriovenous fistula in a forearm, whereas other embodiments may be well-suited for use with deeper vessels, such as the basilic vein in the upper arm. The depth at which the port 100 is located beneath a surface of the skin of the patient also can vary from patient to patient due to differences in anatomy. Sites at which various embodiments of the vascular access port 100 can be implanted include the cephalic, basilic, median antecubital, saphenous, femoral, jugular, subclavian, or other suitable veins; the femoral, radial, ulnar, brachial, femoral, or other suitable arteries; fistulas; the stomach; other organs; or, more generally, any suitable structure where a walled membrane encircles or encapsulates a region.

In some embodiments, it can be desirable for an implanted vascular access port 100 to be beneath an outer surface of the skin of a patient by a sufficient amount to prevent tissue erosion, yet not so deep that palpation of the vascular access port 100 is difficult or provides insufficient information regarding the position or orientation of the port. In various embodiments, a minimum distance between an outer surface of the skin of a patient and an implanted port is no more than about 3, 4, 5, or 6 millimeters, is no less than about 3, 4, 5, or 6 millimeters, or is about 3, 4, 5, or 6 millimeters.

The height H can be defined as a minimum distance between the pinnacle region 122 and the bottom surface 108 of the base 102, and the height H can be selected, adjusted, or otherwise configured so as to achieve a desired depth of the vascular access port 100 beneath the surface of the skin of a patient. In various embodiments, the height H can be no greater than about 2, 3, 4, 5, 6, 7, 8, 9, 10, 11, 12, 13, 14, or 15 millimeters, or can be no less than about 2, 3, 4, 5, 6, 7, 8, 9, 10, 11, 12, 13, 14, or 15 millimeters. In other or further embodiments, the height H can be no more than about 0.1, 0.2, 0.3, 0.4, 0.5, 0.75, 1.0, 1.5, 2.0, 2.5, 3.0, or 3.5 times the width WB of the base 102, or can be no less than about 0.1, 0.2, 0.3, 0.4, 0.5, 0.75, 1.0, 1.5, 2.0, 2.5, 3.0, or 3.5 times the width WB of the base 102. In other or further embodiments, the angle α, as defined above, can vary with the height H. For example, in some embodiments, the angle α increases with increasing height H.

With reference to FIGS. 2-5 and 6, portions of the body 104 and the base 102 define an outermost periphery 160 of the port 100. The outermost periphery 160 represents a maximum extent of the port 100 in each of the lateral and longitudinal directions. As shown in FIGS. 4 and 5, in the illustrated embodiment, the outermost periphery 160 includes a forward continuous region 161 and a rearward continuous region 162 that meet at two discontinuous positions 163 (see also FIG. 1), where the ends of the forward and rearward continuous regions 161, 162 are vertically separated from each another. The forward continuous region 161 is defined by a forward end of the perimeter 106 of the base 102. A portion of the rearward continuous region 162 is defined by a rearward end of the perimeter 106 of the base 102. At two continuous transition points 164, the rearward continuous region 162 extends upwardly and forwardly from the base 102 along an outer periphery of the body 104 and toward the discontinuous positions 163.

With reference again to FIGS. 2, 3, and 6, the outermost periphery 160 can be extended vertically (i.e., upwardly and/or downwardly) so as to define a peripheral extent 166 of the port. As shown in FIGS. 4 and 5, when the port 100 is viewed in a top plan view or a bottom plan view, the three-dimensional nature of the peripheral extent 166 collapses to two dimensions such that the peripheral extent 166 corresponds with an outline of the port 100.

With reference to FIG. 5, the port 100 can define a footprint 168, which is the portion of the port 100 that is configured to come into direct contact with a vessel when the port 100 is connected to the vessel. In the illustrated embodiment, the footprint 168 is coextensive with the bottom surface 108 of the base 102. Moreover, in the illustrated embodiment, the footprint 168 is smaller than the peripheral extent 166 of the port 100. Stated otherwise, an outermost perimeter 169 defined by the footprint 168 is interior to the peripheral extent 166 of the port 100. In the illustrated embodiment, the outermost perimeter 169 of the footprint 168 is also shaped differently from the peripheral extent 166 of the port 100.

It will be appreciated that various features of the embodiments of the vascular access port 100 discussed above can be altered or modified. For example, in some embodiments, the base 102 and the body 104 comprise separate pieces that are joined to each other. By way of illustration, the base 102 may comprise a relatively compliant material that can readily change shape so as to conform to a surface of a vessel, while at least a portion of the body 104 (e.g., the funnel region 132) can comprise a relatively rigid material. In other or further embodiments, the cavity 110 defined by the base 102 can be sized to receive any portion of a circumference of a vessel therein. Different sizes and configurations of the guidance passageway 130 are also possible, as further discussed below.

The vascular access port 100 can be implanted in a patient and used in any suitable methods. As mentioned above, it can be desirable to secure the vascular access port 100 to a vessel in such a manner that the opening 150 defined by the guidance passageway 130 is fixed relative to the vessel, which can allow the guidance passageway 130 and/or the opening 150 to repeatedly direct an access device to the same portion of the vessel.

Figure 8:
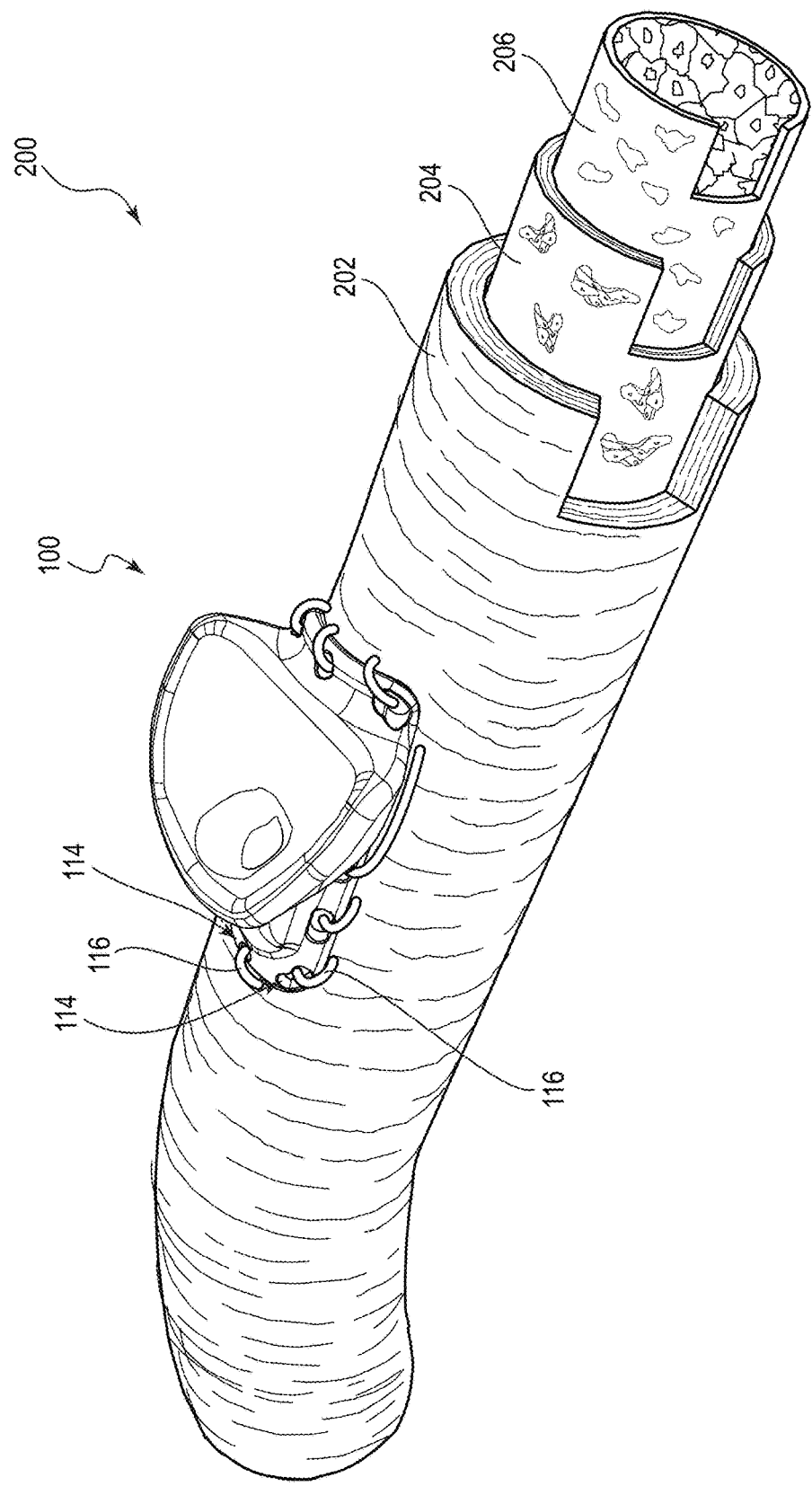
FIG. 8 is a perspective view of the vascular access port of FIG. 1 coupled with a vessel, which is shown in a perspective partial cutaway view.

FIG. 8 depicts an example of one such arrangement. The vascular access port 100 is fixedly and directly secured to a vessel 200, which comprises three layers: the tunica adventitia (or adventitia) layer 202, the tunica media (or media) layer 204, and the tunica intima (or intima) layer 206. The term "direct," when used herein with reference to securing or attaching a vascular access port 100 to the vessel 200, means that some portion of the vascular access port 100 is in abutting contact with the vessel 200 and is fixedly attached thereto. In the illustrated embodiment, an attachment device 116 comprises a running suture that extends through each attachment passage 114 of the vascular access port 100. One or more loops of the suture can extend through all three layers 202, 204, 206 of the vessel 200.

In certain embodiments, it can be desirable to ensure that one or more attachment devices 116 extend through more layers of the vessel 200 than just the adventitia layer 202 (or a portion thereof), or stated otherwise, through the media and/or the intima layers 204, 206. For example, it has been found that attachment of certain ports solely to the adventitia layer 202 (i.e., without attachment to other tissues) can result in mobility of the ports relative to the media and intima layers 204, 206. The ports may shift longitudinally and/or laterally relative to the inner layers 204, 206 of the vessel 200 from such activities as palpation of the ports during cannulation procedures or various day-to-day occurrences. Such mobility of a vascular access port can potentially result in the creation of multiple access sites in the vessel 200 over the course of repeated cannulations, which can weaken the vessel wall over time and potentially result in an aneurysm, vessel stenosis, hematoma, and/or bleeding. In some instances, it can be desirable for one or more attachment devices 116 that are used to attach the port 100 to the vessel 200 to extend through at least the intima layer 206. In further instances, it can be desirable for one or more attachment devices 116 to extend through at least the intima and media layers 206, 204.

Without being limited by theory, it is believed that immobilizing, stabilizing, or fixing the port 100 relative to the media layer 204 permits fibrous tissue to grow between the media layer and into any suitable portion of the port 100, such as an ingrowth-inducing portion. For example, the one or more attachment devices 116 can be used to secure the port 100 relative to the media layer 204. Thereafter, fibrous tissue can further secure the port 100 relative to the media layer 204. The attachment devices 116 thus may primarily be used to facilitate tissue ingrowth, although in some embodiments, long-term presence of the attachment devices 116 may assist in maintaining the port 100 fixed relative to the vessel 100 when extreme loads are applied thereto, such as by an inadvertent bumping or twisting of the implanted port 100.

FIGS. 9A-9E depict various stages of an illustrative method for implanting a vascular access port 100 in a patient 210 such that the vascular access port 100 provides direct access to a vessel within the patient 210. The term "patient" is used broadly herein and includes any animal subject who can or does undergo some process or procedure, whether provided by another or self-administered, and the term is not limited to an individual within a healthcare facility. The vascular access port 100 may be used with any suitable vessel, such as an artery 212, a vein 214 (both shown in FIG. 9A), or an artificial graft (see FIG. 14B). As previously discussed, the vessel may be at any of a variety of positions within the patient 210, such as the neck, the upper arm, the forearm, or the leg, and it may be located at a relatively deep or shallow position relative to the skin 216 of the patient. Numerous uses of an implanted port 100 are possible, including, for example, hemodialysis, chemotherapy, antibiotic therapy, total parenteral nutrition, pain management, aquapheresis, plasmapheresis, hydration, or long-term therapies of any suitable variety. In the illustrated method, a vascular access port 100 is shown being implanted in a forearm of the patient 210—specifically, the vascular access port 100 is shown being connected to a vein 214 that is associated with an arteriovenous fistula 218 for use in hemodialysis. It is noted that the vein 214 is a three-layered vessel such as the vessel 200 depicted in FIG. 8, and thus may be referred to hereafter as a vessel 200 to illustrate the more general applicability of the procedures discussed.

Figure 9A:
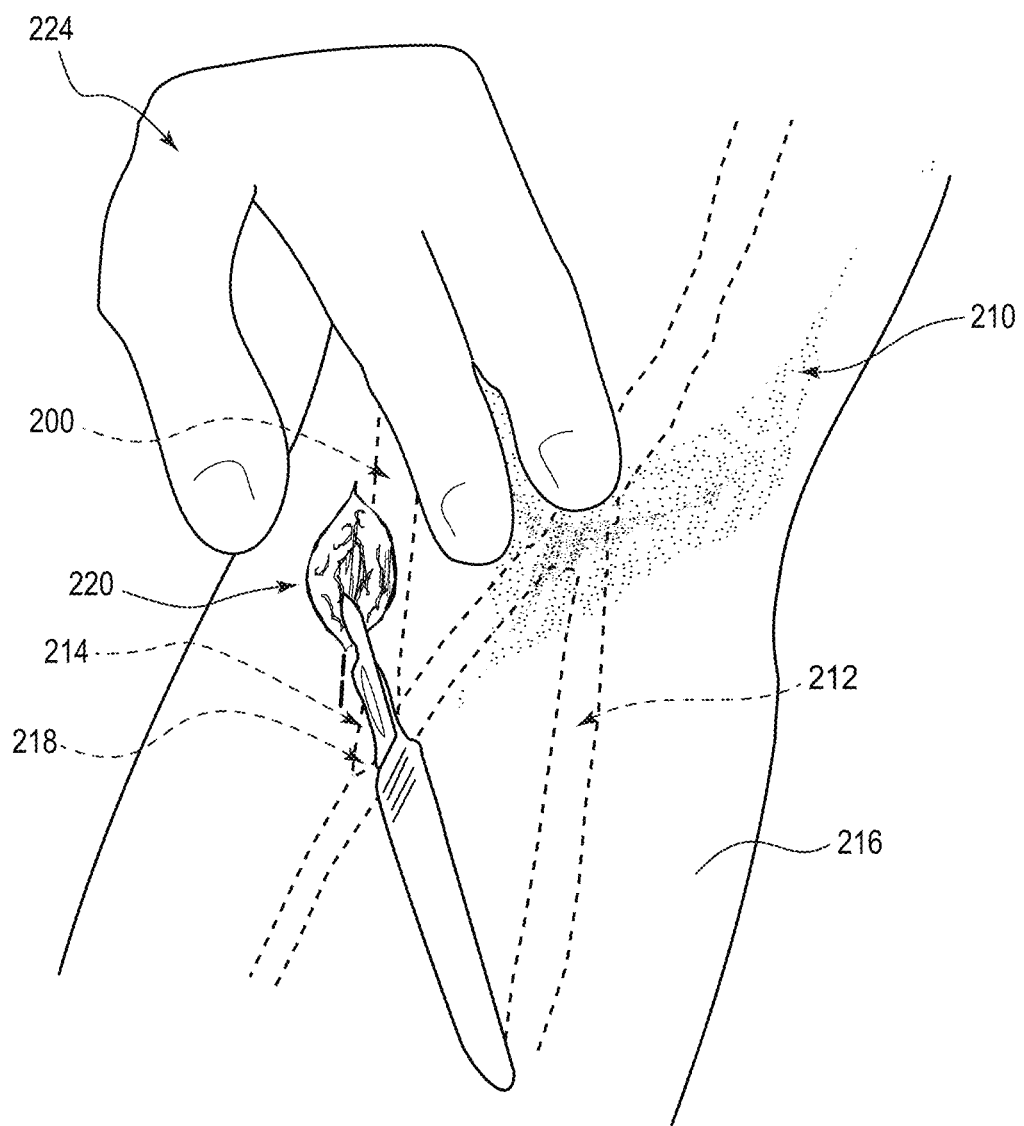
FIG. 9A is a perspective view of a stage of an illustrative method of implanting an embodiment of a vascular access port in a patient depicting the creation of an incision.

With reference to FIG. 9A, an incision 220 can be made in the skin 216 of the patient 210. In the illustrated embodiment, the incision 220 can be from about 4 centimeters to about 5 centimeters in length. The incision 220 can extend substantially parallel to the vessel 200, but can be offset relative thereto (i.e., is not directly over the vessel 200). In the illustrated embodiment, the incision 220 is offset from a position directly over the vessel 200 by a distance of from about 2 centimeters to about 3 centimeters. As discussed further with respect to FIG. 9E, such an orientation of the incision 220 can facilitate access to the vascular access port 100 after the implantation procedure is complete. In other methods, the incision 220 can be directly over the vessel 200 and/or at an angle or entirely transverse relative thereto. The incision 220 can be made by a practitioner 224 using any suitable techniques and instruments.

Figure 9B:
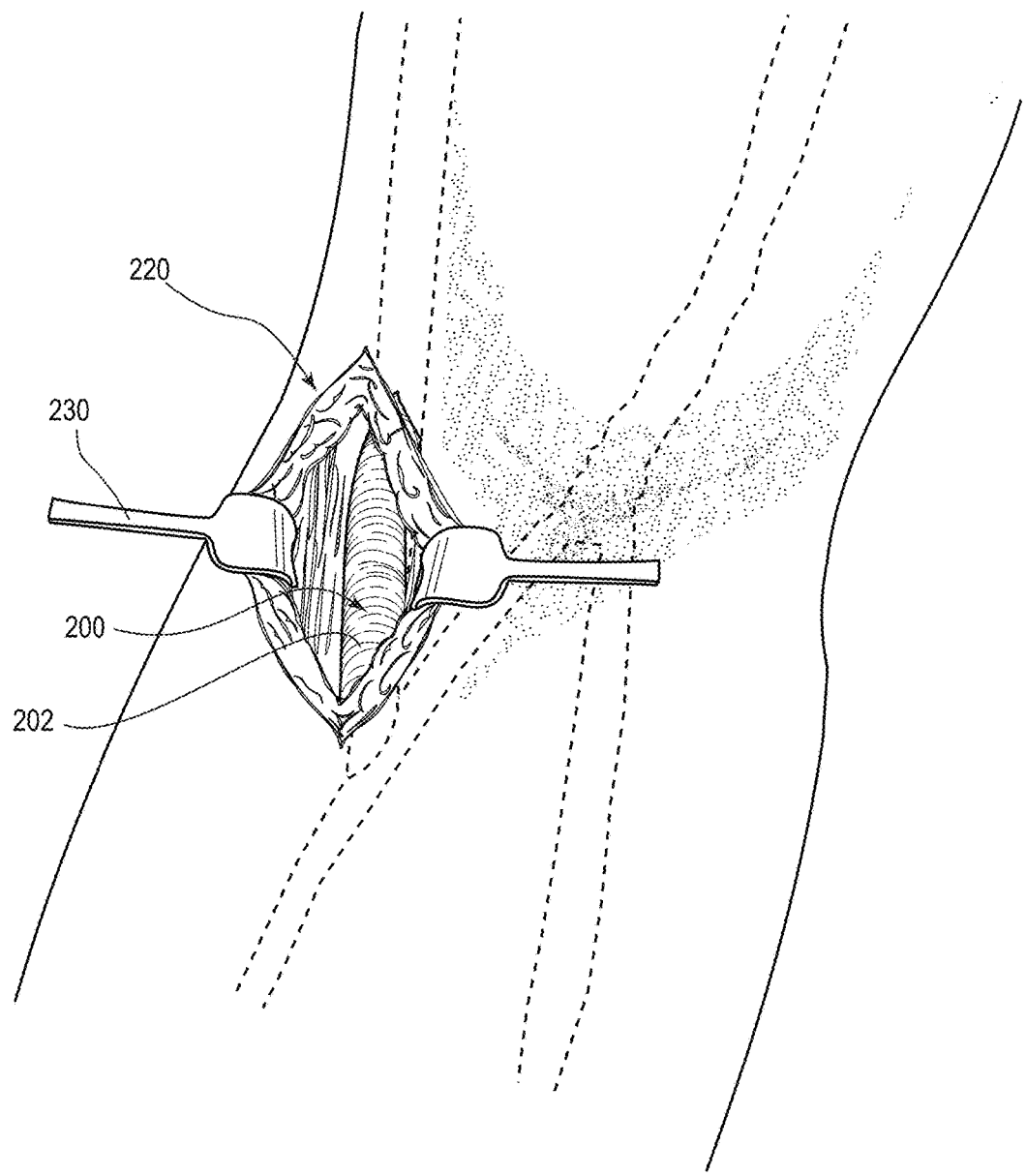
FIG. 9B is a perspective view of another stage of the method of FIG. 9A in which a vessel is exposed.

With reference to FIG. 9B, the vessel 200 can be exposed by removing, partially removing, or separating skin, fat, and fascial layers from the adventitia layer 202 of the vessel 200 at the site of the incision 220. Exposure of the vessel 200 can be maintained in any suitable manner, such as by the use of tissue spreaders 230.

Figure 9C:
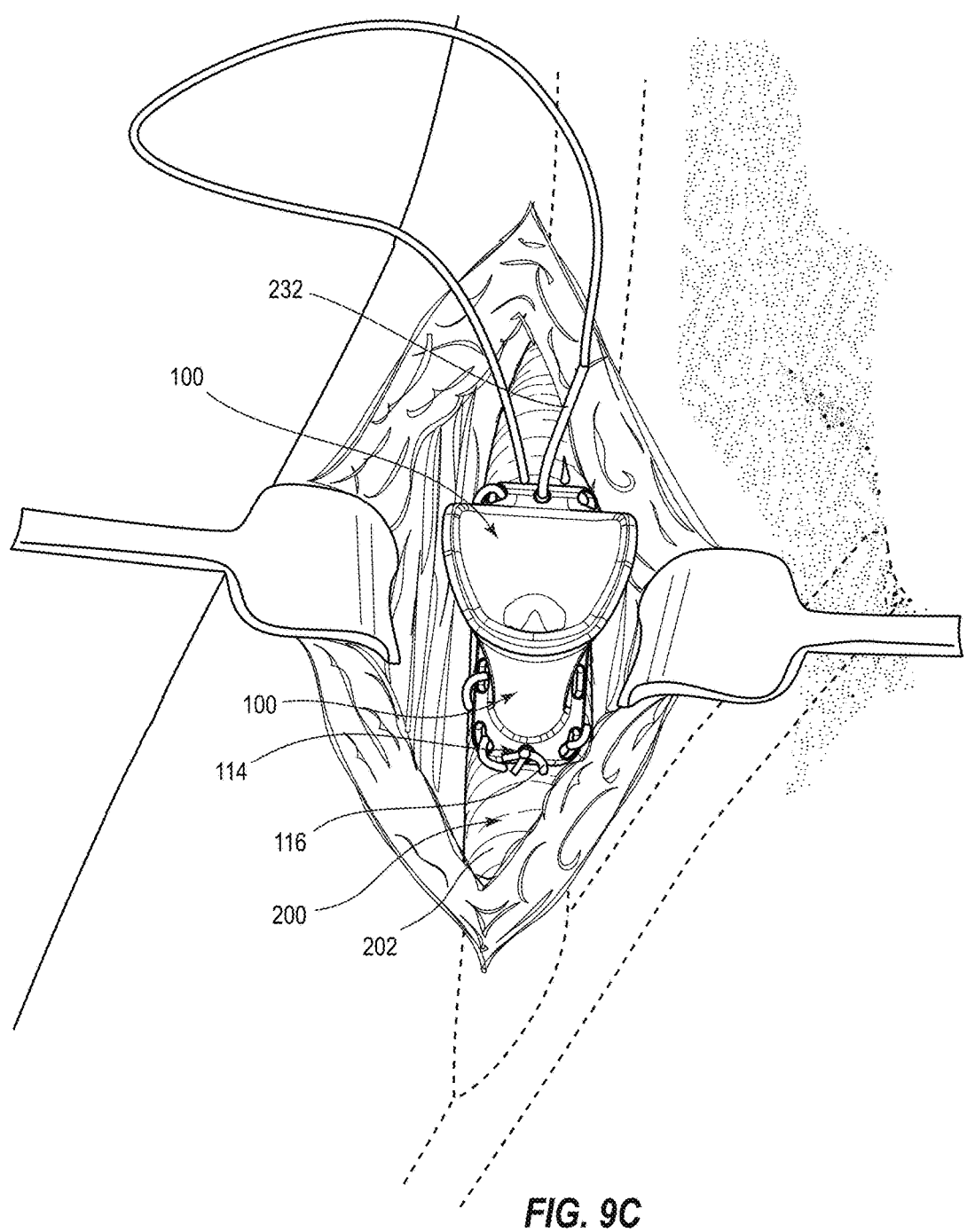
FIG. 9C is a perspective view of another stage of the method of FIG. 9A in which an attachment is made between the vascular access port and the vessel.

With reference to FIG. 9C, an initial attachment of the vascular access port 100 to the vessel 200 can be achieved at the front end or the back end of the vascular access port 100. In some procedures, an attachment device 116 can be inserted through all three layers 202, 204, 206 (see FIG. 8) of the vessel 200 and through an attachment passage 114 at each of the front and back ends of the vascular access port 100 along a lateral center of the port 100 prior to use of any of the remaining attachment passages 114. Initial attachment of the front end and/or the back end of the vascular access port 100 can assist in ensuring that a desired orientation of the vascular access port 100 is achieved and maintained during the course of the implantation procedure.

As previously mentioned, any suitable attachment device (or devices) 116 may be used in securing the vascular access port 100 to the vessel 200. The attachment devices 116 can include, for example, one or more sutures, pinch rings, hooks, or wires. Once an attachment device 116 is in a desired position, it can be securely tied, crimped, twisted, or otherwise fastened.

In the illustrated embodiment, the attachment device 116 comprises a running suture, which can be looped through multiple attachment passages 114. In the illustrated embodiment, a single running suture 116 is used to secure the vascular access port 100 to the vessel 200. In other embodiments, the suture 116 may extend through fewer passages 114 and one or more additional sutures 116 may be used. For example, as previously discussed, in some embodiments, a separate suture 116 is secured at each end of the vascular access port 100 prior to providing sutures in any of the remaining attachment passages 114.

Various options are available for securing one or more sutures 116 in place. For example, in some procedures, a suture needle 232 can be inserted through the wall of the vessel 200 at a position near an attachment passage 114, and can then pass through the attachment passage 114 after having passed through the vessel wall. A suture 116 associated with the suture needle 232 can then be tied using a surgical knot and the excess suture trimmed. In other procedures, a suture 116 can be positioned at a desired location within the wall of the vessel 200 such that at least one leg thereof protrudes from the adventitia layer 202. The protruding leg of the suture 116 can be received through a desired attachment passage 114 of the vascular access port 100 as the port 100 is brought into contact with the vessel 200. The suture 116 can then be tied and trimmed. Either approach may be used to secure sutures 116 through any desired number of attachment passages 114 of the vascular access port 100. Any other suitable suturing or attachment technique may be used. In some embodiments, only a portion of the available attachment passages 114 are used.

Figure 9D:
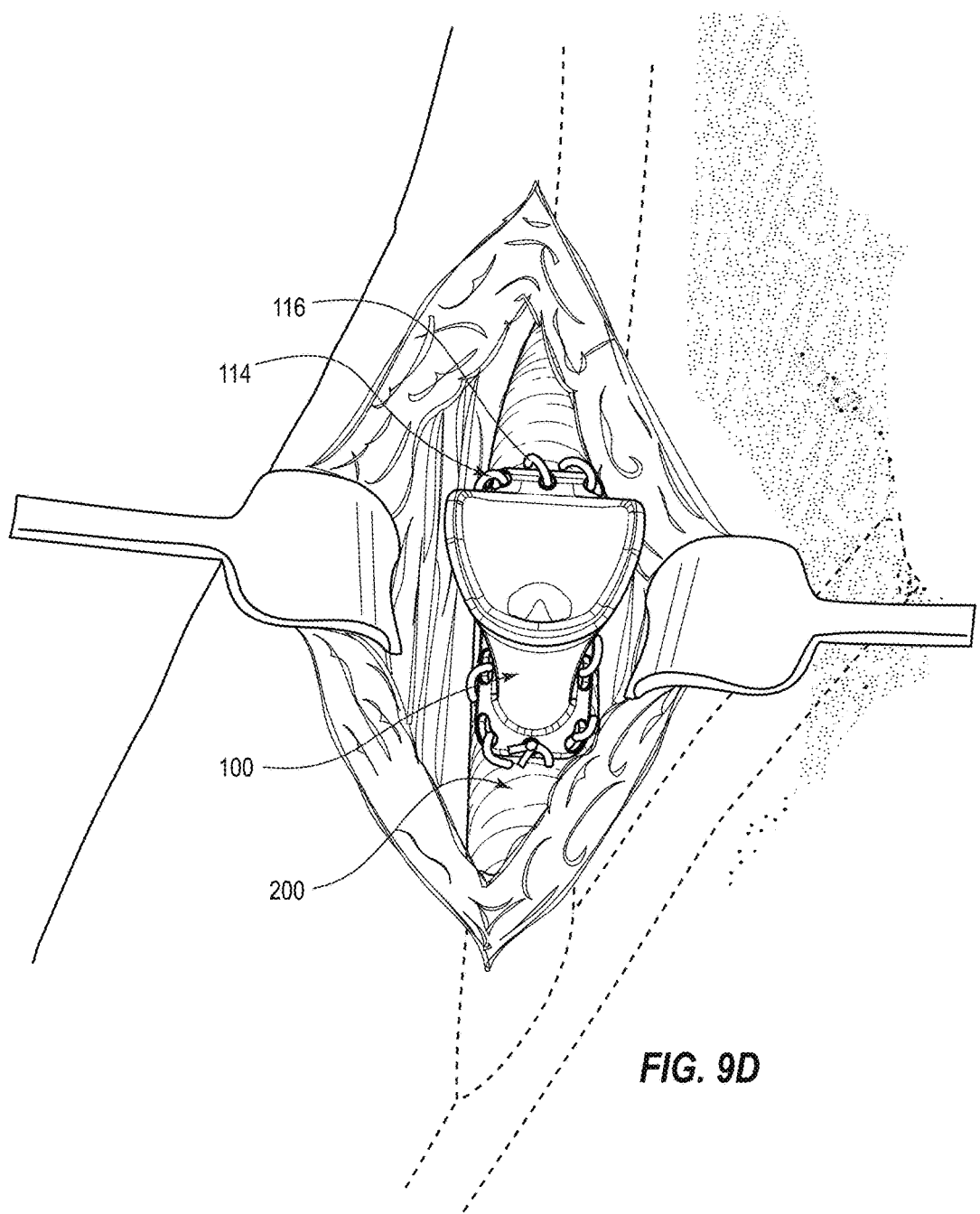
FIG. 9D is a perspective view of another stage of the method of FIG. 9A in which additional attachments have been made between the vascular access port and the vessel.

With reference to FIG. 9D, additional sutures 116 can be used to secure the vascular access port 100 to the vessel 200 via any or all of the remaining attachment passages 114, as desired. In some embodiments, the attachment passages 114 are filled, such as with silicone, so as to prevent ingrowth of tissue. In other embodiments, the attachment passages 114 are left open, which can permit ingrowth of tissue therein or therethrough.

Figure 9E:
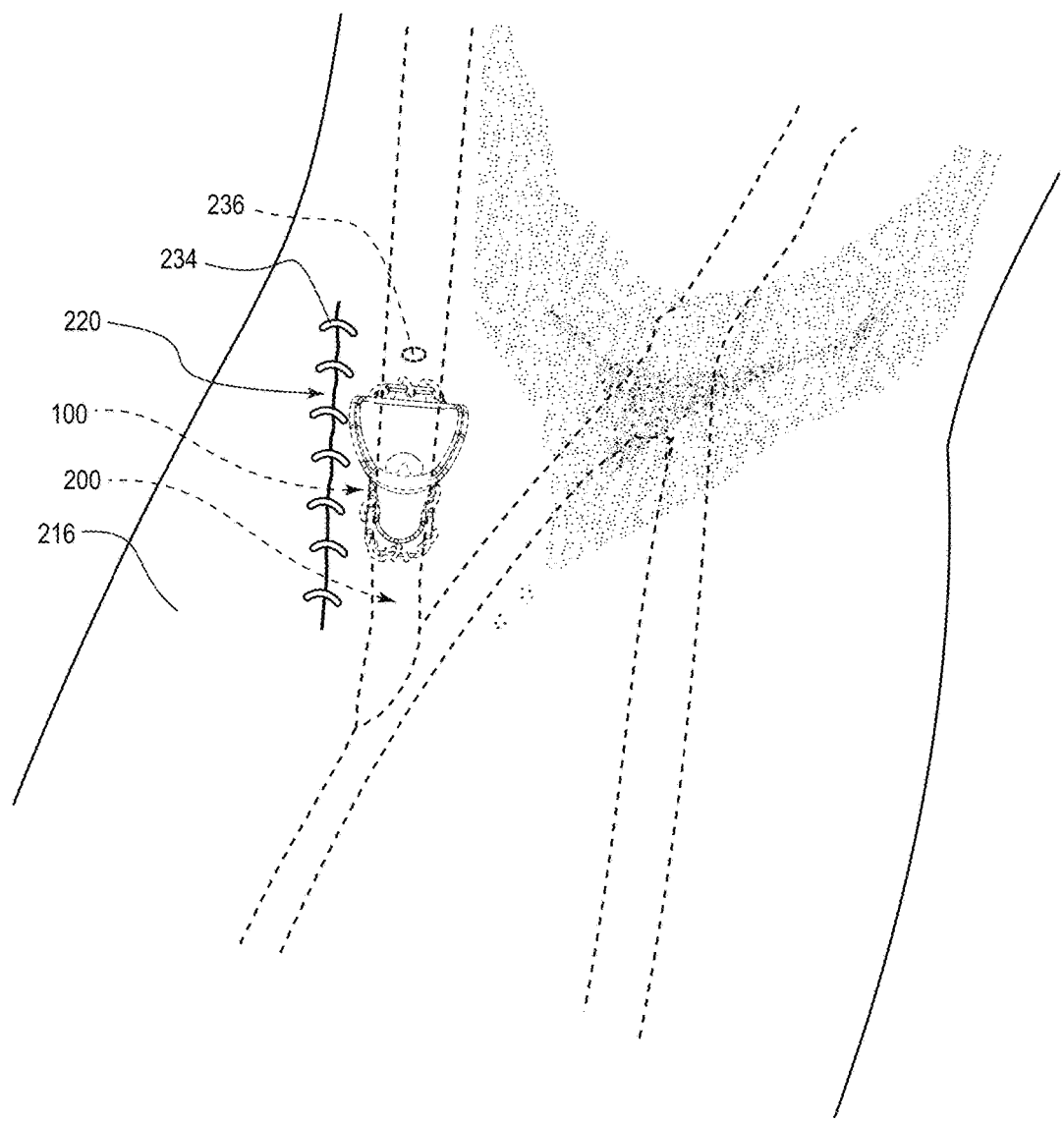
FIG. 9E is a perspective view of another stage of the method of FIG. 9A in which the incision has been closed.

With reference FIG. 9E, the site of the incision 220 can be closed in any suitable manner, such as, for example, via one or more sutures 234. As previously mentioned, the incision 220 can be offset from a position that is directly above the vascular access port 100. In such arrangements, an access device 144 can be inserted through the skin 216 to the vascular access port 100 via a surface insertion site 236 with little or no interaction with the site of the incision 220, or stated otherwise, without contacting any or much scar tissue at or beneath the surface of the skin 216, and this can facilitate the insertion of the access device 144. Likewise, palpation of the port 100 can proceed without interaction with scar tissue, which could otherwise complicate or obscure such palpation.

In certain embodiments, it can be desirable to wait for a period of days or weeks after implantation of the vascular access port 100 before accessing the vessel 200 thereby. The waiting period can provide sufficient time for tissue ingrowth at the appropriate areas of the vascular access port 100, which can provide a more secure connection between the vascular access port 100 and the vessel 200.

FIGS. 10A-10G depict various stages of another illustrative method for implanting a vascular access port 100 in the patient 210 such that the vascular access port 100 provides direct access to the vessel 200 within the patient 210. Although the methods shown in FIGS. 9A-9E and 10A-10G are depicted relative to the same site within the patient 210, it is to be understood that the methods also may be used at other sites.

Figure 10A:
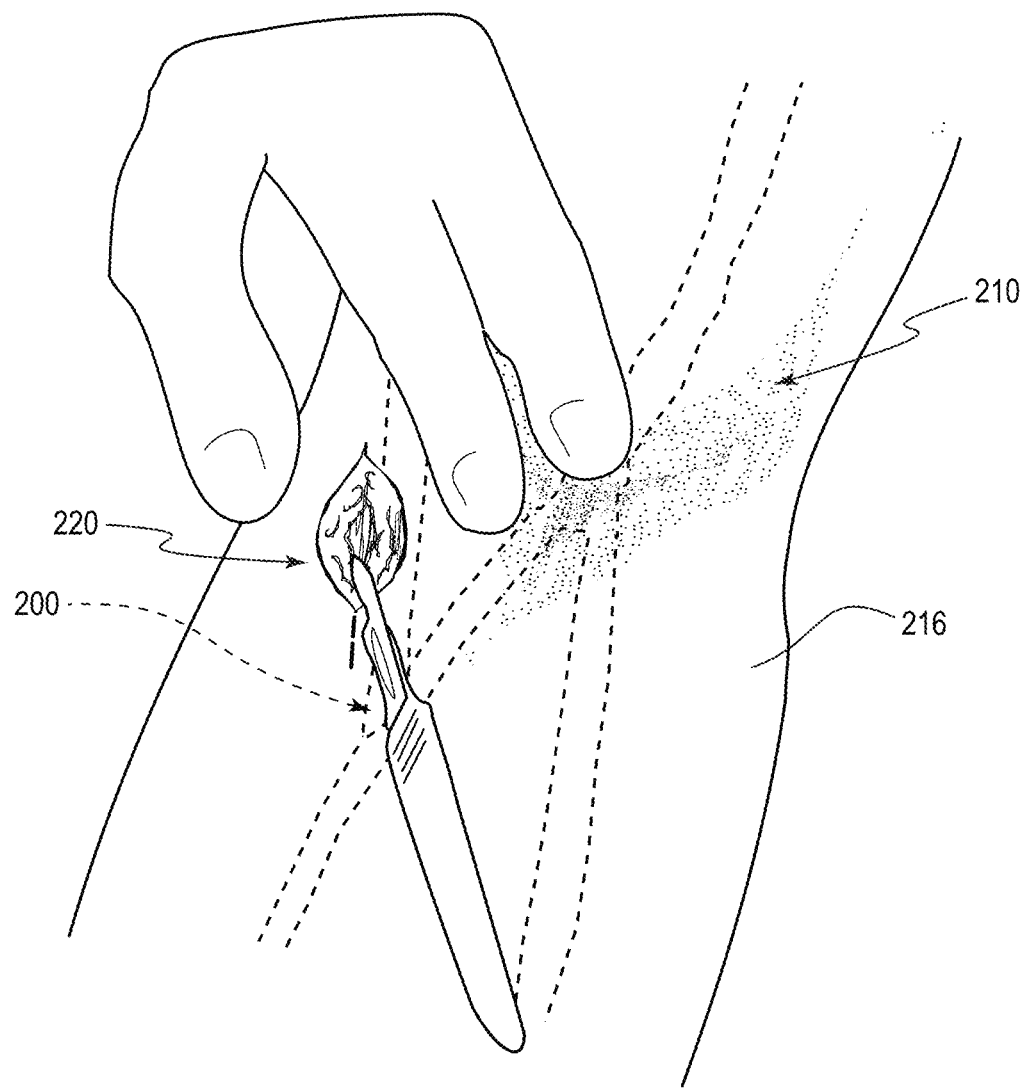
FIG. 10A is a perspective view of a stage of another illustrative method of implanting an embodiment of a vascular access port depicting the creation of an incision in the skin of a patient.

With reference to FIG. 10A, an incision 220 can be made in the skin 216 of the patient 210, which in some embodiments can be from about 4 centimeters to about 5 centimeters in length. The incision 220 can extend substantially parallel to vessel 200 and can be offset relative thereto. In some embodiments, the offset can be by a distance of from about 2 centimeters to about 3 centimeters.

Figure 10B:
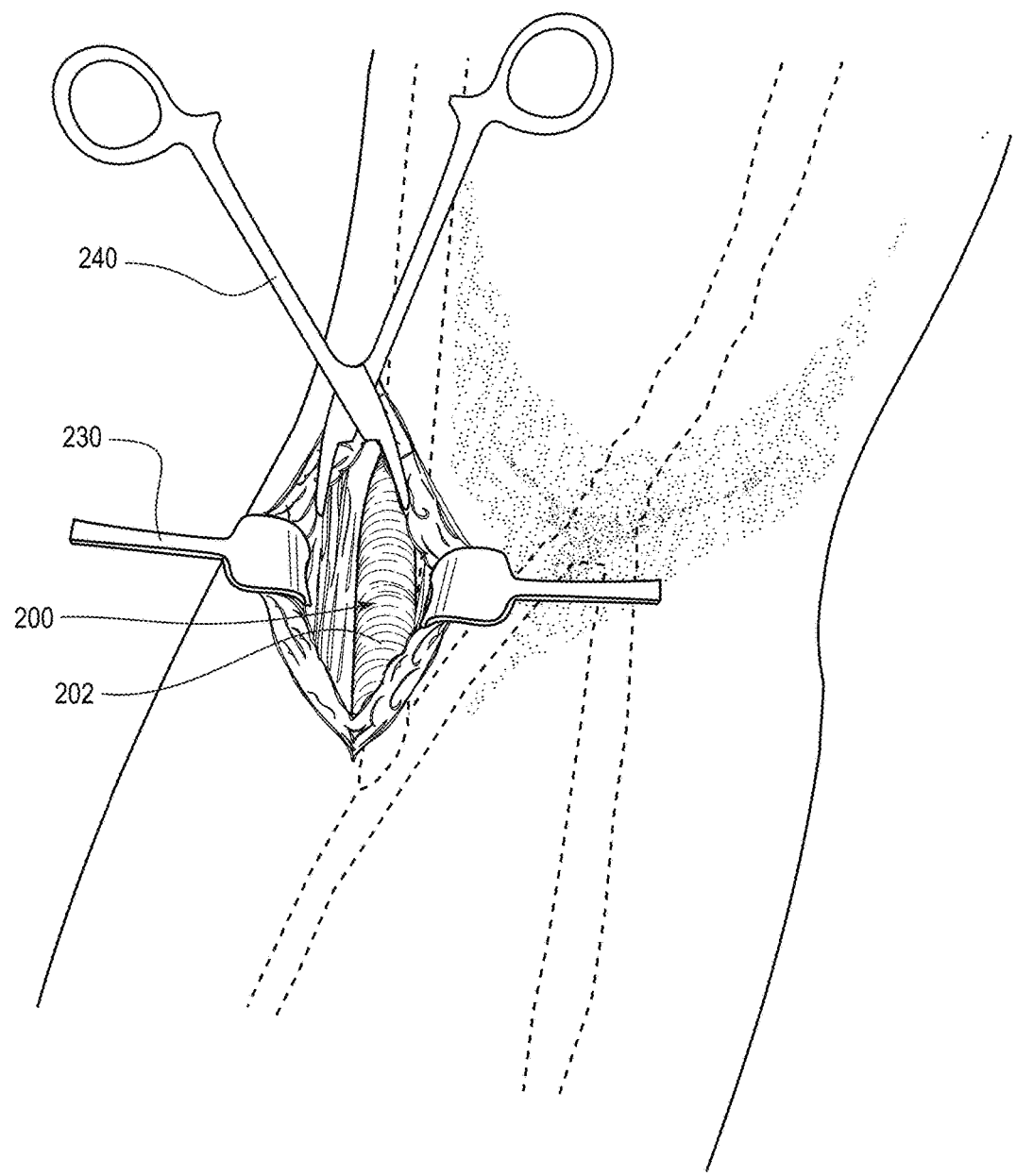
FIG. 10B is a perspective view of another stage of the method of FIG. 10A in which adventitia of a vessel is isolated.

With reference to FIG. 10B, the vessel 200 can be exposed by removing, partially removing, or separating skin, fat, and fascial layers from the adventitia layer 202 of the vessel 200 at the site of the incision 220. In some cases, a hemostat 240 can assist in this process. Exposure of the vessel 200 can be maintained in any suitable manner, such as by the use of tissue spreaders 230.

Figure 10C:
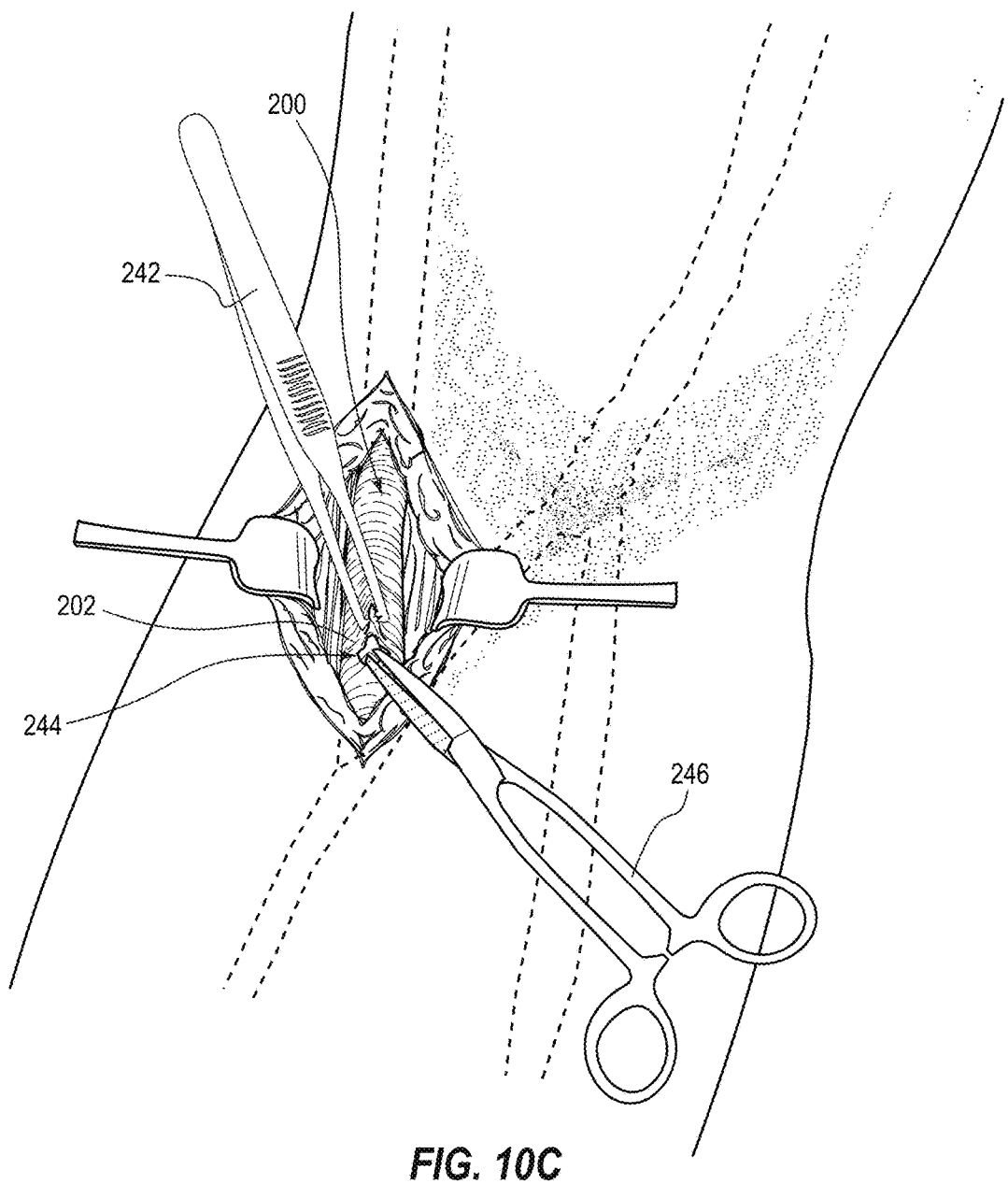
FIG. 10C is a perspective view of another stage of the method of FIG. 10A in which in incision is made in the adventitia.

With reference to FIG. 10C, a portion of the adventitia 202 can be isolated or separated from other portions of the vessel 200 in any suitable manner, such as via one or more forceps 242. Each set of forceps 242 can be used to capture or gather up a portion of the adventitia 202 and/or fascia layers or fat that may not have been removed or spread apart by the tissue spreaders 230.

With reference to FIG. 10C, while the portion of adventitia 202 is being held in its separated state, a small incision 244 can be made therein in any suitable manner, such as via a scalpel or via scissors 246.

Figure 10D:
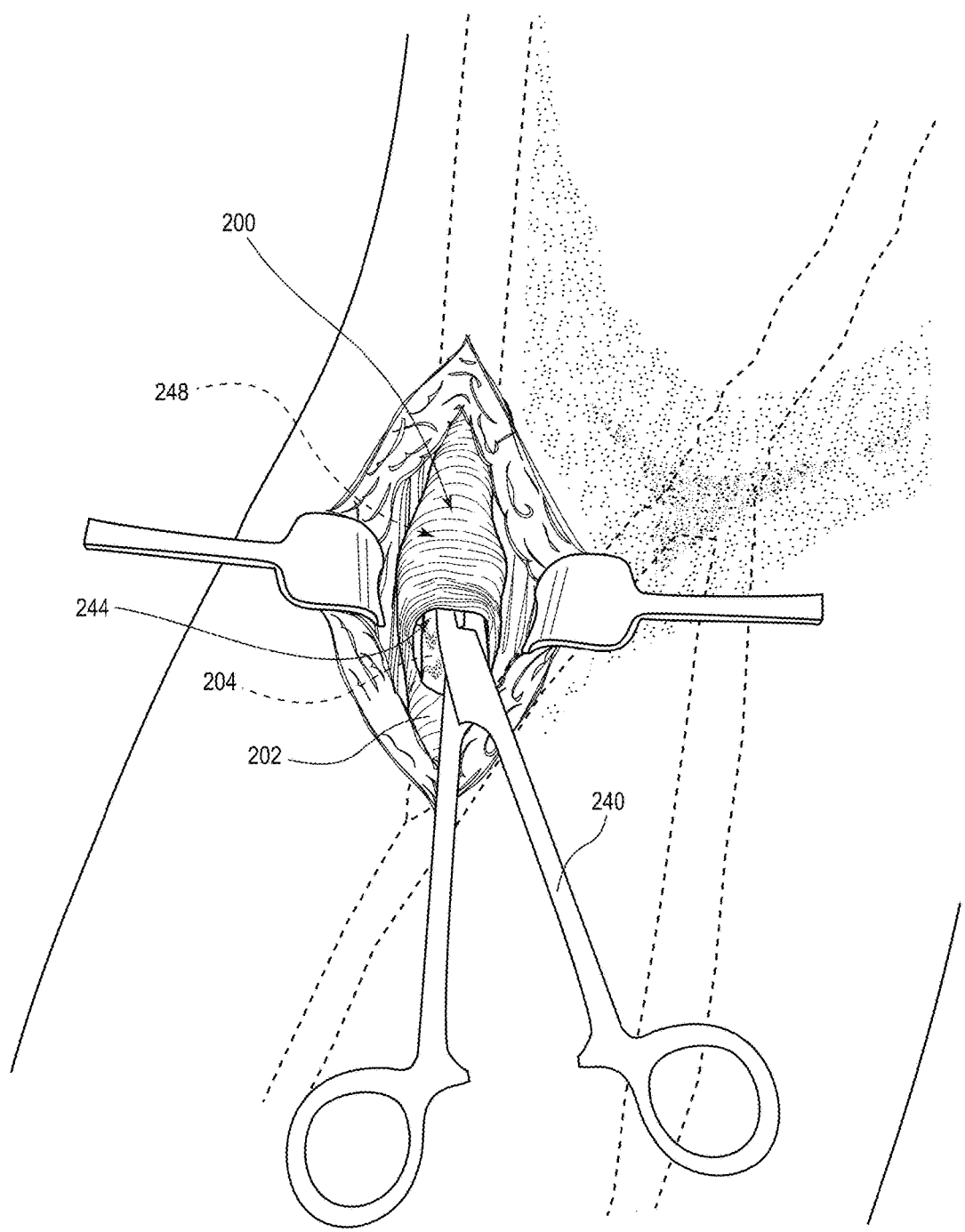
FIG. 10D is a perspective view of another stage of the method of FIG. 10A in which a pocket is formed in the adventitia.

With reference to FIG. 10D, a hemostat 240 can be inserted through the incision 244 so as to slide between the isolated adventitia 202 and the remaining layers of the vessel 200. In some instances, it can be difficult to separate all of the adventitia 202 from the media layer 204 of the vessel 200. This, in the illustrated embodiment, the media layer 204 is shown, but is obscured by a thin layer of adventitia 202.

The hemostat 240 can be used to bluntly dilate a pocket 248 within the adventitia 202 layer. Although not depicted, in some cases, the forceps 242 may be used to maintain control of the adventitia 202 during formation of the pocket 248.

In certain embodiments, the pocket 248 can be sufficiently large to receive the vascular access port 100 therein, while in others, the pocket 248 can be slightly smaller than the vascular access port 100. In some embodiments, the pocket 248 can have a length of no more than about 2.0, 2.5, 3.0, or 3.5 centimeters, and can have a width of no more than about 70, 80, or 90 percent of a width of the outer diameter of the media layer 204.

Figure 10E:
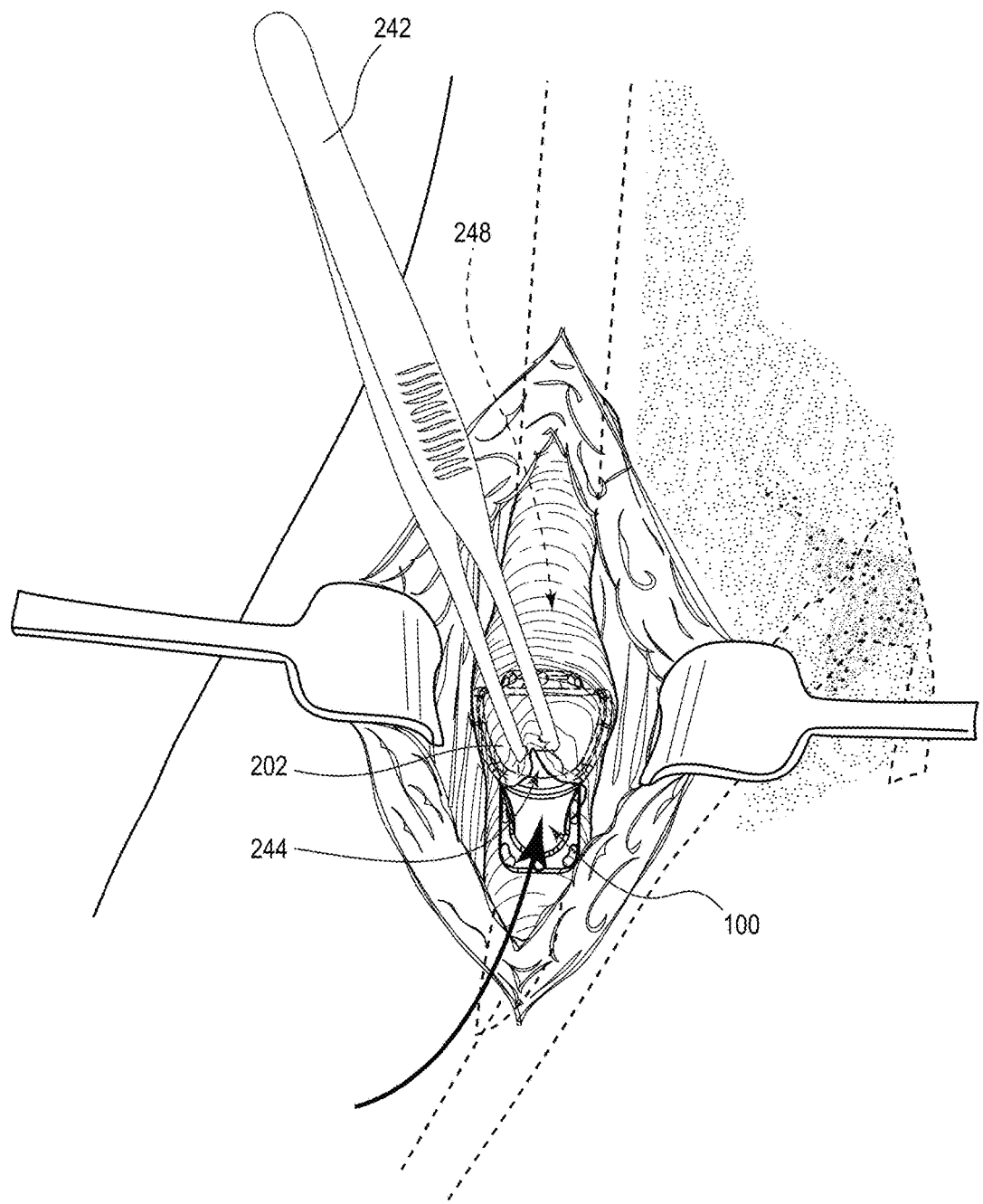
FIG. 10E is a perspective view of another stage of the method of FIG. 10A in which an embodiment of a vascular access port is inserted into the pocket.

With reference to FIG. 10E, the vascular access port 100 can be inserted through the incision 244 into the pocket 248. In some cases, the forceps 242 or other clamping devices are used to maintain control of the adventitia 202 during insertion of the vascular access port 100. The vascular access port 100 can be introduced into the pocket 248 either rearward end first, as shown, or forward end first, and the port 100 can be pushed to the end of the pocket 248 opposite the incision 244.

Figure 10F:
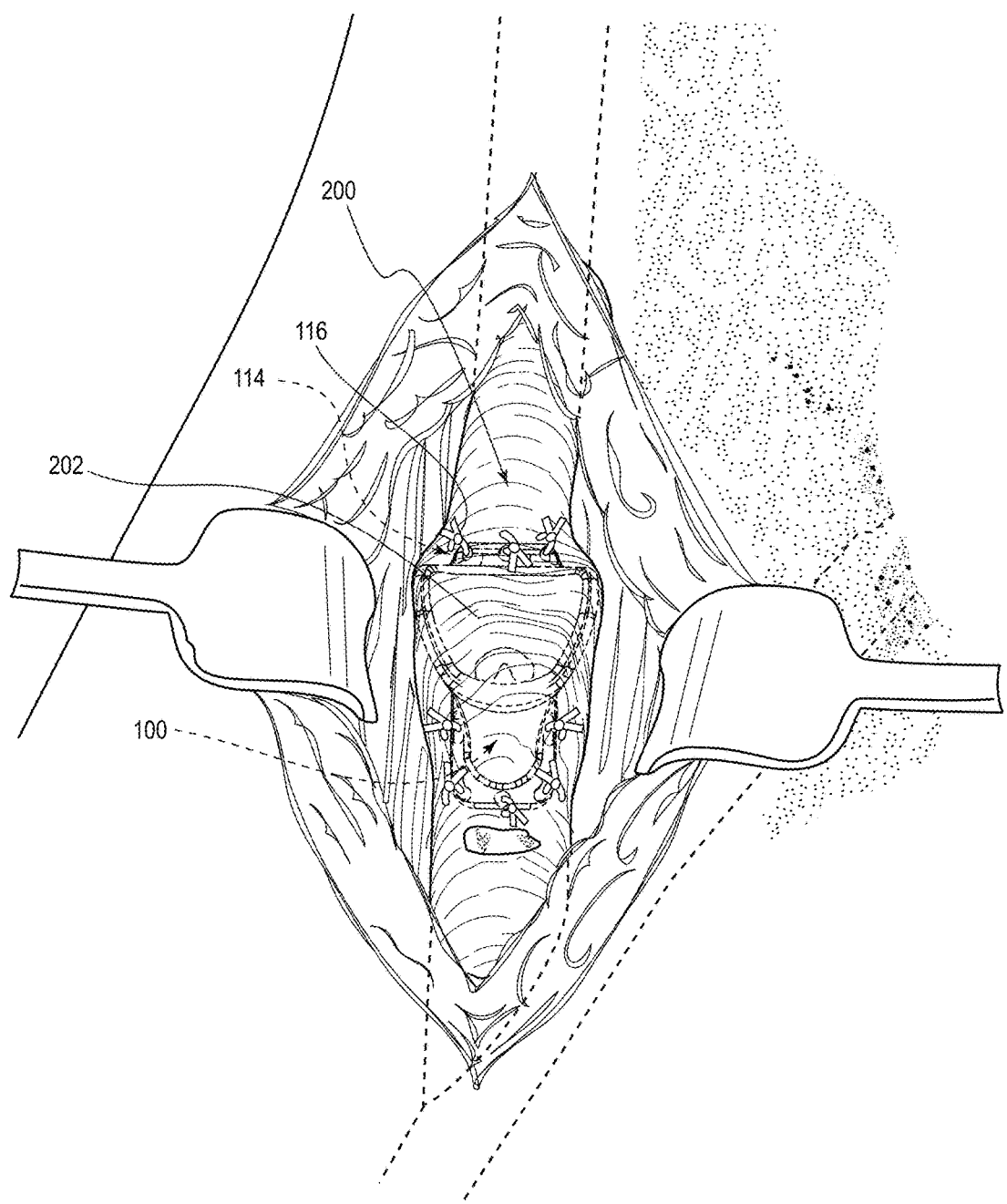
FIG. 10F is a perspective view of another stage of the method of FIG. 10A in which attachments have been made between the vascular access port and the vessel.

With reference to FIG. 10F, the adventitia 202 can cover all or substantially all of the implanted vascular access port 100 when it is within the pocket 248. Sutures 116 can be advanced through the adventitia 202, through the attachment passages 114, and through the remaining portion of the adventitia layer 202, as well as through the entirety of the media and intima layers 204, 206 to attach the vascular access port 100 to the vessel 200. Suture knots thus may be tied outside of the adventitia 202. In other embodiments, the sutures 116 do not pass through the separated portion of the adventitia 202 and may be tied prior to being covered by the adventitia 202.

Figure 10G:
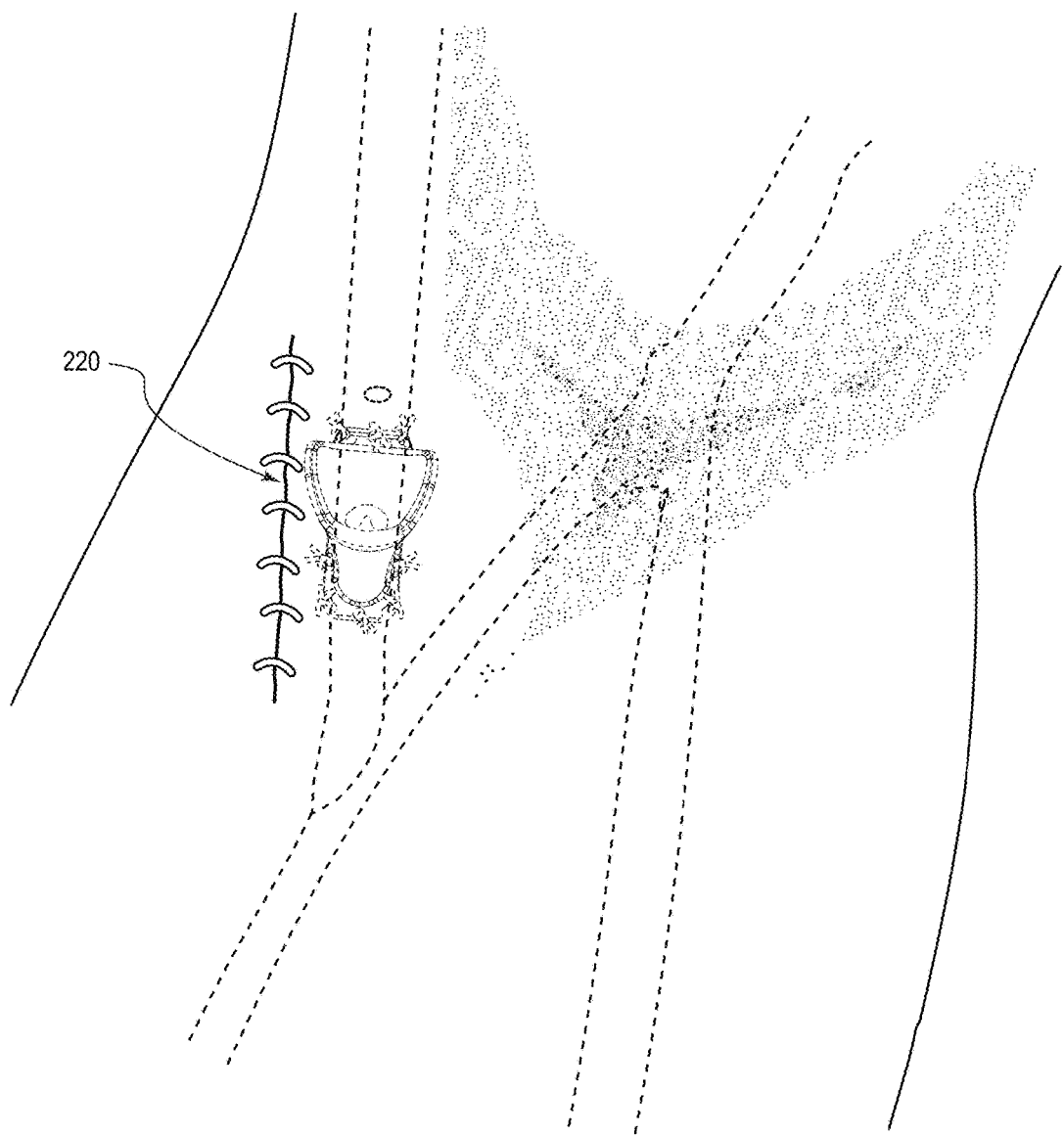
FIG. 10G is a perspective view of another stage of the method of FIG. 10A in which the incision in the skin of the patient has been closed.

FIG. 10G depicts the site of the incision 220 in a closed configuration. The incision 220 can be closed in any suitable manner, such as in any of the manners described above with respect to FIG. 9E.

With reference again to FIGS. 10C-10F, in other methods, at least a portion of the adventitia 202 can be removed rather than forming the pocket 248 therein. The vascular access port 100 may be placed atop a thin layer of the adventitia 202 at a site from which the at least a portion of adventitia 202 has been removed, and sutures 116 may be directly inserted through the attachment passages 114 and through the thinned adventitia layer 202, the media layer 204, and the intima layer 206. The vascular access port 100 may, at least initially, be less stable relative to the vessel 200 when it is implanted in this manner, rather than when it is inserted into the pocket 248.

FIGS. 11A-11E depict various procedures that may be performed relative to an implanted vascular access port 100. As will be discussed, the vascular access port 100 can facilitate the creation of a buttonhole. The vascular access port 100 likewise can facilitate use of the buttonhole once it is formed. These and/or other advantages of the vascular access port 100 will be apparent from the disclosure that follows.

Additionally, as previously mentioned, tissue may grow into or attach to various areas of the vascular access port 100. For example, vessel tissue may grow into the ingrowth-inducing covering 152. In some embodiments, skin tissue may grow into at least a portion of the guidance passageway 130, although such ingrowth is not shown in FIGS. 11A-11E.

Figure 11A:
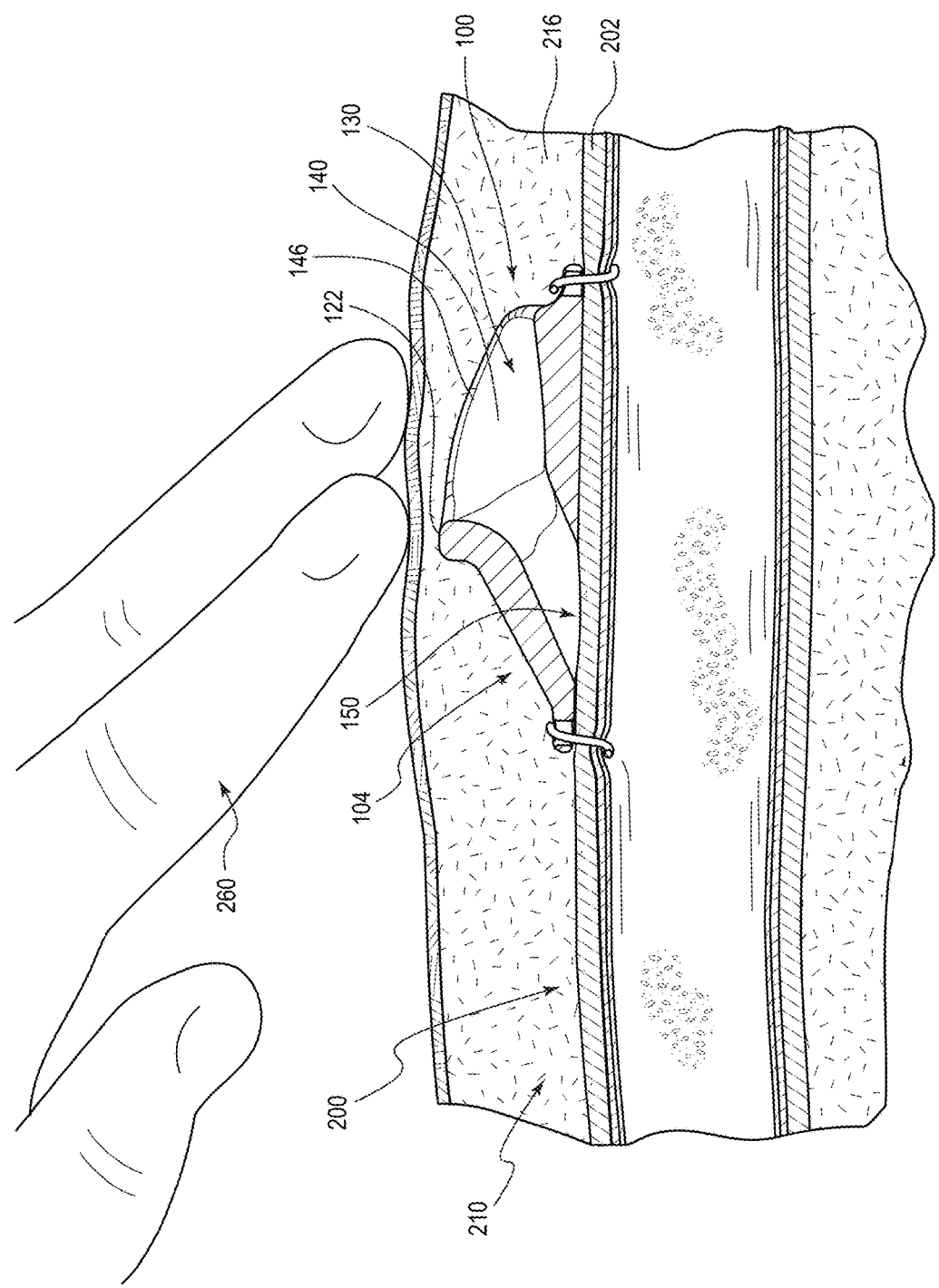
FIG. 11A is a cross-sectional view of a palpation stage of an illustrative method relating to the creation and use of a buttonhole access site to access a lumen of a vessel.

FIG. 11A depicts an embodiment of the vascular access port 100 that has been implanted in the patient 210 in any suitable manner, such as via the method depicted in FIGS.

9A-9E. The opening 150 of the guidance passageway 130 is at or adjacent to the vessel 200. Specifically, in the illustrated embodiment, the opening 150 is at the adventitia layer 202 of the vessel 200.

In the stage that is shown, a clinician 260 palpates the skin 216 to locate and determine the orientation of the vascular access port 100. The term "clinician" is used broadly herein and includes any individual who conducts a process or procedure relative to an implanted access port 100, whether that individual is the individual in whom the access port 100 is implanted (e.g., a patient) or someone else, and the term is not limited to an individual within a healthcare facility. In the illustrated embodiment, the clinician 260 uses fingers to contact the skin 216 located above the pinnacle region 122 of the palpation projection 146. In other instances, the clinician 260 can palpate any other suitable portion of the body 104 to determine the location (e.g., depth) and orientation of the port 100. For example, the clinician 260 may use one or more fingers and/or a thumb to contact the skin 216 that is over or beside other portions of the palpation projection 146, or to squeeze the skin 216 that is at either side of the wings 140. In still other or further embodiments, a clinician may visually determine a location and orientation of the port 100. Prior or subsequent to the stage shown in FIG. 11A, the clinician 260 can clean a surface of the skin with any suitable antiseptic so as to reduce the risk of introducing pathogens into the bloodstream of the patient.

Figure 11B:
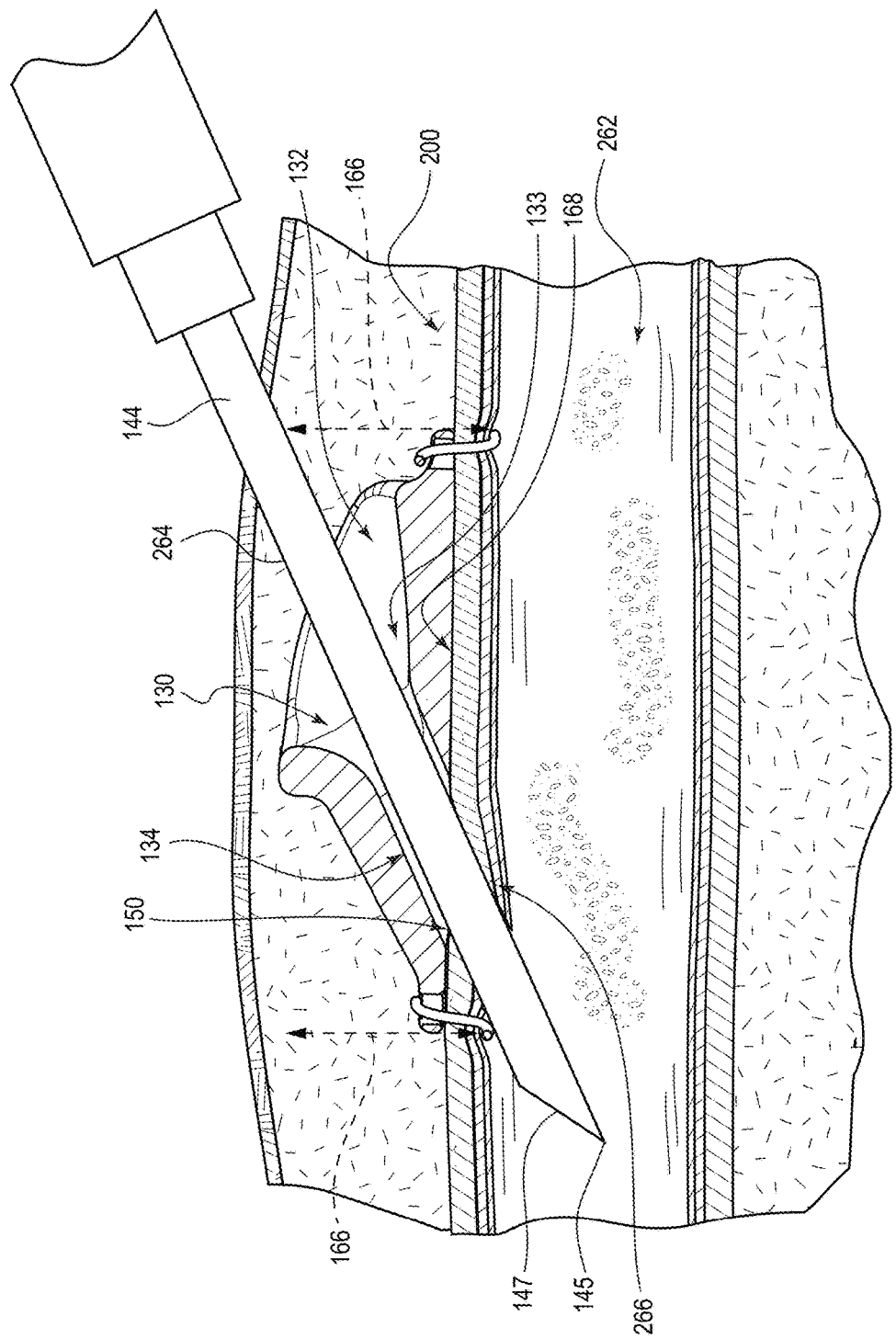
FIG. 11B is a cross-sectional view of another stage of the method of FIG. 11A in which a needle having a sharp tip is inserted into the lumen of the vessel via an embodiment of a vascular access port.

FIG. 11B illustrates an embodiment of an access device 144 directly accessing a lumen 262 of the vessel 200 via the vascular access port 100 for a first time. The access device 144 is advanced through the skin such that an outer surface of the device 144 contacts the skin. The access device 144 is further advanced through the port 100, and then into the vessel 200. Although the fingers of the clinician 260 are not shown in FIG. 11B, the clinician 260 may continue to palpate the vascular access port 100 while inserting the access device 144 into the skin and the vascular access port 100. This can aid in achieving a desired alignment of the access device 144 with the guidance channel 130. The clinician 260 also may make minor adjustments to an orientation of the vascular access port 100 by applying pressure thereto.

The access device 144 can comprise any suitable device configured for fluid communication between a position outside of the skin 216 and the vessel lumen 262 when the device has been introduced into the lumen 262 via the vascular access port 100. For example, in various embodiments, the access device 144 can comprise a needle or a catheter. In many embodiments, the access device 144 can be relatively rigid so as to be able to readily pass through the skin 216. Accordingly, in some embodiments, the catheter may be an over-the-needle catheter.

Standard needles that are presently used in hemodialysis or other procedures may be used with embodiments of the vascular access port 100, which may facilitate use of such ports. For example, standard protocols for making and using buttonholes in vessels via known freehand methods may be readily adapted to "device-assisted" buttonhole techniques that employ the vascular access ports 100, and this can take place without alteration to the instruments called for by the existing protocols.

As the procedural stage depicted in FIG. 11B represents an initial access of the vessel lumen 262, the access device 144 is shown as having a sharp tip or cutting edge 145, which can allow the access device 144 to more readily be inserted through the unbroken skin so as to form an insertion tract 264, and also so as to create an insertion site 266 of the vessel 200. As further discussed below, however, other embodiments of an access device 144 that have blunt ends may be used after at least an initial access event with a sharp access device has occurred. For example, as discussed hereafter, in some embodiments, sharp access devices 144 can be used for a number of access events (e.g., 6, 7, 8, 9, or 10 access events) until an insertion tract may have been formed through the skin of a patient, and blunt access devices 144 can be used thereafter. In other embodiments, a sharp access device 144 is used for an initial insertion event, and blunt access devices 144 can be used thereafter.

In certain embodiments, the access device 144 can comprise a needle sized from 14 gauge to 20 gauge. As previously mentioned, the diameter and length of the channel 134 can be configured to constrain movement of the access device 144 along a path that is coaxial with the channel 134 so as to direct the access device 144 to a specific region of the vessel 200. This may be achieved by a relatively close fit between the channel 134 of the vascular access port 100, which can provide for a predictable orientation at which the access device 144 will exit the channel 134 through the opening 150. In some instances, it may be desirable for the channel 134 to be sized such that at least a small amount of space exists between an inner wall thereof and an access device 144 when the access device 144 is inserted therein. This can prevent or reduce binding of the access device 144 within the channel 134, which may be more likely to occur if tissue has grown into at least a portion of the channel 134. In some embodiments, a balancing or optimization may be achieved with respect to the spacing between the channel 134 and an access device 144 such that a sufficiently tight fit is achieved to allow the vascular access device 144 to be directed repeatedly to substantially the same area of the vessel 200 and to achieve hemostasis when the vascular access device 144 is inserted into the vessel 200, while inhibiting, reducing the occurrence of, or preventing binding of the vascular access device 144 within the channel 134. In various embodiments, an inner diameter of the channel 134 is larger than an outer diameter of an access device 144 with which it is configured to be used by an amount within a range of from about 0.25 gauge to about 3.0 gauge, from about 0.5 gauge to about 2.0 gauge, from about 0.75 gauge to about 1.5 gauge, or from about 0.75 gauge to about 1.25 gauge; by an amount that is no less than about 0.25, 0.5, 0.75, 1.0, 1.25, 1.5, 1.75, 2.0, 2.5, or 3.0 gauge; or by an amount that is no greater than about 0.25, 0.5, 0.75, 1.0, 1.25, 1.5, 1.75, 2.0, 2.5, or 3.0 gauge. In some embodiments, the channel 134 is about 1 gauge larger than access devices 144 with which it is configured to be used. For example, in the illustrated embodiment, the channel 134 may be sized at approximately 14 gauge and the access device 144 can comprise a 15 gauge fistula needle.

Other configurations for the channel 134 and the access device 144 are also possible. For example, one or more of the channel 134 and the access device 144 may have geometries other than cylindrical. In certain of such embodiments, the geometries of the channel 134 and of the access device 144 may be complementary to each other, whereas in other embodiments, a cross-sectional shape of the channel 134 may be different from a cross-sectional shape of the access device 144.

In some instances, it can be desirable to insert the access device 144 into the vessel in a bevel-up orientation, as shown in FIG. 11B. In particular, the illustrated access device 144 includes a bevel 147 at a distal end thereof. When the access device 144 is inserted in the bevel-up orientation, the bevel 147 extends upwardly from a distal-most point of the access device 144. Many protocols for accessing a vessel with a needle or other access device indicate a preference for inserting the access device in such a bevel-up orientation. As can be appreciated from FIG. 11B, when the access device 144 is in a bevel-down orientation it would be rotated by approximately 180 degrees relative to the illustrated orientation, such that the bevel 147 would extend primarily rearwardly in the longitudinal direction rather than primarily upwardly in the vertical direction, as shown.

As can be seen in FIG. 11B, when the access device 144 is advanced through the guidance passageway 130 in a proximal-to-distal direction, the cutting edge 145 of the access device 144 proceeds through the opening 150 and into contact with a wall of the vessel 200. Upon further advancement of the access device 144, the cutting edge 145 cuts through the vessel wall and progresses into the lumen 262 of the vessel 200. In some embodiments, the cut or incision thus created by the cutting edge 145 can be semi-circular, which can result in a convexly shaped flap portion of the vessel wall.

With continued reference to FIG. 11B, the cutting edge 145 of the access device 144 has been advanced into the lumen 262 of the vessel 200 sufficiently far such that it is outside of the peripheral extent 166 of the port 100. However, it can be seen that when the cutting edge 145 of the access device 144 is at a position that is vertically even with an apex of the footprint 168, it is also approximately at a surface of the vessel wall. At this position, the cutting edge 145 is at an interior of the peripheral extent 166 of the port 100.

In the illustrated embodiment, the guidance passageway 130 defines a closed loop about the access device 144 when it has been advanced through the passageway. Stated otherwise, the guidance passageway 130 is enclosed so as to fully encircle the access device 144 once it has been advanced through the opening 150. Stated in yet another manner, the guidance passageway 130 fully encircles the opening 150. Such an arrangement can, for example, assist in directing the access device 144 toward the opening 150 when the distal tip of the access device 144 is brought into contact with any portion of the guidance passageway 130 as it is advanced toward the vessel 200.

As previously mentioned, some protocols for the creation and use of buttonhole cannulation sites can require introduction of a needle into a vessel at a designated acute angle. In some embodiments, the angle α defined by the channel 134 (see FIG. 7) can be matched to this specified angle, and the channel 134 can constrain the access device 144 to enter the vessel 200 at the angle α, such that the vascular access port 100 can be configured for use with such protocols.

Tenting of the vessel wall can be inhibited by the formation of a seal about the opening 150, as tissue can tightly grab or integrate into the port 100 in this region as discussed above. The vessel wall thus can be held relatively taut within the area that is internal to an outer edge of the opening 150. The taut vessel wall can be relatively resilient as the access device 144 is passed therethrough. This resilience, which may result from the seal or tissue integration about the opening 150, can be referred to as a trampoline effect. Accordingly, where sufficient time has passed for formation of the seal, an initial access event via the access device 144 may cause relatively little deformation of the vessel wall as the access device 144 passes therethrough. Deformation is also reduced by the use of a sharp-tipped device for the initial access. As can be appreciated from the discussion that follows, in some embodiments, a reduction in tenting can also be advantageous where subsequent access events are performed with blunt-tipped devices.

Figure 11C:
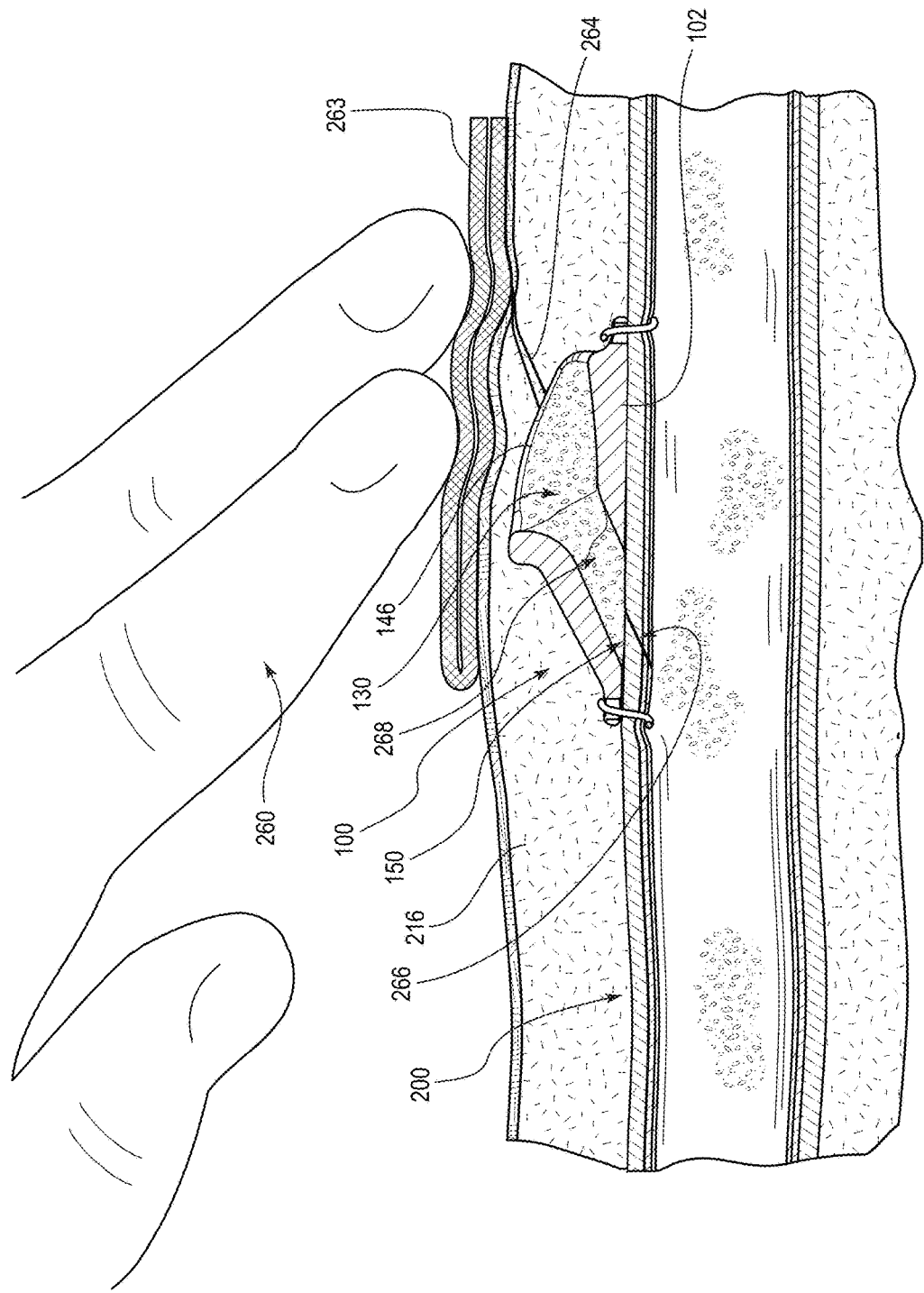
FIG. 11C is a cross-sectional view of another stage of the method of FIG. 11A in which pressure is applied to the skin of the patient.

FIG. 11C illustrates a stage of the procedure after removal of the access device 144. The insertion site 266 is shown in a closed state, in which it is allowed to heal. Prior to closure and/or healing of the insertion site 266, however, blood 268 can be permitted to exit thereby, and may fill at least a portion of the guidance passageway 130 and the insertion tract 264. The practitioner 260 can apply pressure above the vascular access port 100 to close the insertion tract 264 until bleeding subsides at the surface of the skin 216. For example, the practitioner 260 can apply pressure while simultaneously applying a pad 269 (e.g., gauze) to the upper end of the insertion tract 264. As previously mentioned, the entry mouth 136 of the guidance passageway 130 can be configured to assist in achieving hemostasis. For example, the entry mouth 136 may be relatively planar, and application of pressure above the entry mouth 136 can cause tissue surrounding the guidance passageway 130 to effectively seal the guidance passageway 130 about the entry mouth 136. In some embodiments, a two-finger technique may be used to close the insertion tract 264 while applying pressure to the tissue positioned above the guidance passageway 130. In some embodiments, pressure may be applied for a period of no more than about 5, 6, 7, 8, 9, or 10 minutes in order to achieve hemostasis.

It is also noted that removal of the access device 144 from the vessel 200 can be achieved without removing a portion of the vessel wall from the patient. For example, when a sharp-tipped needle is used, the needle can cut the wall of the vessel 200 as described above, and removal of the needle can allow the cut edges in the wall to come back into close proximity or contact with each other.

A relatively tight attachment between the vascular access port 100 and the vessel 200 so as to achieve a seal (whether acute or long-term) as described above within the attachment area AR (see FIG. 5) likewise can assist in reaching hemostasis. For example, tightly attached sutures or other attachment devices and/or tissue ingrowth about the opening 150 can inhibit or prevent blood 268 from seeping outwardly between the base 102 of the vascular access port 100 and the vessel 200. The seal can at least partially encompass the opening 150.

In some instances, the procedures discussed with respect to FIGS. 11A-11C can be repeated multiple times. For example, with reference again to FIG. 11B, a second access device 144 having a sharp tip 145 can be inserted through the insertion tract 264 toward the vascular access port 100 for a second insertion event. However, during the time between the first and second access events and/or as a result of palpation of the vascular access port 100 during the second access event, the vascular access port 100 and the vessel 200 to which it is attached may have shifted relative to the insertion tract 264 such that the channel 134 is no longer aligned with the insertion tract 264. As the access device 144 is advanced through the insertion tract 264, the tip of the access device 144 can contact the funnel region 132. The funnel region 132 then can direct the tip of the access device 144 into the channel 134 as the access device 144 is further advanced through the insertion tract 264. In some cases, this redirection of the tip of the access device 144 relative to the vascular access port 100 may urge the insertion tract 264 and the channel 134 into alignment with each other. Once the tip of the access device 144 enters the channel 134, the channel 134 directs the tip of the access device 144 to the insertion site 266 of the vessel 200. The vascular access port 100 thus can direct the access device 144 to the same insertion site 266 via which the vessel lumen 262 was accessed in the first access event. As further discussed below with respect to FIGS. 23A-23E, in some instances, a similar result can be achieved without direct contact between the access device 144 and the funnel region 132. For example, the funnel region 132 can be coated with tissue ingrowth, and the funnel region 132 can constrain movement of the access device 144 so as to direct it toward the single insertion site 266.

Figure 11D:
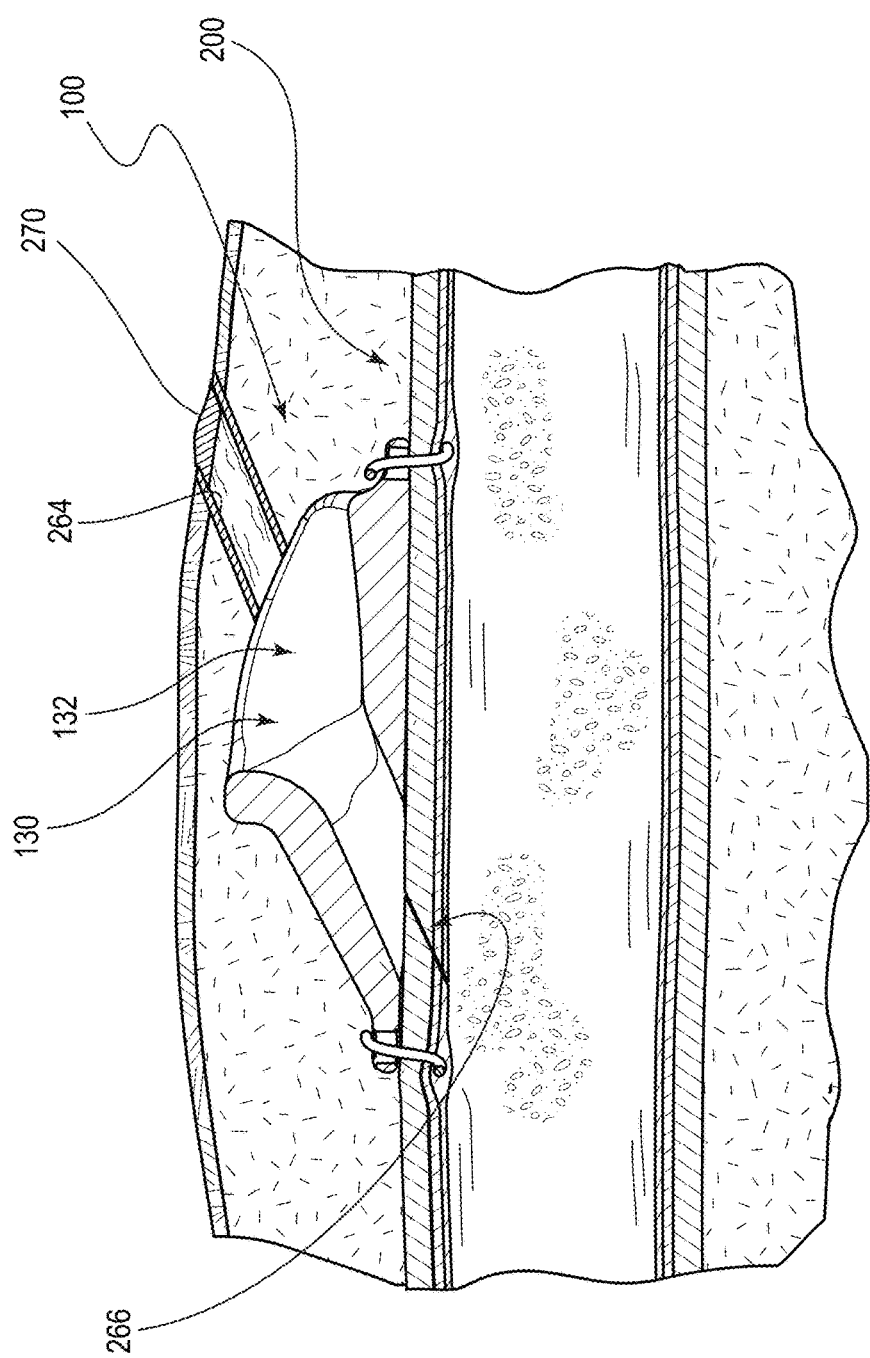
FIG. 11D is a cross-sectional view of another stage of the method of FIG. 11A in which an insertion tract and a buttonhole access site have been formed.

FIG. 11D depicts the insertion tract 264 and the insertion site 266 after multiple access events. As shown, the insertion tract 264 may become more well-defined over time. Without being limited by theory, the well-defined insertion tract 264 may result, for example, from the formation of scar tissue or connective tissue. Similarly, the insertion site 266 may become more well-defined over time such that it may become easier to insert an access device 144 therethrough. Such an insertion site 266 through a vessel wall can be referred to as a buttonhole access site, or more commonly, as a buttonhole. Accordingly, the insertion site 266 may also be referred to herein as a buttonhole 266. In some embodiments, the well-defined insertion tract 264 and/or the buttonhole 266 may be established after 6, 7, 8, 9, or 10 access events. In some embodiments, the buttonhole 266 may be formed more quickly. For example, the buttonhole insertion site 266 may be present upon insertion of a sharp access device 144 into the vessel 200. So long as the insertion site 266 is not allowed to completely heal, a blunt access device 144 may readily be inserted through the insertion site 266. For example, it may be desirable to permit the insertion site 266 to heal for no more than one, two, three, or four days before a subsequent access event.

In other embodiments, the insertion tract 264 and/or the buttonhole 266 can be formed by inserting an over-the-needle catheter (not shown) through the vascular access port 100. The needle portion can be removed and the catheter portion can be left in place until the insertion tract 264 is well-defined. The catheter then can be removed.

As previously discussed, the vascular access port 100 and the vessel 200 may shift relative to the insertion tract 264 between access events. However, in certain embodiments, the funnel region 132 of the guidance passageway 130 is sufficiently large that a distal end of the insertion tract 264 opens into, or extends through at least a portion of, the funnel region 132 despite any such shifting. Accordingly, the vascular access port 100 may act as a mobile extension of the insertion tract 264, which is configured to ensure that access devices 144 are consistently directed to the buttonhole 266, despite any relative movement between the insertion tract 264 and the vessel 200. In some instances, however, relatively little shifting may occur between the insertion tract 264 and the vascular access port 100, and an access device 144 may be inserted through the insertion tract 264 and directly into the channel 134 with little or no contact with either the funnel region 132 or the channel 134. As previously mentioned, the guidance passageway 130 may be covered by tissue, which can further ensure that certain access events may take place without direct contact between the access device 144 and the guidance passageway 130.

FIG. 11D also illustrates that a scab 270 may form over the insertion tract 264 between access events. The scab 270 may be removed prior to an access event. In other embodiments, a synthetic covering may be provided over or in place of the scab 270.

Figure 11E:
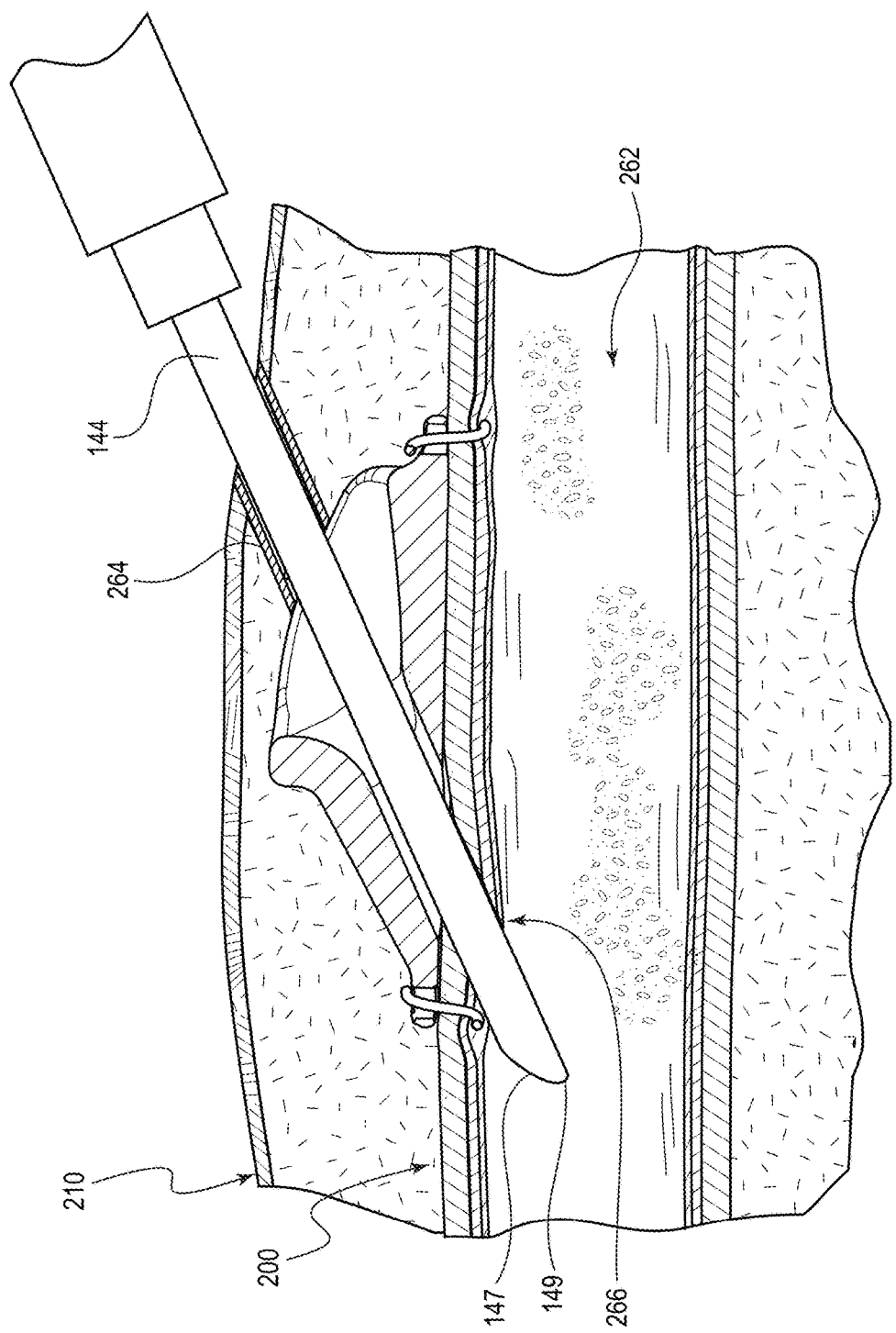
FIG. 11E is a cross-sectional view of another stage of the method of FIG. 11A in which a needle having a blunt tip is inserted into the lumen of the vessel via the insertion tract, the vascular access port, and the buttonhole access site.

FIG. 11E illustrates the use of an access device 144 having a blunt distal tip 149 after formation of the insertion tract 264 and the buttonhole 266. The blunt tip 149 of the access device 144 can guide the device 144 through the insertion tract 264 and through the buttonhole 266, and may do so in a less traumatic or more comfortable manner for the patient 210. Use of a blunt-tipped access device 144 also can reduce the risk of striking through an opposing side of the vessel 200. In the illustrated embodiment, the access device 144 includes a bevel 147, and the access device 144 is inserted in a bevel-up orientation.

As previously discussed, in some embodiments, a seal forms about the opening 150 prior to access events in which a blunt-tipped access device 144 is used. Such a seal can hold the vessel wall in a relatively taut and/or resilient fashion and can inhibit tenting of the vessel wall. This effect, also referred to as a trampoline effect, can facilitate insertion of the blunt-tipped device through the buttonhole 266. For example, without being limited by theory, the blunt-tipped access device 144 may force open the buttonhole 266 so that the device can be inserted into the vessel lumen 262, rather than cut open the buttonhole 266. The buttonhole 266 thus may be more resistant to a forced opening, as opposed to a cutting event. Accordingly, the seal can steady the vessel wall and allow the wall to resist the forced opening without a large degree of deformation up to the point where the buttonhole 266 yields and the access device 144 is advanced therethrough. This can aid in the continued use and maintenance of a single buttonhole access site 266.

As previously mentioned, in some embodiments, an over-the-needle catheter can be used with an implanted vascular access port 100. In certain procedures, a needle/catheter assembly can be inserted through the insertion tract 264 into the vessel 200 (e.g., the jugular vein) and then the catheter can be advanced through the vessel to the desired position (e.g., the superior vena cava for certain central venous system applications). An infusion or other desired procedure can then be conducted. The catheter can be removed from the patient after completion of the procedure.

Figure 12:
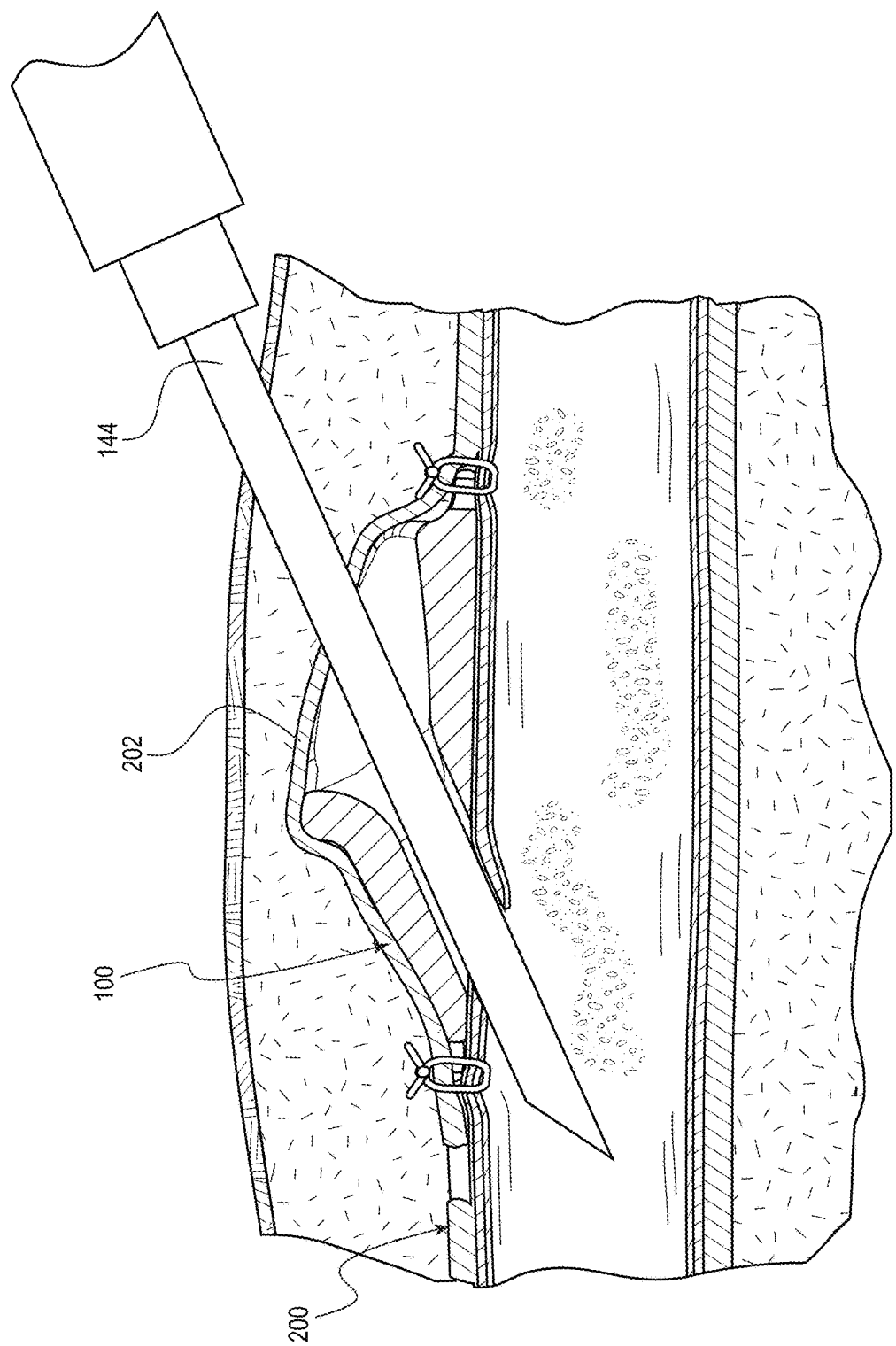
FIG. 12 is a cross-sectional view of a stage of another illustrative method relating to the creation and use of a buttonhole access site to access a lumen of a vessel.

FIG. 12 depicts an embodiment of the vascular access port 100 that has been implanted in the patient 210 via a method such as that depicted in FIGS. 10A-10G. A portion of the adventitia layer 202 of the vessel 200 thus extends over the vascular access port 100. Accordingly, when an access device 144 is inserted into the vessel 200 via the access port 100, it passes through the adventitia layer 202 before entering the vascular access port 100. Otherwise, procedures for creating and using buttonholes can be similar to those described above with respect to FIGS. 11A-11E.

Figure 13:
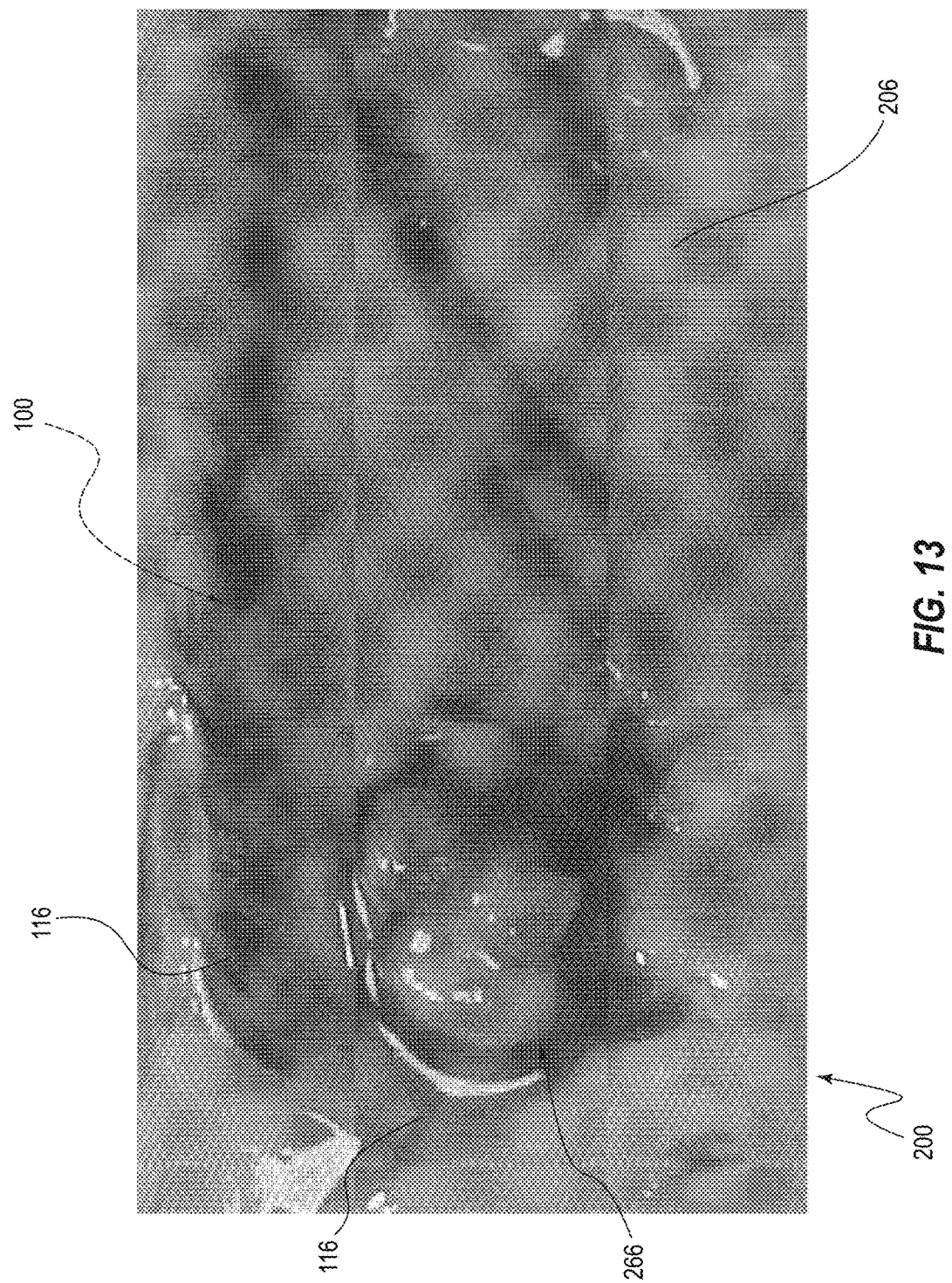
FIG. 13 is a bottom plan view of a filleted vessel that bears an embodiment of a buttonhole access site that has been created via an embodiment of a vascular access port.

FIG. 13 depicts an illustrative example of an embodiment of a buttonhole access site 266 in a vessel 200 that was formed by repeated insertion of access devices 144 through an embodiment of a vascular access port 100. FIG. 13 is a photograph of a filleted portion of the vessel 200, and is shown from a bottom plan view thereof (i.e., a view directed toward the intima layer 206). A contour of the vascular access port 100 is visible in the photograph, as are portions of a running suture 116 that extend through the initima layer 206.

In this particular example, the vascular access port 100 was implanted in a sheep for a period of 9 weeks. After a waiting period to permit for tissue ingrowth, a sharp needle was inserted through the vascular access port 100 to access the vessel 200. Six (6) additional access events were conducted thereafter using a sharp needle, followed by twelve (12) access events using a blunt needle. Accordingly, a total of nineteen (19) cannulations were performed. The access events were conducted at a frequency of three per week.

Figure 14A:
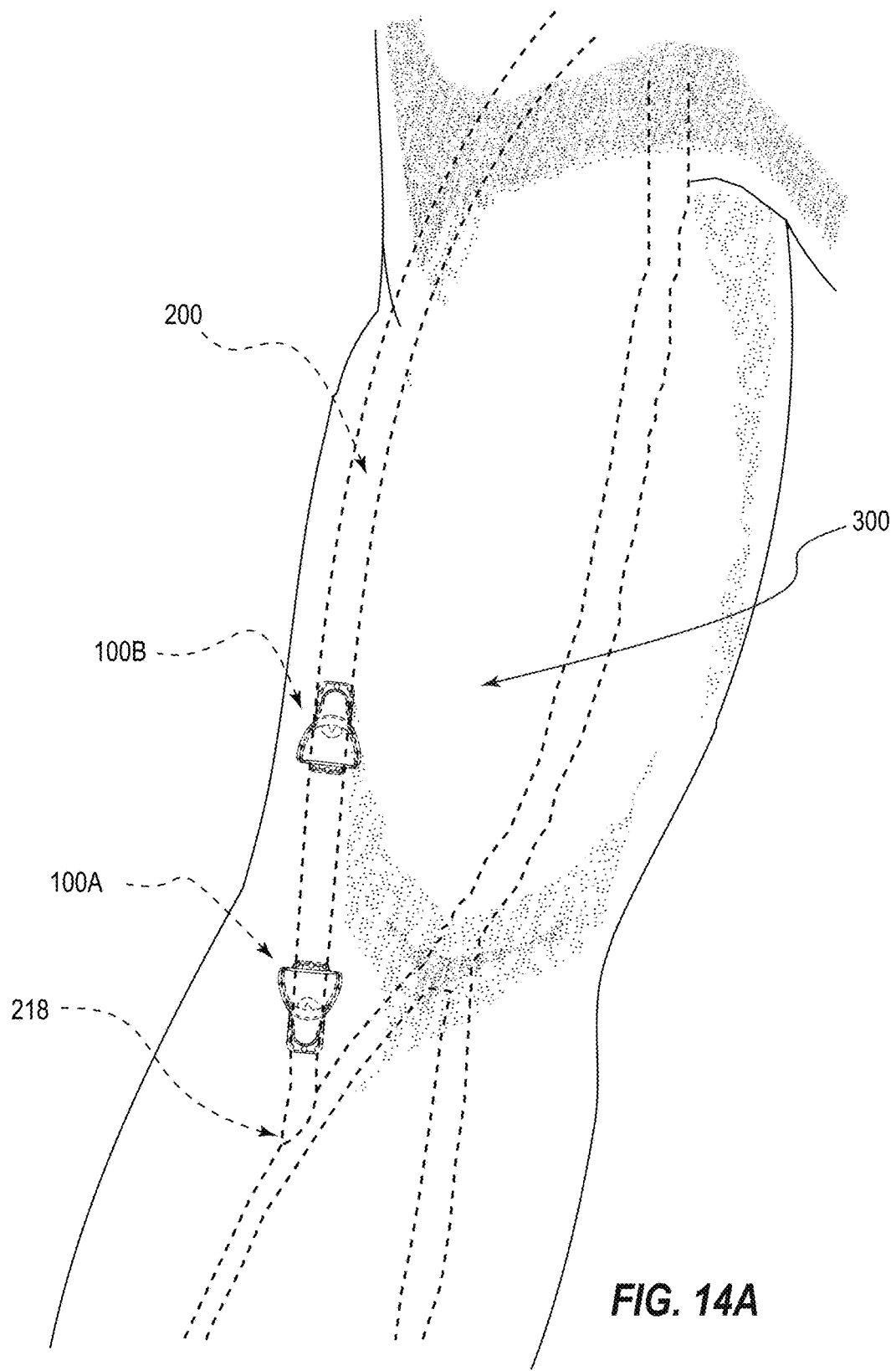
FIG. 14A is a perspective view of an embodiment of a vascular access system that can be used for hemodialysis.

FIG. 14A depicts an embodiment of a hemodialysis system 300 that includes two vascular access ports 100A, 100B, which can resemble any of the vascular access ports described herein. Both of the ports 100A, 100B are shown attached to a vessel 200 that is associated with an arteriovenous fistula 218. One port 100A is directed upstream such that a forward end thereof points in a direction opposite to the flow of blood through the vessel 200 (e.g., points in a retrograde direction), and the other port 100B is directed downstream such that a forward end thereof points in the direction of the blood flow through the vessel 200 (e.g., points in an antegrade direction). A fistula needle may be introduced into each of the ports 100A, 100B and hemodialysis performed. The first port 100A can be an uptake port through which blood is removed from the vessel 200 and delivered to a hemodialysis machine, and the second port 100B can be a return port through which filtered blood is returned to the vessel 200 from the hemodialysis machine.

In other embodiments, the hemodialysis system 300 can comprise only a single vascular access port 100A or 100B. Hemodialysis may be conducted thereby via any suitable method, such as a single-needle hemodialysis technique.

In still other embodiments, the hemodialysis system 300 includes more than two vascular access ports 100A, 100B. A clinician thus can rotate among the ports 100A, 100B, thereby leaving one or more of the ports unused during any given hemodialysis session.

Figure 14B:
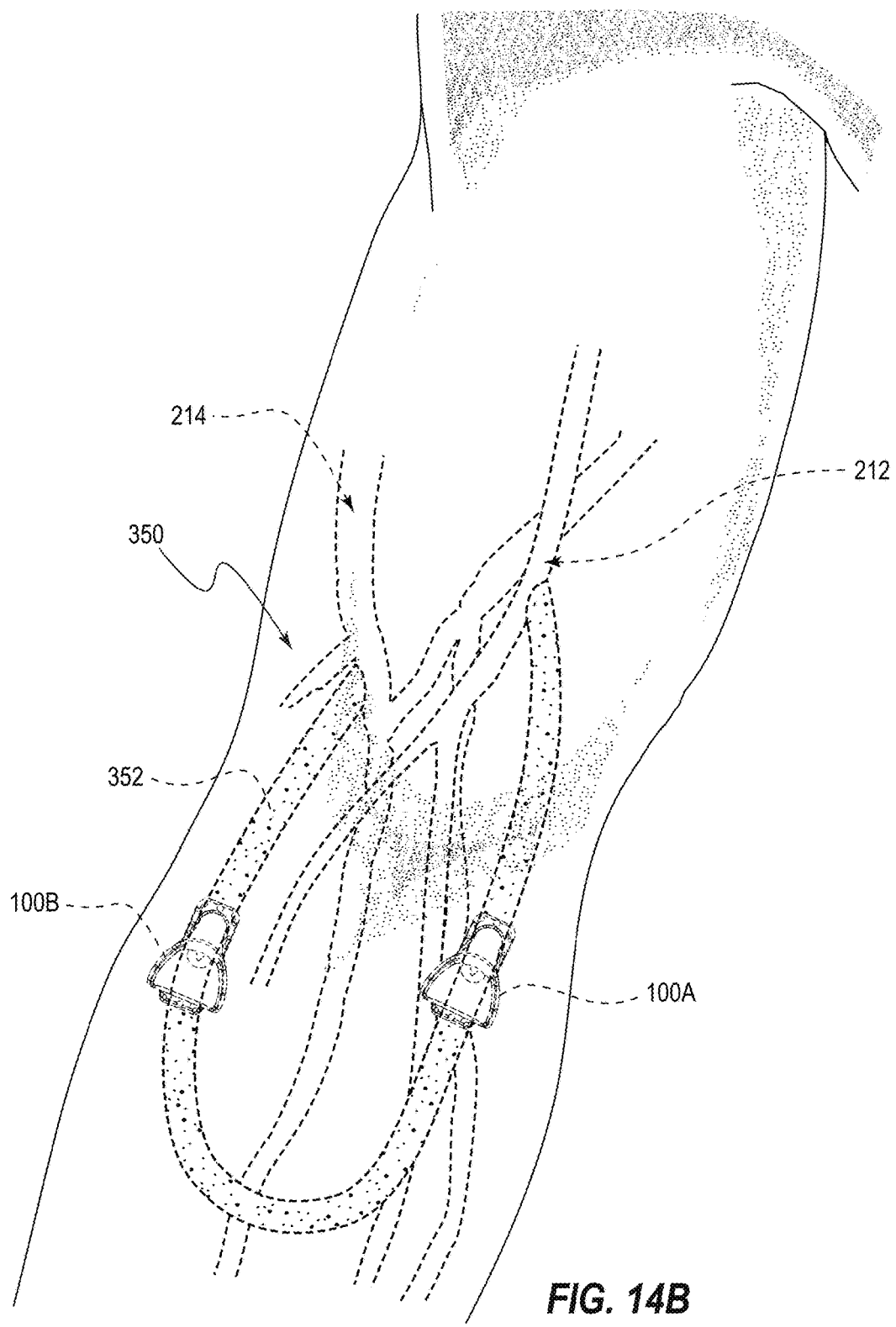
FIG. 14B is a perspective view of another embodiment of a vascular access system that can be used for hemodialysis.

FIG. 14B depicts another embodiment of a hemodialysis system 350. The illustrated embodiment includes two vascular access ports 100A, 100B, but more or fewer ports are possible. Both of the ports 100A, 100B are shown attached to an artificial graft vessel 352 that serves as a shunt between an artery 212 and a vein 214. The graft vessel 352 can comprise any suitable material, such as e-PTFE. The ports 100A, 100B can be attached to the graft vessel 352 prior to its implantation, or may be attached to the graft vessel 352 after it has been implanted. The hemodialysis system 350 can function similarly to the system 300 described above, with the port 100A serving as an uptake port and the port 100B serving as a return port.

Figure 15:
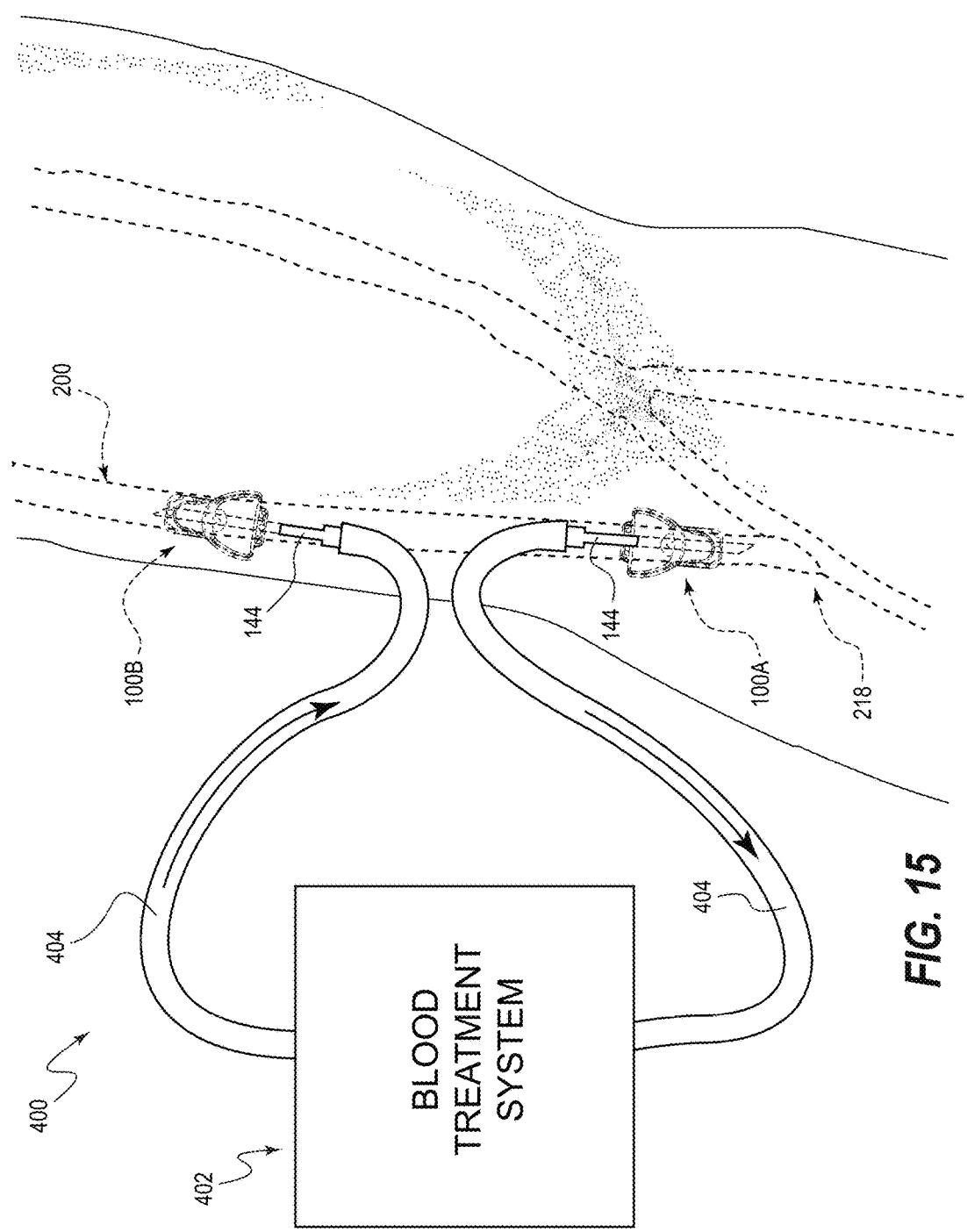
FIG. 15 is a perspective view of an embodiment of a vascular access system that can be used for the external treatment of blood.

FIG. 15 illustrates an embodiment of a system 400 configured for the external treatment of blood. The system 400 is similar to the system 300 described above. The system 400 includes two vascular access ports 100A, 100B, which can resemble any of the ports described herein. Both of the ports 100A, 100B are shown attached to a vessel 200 that is associated with an arteriovenous fistula 218. One port 100A is directed upstream such that a forward end thereof points in a direction opposite to the flow of blood through the vessel 200, and the other port 100B is directed downstream such that a forward end thereof points in the direction of the blood flow through the vessel 200, although other arrangements are possible. A separate access device 144 (e.g., fistula needle or over-the-needle catheter) may be introduced into each of the ports 100A, 100B via any of the methods described above and connected to a blood treatment system 402 (e.g., hemodialysis machine) via any suitable passageways 404 (e.g., tubing).

Blood treatment then can then be performed. The first port 100A can be an uptake port through which blood is removed from the vessel 200 and delivered to the blood treatment system 402, and the second port 100B can be a return port through which treated blood is returned to the vessel 200 from the blood treatment system 402. Accordingly, in use, blood is removed from the patient via an access device 144 that is within the first port 100A and delivered to the blood treatment system 402. The removed blood is treated in any suitable manner via the blood treatment system 402. Treated blood is returned to the patient via an access device 144 that is within the second port 100B.

In other embodiments, the system 400 can comprise only a single vascular access port 100A or 100B. Blood treatment may be conducted thereby via any suitable method (e.g., a single-needle hemodialysis technique). In still other embodiments, the system 400 includes more than two vascular access ports 100A, 1006. A clinician thus can rotate among the ports 100A, 1006, thereby leaving one or more of the ports unused during any given blood treatment session.

FIGS. 16A-16G illustrate another embodiment of a vascular access port 500, which can resemble the vascular access port 100 described above in certain respects. Accordingly, like features are designated with like reference numerals, with the leading digits incremented to "5." Relevant disclosure set forth above regarding similarly identified features thus may not be repeated hereafter. Moreover, specific features of the vascular access port 500 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access port 500. Any suitable combination of the features and variations of the same described with respect to the vascular access port 100 can be employed with the vascular access port 500, and vice versa. This pattern of disclosure applies equally to further embodiments depicted in subsequent figures and described hereafter.

The vascular access port 500 can include a base 502 and a body 504. The base defines a perimeter 506 that is substantially rectangular, except for a rounded front end. An outermost periphery 560 of the port 500 can be continuous about an entirety thereof. In the illustrated embodiment, the outermost periphery 560 is defined entirely by the perimeter 506 of the base 502. Stated otherwise, the body 504 does not extend outwardly to a greater lateral or longitudinal extent than does the base 502. However, at two regions 570 of the port 500, the body 504 and the base 502 extend outwardly to the same lateral position so as to be even with each other thereat. Accordingly, it could be said that the body 504 cooperates with the base 502 to define a portion of the outermost periphery 560 of the port 500. A vertical extension or projection of the outermost periphery 560 defines a peripheral extent 566 of the port 500.

Figure 16A:
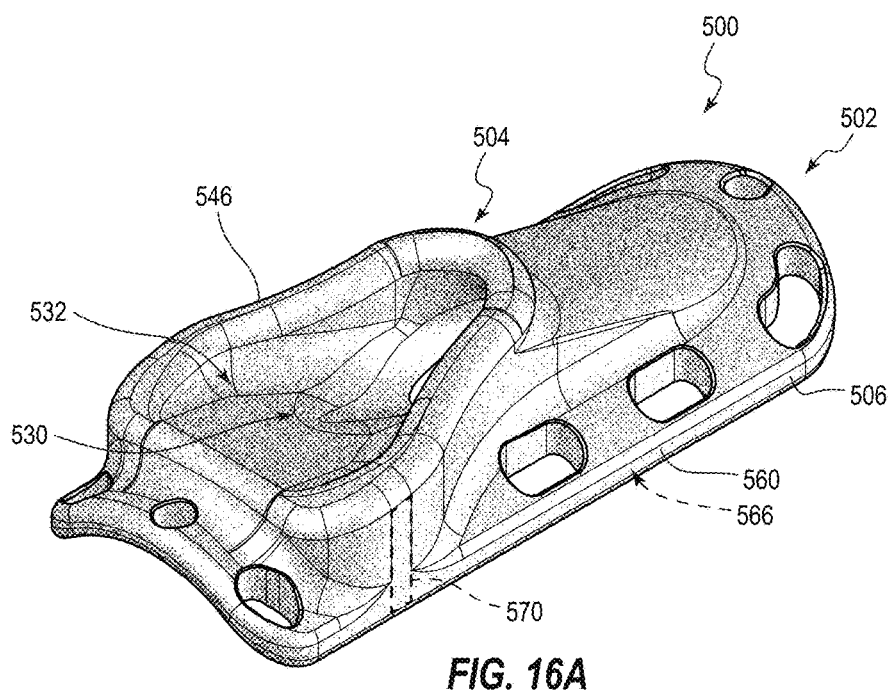
FIG. 16A is a perspective view of another embodiment of a vascular access port.
Figure 16B:
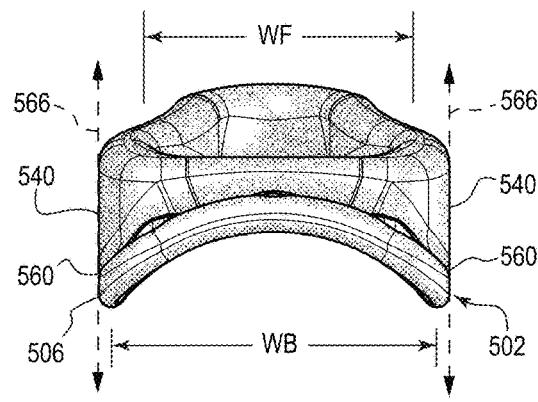
FIG. 16B is a rear elevation view thereof.
Figure 16C:
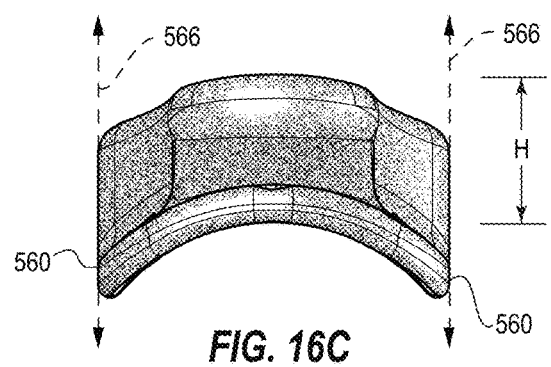
FIG. 16C is a front elevation view thereof.

As can be seen in FIGS. 16A and 16B, a width WF of the funnel region 532 of the vascular access port 500 can be less than a width WB of the base 502. Wings 540 of the body 504 may not extend past a perimeter 506 of a base 502 of the port 500. In the illustrated embodiment, the outer edges of the wings 540 are substantially parallel to each other and extend upwardly from the base 502. The narrower arrangement of the wings 540 thus can result in a smaller entry to or proximal opening of the funnel region 532, as compared with the port 100.

The port 500 can include a palpation projection 546 that fully encompasses the funnel region 532. As shown, for example, in FIG. 16F, the palpation projection 546 can be substantially planar. A plane defined by the palpation projection 546 can define an acute angle relative to a bottom end of the base 502 such that a forward end of the palpation projection 546 is at a greater vertical height than is a rearward end thereof. Additionally, a forward face 556 of the port 500 can define an acute angle relative to a bottom surface 508 of the base 502. In the illustrated embodiment, the port 500 includes a channel 534 that defines a central axis AX that is at an acute angle relative to the bottom surface 508 of the base 502. The acute angles defined by the forward face 556 and the central axis AX both open rearwardly, or stated otherwise, are both directed forwardly. However, the acute angle defined by the forward face 556 is smaller than the acute angle defined by the central axis AX.

FIG. 17A illustrates another embodiment of a vascular access port 600, which can resemble the vascular access ports described above in certain respects. The port 600 can include a base 602 that comprises a graft extension 605, which can aid in securely attaching the port 600 to a vessel. In the illustrated embodiment, the graft extension 605 can be fixedly attached to a remainder of the base 602 via one or more sutures 116. Any other suitable method for attaching the graft extension 605 to the base 602 may be used. The graft extension 605 can comprise any suitable material, which may be flexible so as to permit natural fluctuations in the vessel diameter. The material may also promote tissue ingrowth. In some embodiments, the graft extension 605 comprises e-PTFE. In the illustrated embodiment, a first side of the graft extension 605 (not shown) is coupled with the port 600 and a second side 609 is unattached thereto.

As shown in FIG. 17B, the graft extension 605 can be positioned about a at least a portion of a vessel 200 and one or more attachment devices 116 can be inserted through the port 600, through the various layers of the vessel 200, and through the graft extension 605 and then secured (e.g., tied off). Additional attachment devices 116 may also be used relative to the port 600 in manners such as discussed above.

In some embodiments, the vascular access port 600 can be used to repair a fistula. For example, in some embodiments, the base 602 (e.g., the graft extension 605) can be positioned about an aneurism in a vessel wall.

In certain embodiments, the graft extension 605 may be replaced with a housing element (not shown) that is configured to encompass at least a portion of the vessel 200 in a manner such as that depicted in FIG. 17B. The housing element can comprise any suitable biocompatible material, and may be sufficiently rigid to prevent an access device 144 from striking through a side of a vessel that is opposite the port 600.

In various embodiments, at least a portion of the graft extension 605 or the housing element can include a covering (not shown), such as a coating and/or an embedded portion, that comprises one or more materials or agents that provide antiseptic, antimicrobial, antibiotic, antiviral, antifungal, anti-infection, or other desirable properties to the vascular access port 600, such as the ability to inhibit, decrease, or eliminate the growth of microorganisms at or near a surface of the port. For example, any suitable covering material listed above may be used.

Figure 18:
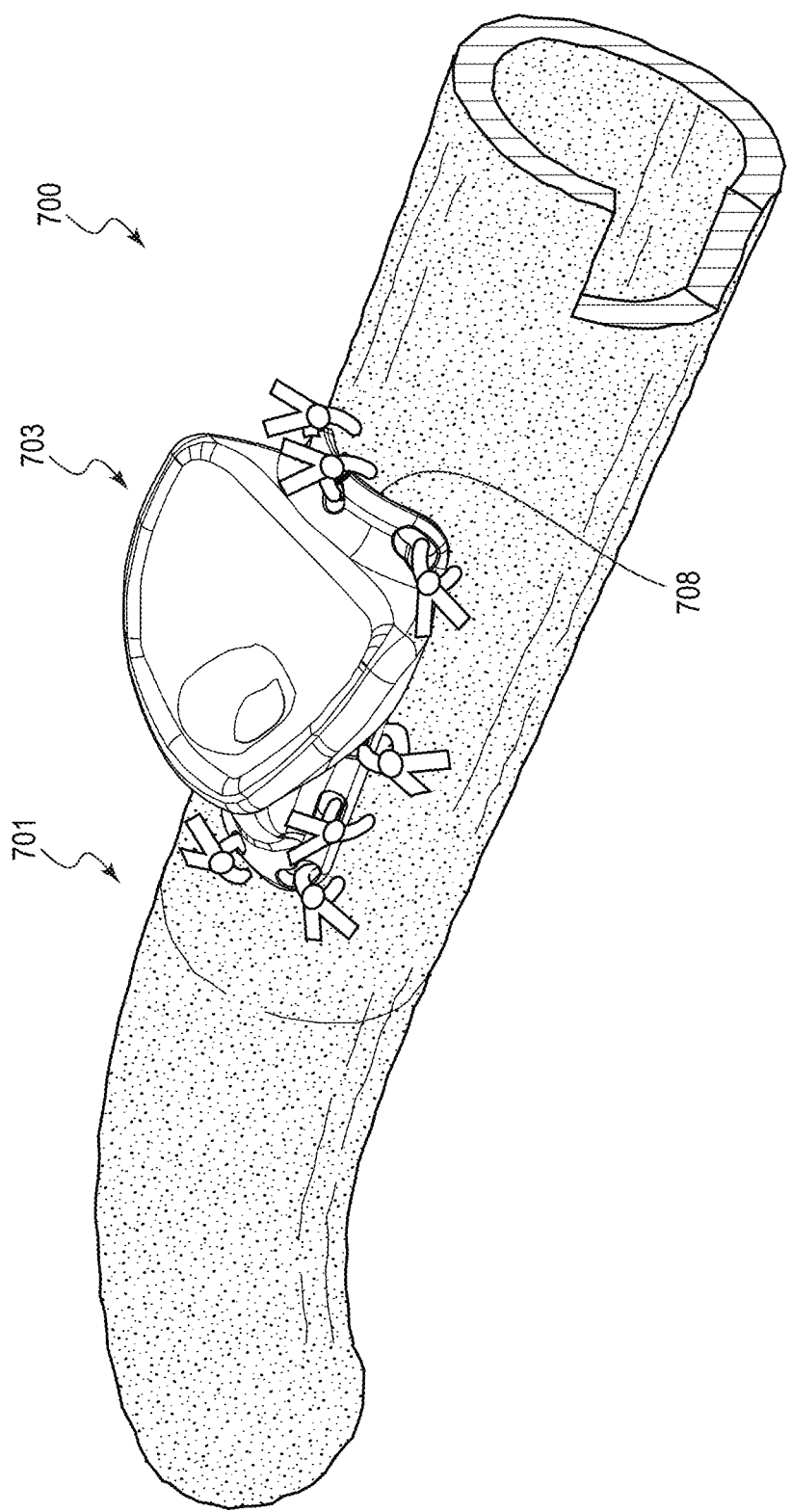
FIG. 18 is a perspective view of an embodiment of a vascular access system.

FIG. 18 illustrates an embodiment of a vascular access system 700. The system 700 includes an artificial graft vessel 701 and a vascular access port 703 attached thereto. The vascular access port 703 can resemble any of the access ports described above. However, in some embodiments, a bottom surface 708 of the port 703 may be devoid of an ingrowth-inducing covering. The bottom surface 708 may be provided with an adhesive to create a tight bond between the port 703 and the graft vessel 701. In some embodiments, a fluid-tight seal is provided between the port 703 and the graft vessel 701, which can prevent blood or other fluids from seeping between the port 703 and the graft vessel 701 during or after an access event. One or more attachment devices 116 may be used to attach the port 703 to the graft vessel 701. The graft vessel 701 can comprise any suitable material, such as, for example, e-PTFE.

Figure 19:
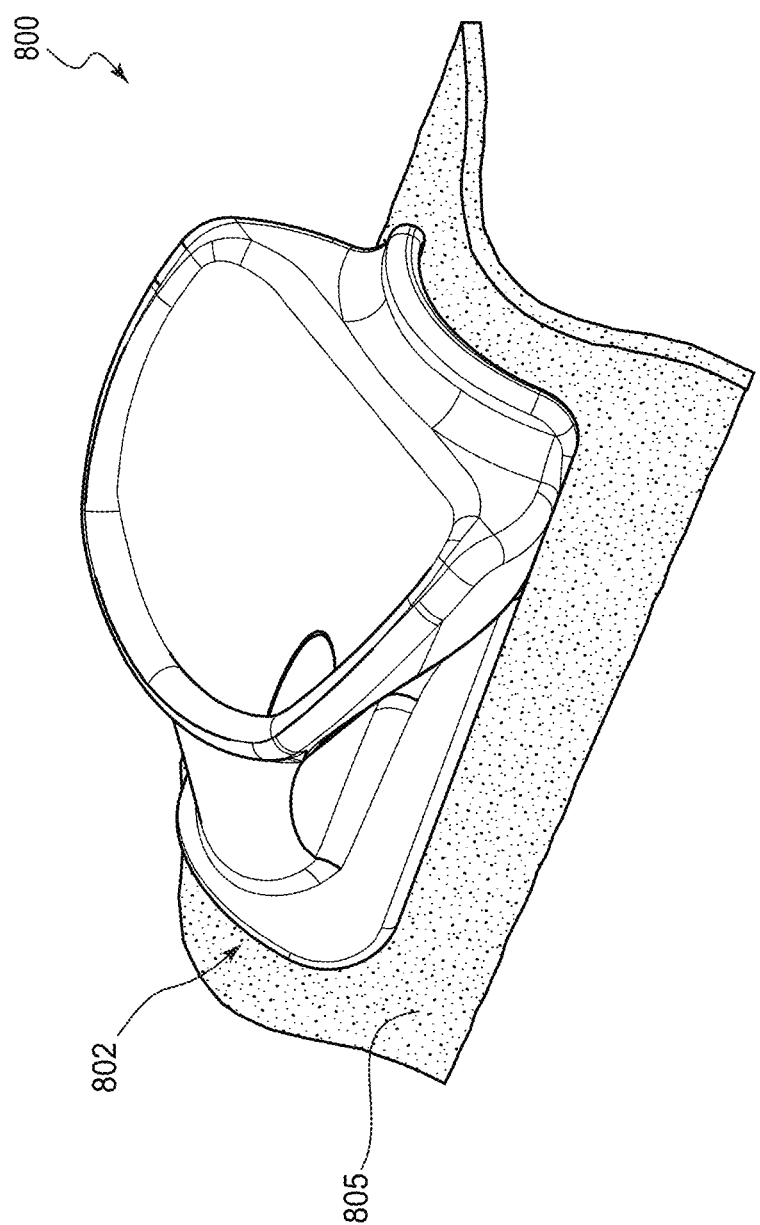
FIG. 19 is a perspective view of another embodiment of a vascular access port.

FIG. 19 illustrates another embodiment of a vascular access port 800. The vascular access port 800 includes a flexible patch 805 connected to a base 802 thereof. The patch 805 extends outwardly beyond a periphery of the body 802. The patch 805 can comprise any suitable biocompatible material, and can promote tissue ingrowth therein. For example, in various embodiments, the patch 805 comprises one or more of Dacron, e-PTFE, or polyurethane foam. The patch 805 can be conformable to an exterior surface of a vessel to which it is attached, and it may be attached to the vessel by one or more of sutures, clips, or other suitable devices. The patch 805 can be configured to encompass at least a portion of the vessel to which it is attached.

In the illustrated embodiment, the base 802 is bowed so as to conform to a wall of a vessel. As with other ports described herein, in other embodiments, the base 802 may be substantially planar or shaped in another configuration. For example, in some embodiments, at least a portion of the base 802 may be formed of a flexible or conformable material. In certain of such embodiments, the base 802 can be configured to conform to an outer surface of a vessel wall. For example, in some embodiments, the base 802 can comprise the patch 805, which may naturally have a substantially planar configuration, and the patch 805 can be bowed when it is joined to a vessel wall.

Figure 20:
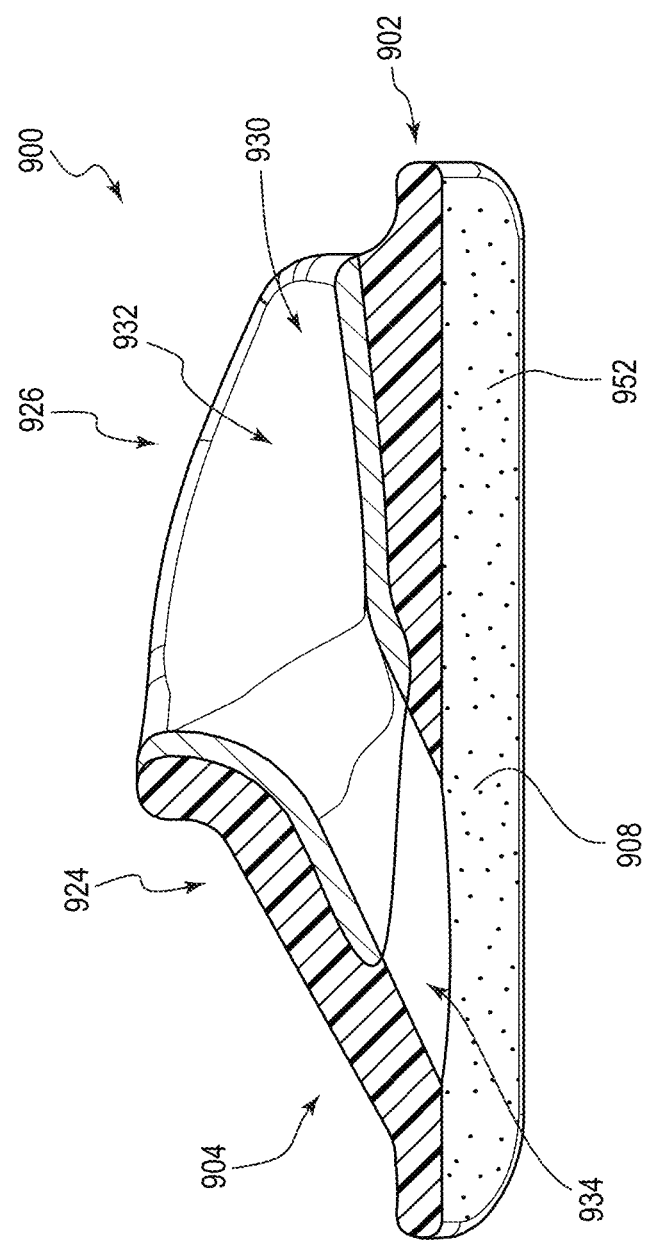
FIG. 20 is a cross-sectional view of another embodiment of a vascular access port.

FIG. 20 illustrates another embodiment of a vascular access port 900. The vascular access port 900 includes a supportive component 924 and a directive component 926 that have different properties, such as, for example, different resistances to puncturing, duration times once implanted in a patient, and/or material costs. In various embodiments, each of the supportive and directive components 924, 926 can form at least a portion of one or more of a base 902 and a body 904 of the vascular access port 900. For example, in the illustrated embodiment, each of the supportive and directive components 924, 926 help form the body 904, whereas, of the two, only the supportive component 924 contributes to the base 902.

In some embodiments, the supportive and directive components 924, 926 are configured to maintain a predetermined form within a patient for different periods of time once the vascular access port 900 has been implanted. For example, in some embodiments, the supportive component 924 is configured to be resorbed within a patient more quickly than is the directive component 926. For example, in various embodiments, the supportive component 924 is resorbed at a rate that is no more that about 1.5, 2, 3, 4, 5, 6, 7, 8, 9, or 10 times the rate at which the directive component 926 is resorbed, or the supportive component 924 is resorbed at a rate that is no less than about 1.5, 2, 3, 4, 5, 6, 7, 8, 9, or 10 times the rate at which the directive component 926 is resorbed. In some embodiments, the directive component 926 is configured to resist resorption, and may remain within a patient indefinitely without being resorbed. In some embodiments, the supportive component is configure to be fully resorbed within a period of no more than about 1, 2, 3, 4, 5, or 6 months or no less than about 1, 2, 3, 4, 5, or 6 months.

In various embodiments, one or both of the supportive and directive components 924, 926 can comprise a resorbable material, such as, for example, any suitable resorbable material described above. In other or further embodiments, the directive component 926 can comprise a non-resorbable material, such as stainless steel, titanium, or the like.

A substantial portion of a guidance passageway 930 can be defined by the directive component 926. For example, in the illustrated embodiment, an entire funnel region 932 and an entrance end of a channel 934 are formed by the directive component 926. In contrast, only an exit end of the channel 934 is formed by the supportive component 924. As it is more resistant to being resorbed, the directive component 926 can resist coring and scraping by a needle or other insertion device 144 for a longer duration, and thus can assist in creating an insertion tract through the skin of a patient to a buttonhole and/or can assist in the creation of the buttonhole itself.

The supportive component 924 can encompass a forward end of the directive component 926, as shown. The supportive and directive components 924, 926 can be joined to each other in any suitable manner. For example, the components 924, 926 can be adhered or welded to each other. In some embodiments, the supportive component 924 is overmolded onto the directive component 926.

Tissue that replaces the supportive component 924 can in turn support the directive component 926 in a similar manner such that the directive component 926 can generally maintain the same orientation within a patient once the supportive component 924 has been resorbed. In some embodiments, an outer surface of the directive component 926 (e.g., a surface opposite the guidance passageway 930) can include any suitable ingrowth-inducing features, such as the ingrowth-inducing covering 152 described above. Accordingly, as the supportive component 924 is replaced with tissue, the tissue can be firmly attached to the directive component. Additionally, as with the ports discussed above, at least a bottom surface 908 of the vascular access port 900 can include an ingrowth-inducing covering 952.

In some embodiments, different materials may be used for the supportive and directive components 924, 926 as a cost-saving measure. For example, a less durable, less expensive material may be used for the supportive component 924 with little or no difference in the performance of certain embodiments of vascular access ports described above. In some embodiments, the directive component 926 may comprise a coating or layer of a material having intrinsic strength and/or that is capable of imparting strength to the supportive component 924.

FIGS. 21A-21G illustrate another embodiment of a vascular access port 1000, which can resemble the vascular access ports described above in certain respects. The vascular access port 1000 can comprise a base 1002 that is devoid of attachment passages. Accordingly, the port 1000 may be attached to a vessel by some method other than suturing or the like, such as via a biocompatible adhesive. However, in other embodiments, the vascular access port 1000 includes attachment passages such as the attachment passages 114 discussed above.

The port 1000 can include a guidance passageway 1030 that varies from the guidance passageway 130 depicted in FIGS. 1-7. In particular, the guidance passageway 1030 comprises a funnel region 1032 that extends from one or more of a palpation projection 1046 and an entry mouth 1036 to an opening 1050 in the base 1002. The funnel region 1032 decreases in size in a vertically downward direction such that a width of the funnel region becomes smaller toward the opening 1050. The funnel region 1032 also decreases in size in a longitudinally forward direction such that a width of the funnel becomes smaller in a rearward-to-forward direction.

Figure 21D:
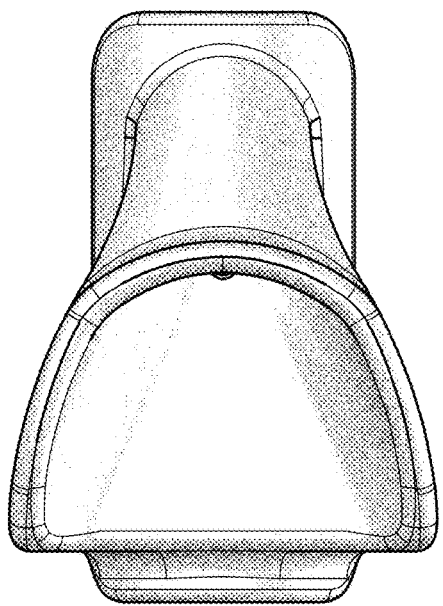
FIG. 21D is a top plan view thereof.
Figure 21E:
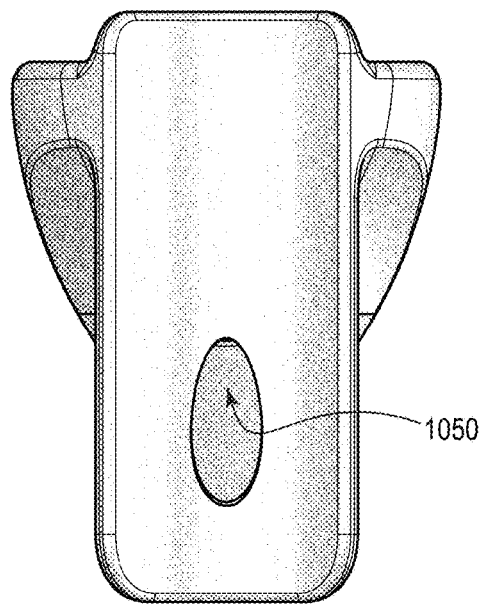
FIG. 21E is a bottom plan view thereof.
Figure 21F:
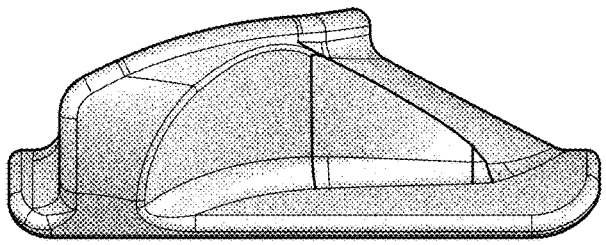
FIG. 21F is a right side elevation view thereof, wherein a left side elevation view thereof is a mirror image of the right side elevation view.
Figure 21G:
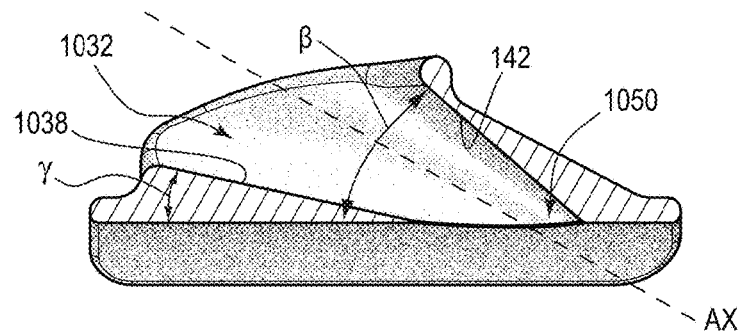
FIG. 21G is a cross-sectional view thereof.

As can be seen in FIG. 21G, a backstop portion 1042 of the funnel region 1032 is angled rearwardly and extends over (e.g., is positioned above) the opening 1050. A base surface 1038 of the funnel region is also angled rearwardly. The funnel region 1032 thus can be said to be angled rearwardly in its entirety.

The guidance passageway 1030 does not include a channel portion, such as the channel 134 described above, that defines a substantially constant cross-sectional area along a given length. In some instances, the absence of a channel can prevent or inhibit binding of an access device 144 as it is inserted through the passageway 1030 and/or removed therefrom. As can be seen from a comparison of FIG. 5 and FIG. 21E, the opening 1050 can define the same ovoid shape as the opening 150 that is at the end of the cylindrical channel 134. Accordingly, the opening 150 can be configured to closely conform to an outer surface of a cylindrical access device 144 that is inserted therethrough at a preferential angle, or at an angle within a preferential range. In some instances, such as where the size of the access device 144 is closely matched to the size of the opening 150, binding may occur when the access device 144 is inserted or removed from the opening 150 at an angle that is not within a preferential range. Such close matching may occur where an outer diameter of the access device 144 is smaller than a maximum lateral width of the opening 150 by any of the gauge values described above with respect to the channel 134.

The funnel region 1032 can define multiple angles relative to the base 1002. With reference to FIG. 21G, which represents a cross-section of the port 1000 along a central vertical-longitudinal plane thereof, a front surface of the funnel region 1032 can define a maximum angle $\beta$ relative to the base 1002, and a rear surface of the funnel region 1032 can define a minimum angle $\gamma$ relative to the base 1002. A central axis AX of the guidance passageway 1030 can pass through a center of the opening 1050 along the central vertical medial plane at an angle relative to the base that has a value defined by $(\beta+\gamma)/2$. In some embodiments, a preferential range of angles over which an access device 144 may be inserted through the opening 1050 with little or no binding can include the angle $(\beta+\gamma)/2$ defined by the central axis AX. In other embodiments, the angle $(\beta+\gamma)/2$ may be outside of the preferential range such that the central axis AX does not necessarily correspond with (e.g., is not aligned or coaxial with) a longitudinal, central axis of an access device 144 when the access device 144 has been inserted through the opening 1050. For the embodiment illustrated in FIGS. 21A-21G, the angle $(\beta+\gamma)/2$ defined by the central axis AX can be acute. For example, a value of the angle $(\beta+\gamma)/2$ can be the same as any of the values discussed above with respect to the angle $\alpha$ defined by the central axis AX of the port 100.

FIGS. 22A-22G illustrate another embodiment of a vascular access port 1100, which can resemble the vascular access ports described above in certain respects. The vascular access port 1100 can comprise a base 1102 similar to the base 102 described above. The vascular access port 1100 can further comprise a body 1104 that extends vertically and, in some regions, laterally away from the base 1102.

Figure 22A:
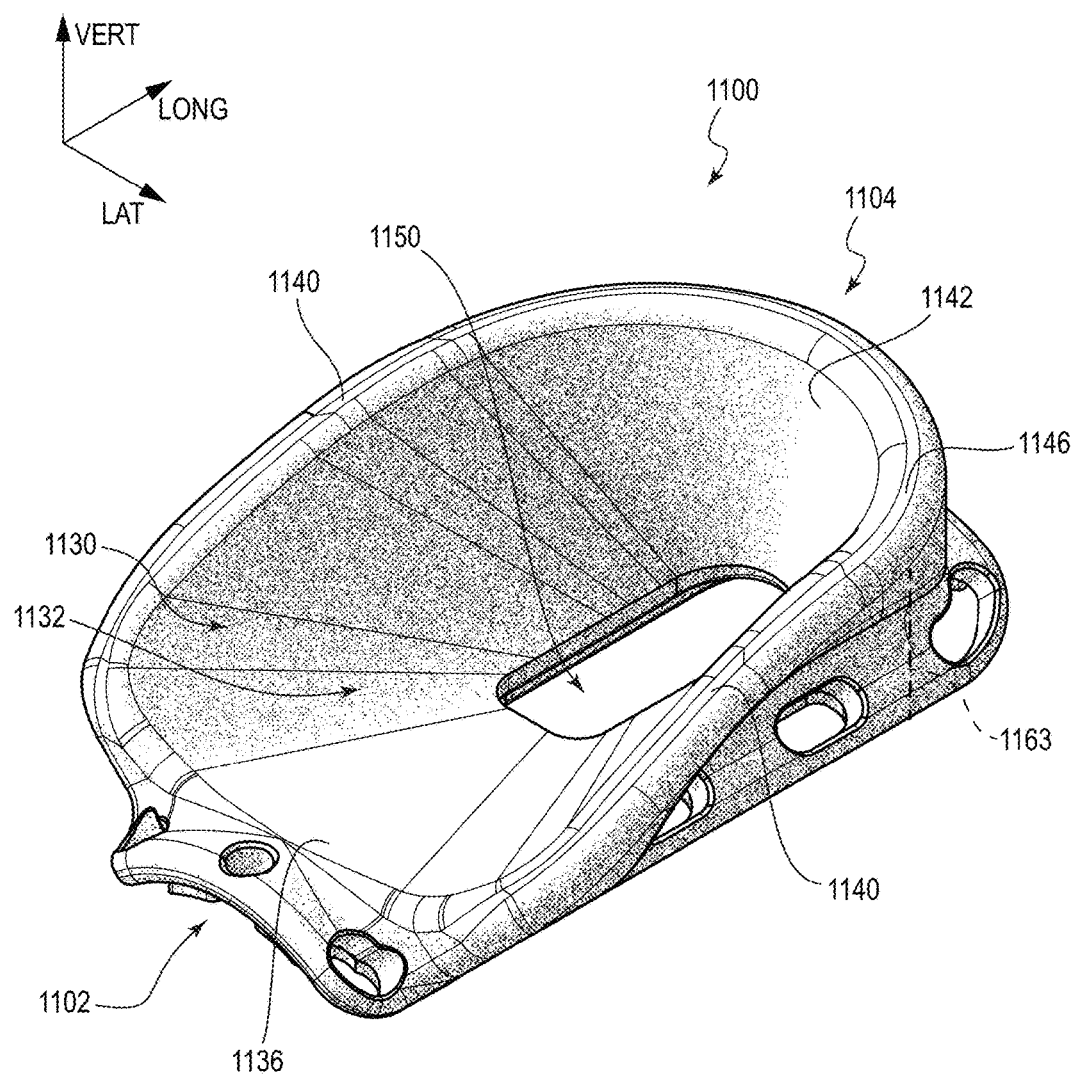
FIG. 22A is a perspective view of another embodiment of a vascular access port.
Figure 22B:
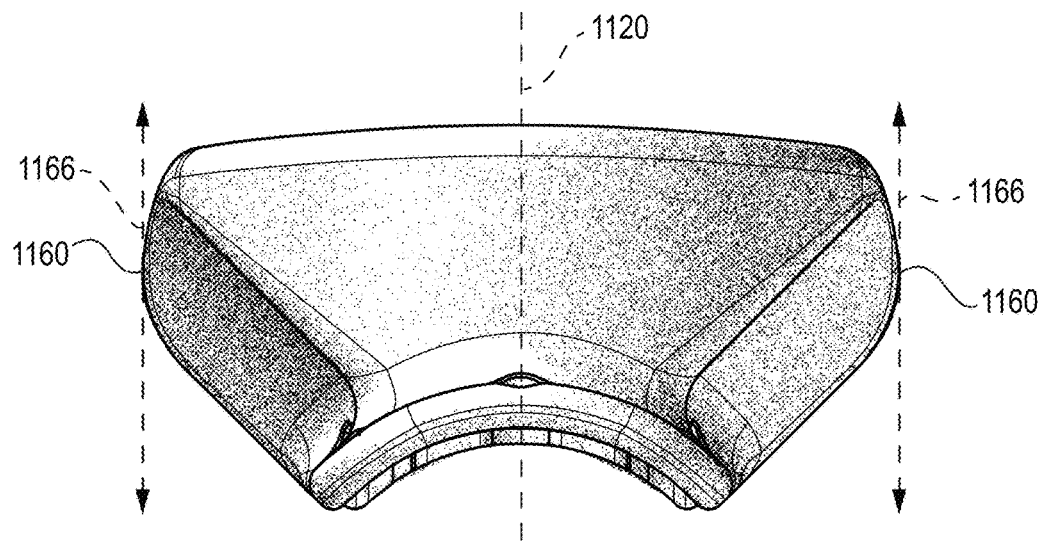
FIG. 22B is a front elevation view thereof.
Figure 22C:
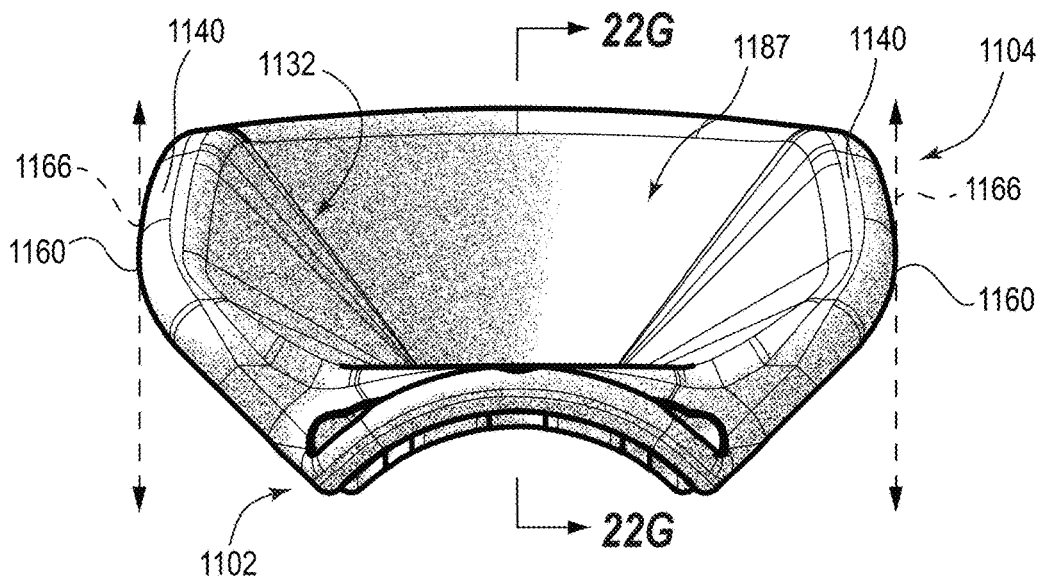
FIG. 22C is a rear elevation view thereof.
Figure 22D:
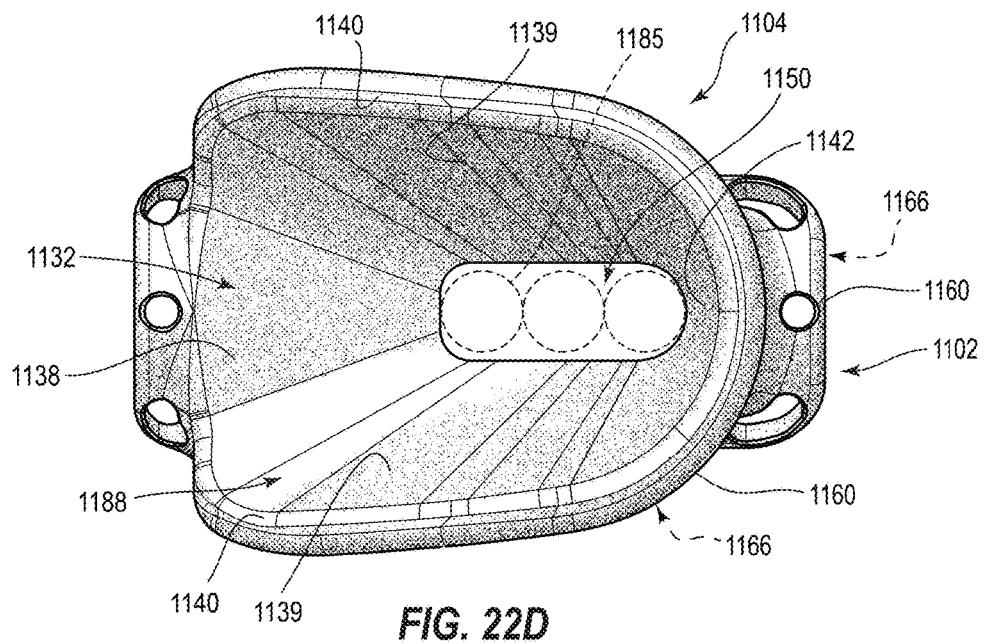
FIG. 22D is a top plan view thereof.
Figure 22E:
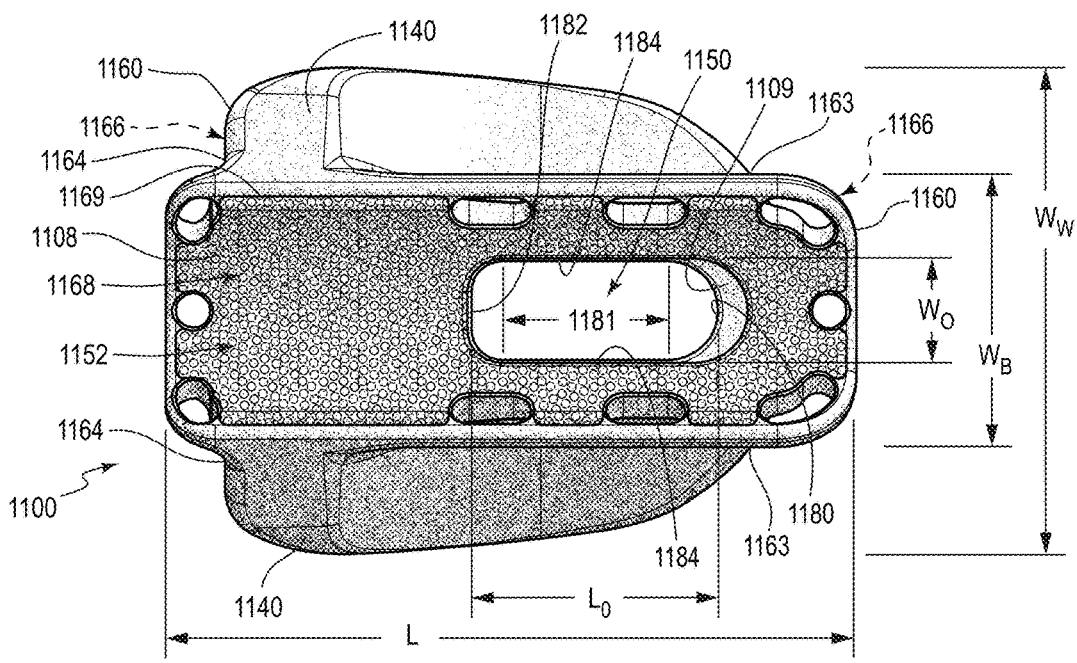
FIG. 22E is a bottom plan view thereof.

Similar to the outermost periphery 160 of the port 100, an outermost periphery 1160 of the port 1100 is discontinuous, as it transitions from the body 1104 to the base 1102 at various discontinuous positions 1163, 1164 (see FIGS. 22A and 22E). In the illustrated embodiment, a large majority of the outermost periphery 1160 is defined by a perimeter of the body 1104, as the body 1104 includes large wings 1140 that extend laterally outward beyond the base 1102 and are also elongated in the longitudinal direction. Only a small portion of the outermost periphery 1160 is defined by the front and rear ends of the base 1102. A vertical projection or extension of the outermost periphery 1160 defines a peripheral extent 1166 of the port 1100 (see FIGS. 22B, 22C, and 22F).

The port 1100 includes a guidance passageway 1130 that comprises a funnel region 1132 that extends from one or more of a palpation projection 1146 and an entry mouth 1136 to an opening 1150 in the base 1102. The funnel region 1132 decreases in size in a vertically downward direction such that a width of the funnel region becomes smaller toward the opening 1150. The funnel region 1132 also decreases in size in a longitudinally forward direction such that a width of the funnel becomes smaller in a rearward-to-forward direction.

Figure 22F:
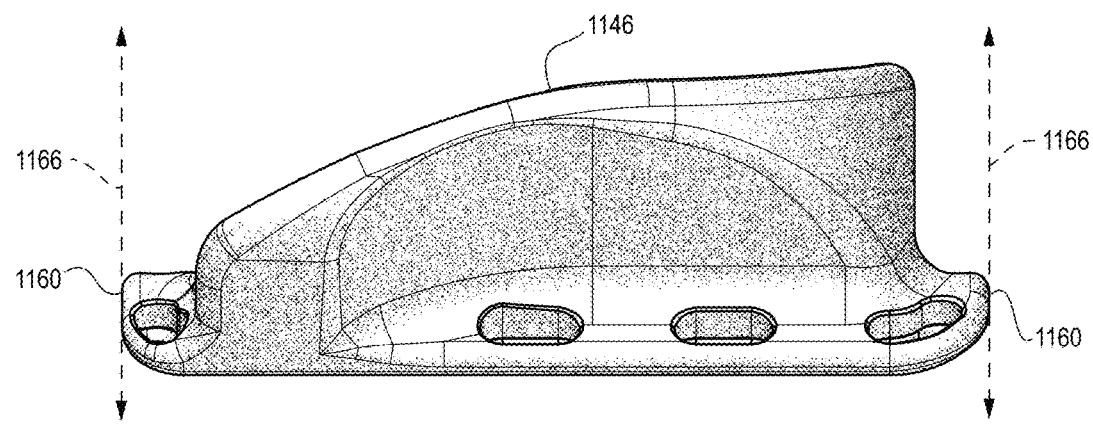
FIG. 22F is a right side elevation view thereof, wherein a left side elevation view thereof is a mirror image of the right side elevation view.
Figure 22G:
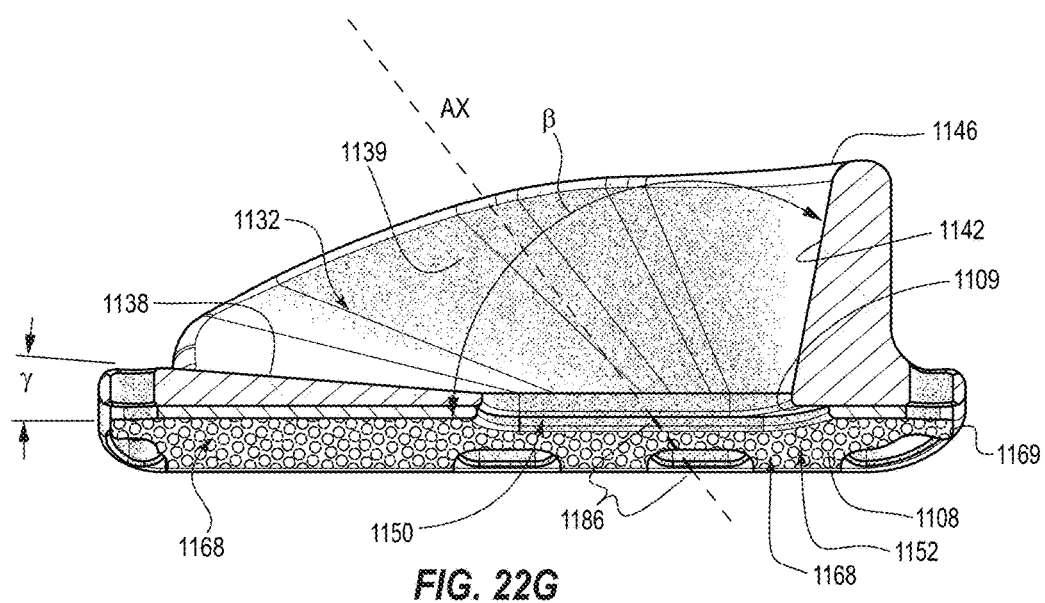
FIG. 22G is a cross-sectional view thereof.

With reference to FIGS. 22D and 22G, a backstop portion 1142 of the funnel region 1132 is angled forwardly such that at least a portion thereof is forward of the opening 1150. The backstop portion 1142 may also be said to angle outwardly from the opening 1150 in an upward direction. A base surface 1138 of the funnel region is also angled rearwardly or outwardly from the opening 1150 in the upward direction, and may extend to a vertical height that is less than a vertical height to which the backstop portion 1142 extends. Side regions 1139 of the funnel region 1132 likewise are angled outwardly from the opening 1150 in the upward direction. The funnel region 1132, in its entirety, thus can be said to be angled outwardly from the opening in the upward direction. Stated otherwise, the funnel region 1132 can constrict inwardly from all sides in a downward direction. In other embodiments, the backstop portion 1142 may extend in a true vertical direction, so as not to be angled outwardly or inwardly, or it may extend vertically and rearwardly, so as to be angled rearwardly (as discussed below with respect to FIG. 28G). As can be seen in FIG. 22D, the backstop portion 1142 can be rounded and, in the illustrated embodiment, is substantially conically shaped.

With reference to FIGS. 22F and 22G, the palpation projection 1146 can define a substantially planar surface that is angled relative to the longitudinal direction. In the illustrated embodiment, the substantially planar surface is gently bowed so as to be convexly rounded at a central region of the port 1100. The palpation projection 1146 increases in height in the forward direction so as to reach a maximum height at a forward end of the port 1100. As can be seen in FIG. 22G, at least a portion of the palpation projection 1146 can be at a position that is forward of the opening 1150.

With reference to FIGS. 22D and 22E, the opening 1150 can be larger than the opening 1050 discussed above. For example, where the ports 1000, 1100 are configured for use with an access device 144 of a given outer diameter, the opening 1150 can be longer than the opening 1050, or stated otherwise, can be more elongated in the longitudinal direction. Due to the greater length of the opening 1150, an access device 144 can be inserted through the opening 1150 at a larger variety of angles. Moreover, the opening 1150 can inhibit, reduce, or eliminate binding of the access device 144 after it has been inserted, particularly where the device is inserted through the opening 1150 such that a central axis thereof is aligned with a central vertical-longitudinal plane 1120 (see FIG. 22B). As discussed further below, such binding can be inhibited, reduced, or eliminated when the access device 144 is at an angle relative to a bottom surface 1108 of the base 1102 that is within a wide range of angles. A larger opening 1150 also can allow for greater or more consistent tissue ingrowth through the opening 1150 and may prevent direct contact between an access device 144 and the edges of the opening 1150.

In the illustrated embodiment, the opening 1150 includes a semicircular forward end 1180 and a rectangular rearward end 1182, which has rounded corners. Stated otherwise, a portion of the rearward end 1182 of the opening 1150 is defined by a non-curved or straight portion. Opposite sides 1184 extend between the forward and rearward ends 1180, 1182. In the illustrated embodiment, the sides 1184 define substantially straight lines that are substantially parallel to each other. Accordingly, a contour or periphery of the opening 1150 can include one or more non-curved, straight, or linear portions. The sides 1184 can provide a spacing between the forward and rearward ends 1180, 1182 that can reduce binding of an access device 144.

As shown in FIG. 22E, a maximum length $L_O$ of the opening 1150 can be greater than a maximum width $W_O$ of the opening. In various embodiments, the length $L_O$ can be greater than the width $W_O$ by no less than a factor of 1.5, 2.0, 2.5, 3.0, or 3.5, by a factor that is within a range of from about 1.5, 2.0, 2.5, or 3.0 to about 3.5, or by a factor that is within a range of from about 1.5, 2.0, or 2.5 to about 3.0. In other or further embodiments, the width $W_O$ can be greater than an outer diameter of an access device 144 that is used with port 1100 by an amount within a range of from about 0.1 gauge to about 3.5 gauge, from about 0.25 gauge to about 3.0 gauge, from about 0.5 gauge to about 2.0 gauge, from about 0.75 gauge to about 1.5 gauge, or from about 0.75 gauge to about 1.25 gauge; by an amount that is no less than about 0.1, 0.25, 0.5, 0.75, 1.0, 1.25, 1.5, 1.75, 2.0, 2.5, or 3.0 gauge; or by an amount that is no greater than about 0.1, 0.25, 0.5, 0.75, 1.0, 1.25, 1.5, 1.75, 2.0, 2.5, or 3.0 gauge. In some embodiments, the width $W_O$ is about 1.0 or about 2.0 gauge larger than an outer diameter of the access devices 144 with which it is configured to be used. In other or further embodiments, the length $L_O$ of the opening 1150 is greater than an outer diameter of the access device 144 by no less than a factor of 1.5, 2.0, 2.5, 3.0, 3.5, or 4.0.

In some embodiments, a relatively close fit between the width $W_O$ of the opening 1150 and an outer diameter of the access devices 144 with which the port 1100 is configured to be used can help to prevent or inhibit an access device 144 from penetrating through a sidewall of a vessel 200 after having been introduced into the lumen of the vessel through the opening 1150. In particular, such a relatively close fit can cause the access device 144 to enter a lumen of the vessel 200 in a direction that is aligned, substantially aligned, or defines a relatively small angle with the central vertical-longitudinal plane 1120 of the port 1100, and the central vertical-longitudinal plane 1120 of the implanted port 1100 can be aligned, or substantially aligned, with a longitudinal axis of the vessel 200. Such an arrangement can constrict movement of the access device 144 such that a tip thereof remains spaced from the lateral sides of the vessel 200.

The funnel region 1132 can define multiple angles relative to the base 1102. With reference to FIG. 22G, which represents a cross-section of the port 1100 along the central vertical-longitudinal plane 1120, a front surface of the funnel region 1132 (i.e., the backstop portion 1142) can define a maximum angle β relative to the bottom surface 1108 of the base 1102 within the plane 1120, and a rear surface of the funnel region 1132 can define a minimum angle γ relative to the bottom surface 1108 of the base 1102 within the plane 1120. A central axis AX of the guidance passageway 1130 can pass through a center of the opening 1150 along the central vertical medial plane at an angle relative to the bottom surface 1108 of the base 1102 that has a value defined by (β+γ)/2. In the illustrated embodiment, the angle (β+γ)/2 is acute. As with the port 1000 discussed above, the value of the angle (β+γ)/2 can be the same as any of those discussed above with respect to the angle α defined by the central axis AX of the port 100.

In some embodiments, a range of angles over which an access device 144 may be inserted through the opening 1150 with little or no binding can include the angle (β+γ)/2 defined by the central axis AX. Moreover, other angles that are greater or smaller in value than the angle (β+γ)/2 also may result in little or no binding such that the central axis AX does not necessarily correspond with (e.g., is not aligned or coaxial with) a central axis of an access device 144 when the access device 144 has been inserted through the opening 1150. For example, a substantially cylindrical access device having an outer diameter that is only slightly smaller than the width $W_O$ of the opening 1150, such that it can be inserted through the opening 1150 along the central vertical longitudinal plane 1120 and contact opposing lateral sides of the opening 1150, can be inserted through or removed from the opening 1150 without binding over a range of angles. As can be appreciated from the foregoing, in such an arrangement, binding can occur due to contact between the access device 144 and one or more of the forward and rearward ends 1180, 1182 of the opening 1150. Stated otherwise, the forward and rearward ends 1180, 1182 can interact with the access device 144 to define a minimum angle and a maximum angle at which no binding of the access device 144 occurs. A difference between the maximum and minimum angles at which no binding occurs can be no less than about 5, 10, 15, 20, 25, 30, 35, 40, 45, 50, 55, 60, 65, 70, 75, 80, 85, or 90 degrees, can be no more than about 5, 10, 15, 20, 25, 30, 35, 40, 45, 50, 55, 60, 65, 70, 75, 80, 85, or 90 degrees, or can be within a range of from about 5, 10, 15, 20, 25, 30, 40, 45, 50, 55, 60, 65, 70, or 75 degrees to about 90 degrees, from about 5, 10, 15, 20, 25, 30, 40, or 45 degrees to about 60 degrees, or from about 5, 10, 15, 20, 25, 30 degrees to about 45 degrees.

With reference to FIG. 22D, in some embodiments, the opening 1150 is sufficiently elongated to permit a single access device 144 to create multiple discreet insertion sites 266 in a vessel to which the port 1100 is attached, depending on the angle at which the access device 144 is inserted. For example, in the illustrated embodiment, a large number of separate insertion sites 266 (see FIGS. 11C-11E) can be created in each of three distinct insertion regions 1185 that are shown as phantom circles in FIG. 22D. The contours of the three distinct insertion regions 1185 represent an outer surface of an access device 144 that is inserted vertically through the opening 1150. Fewer insertion regions 1185 that have larger outer contours are possible with increasingly shallower angles of the access device 144 relative to the base 1102. For example, the contours of the insertion regions 1185 can become more ovoid than the circular contours illustrated in FIG. 22D when the access device 144 is inserted at shallower angles. At a minimum insertion angle at which no binding occurs (i.e., at angles less than the minimum insertion angle, the insertion device 144 will bind), the opening 1150 can accommodate only a single insertion region 1185, which can define an ovoid contour such as, for example, the periphery defined by the opening 150 (see FIG. 5). The forward and rearward ends of such a single insertion region 1185 can be substantially even with the forward and rearward ends 1180, 1182 of the opening 1150. Accordingly, at the minimum insertion angle, only a single insertion site 266 may be formed in a vessel via the port 1100. In various embodiments, where a substantially cylindrical access device is used that has an outer diameter that is only slightly smaller than the width $W_O$ of the opening 1150, such that it can be inserted through the opening 1150 along the central vertical longitudinal plane 1120 and contact opposing lateral sides of the opening 1150, the minimum insertion angle can be no less than about 10, 13, 15, 17, 20, 25, 30, 35, or 45 degrees. In some illustrative embodiments, a minimum insertion angle (i.e., the angle at which a single insertion region is present) can be about 17 degrees, and when an access device 144 is inserted at an angle of 20, 25, 30, or 35 degrees, about 1.1, 1.4, 1.6, and 1.9 insertion regions are possible, respectively.

As shown in FIG. 22E, the non-curved sides 1184 of the opening 1150 define an elongated region 1181 of the opening 1150 that can allow not only for the range of insertion positions in the longitudinal direction, as just discussed, but also provide a substantially constant constraint relative to the access device 144 in the lateral direction at any of the possible insertion positions. Stated otherwise, the opening 1150 can be sufficiently elongated to permit a single access device 144 to create multiple discreet insertion sites 266 in a vessel to which the port 1100 is attached (e.g., at a given insertion angle, more than one insertion region 1185 may be present). The non-curved sides 1184 of the opening 1150 that define the elongated region 1181 can permit the access device 144 to experience the same amount of constraint or guidance in the lateral direction at any of the longitudinal insertion positions just discussed.

Standard vascular access procedures often call for inserting an access device 144 into a lumen of a vessel at an angle within a range of from any of about 20, 25, or 30 degrees to any of about 35, 40, or 45 degrees. Accordingly, practitioners may be trained to cannulate a vessel at any of a number of angles that fall within any of the foregoing ranges. In various embodiments, the opening 1150 thus can readily accommodate any of the angles at which cannulation may proceed without binding of the access device 144. Larger insertion angles can result in a greater range of possible longitudinal positions within the opening 1150 through which the access device 144 can be inserted, as previously discussed. However, since many cannulations take place at relatively small angles (e.g., about 20 to about 30 degrees), the range of possible longitudinal positions is also small.

Moreover, in some instances, the range of possible longitudinal positions can be a factor primarily with respect to an initial insertion of an access device 114. That is, although the opening 1150 may be sufficiently elongated to allow the creation of an insertion site 266 at any of a variety of positions within the longitudinal range, repeated use of the port 1100 can nevertheless result in only a single insertion site 266. For example, in an initial access event, the access device 114 may be inserted through the opening 1150 at any of a variety of suitable positions. However, in subsequent access events, surrounding tissue can help guide the access device 144 along a path that was traveled by the previous access device 144 such that the previous insertion site 266 into the vessel is used in the subsequent access event. Formation of a buttonhole access site thus may proceed in manners similar to those of standard methods.

With reference to FIGS. 22E and 22G, the ingrowth-inducing covering 1152 can be recessed at the forward end 1180 of the opening 1150 so as to expose a lip 1109 of the base 1102. Such an arrangement can also reduce binding of an access device 144.

With reference to FIGS. 22E and 22G, the port 1100 can define a footprint 1168 that has an outermost perimeter 1169. As shown in FIG. 22G, a region 1186 of the central axis AX can be vertically even with the footprint 1168. In the illustrated embodiment, the region 1186 of the central axis AX extends a finite distance in the vertical direction, as the footprint 1168, which corresponds with the bottom surface 1108 of the base 1102, is bowed. The entirety of the region 1186 is interior to the outermost perimeter 1169 of the footprint 1168. Moreover, as can be seen by comparing FIG. 22G with FIG. 22F, the entirety of the region 1186 is also interior to the peripheral extent 1166 of the port 1100. As discussed below, in other embodiments, at least a portion of the region 1186 can be exterior to one or more of the outermost perimeter 1169 of the footprint 1168 and the peripheral extent 1166 of the port 1100.

With reference to FIG. 22E, a width Ww of the wings 1140 can be significantly greater than a width $W_B$ of the base 1102. For example, in various embodiments, the width Ww can be no less than 1.5, 2.0, or 2.5 times greater than the width $W_B$. In some instances, the wings 1140 the width Ww is greater than a width of a vessel to which the port 1100 is attached. The width Ww of the wings 1140 can assist a clinician in holding or steadying the port 1100 during an access event. A height of the wings 1140, which also can be significantly greater than a thickness or height of the base 1102, also can assist in locating, holding, and/or steadying the port 1100, as discussed further below.

The funnel region 1132 can serve as a target toward which an access device 144 can be directed and, as further discussed below, the funnel region 1132 can constrain movement of the access device 144 as it is advanced therethrough. The target-like nature of the funnel region 1132 can be particularly helpful where the port 1100 is implanted deeply below an outer surface of skin of a patient. A rear plan view target area 1187 of the funnel region 1132 can be defined as the area of the funnel region 1132 that is visible in a two-dimensional projection of the port 1100 such as that in FIG. 22C. Similarly, a top plan view target area 1188 of the funnel region 1132 can be defined as the area of the funnel region 1132 (exclusive of the opening 1150) that is visible in a two-dimensional projection of the port 1100 such as that in FIG. 22D. In various embodiments, an area defined by the rear plan view target area 1187 can be no less than about 0.25, 0.5, 0.75, 1.0, 1.25, or 1.5 times that defined by the top plan view target area 1188, no greater than about 0.25, 0.5, 0.75, 1.0, 1.25, or 1.5 times that defined by the top plan view target area 1188, or within a range of from about 0.25, 0.5, 0.75, 1.0, or 1.25 to about 1.5 times that defined by the top plan view target area 1188.

With reference to FIG. 22C, because the wings 1140 of the body 1104 extend outwardly beyond the base 1102, the rear plan view target area 1187 can be relatively large, as compared with arrangements such as that of the port 500 (see FIG. 16B). Similarly, the top plan view target area 1188 can be relatively large. As discussed further below, the rear plan target area 1187 can be enlarged for ports that are configured for deep implantation. Such an arrangement can facilitate cannulation of the vessel, due to the increased target size, and also can position the palpation projection 1146 closer to the surface of the skin when the port is implanted.

FIGS. 23A-23E resemble FIGS. 11A-11E above, and depict various procedures that may be performed relative to an implanted vascular access port 1100. As with the port 100, the vascular access port 1100 can facilitate the creation of a single-site buttonhole. The vascular access port 1100 likewise can facilitate use of the buttonhole once it is formed. Many of the features discussed above with respect to FIGS. 11A-11E can be similar or identical to uses of the port 1100, and thus may not be repeated hereafter. Other features and advantages of the port 1100 are discussed, some of which may vary from those discussed above with respect to FIGS. 11A-11E, while others may be common to both ports 100, 1100.

As shown in FIGS. 23A-23E, tissue 217 may grow into, attach to, or otherwise cover various areas of the vascular access port 1100. For example, skin tissue may grow into at least a portion of the guidance passageway 1130. In the illustrated embodiment, tissue covers the entirety of the guidance passageway 130. Accordingly, in the illustrated embodiment, sufficient time has passed between implantation of the port 1100 (e.g., via procedures such as those depicted in FIGS. 9A-9E) and a first access event (depicted in FIG. 23B) to permit growth of the tissue 217. In other instances, at least a first such access event may take place prior to any or full ingrowth or overgrowth of the tissue 217.

In some instances, a large amount of tissue ingrowth relative to the port 1100, or in further instances, a complete covering of tissue over the port 1100, can reduce, inhibit, or prevent direct contact between the access device 144 and the port 1100 during an access event. The tissue 217 thus can act as a barrier between the access device 144 and the port 1100, which can reduce or eliminate a risk of infection that might otherwise arise from contact between the foreign access device 144 and the implanted port 1100.

As previously discussed, in some embodiments, the opening 1150 of the port 1100 is relatively large, which can facilitate ingrowth of the tissue into the guidance passageway 1130. The relatively large opening 1150 can be significantly longer and/or wider than an outer diameter of the access device 144 (see FIG. 23B), which can facilitate insertion of the access device 144 without directly contacting the edges of the opening 1150. The large opening 1150 also can serve to inhibit or prevent binding of the access device 144, particularly in the presence of such ingrowth.

Despite relatively large size of the opening 1150 as compared with an outer diameter of the access device 144, in many embodiments, the port 1100 can nevertheless assist in the creation of only a single insertion site or buttonhole 266 through the wall of the vessel 200. In some embodiments, the guidance passageway 1130 constrains movement of various access devices 140, which may be inserted individually through the port 1100 on separate occasions, toward the opening 1150 and along a path that is directed toward the single insertion site 266. In some embodiments, the constraint may be indirect due to tissue 217 that is positioned between the port 1100 and the access device 144.

Figure 23A:
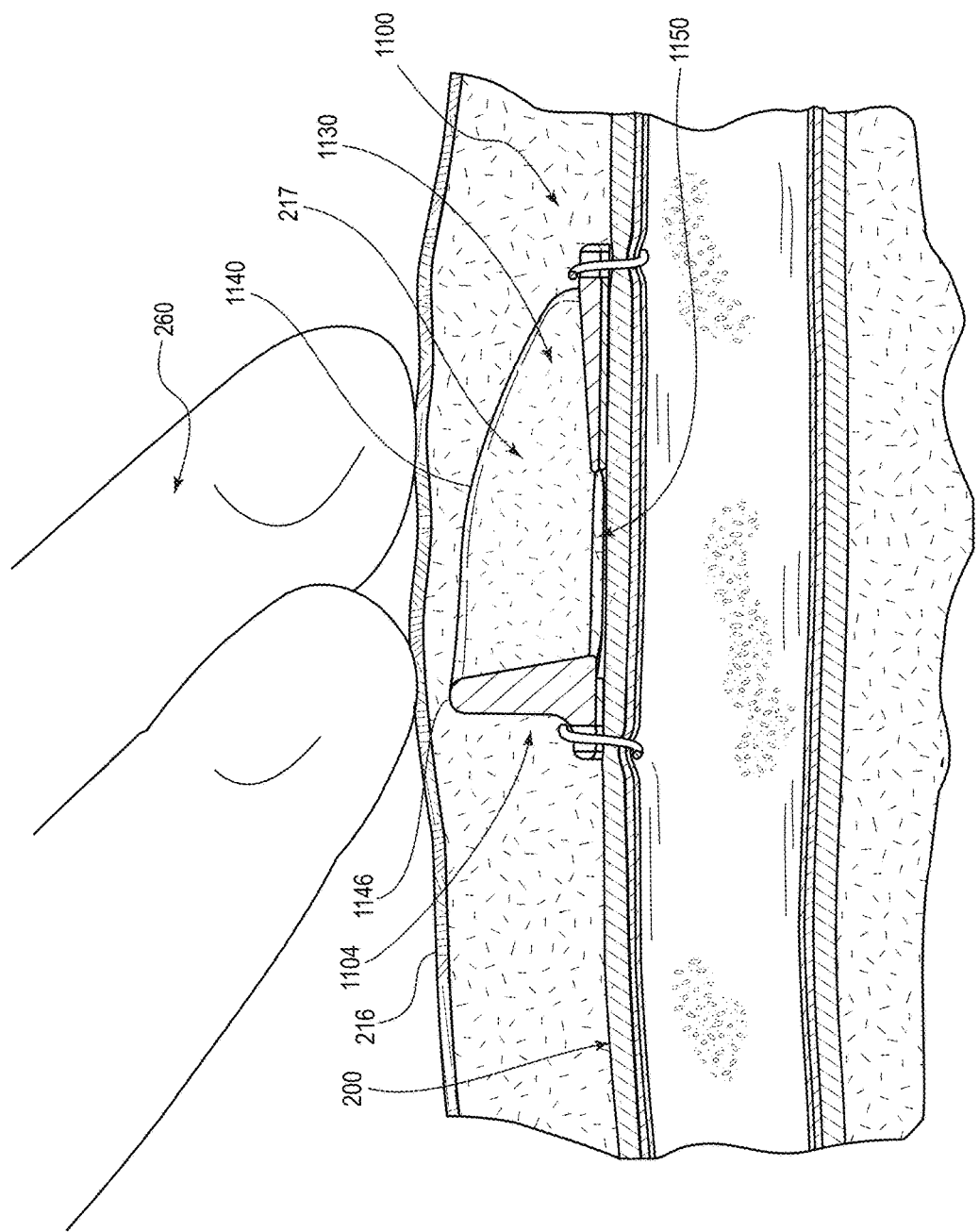
FIG. 23A is a cross-sectional view of a palpation stage of an illustrative method relating to the creation and use of a buttonhole access site to access a lumen of a vessel.

With reference to FIG. 23A, for an initial access event, a clinician 260 can palpate an outer surface of the skin 216 to locate and determine the orientation of the vascular access port 1100. In the illustrated embodiment, the clinician 260 is using fingers to contact the skin 216 that is positioned above a forward end of the palpation projection 1146. In other instances, the clinician 260 can palpate any other suitable portion of the body 1104 to determine the location (e.g., depth) and orientation of the port 1100. For example, the clinician 260 may use one or more fingers and/or a thumb to contact the skin 216 that is over or beside other portions of the palpation projection 1146, or to squeeze the skin 216 that is at either side of the wings 1140. In still other or further embodiments, a clinician may visually determine a location and orientation of the port 1100. Prior or subsequent to the stage shown in FIG. 23A, the clinician 260 can clean a surface of the skin with any suitable antiseptic so as to reduce the risk of introducing pathogens into the bloodstream of the patient.

Figure 23B:
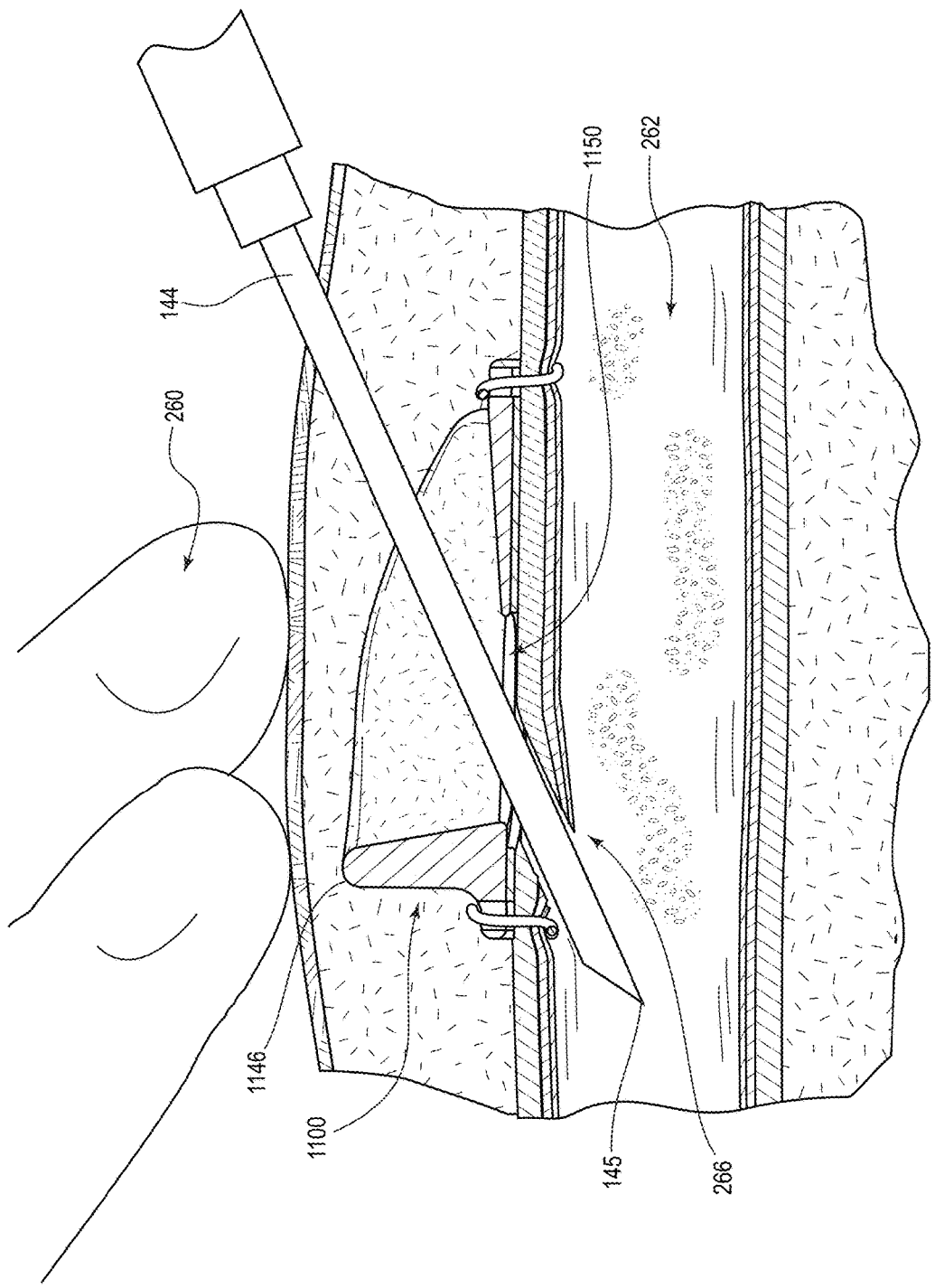
FIG. 23B is a cross-sectional view of another stage of the method of FIG. 23A in which a needle having a sharp tip is inserted into the lumen of the vessel via an embodiment of a vascular access port.

FIG. 23B illustrates an embodiment of an access device 144 directly accessing a lumen 262 of the vessel 200 via the vascular access port 1100 for a first time. In the illustrated embodiment, the fingers of one hand of the clinician 260 remain positioned over the forward end of the palpation projection 1146 so as to maintain an understanding of the position of the port 1100 and/or so as to steady the port 1100 during insertion of the access device 144 using another hand (not shown). In other or further instances, continued palpation of the port 1100 may take place at side regions of the port 1100, such as the wings 1140 and their associated portion of the palpation projection 1146. For example, skin on either side of the wings 1140 can be compressed inwardly so as to align and/or steady the port 1100. Continued palpation of the port 1100 can aid in achieving a desired alignment of the access device 144 with the guidance channel 1130 and/or preventing movement of the port 1100 during insertion.

The port 1100 can guide the access device 144 into the vessel 200 in manners such as previously described. It is also noted that, in so doing, the port 1100 can protect the vessel 200 from undesired cannulations. For example, by isolating a small portion of the vessel 200 to which a tip of the access device 144 is directed, the port 1100 can prevent the tip from contacting other portions of the vessel 200. Thus, as shown in FIG. 23B, the port 1100 not only directs the access device 144 to the opening 1150, but also prevents the access device 144 from cannulating the vessel 200 at positions that are forward of, rearward of, and lateral to the opening 1150.

As previously mentioned, some protocols for the creation and use of buttonhole cannulation sites can require introduction of a needle into a vessel at a designated acute angle. In some embodiments, the angle defined by a central axis AX of the funnel region 1132 (see FIG. 22G) can correspond with this specified angle. In many embodiments, an access device 144 can be inserted through the opening 1150 at any of a wide range of angles without binding, such that exact alignment with the central axis AX is not necessary. Moreover, in some embodiments, the central axis AX may not necessarily be within the preferred range of angles. For a first access event, a clinician thus may have a degree of liberty in introducing the access device 144 at an angle that is consistent with a desired protocol.

Figure 23C:
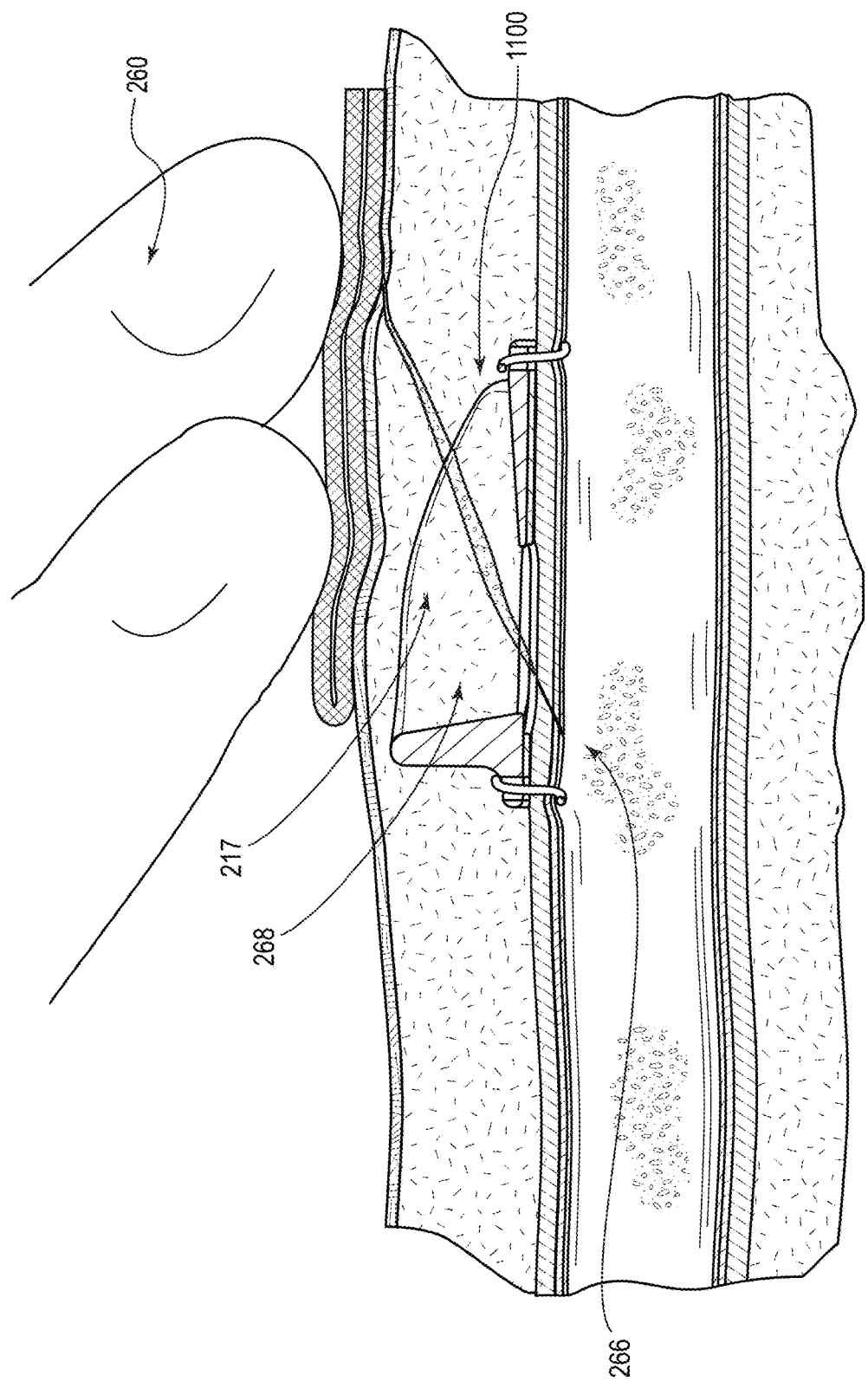
FIG. 23C is a cross-sectional view of another stage of the method of FIG. 23A in which pressure is applied to the skin of the patient.

FIG. 23C illustrates a stage of the procedure after removal of the access device 144. The insertion site 266 is shown in a closed state, in which it is allowed to heal. Prior to closure and healing of the insertion site 266, however, blood 268 can be permitted to exit thereby, and may fill at least a portion of the guidance passageway 1130. The practitioner 260 can apply pressure above the vascular access port 1100 to achieve hemostasis. In the illustrated embodiment, pressure from above the port 1100 can achieve hemostasis readily easily, as the pressure transfers to the tissue 217 that is directly above the opening 1150. Such an arrangement may, in some instances, more readily achieve hemostasis, as compared with arrangements such as that illustrated in FIG. 11C. In some embodiments, pressure may be applied for a period of no more than about 3, 4, 5, 6, 7, 8, 9, or 10 minutes in order to achieve hemostasis.

Figure 23D:
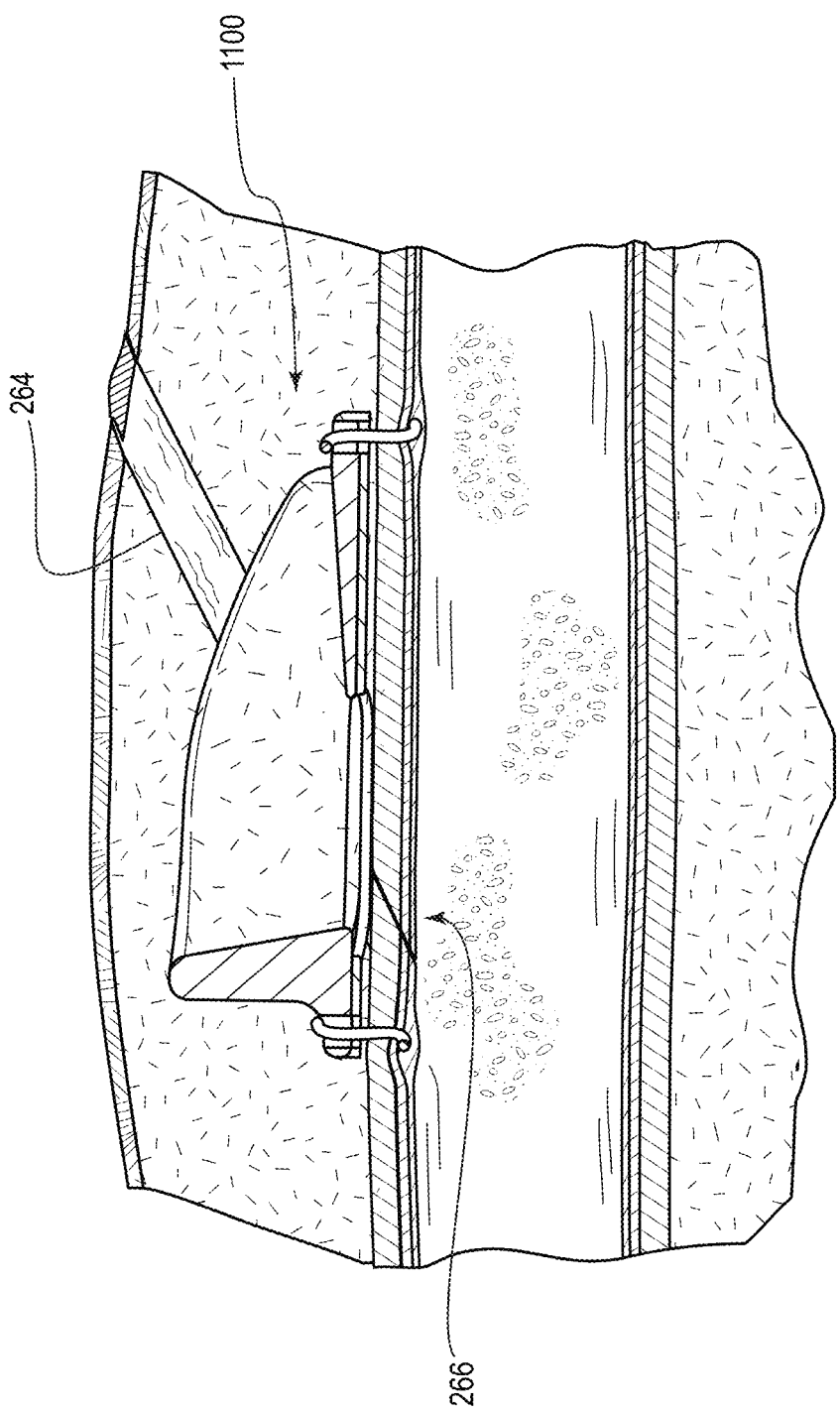
FIG. 23D is a cross-sectional view of another stage of the method of FIG. 23A in which a buttonhole access site has been formed.

FIG. 23D depicts the port 1100 after removal of the access device 144 therefrom at the completion of an initial access event. Without being limited by theory, the insertion site 266 and the insertion tract 264 can begin to heal. It may be desirable to conduct another access event before too much time has passed, which would result in the insertion site 266 completely healing. For example, in various instances, it can be desirable to allow no more than 2, 3, 4, 5, or 6 days to pass between access events to ensure that the single insertion site 266 can readily be used in the latter access event.

Figure 23E:
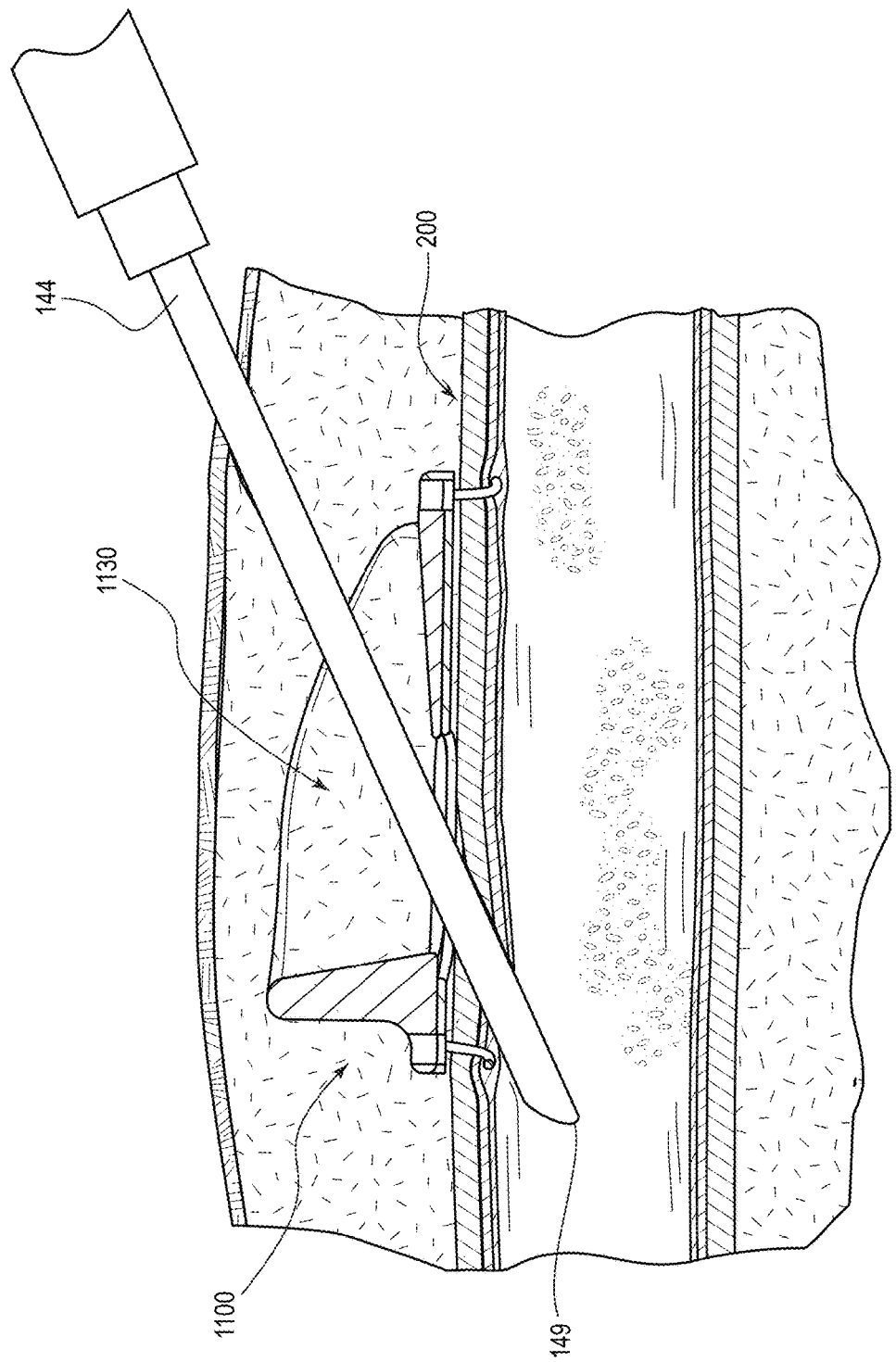
FIG. 23E is a cross-sectional view of another stage of the method of FIG. 23A in which a needle having a blunt tip is inserted into the lumen of the vessel via the vascular access port and the buttonhole access site.
Figure 24A:
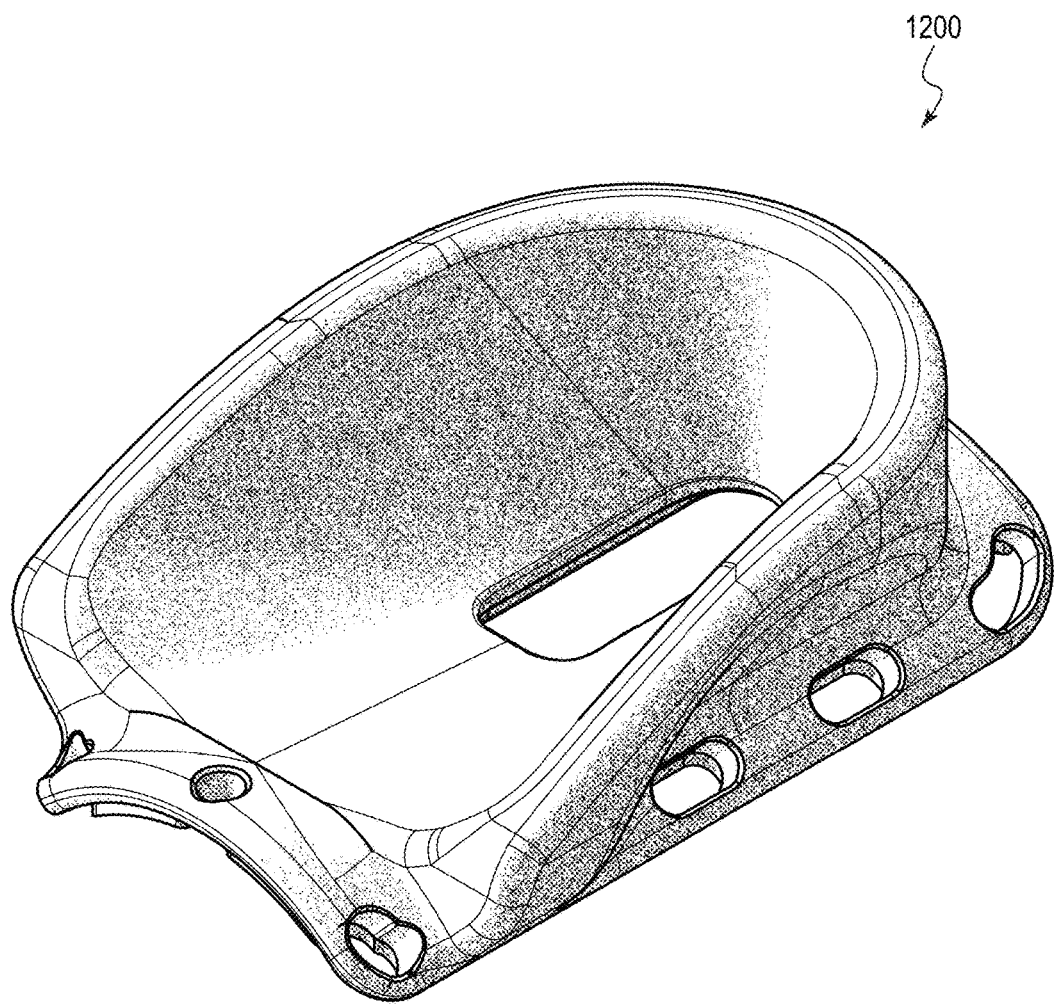
FIG. 24A is a perspective view of another embodiment of a vascular access port.
Figure 24B:
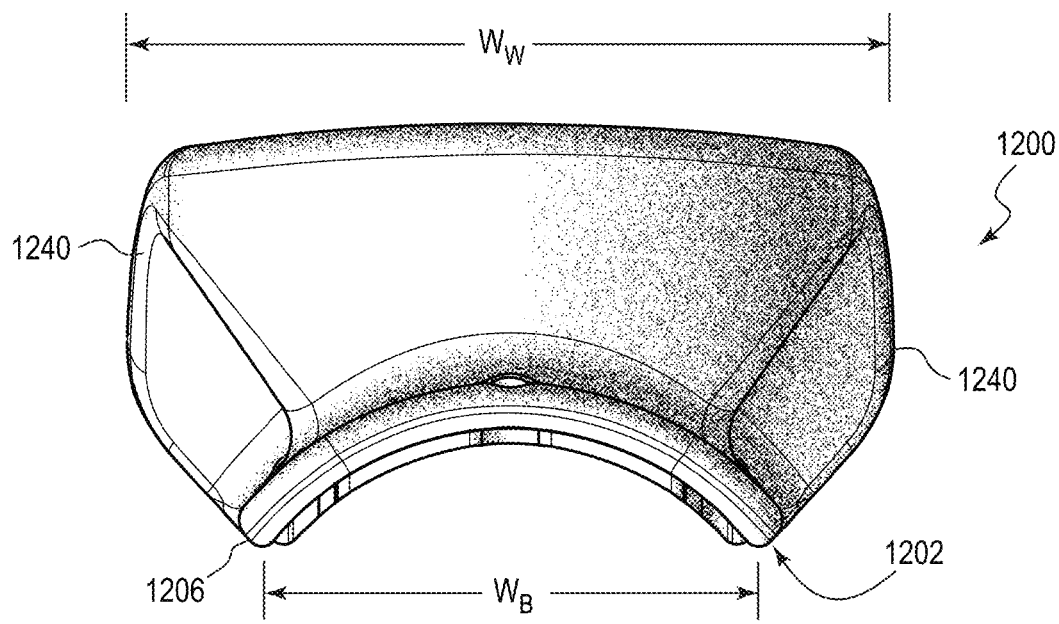
FIG. 24B is a front elevation view thereof.
Figure 24C:
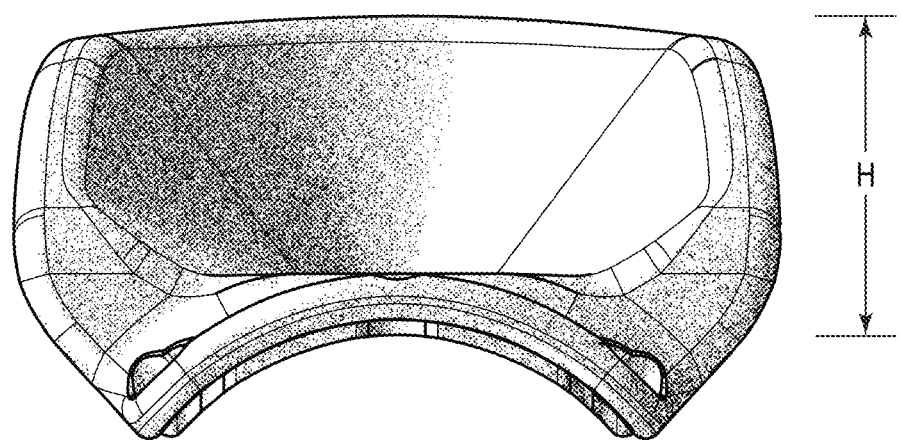
FIG. 24C is a rear elevation view thereof.
Figure 24D:
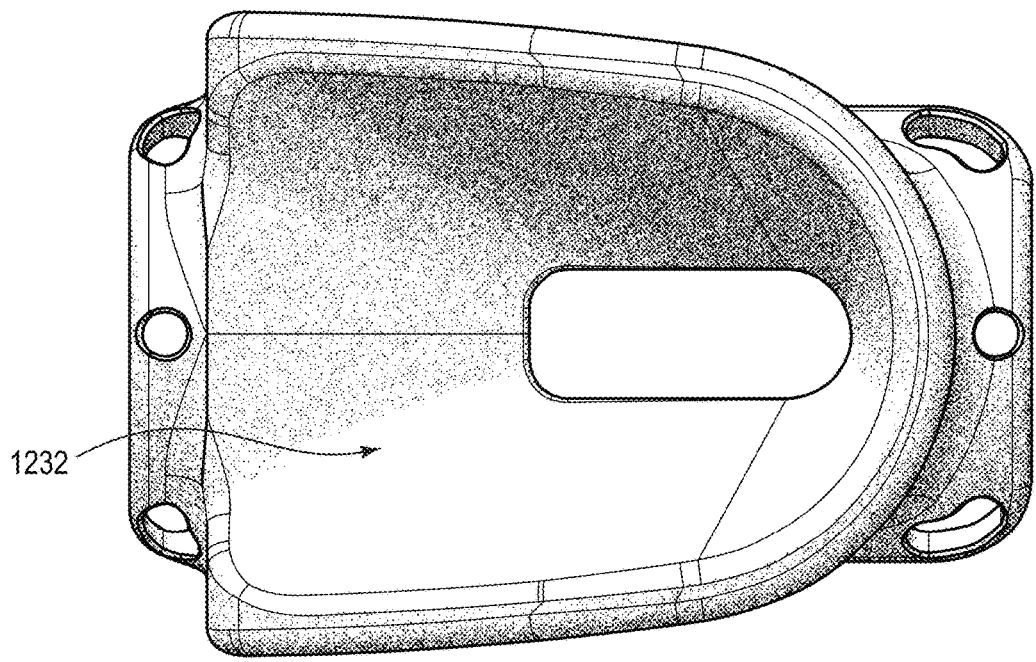
FIG. 24D is a top plan view thereof.
Figure 24E:
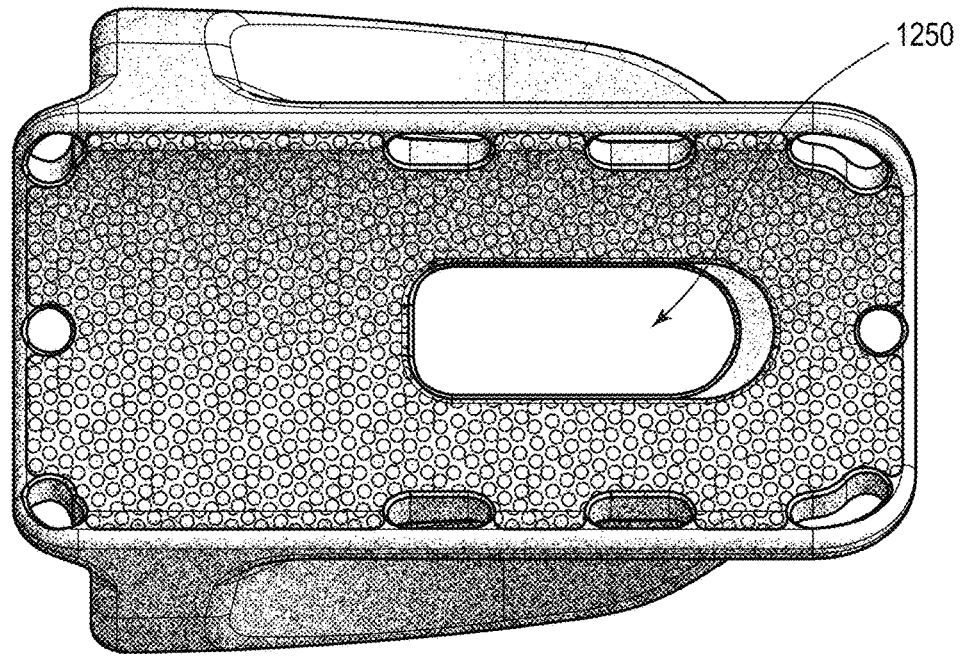
FIG. 24E is a bottom plan view thereof.
Figure 24F:
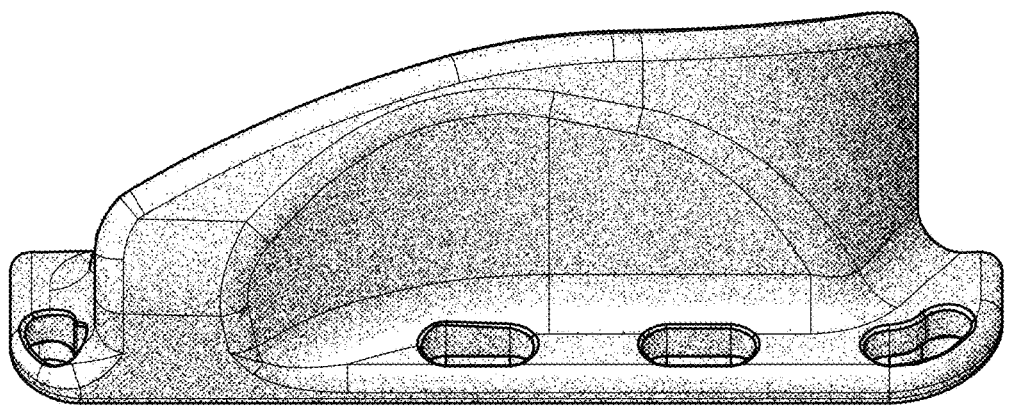
FIG. 24F is a right side elevation view thereof, wherein a left side elevation view thereof is a mirror image of the right side elevation view.
Figure 24G:
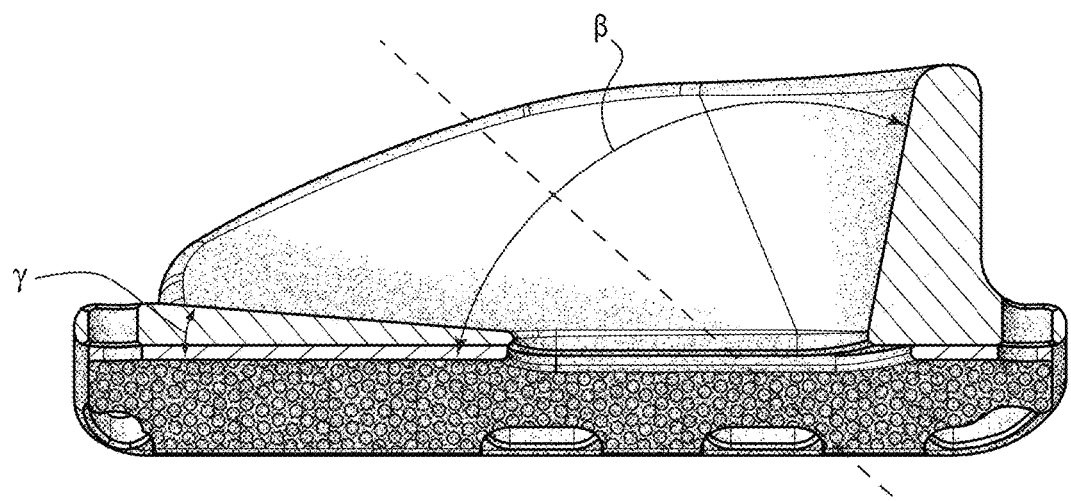
FIG. 24G is a cross-sectional view thereof.
Figure 25A:
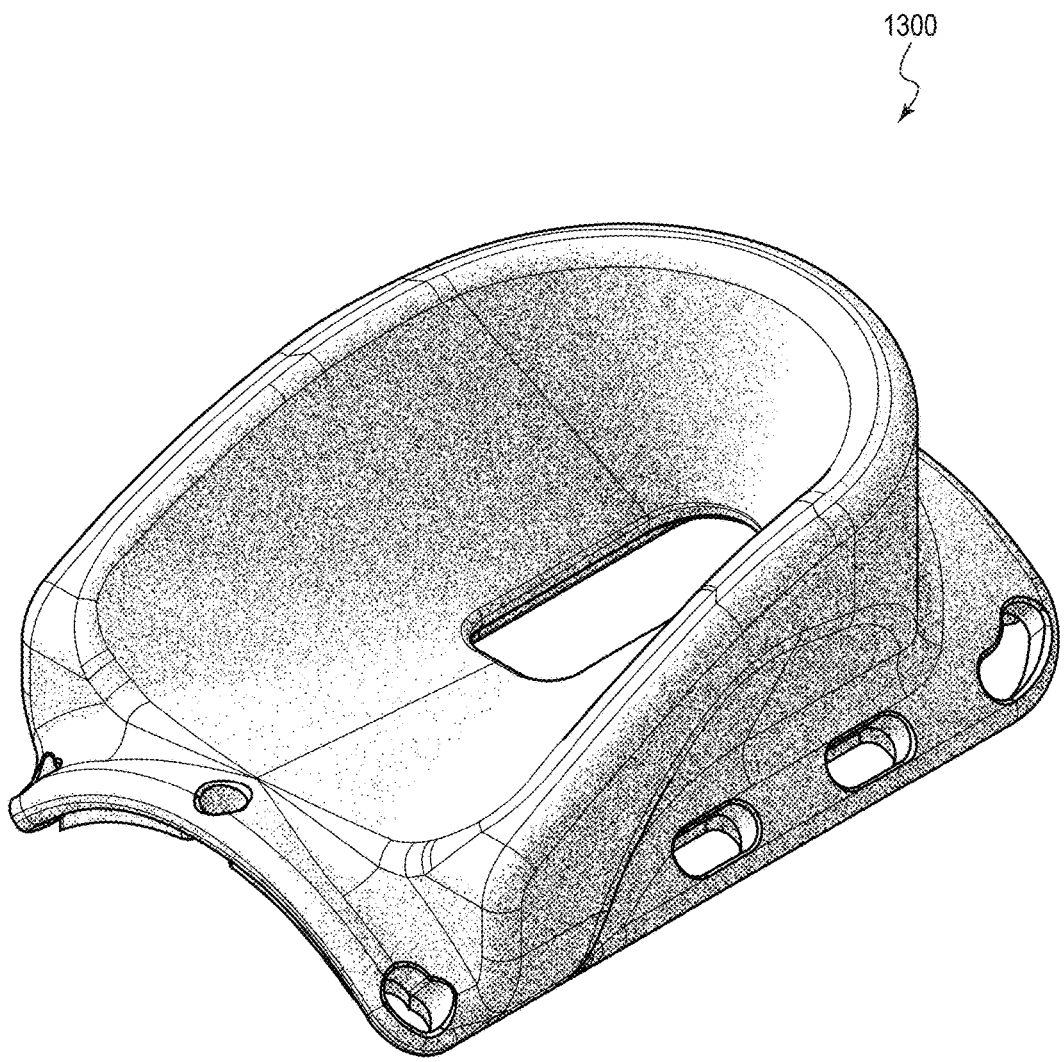
FIG. 25A is a perspective view of another embodiment of a vascular access port.
Figure 25B:
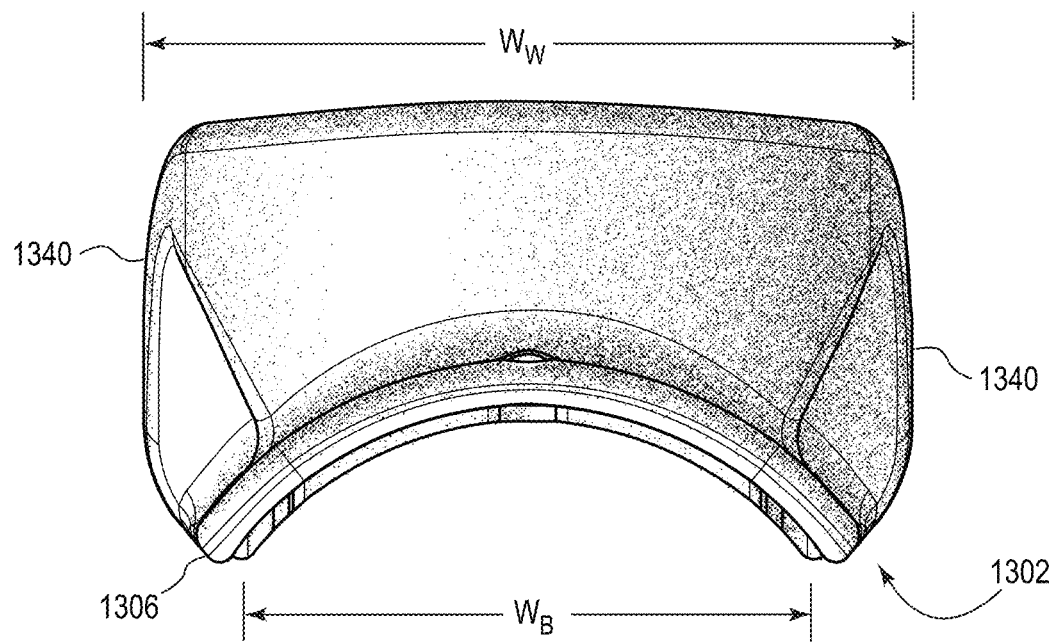
FIG. 25B is a front elevation view thereof.
Figure 25C:
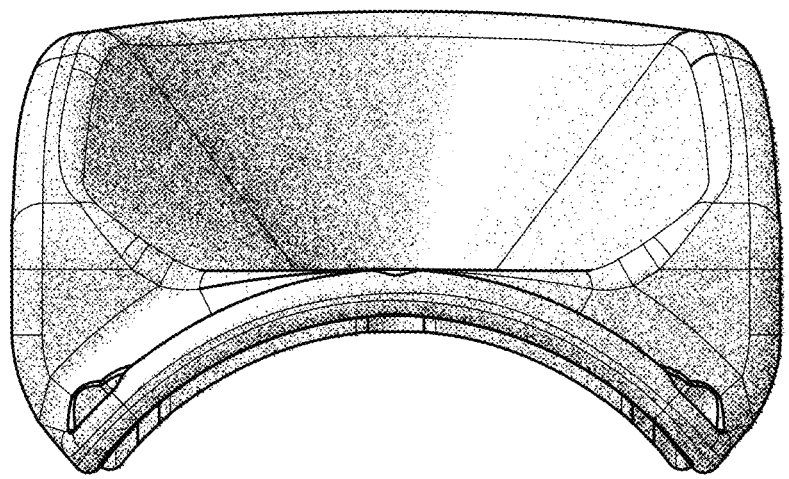
FIG. 25C is a rear elevation view thereof.
Figure 25D:
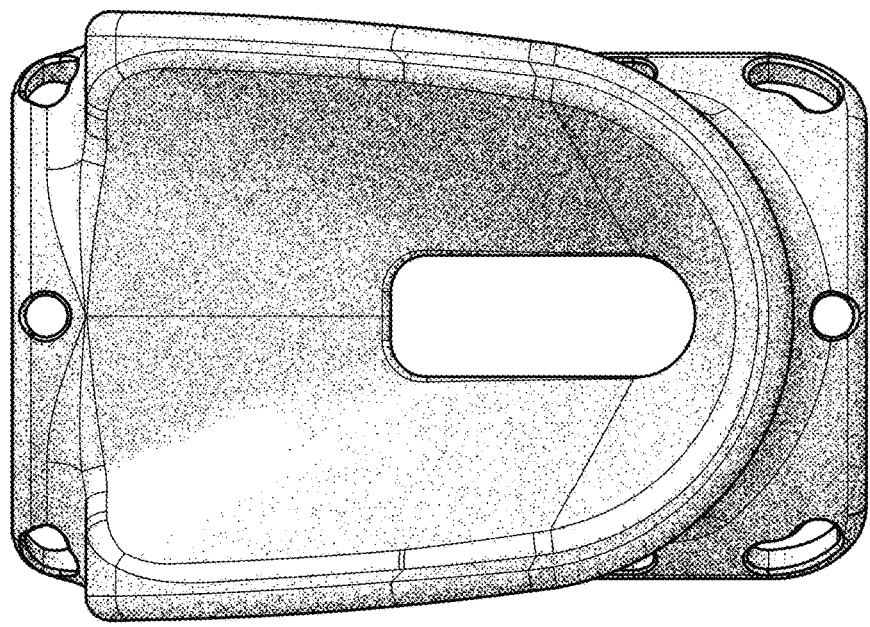
FIG. 25D is a top plan view thereof.
Figure 25E:
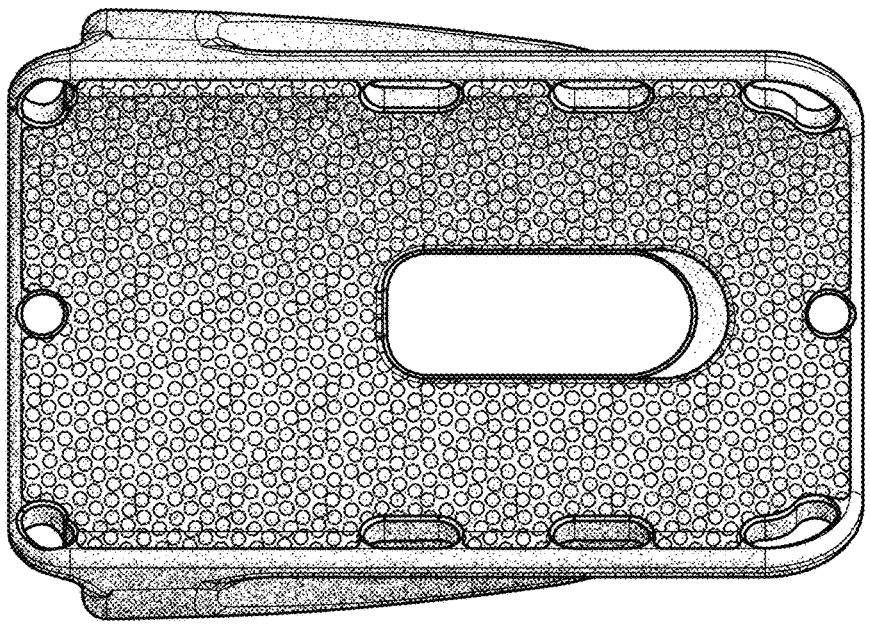
FIG. 25E is a bottom plan view thereof.
Figure 25F:
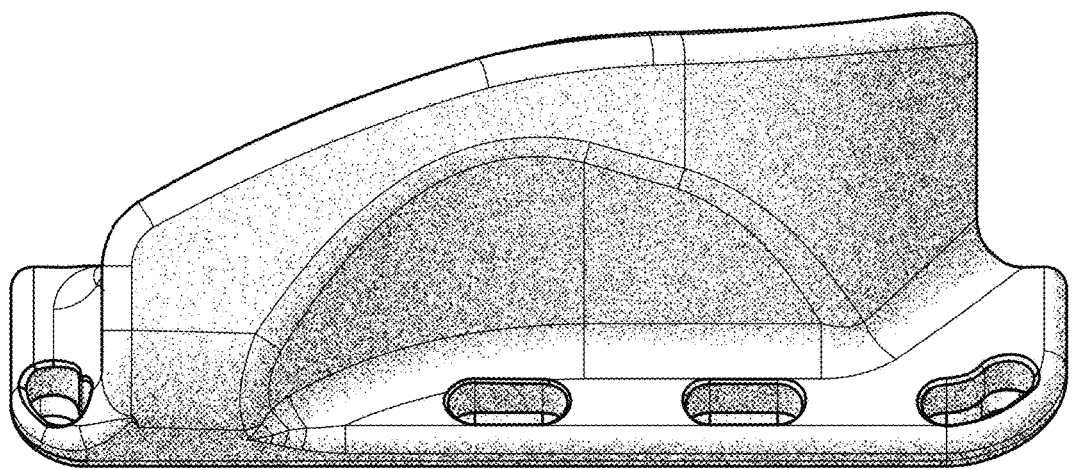
FIG. 25F is a right side elevation view thereof, wherein a left side elevation view thereof is a mirror image of the right side elevation view.
Figure 25G:
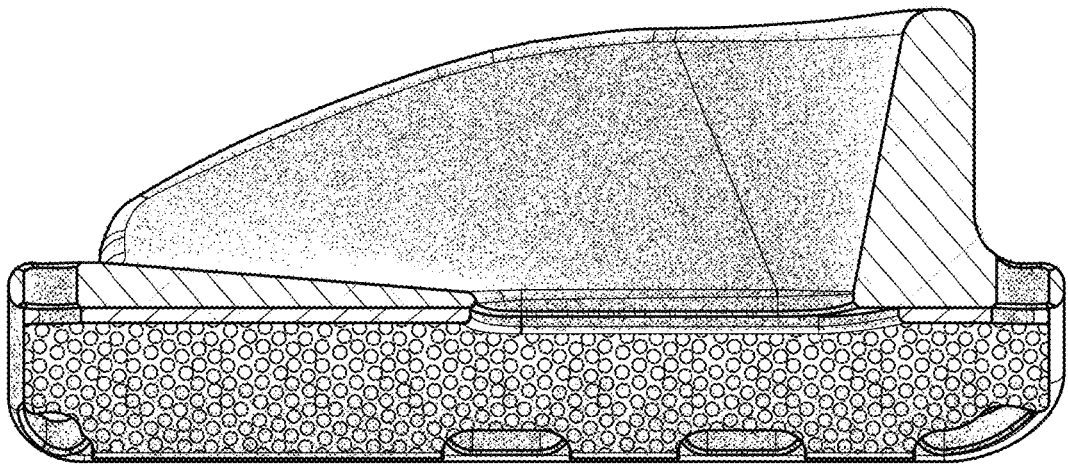
FIG. 25G is a cross-sectional view thereof.

FIG. 23E illustrates the use of a blunt-tipped access device 144 for a second access event—specifically, an access event that is subsequent to the initial access event depicted in FIG. 23B, where no other access events have occurred between the access events depicted in FIGS. 23B and 23E. In the illustrated embodiment, the guidance passageway 1130 constrains movement of the access device 144 along a path so as to direct a distal tip 149 of the device 144 to the insertion site 266. The constrained movement may be indirect, as tissue can cover an interior of the guidance passageway 1130. Without being limited by theory, the blunt tip 149 can force open the insertion site 266 at a position where the wall was previously cut by the sharp-tipped access device 144 (FIG. 23B) so as to access an interior of the vessel 200. Moreover, use of the blunt-tipped access device 144 may improve the likelihood that access will be achieved via the insertion site 266, as the blunt-tipped needle may be less likely to cut a new insertion site 266 in the vessel wall.

In the illustrated embodiment, a seal can form about the opening 1150 due to the ingrowth of tissue into the ingrowth-inducing covering 1152 (FIG. 22E). The seal can be hemostatic, so as to inhibit or prevent bleeding from the insertion site 266 along a path between the port 1100 and the vessel wall. The seal also can inhibit tenting of the vessel wall during insertion of an access device 144 therethrough. In some embodiments, this feature can be particularly useful in creating a single-site buttonhole 266, such as where blunt-tipped access devices 144 are used relatively soon after an initial access event. This may also be advantageous where the port 1100 has a relatively larger opening 1150, as compared with the size of the access device 144.

FIGS. 24A-24G illustrate another embodiment of a vascular access port 1200. A width Ww of the vascular access port 1200 can be approximately the same as the width Ww of the vascular access port 1100 described above, but a width $W_B$ thereof may be somewhat larger than the width $W_B$ of the vascular access port 1100. Accordingly, wings 1240 may extend past a perimeter 1206 of a base 1202 to a lesser extent than do the wings 1140 of the port 1100. Additionally, a radius of curvature of the base 1202 can be larger than a radius of curvature of the base 1102. A height H of the port 1200 may be approximately the same as the height H of the port 1100. An opening 1250 of the port 1200 may have the same configuration and dimensions as the opening 1150.

The port 1200 thus can be configured for use with a somewhat larger vessel than the port 1100. However, the port 1200 can be implanted in a patient at approximately the same depth as the port 1100 without substantially changing an observable profile at the surface of the skin of the patient. A funnel region 1232 of the port 1200 can be about the same size and configuration of the funnel region 1132. For example, the funnel region 1232 may define a central axis AX that defines the same angle relative to the base 1202 as the central axis AX of the port 1100 does relative to the base 1102.

The port 1200 thus may be configured for use with the same type of vessel as the port 1100, but with a different patient who may have larger vessels. By way of example, the port 1100 may be configured for use with vessels having an outer diameter of approximately 7 millimeters, whereas the port 1200 may be configured for use with vessels having an outer diameter of approximately 9 millimeters. Similar methods for implantation and use thus may be performed for each port 1100, 1200.

A system for providing a selection of vascular access ports for a given use thus may comprise both of the ports 1100, 1200. For example, a distributor may offer both types of ports 1100, 1200 as alternatives to accommodate varying needs of a customer, and/or may deliver one or both ports 1100, 1200 to a customer so as to be used with any of a variety of patients having differing anatomies. Such systems can include other or further ports of differing lengths, heights, base sizes, funnel widths, and/or funnel configurations.

FIGS. 25A-25G illustrate another embodiment of a vascular access port 1300. A width Ww of the vascular access port 1300 can be approximately the same as the width Ww of each of the vascular access ports 1100, 1200 described above, but a width WB thereof may be somewhat larger than the width WB of the vascular access port 1200. Accordingly, wings 1340 may extend past a perimeter 1306 of a base 1302 to a lesser extent than do the wings 1240 of the port 1200. Additionally, a radius of curvature of the base 1302 can be larger than a radius of curvature of the base 1202. A height H of the port 1300 may be approximately the same as the height H of the ports 1100, 1200. Other aspects of the port 1300 may be the same as or similar to those of the ports 1100, 1200.

The port 1300 thus may be configured for use with the same type of vessel as the ports 1100, 1200 but with a different patient who may have even larger vessels. Or the port 1300 may be configured for use with a different type of vessel that has a larger diameter but is positioned approximately the same distance beneath an outer surface of the skin. By way of example, the ports 1100, 1200 may be configured for use with vessels having outer diameters of approximately 7 and 9 millimeters, respectively, whereas the port 1300 may be configured for use with vessels having an outer diameter of approximately 11 millimeters. Similar methods for implantation and use thus may be performed for each port 1100, 1200, 1300.

FIGS. 26A-26G illustrate another embodiment of a vascular access port 1400, which can resemble the vascular access ports described above in certain respects. The vascular access port 1400 can particularly resemble the access port 1100, but may be configured for deeper implantation within a patient. For example, in some embodiments, a width WB of the base 1402 of the port 1400 is approximately the same as the width WB of the base 1102. Similarly, each port 1100, 1400 may define a length L that is approximately the same. However, a height H of the port 1400 can be greater than the height H of the port 1100. The height H can be greater than the width WB of the base 1102. In various embodiments, the height H can be no less than about 1.0, 1.25, 1.5, 1.75, or 2.0 times the width WB of the base 1102.

As a result of the greater height H of the port 1400, yet similarities between the ports 1100, 1400 in other dimensions, the port 1400 may define a rear plan view target area 1487 that is significantly larger than the rear plan view target area 1187 of the port 1100. However, the port 1400 can define a top plan view target area 1488 that is approximately the same size as the top plan view target area 1188. Depending on how much more deeply the port 1400 is configured for implantation, as compared with the port 1100, the size of the target areas 1487, 1488 may be relatively larger or smaller. In various embodiments, the rear plan view target area 1487 of the port 1400 can be no less than about 1.1, 1.2, 1.3, 1.4, 1.5, 1.6, 1.75, or 2.0 times greater than the target area 1187 of the port 1100, and in other or further embodiments, the top plan view target area 1488 of the port 1400 can be no more than about 1.0, 1.2, 1.3, 1.4, 1.5, 1.6, 1.75, or 2.0 times greater than the top plan view target area 1188 of the port 1100.

Figure 26A:
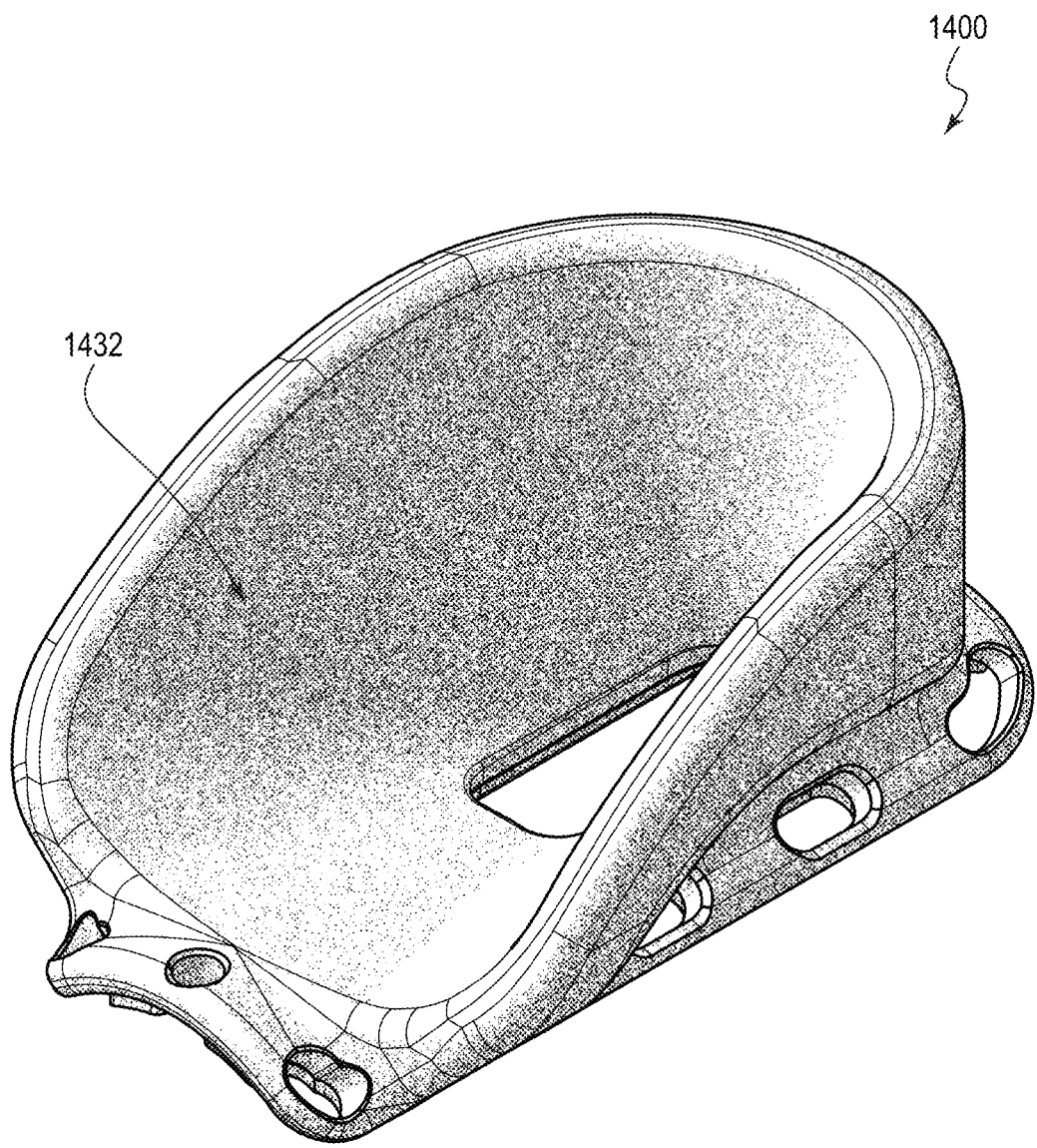
FIG. 26A is a perspective view of another embodiment of a vascular access port.
Figure 26B:
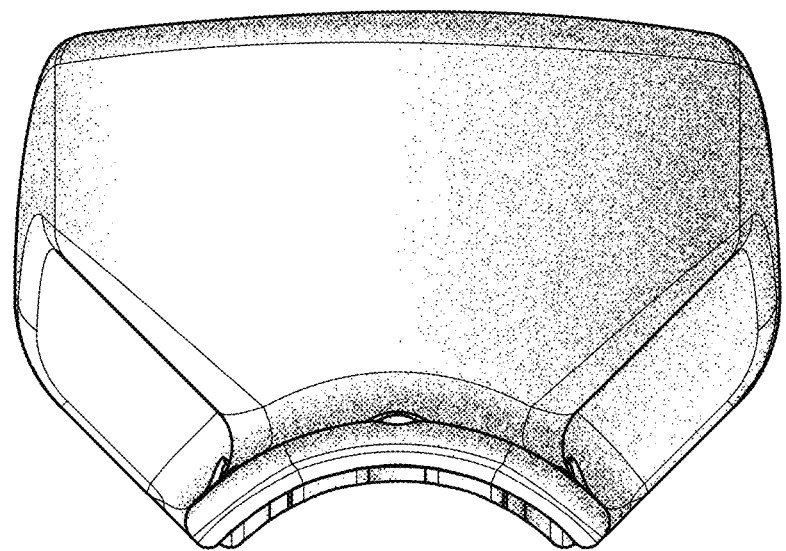
FIG. 26B is a front elevation view thereof.
Figure 26C:
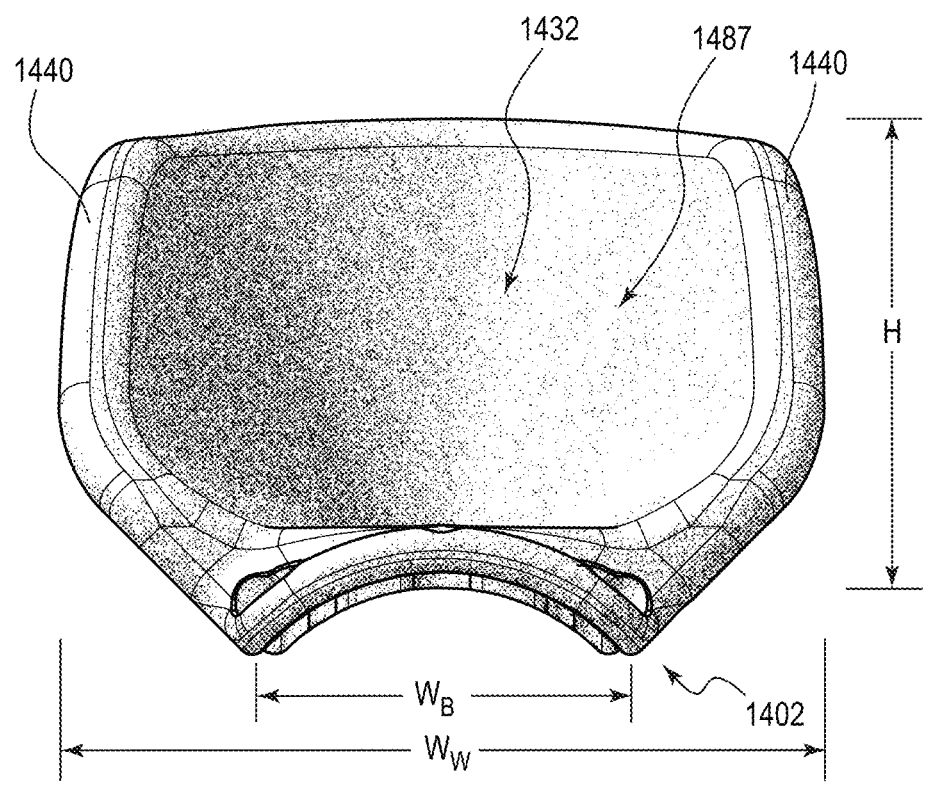
FIG. 26C is a rear elevation view thereof.
Figure 26D:
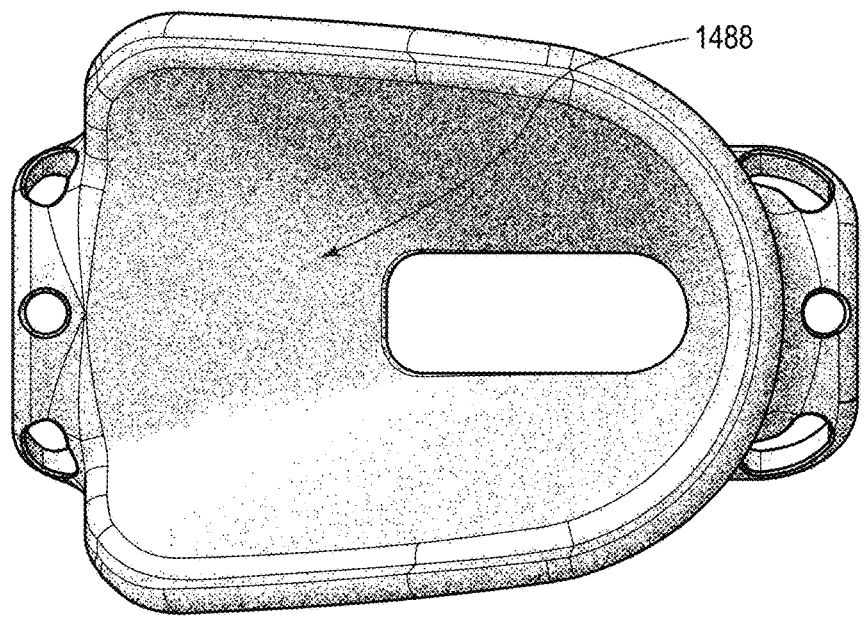
FIG. 26D is a top plan view thereof.
Figure 26E:
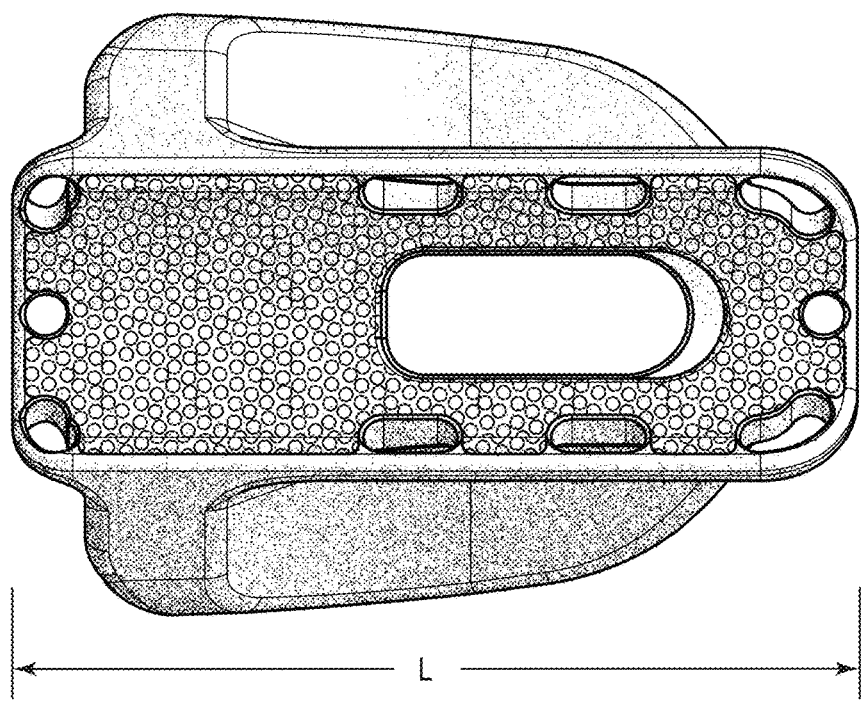
FIG. 26E is a bottom plan view thereof.

As can be appreciated from FIG. 26C, in the illustrated embodiment, the maximum width $W_W$ of the port 1400, which is defined by wings 1440, can be about the same as the maximum width $W_W$ of the port 1100. Similarly, the bottom contour of the rear plan view can be substantially the same between the two ports 1100, 1400. However, the wings 1440 of the port 1400 can extend upward to a greater height than those of the port 1100, and can slant inwardly. In the illustrated embodiment, the funnel region 1432 extends transversely outward past the maximum width WB of the base 1102.

Figure 26F:
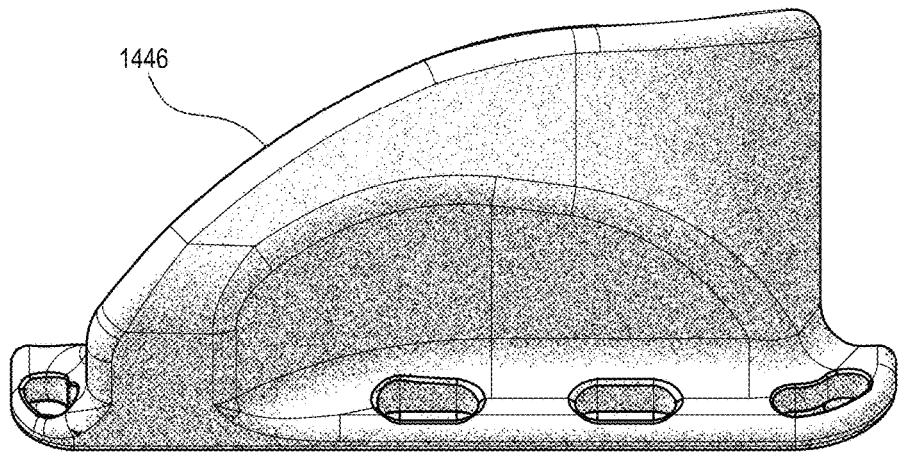
FIG. 26F is a right side elevation view thereof, wherein a left side elevation view thereof is a mirror image of the right side elevation view.
Figure 26G:
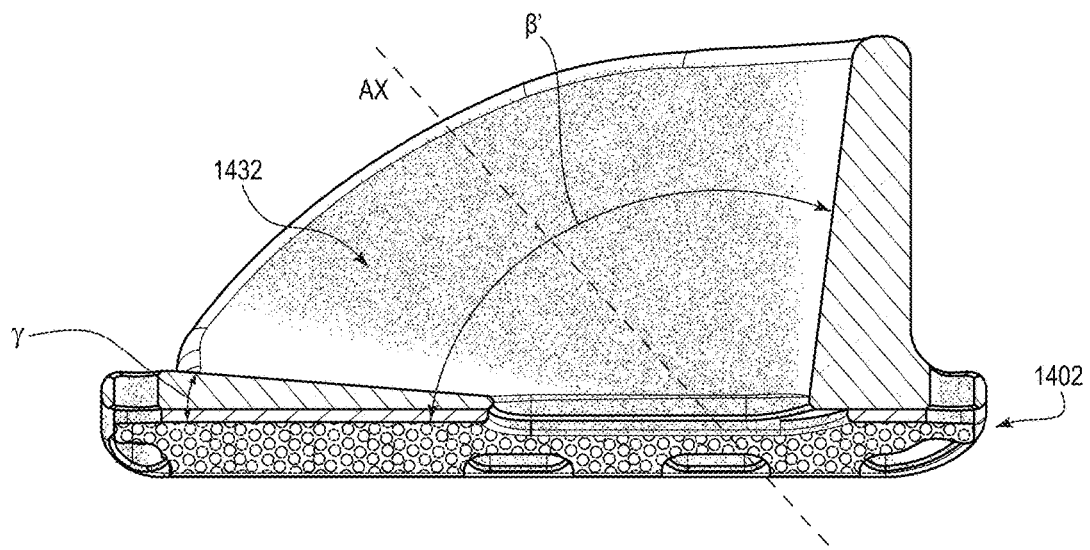
FIG. 26G is a cross-sectional view thereof.

As shown in FIG. 26F, a palpation projection 1446 of the port 1400 can be more curved or convexly rounded in the longitudinal direction than the palpation projection 1146 of the port 1100. As shown in FIG. 26G, a forward face of the funnel region 1432 can be more vertically oriented than that of the funnel region 1132, whereas a rearward face can be at approximately the same orientation relative to a base 1402 of the port 1400. Accordingly, the forward face of the funnel region 1432 may define a maximum angle $\beta'$ relative to the base 1402, and the rearward face can define a minimum angle $\gamma$ relative to the base 402. A central axis AX of the funnel region 1432 thus can define a slightly more shallow angle $(\beta'+\gamma)/2$ relative to the base 1402, as compared with the angle $(\beta+\gamma)/2$ of the port 1100.

The port 1400 can be configured for use with a somewhat deeper yet similarly sized vessel, as compared with the port 1100. By way of example, the ports 1100, 1400 may each have a base width WB of approximately 7 millimeters, yet the port 1100 may have a height within a range of from about 2 millimeters to about 3 millimeters, while the port 1400 may have a height within a range of from about 4 millimeters to about 5 millimeters. Similar methods for implantation and use may be performed for each port 1100, 1400.

Similarities and differences such as those just described with respect to the ports 1100, 1400 may also exist between the port 1100 and the port 1500 depicted in FIGS. 27A-27G. In particular, the port 1500 may be configured for even deeper implantation, as compared with the port 1100. The port 1500 may have a larger rear plan view target area 1587 than that of the port 1400, but may have a top plan view target area 1588 that is about the same as that of the port 1400. The port 1500 may have a palpation projection 1546 that is even more curved than that of the palpation projection 1446. A funnel region 1532 of the port 1500 may define a central axis AX that is at the same angle $(\beta'+\gamma)/2$ as that of the central axis of the port 1400.

Figure 27A:
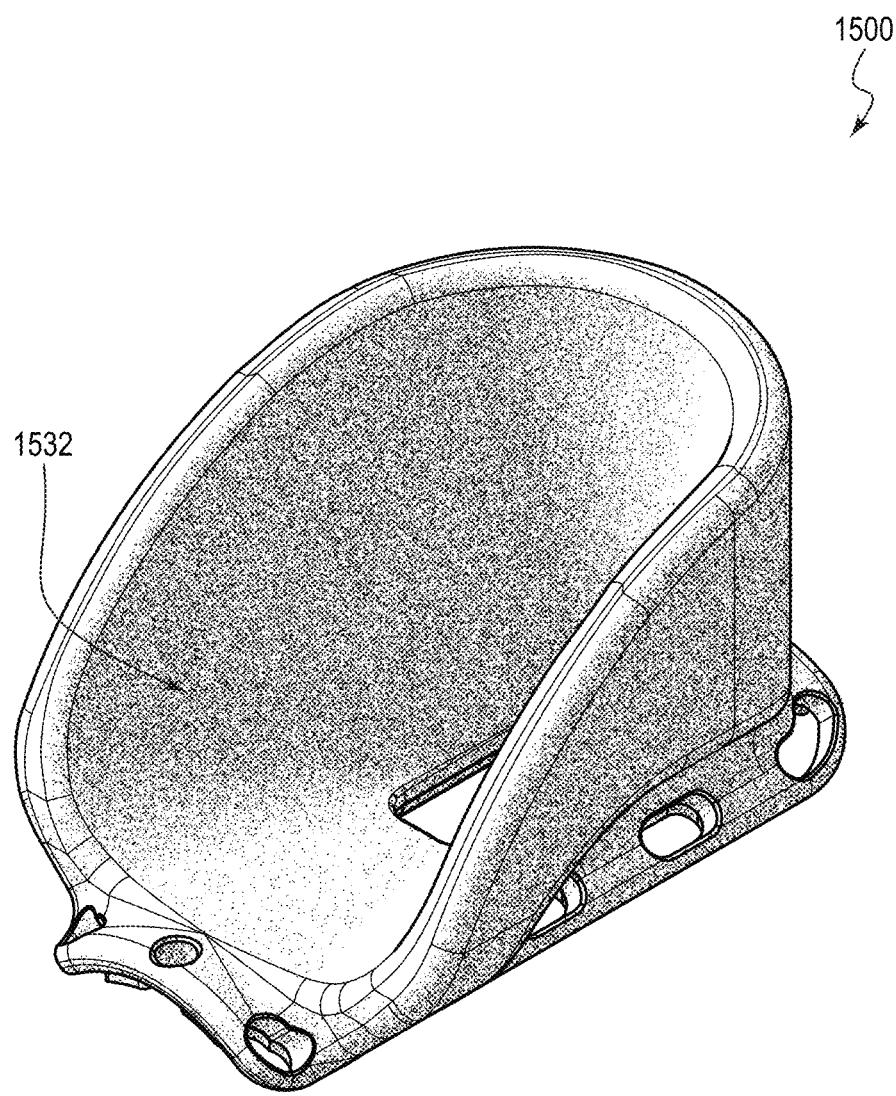
FIG. 27A is a perspective view of another embodiment of a vascular access port.
Figure 27B:
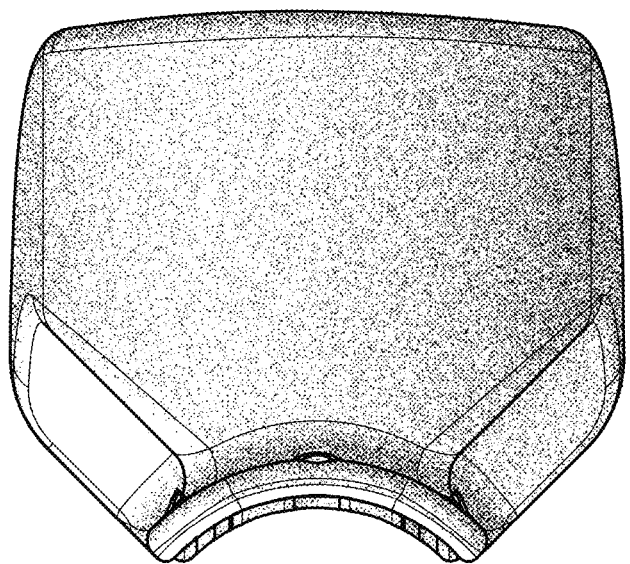
FIG. 27B is a front elevation view thereof.
Figure 27C:
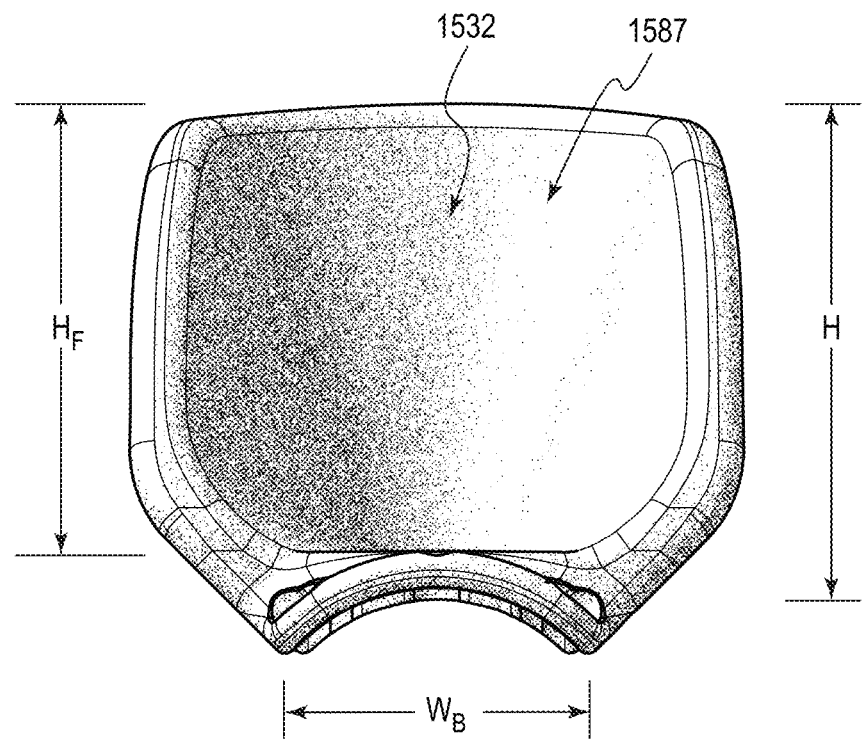
FIG. 27C is a rear elevation view thereof.
Figure 27D:
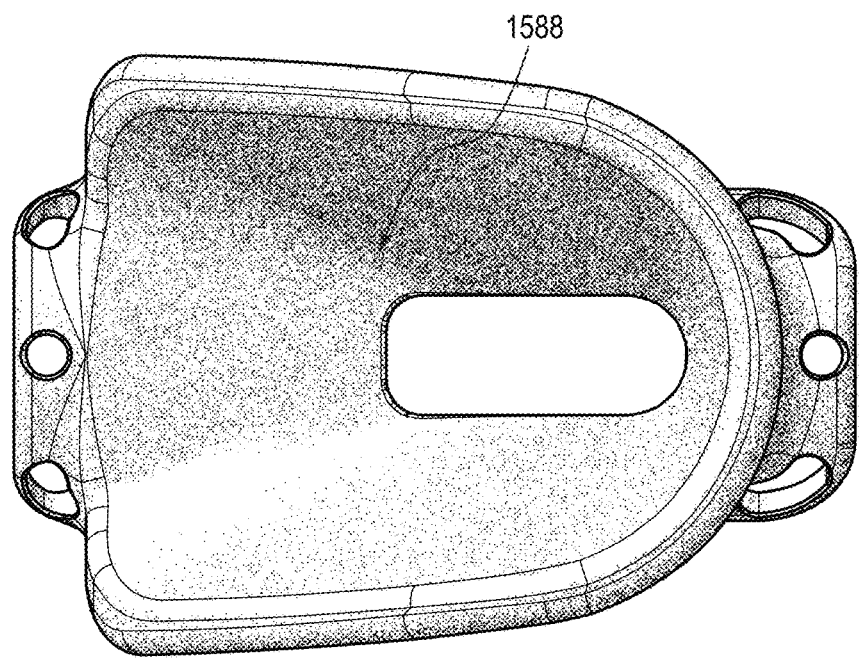
FIG. 27D is a top plan view thereof.
Figure 27E:
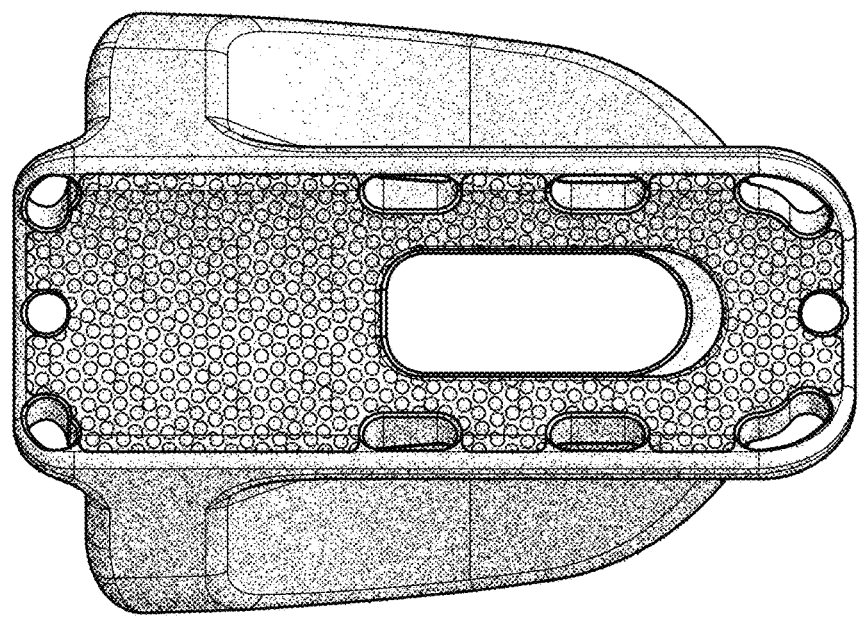
FIG. 27E is a bottom plan view thereof.
Figure 27F:
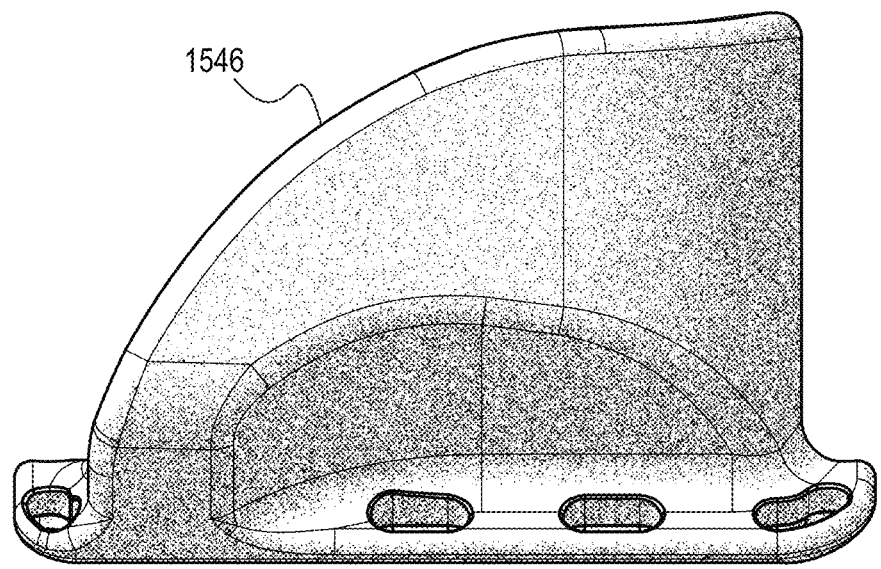
FIG. 27F is a right side elevation view thereof, wherein a left side elevation view thereof is a mirror image of the right side elevation view.
Figure 27G:
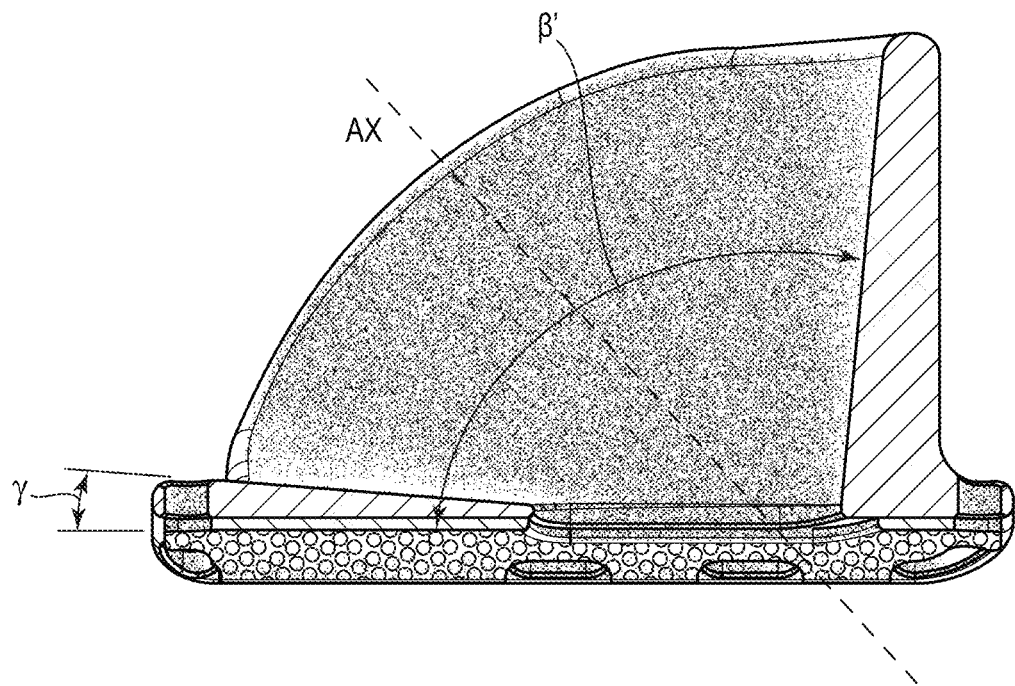
FIG. 27G is a cross-sectional view thereof.

With reference to FIG. 27C, a funnel region 1532 of the port 1500 can extend laterally outward past a maximum base width WB of the port 1500. The rear plan view target area 1587 likewise can extend laterally outward past the base width WB. The target area 1587 (which can be defined by the funnel region 1532) can define a height $H_F$ that is greater than the width of the base WB. Moreover, the target area 1587 can extend laterally outward over the base width WB along a portion of the height $H_F$ that is greater than the width of the base WB. Such an arrangement can be of particular assistance in directing an access device through the port 1500 when the port is implanted deeply within a patient.

In certain embodiments, the base width WB of the port 1500 may be approximately 7 millimeters, yet the port 1500 may have a height within a range of from about 6 millimeters to about 7 millimeters. Other dimensions of the ports 1100, 1400, 1500 are also possible. For example, in various embodiments, the base width WB may be within a range of from about 5 millimeters to about 15 millimeters, about 6 millimeters to about 10 millimeters, or no less than about 5, 6, 7, 8, 9, 10, or 11 millimeters. In other or further embodiments, the height may be within a range of from about 2 millimeters to about 15 millimeters, about 5 millimeters to about 10 millimeters, or no less than about 2, 3, 4, 5, 6, 7, 8, 9, 10, 11, 12, 13, 14, or 15 millimeters. Other dimensions are also possible. Additionally, relationships between the width $W_B$ and the height H for various embodiments of the ports 1100, 1400, 1500 can be the same as those described above with respect to the port 100.

Similar methods for implantation and use may be performed for each port 1100, 1400, 1500. However, as previously mentioned, the ports 1400, 1500 can be configured for use with deeper vessels than those with which the port 1100 may be used. The vessels may be positioned so deeply that they cannot be detected by external palpation. Such vessels may be at a native position that is directly below an outer surface of the skin of the patient by a distance of no less than about 5, 6, 7, 8, 9, or 10 millimeters. The ports 1400, 1500 can be implanted in any suitable manner, such as those described above with respect to FIGS. 9A-9E and 10A-10G. As can be appreciated from the techniques described with respect to these drawings, the ports 1400, 1500 can be implanted on any suitable vessel, such as a blood vessel within any suitable limb of a patient. In some embodiments, the vessel is allowed to remain in its native position after implantation of the port 1400, 1500, which can prevent complications that might otherwise arise from modification of the position of the vessel relative to an outer surface of the skin. For example, in certain prior art techniques that are used to make natively deep vessels accessible for hemodialysis or other procedures, the deep vessel may be transposed (e.g., moved from a native position beside a muscle to a different position over the muscle) or elevated. In other or further prior art procedures, tissue may be removed from the patient such that a distance between the vessel and the outer surface of the skin is reduced. Such modification of the relative position between the vessel and the outer surface of the skin may be undesirable, in certain circumstances. Accordingly, in some cases, it can be desirable to implant a port 1400, 1500 within the patient without modifying the native position of the vessel. Once implanted, the port 1400, 1500 can be externally palpated through the skin so as to determine a location and orientation of the vessel, and the port 1400, 1500 can otherwise be used in manners such as described above.

In other embodiments, a shorter port (e.g., the port 1100) can be used with a vessel that has been modified from its native position relative to the outer surface of the skin. For example, the port 1100 can be used with a vessel that has been transposed or elevated, or one that is relatively closer to an outer surface of the skin due to removal of tissue from a position between the outer surface and the vessel. Accordingly, in some embodiments, techniques such as those described with respect to FIGS. 9A-9E and 10A-10G can be suitably combined with the prior art techniques of transposition, elevation, or tissue removal so as to achieve such a shallow implantation of the shorter port.

In some embodiments, any suitable port described herein can be used for hemodialysis. In some instances, ports that can be implanted at a deep position within a patient can be particularly advantageous. For example, some patients may have thick layers of tissue that obscure the location of their blood vessels so as to prevent the palpation thereof, even at positions that would allow palpation for other patients. As a further example, some vessels may be readily accessible at the forearm of a patient, but much less accessible in the upper arm. Deep implantation thus can allow for use of vessels, or greater portions thereof, than would be possible otherwise.

In some instances, ateriovenous fistulas may be used for such hemodialysis procedures. Ports such as described above can be particularly useful with such fistulas, and can allow such fistulas to be used more effectively. Illustrative examples of such arteriovenous fistulas include fistulas of the radial artery and the cephalic vein, the radial artery and the basilic vein, the ulnar artery and the basilic vein, the brachial artery and the cephalic vein, the brachial artery and the basilic vein, the brachial artery and the median antecubital vein, the femoral artery and the saphenous vein, and the femoral artery and the femoral vein.

A system for providing a selection of vascular access ports for a given use may comprise any suitable combination of the ports 1100, 1200, 1300, 1400, 1500. For example, a distributor may offer two or more of the ports 1100, 1200, 1300, 1400, 1500 as alternatives to accommodate varying needs of a customer (e.g., for differently sized vessels and/or vessels at different depths), and/or the distributor may deliver one or more of the ports 1100, 1200, 1300, 1400, 1500 to the customer. One or more of the ports may be used with patients having differing anatomies.

Figure 28A:
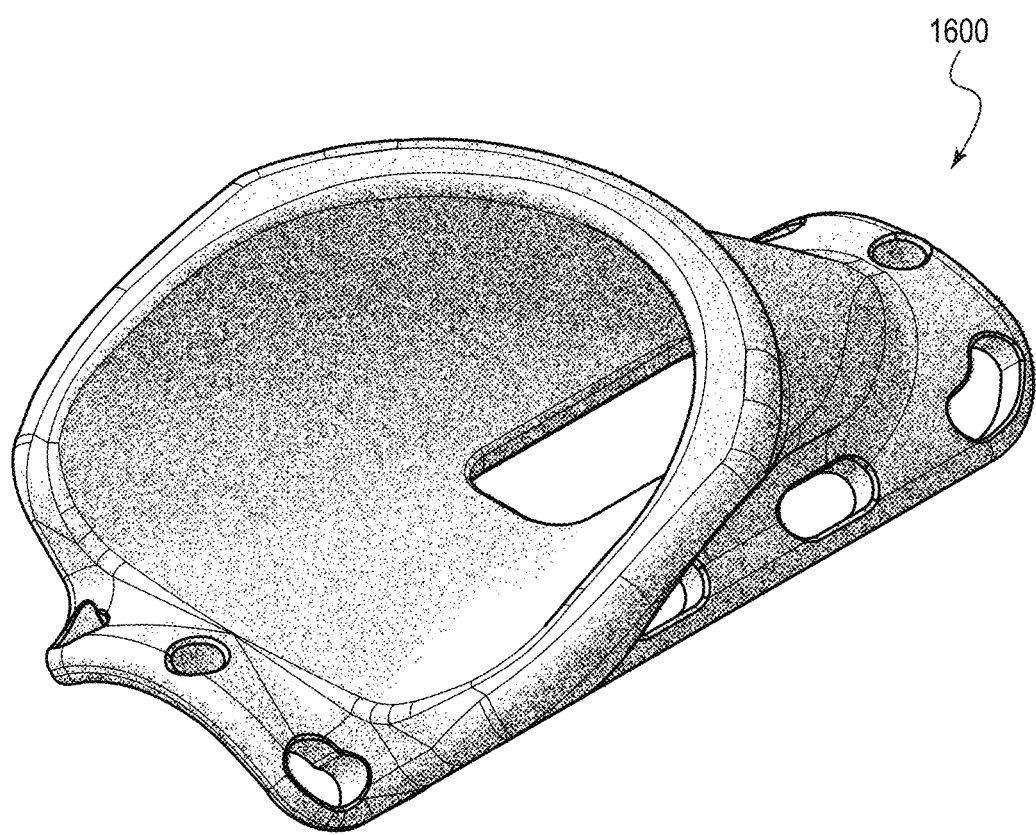
FIG. 28A is a perspective view of another embodiment of a vascular access port.
Figure 28B:
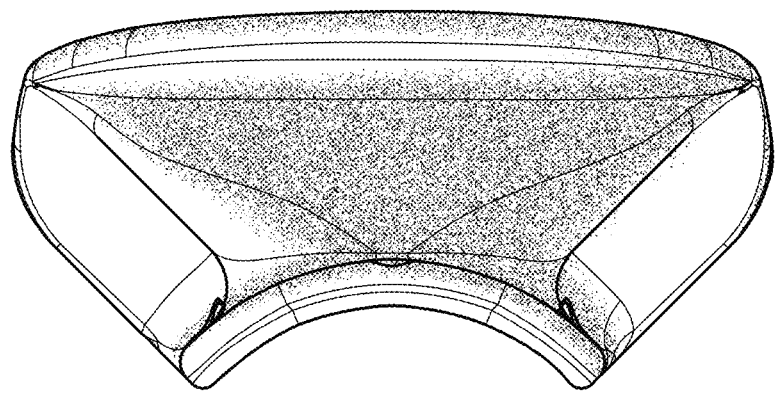
FIG. 28B is a front elevation view thereof.
Figure 28C:
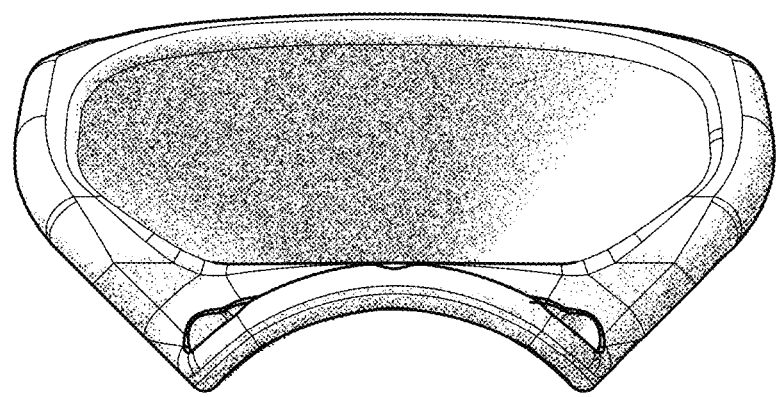
FIG. 28C is a rear elevation view thereof.
Figure 28D:
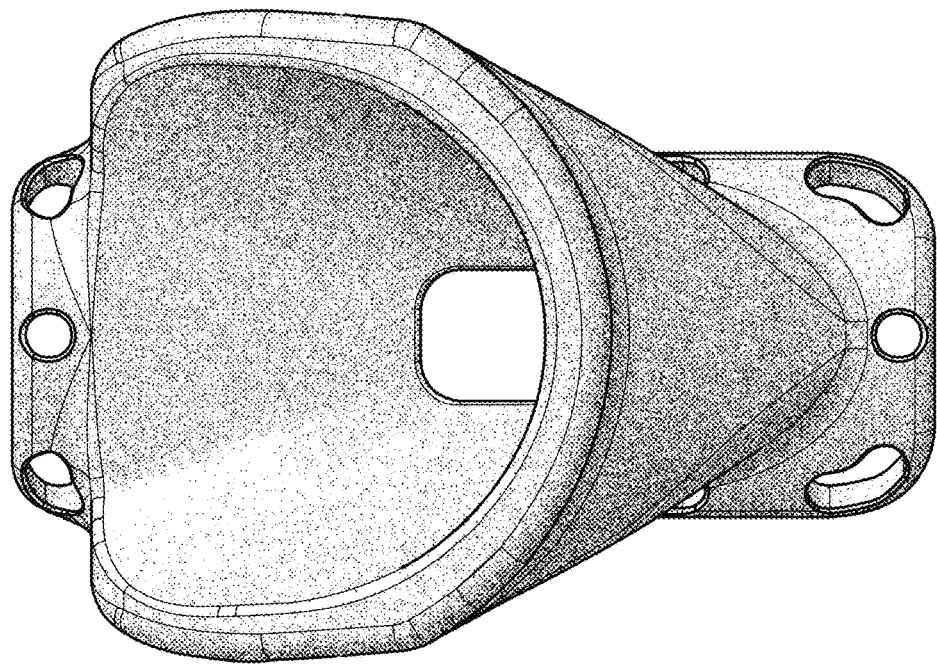
FIG. 28D is a top plan view thereof.
Figure 28E:
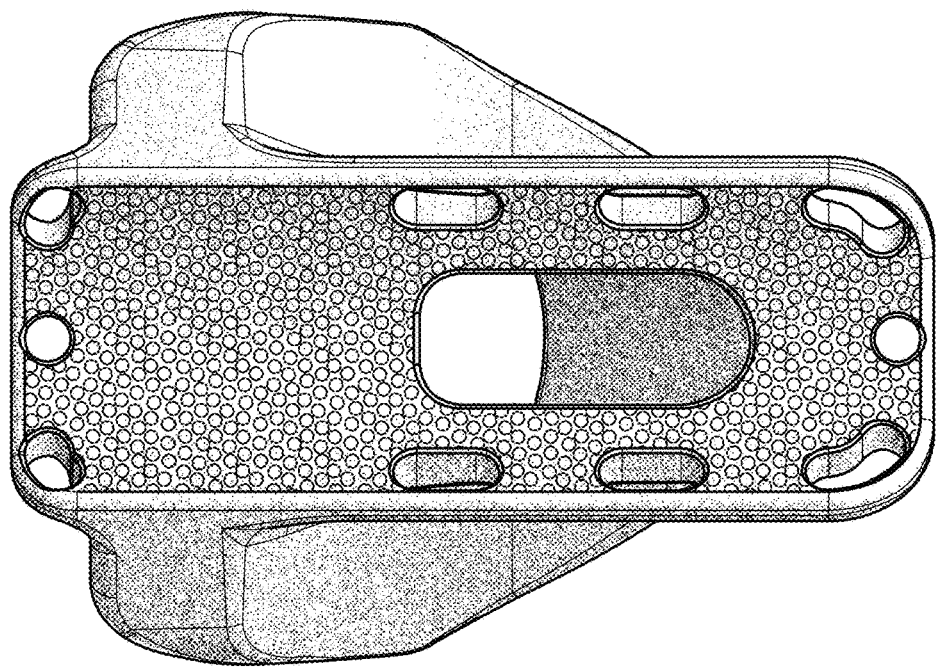
FIG. 28E is a bottom plan view thereof.
Figure 28F:
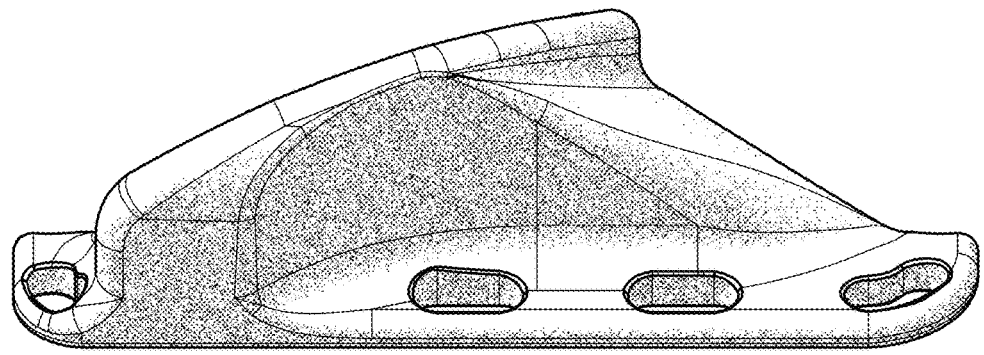
FIG. 28F is a right side elevation view thereof, wherein a left side elevation view thereof is a mirror image of the right side elevation view.
Figure 28G:
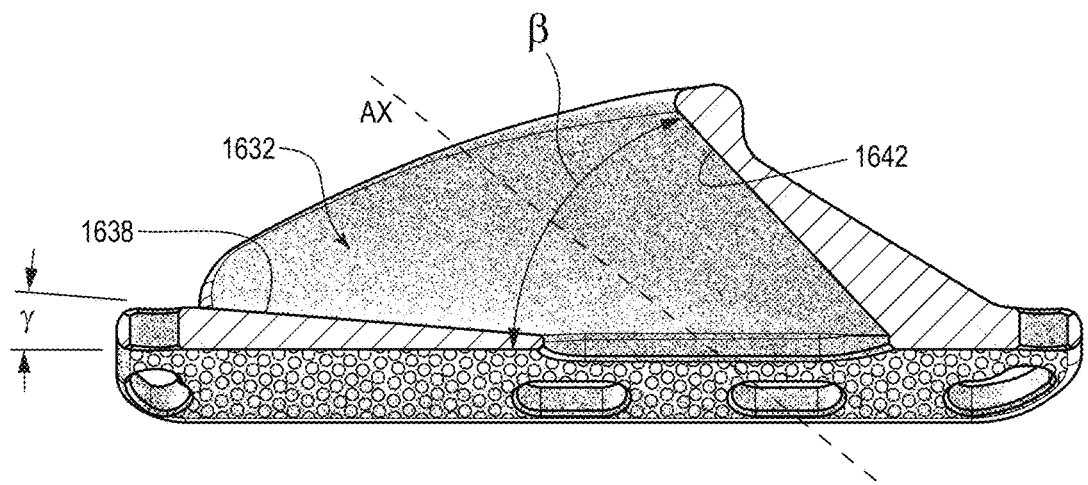
FIG. 28G is a cross-sectional view thereof.

FIGS. 28A-28G illustrate another embodiment of a vascular access port 1600, which can resemble the vascular access ports described above in certain respects. The vascular access port 1600 can particularly resemble the access port 1100, but can have a differently shaped funnel region 1632. As shown in FIG. 28G, the funnel region 1632 can include a base surface 1638 that defines an angle γ relative to a base 1602 of the port 1600, and can include a backstop portion 1642 that defines an angle β relative to the base 1602. The backstop portion 1642 can be angled rearwardly such that the angle β is acute. A central axis AX of the funnel region 1632 thus can be at an angle (β+γ)/2 relative to the base 1602 that is more shallow than a similar angle defined by the central axis AX of the port 1100.

Figure 29A:
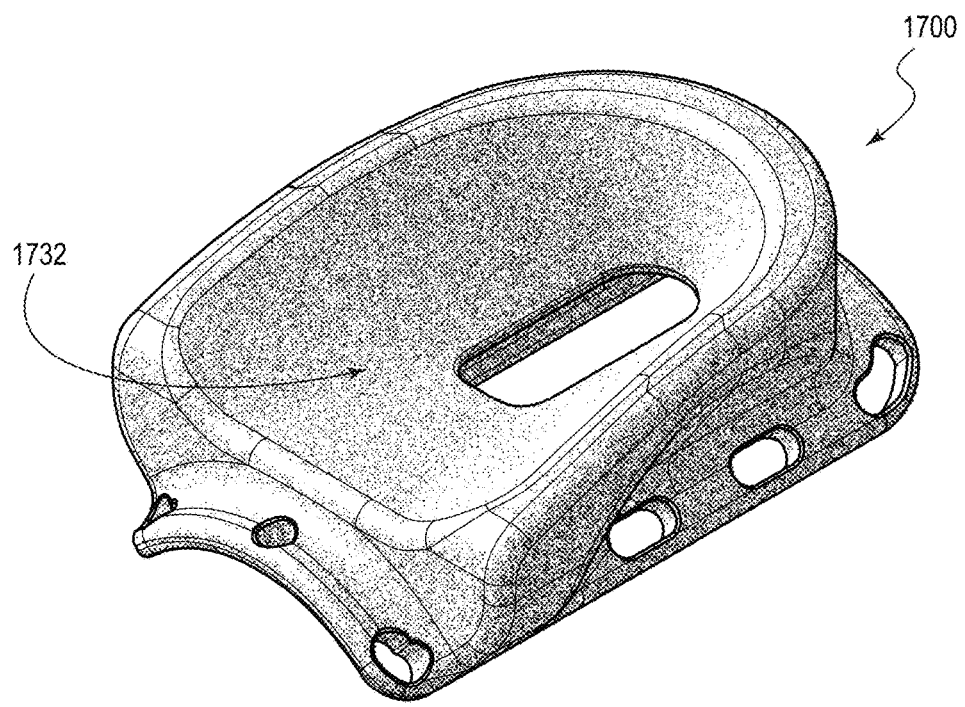
FIG. 29A is a top perspective view of another embodiment of a vascular access port.
Figure 29B:
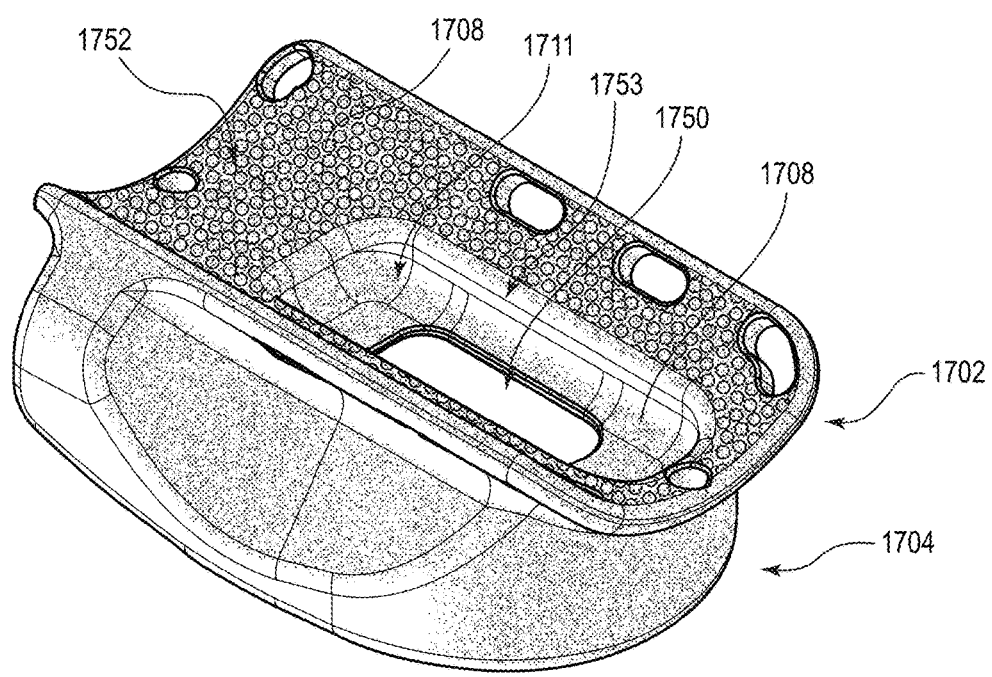
FIG. 29B is a bottom perspective view thereof.
Figure 29C:
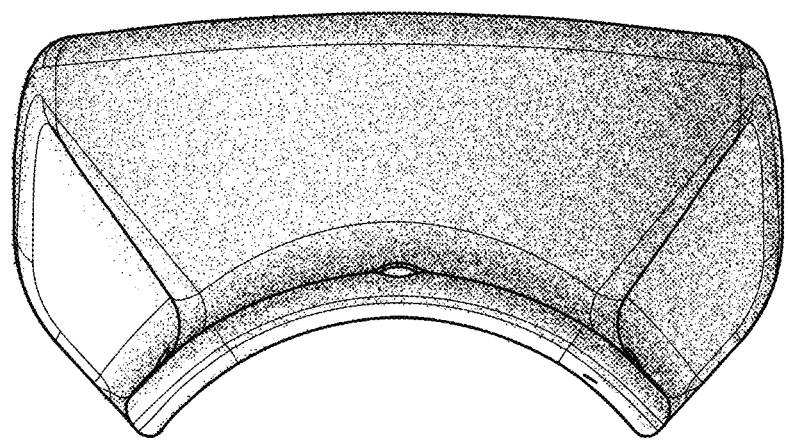
FIG. 29C is a front elevation view thereof.
Figure 29D:
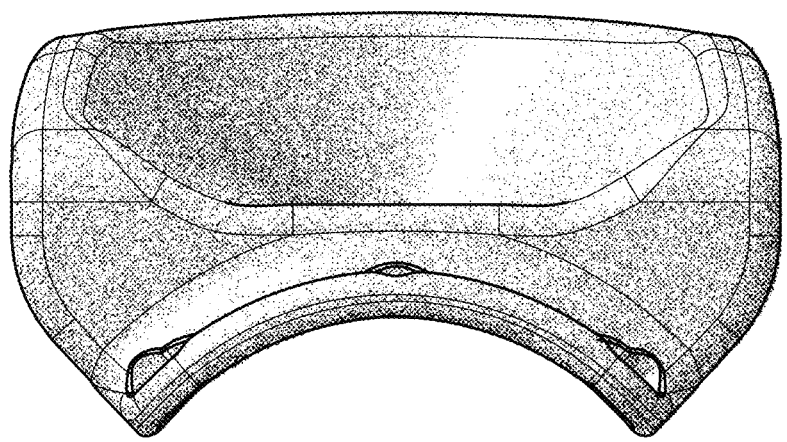
FIG. 29D is a rear elevation view thereof.
Figure 29E:
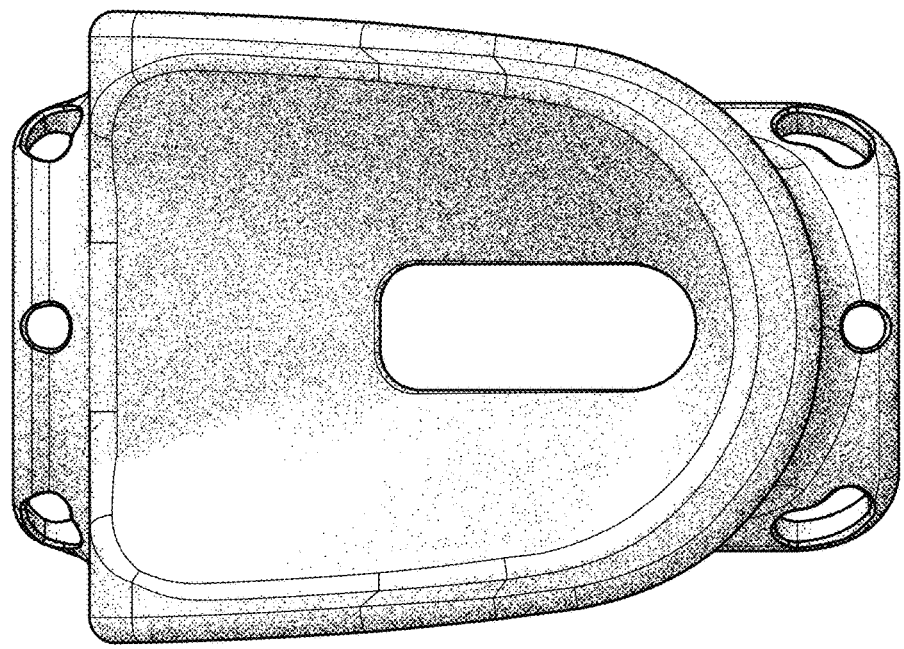
FIG. 29E is a top plan view thereof.
Figure 29F:
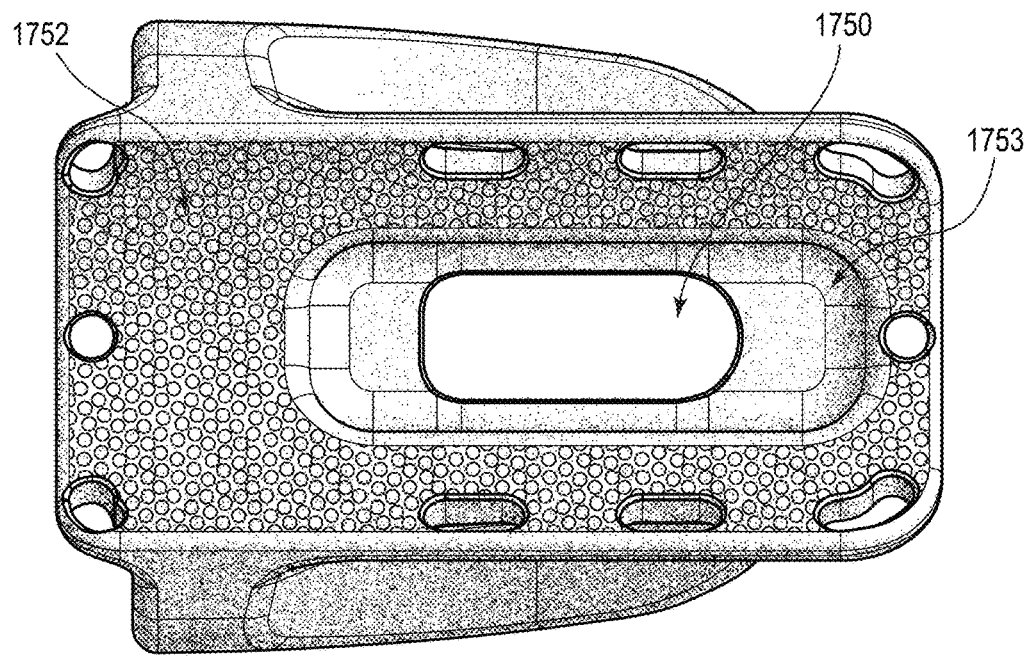
FIG. 29F is a bottom plan view thereof.
Figure 29G:
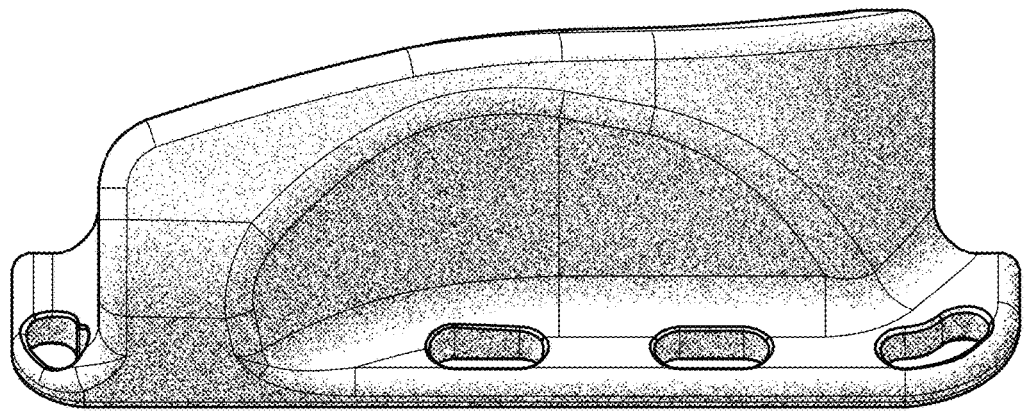
FIG. 29G is a right side elevation view thereof, wherein a left side elevation view thereof is a mirror image of the right side elevation view.
Figure 29H:
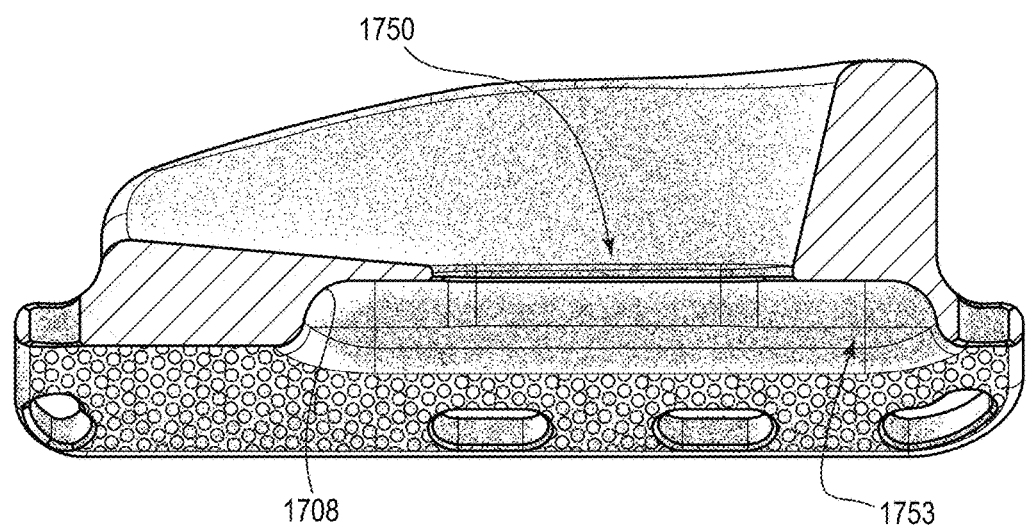
FIG. 29H is a cross-sectional view thereof.

FIGS. 29A-29G illustrate another embodiment of a vascular access port 1700, which can resemble the vascular access ports described above in certain respects. The port 1700 includes a funnel region 1732 that is higher than the funnel region 1132 of the port 1100, relative to a base 1702 of the port 1700. As can be seen in FIG. 29B, the port 1700 includes an atrium, chamber, or cavity 1711, which encompasses at least a portion of an opening 1750 at a distal end of the funnel region 1732. The base 1702 likewise can define an opening 1753 at the bottom end of the cavity 1711. In the illustrated embodiment, the cavity 1711 extends outwardly and downwardly from the opening 1750. The cavity 1711 can be defined by a bottom surface 1708 of the port 1700; in particular, the bottom surface 1708 of the port 1700 can extend inwardly from the outer edges of the base 1702, upwardly through the base 1702, and either adjacent to or at an interior of a body 1704 of the port. The bottom surface 1708 of the port 1700 can alternatively be described as a surface that extends outwardly and/or downwardly from the opening 1750 to a peripheral edge of the base 1702. As shown in FIG. 29H, the opening 1750 can be suspended or elevated relative to the portion of the bottom surface 1708 that is configured to contact a vessel wall. As shown in FIG. 29F, in some embodiments, the opening 1750 can otherwise resemble the opening 1150 described above.

In the illustrated embodiment, an ingrowth-inducing covering 1752 is restricted to the portion of the bottom surface 1708 that will contact the wall of a vessel, and does not cover an inner surface of the cavity 1711. In other embodiments, the cavity 1711 may include an ingrowth-inducing covering. As shown in FIG. 29F, the ingrowth-inducing covering 1752 can fully encompass the opening 1750. In other embodiments, the ingrowth-inducing covering 1752 may only partially encompass the opening 1750. As with other embodiments described herein, ingrowth-inducing features other than a covering or coating are possible. When the port 1700 is implanted in a patient, tissue may eventually fill the cavity 1711. A greater space between the bottom surface 1708 of the port 1700 and a vessel to which it is attached within the cavity 1711 region can allow a more natural healing response after access events. For example, the vessel wall may thicken upon formation of button hole site, and such thickening may be accommodated by the cavity 1711.

Figure 30A:
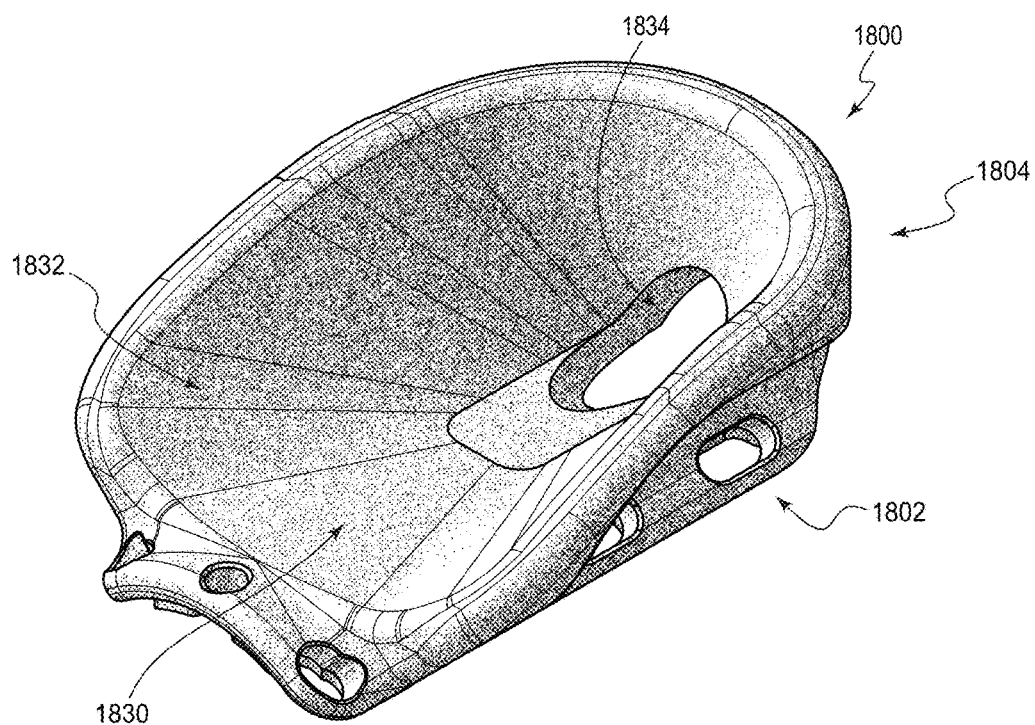
FIG. 30A is a perspective view of another embodiment of a vascular access port.
Figure 30B:
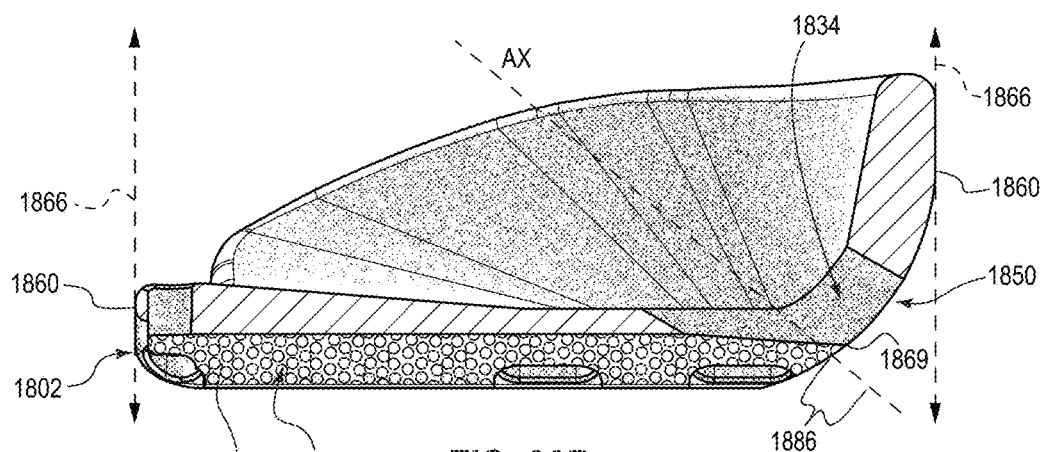
FIG. 30B is a cross-sectional view thereof.
Figure 30C:
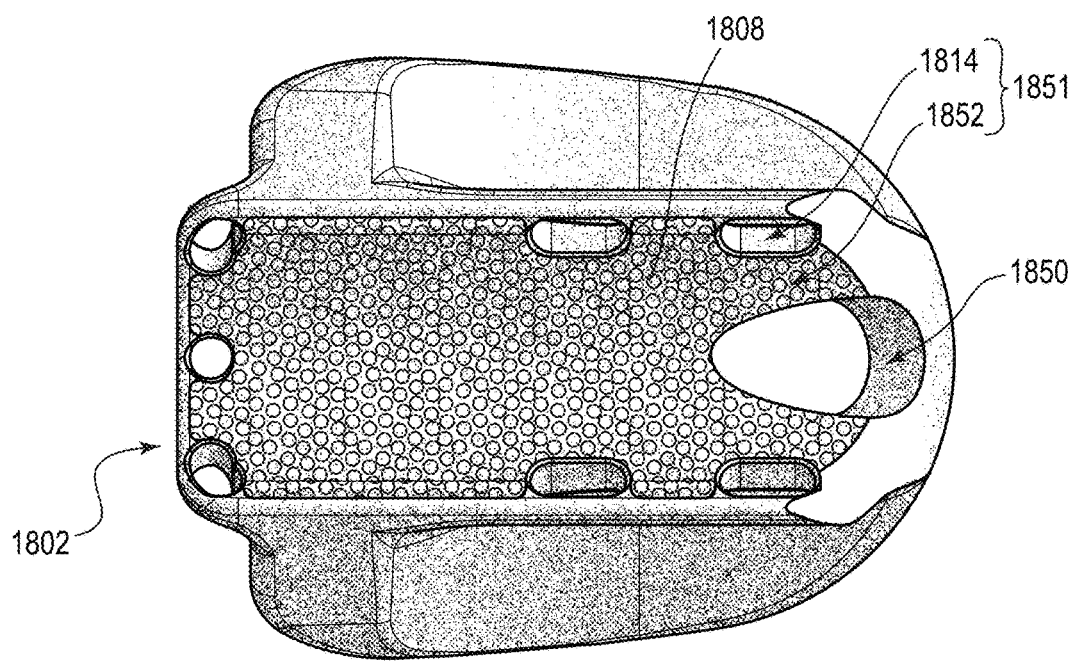
FIG. 30C is a bottom plan view thereof.

FIGS. 30A-30C illustrate another embodiment of a vascular access port 1800, which can resemble the vascular access ports described above in certain respects. The port 1800 can include a guidance passageway 1830, which can include a funnel region 1832 and a channel 1834. The channel 1834 is situated at a front end of the port 1800. As shown in FIG. 30B, the channel 1834 can have a substantially cylindrical outer profile and can define a central axis AX that extends through a center of the cylinder. A distal end of the channel 1834 defines an opening 1850. As shown in FIGS. 30B and 30C, a portion of the distal opening 1850 is at a bottom surface 1808 of the port 1800. Another portion of the opening 1850 extends upwardly away from the bottom surface 1808. Accordingly, only a portion of the opening 1850 is encompassed by ingrowth-inducing features 1802 that are incorporated into a base 1802 of the port 1800. In particular, attachment passages 1814 and an ingrowth-inducing covering 1852 extend about only a rearward portion of the opening 1850.

With reference to FIG. 30B, the base 1802 can define a footprint 1868 that has an outermost perimeter 1869. Both a body 1804 and the base 1802 of the port 1800 can define an outermost periphery 1160 which, when projected vertically, defines a peripheral extent 1866 of the port 1800. The central axis AX can have a region 1886 that is vertically even with the footprint 1868. An upper portion of the region 1886 is interior to the outermost perimeter 1869 of the footprint 1868. A lower portion of the region 1886 is exterior to the outermost perimeter 1869 of the footprint 1868. However, the entire region 1886 is interior to the peripheral extent 1866 of the port 1800.

Figure 31A:
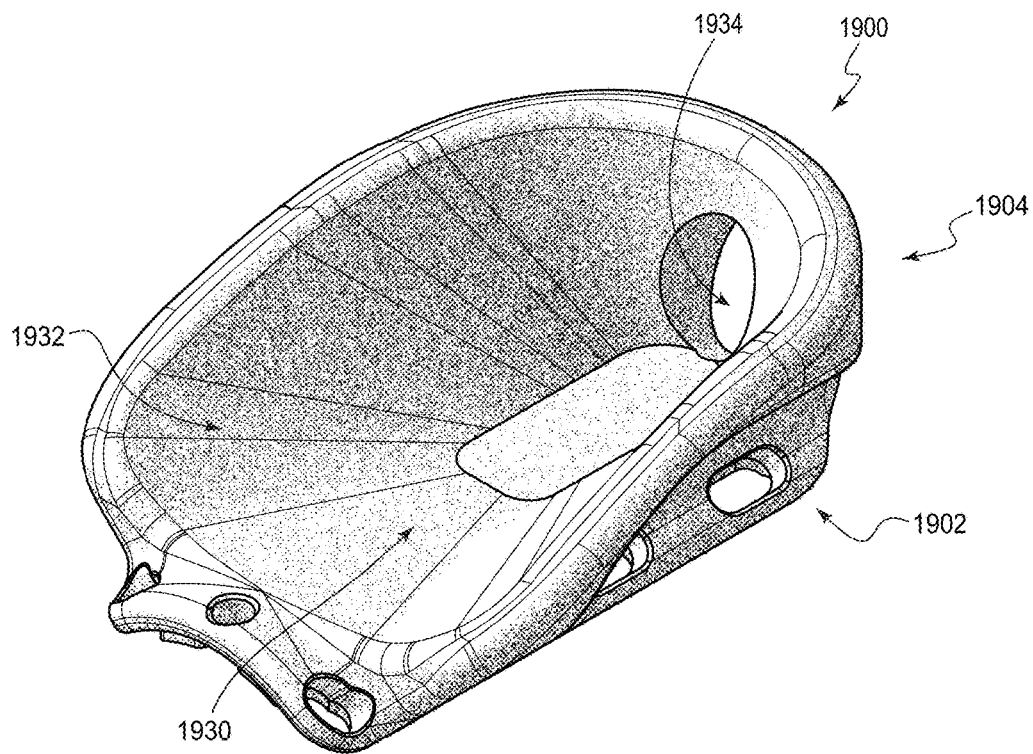
FIG. 31A is a perspective view of another embodiment of a vascular access port.
Figure 31B:
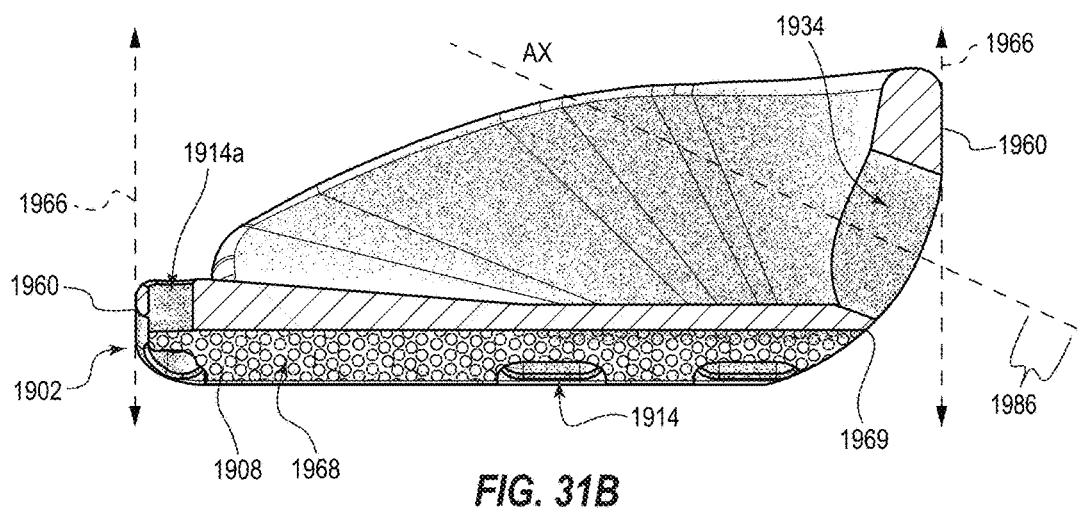
FIG. 31B is a cross-sectional view thereof.
Figure 31C:
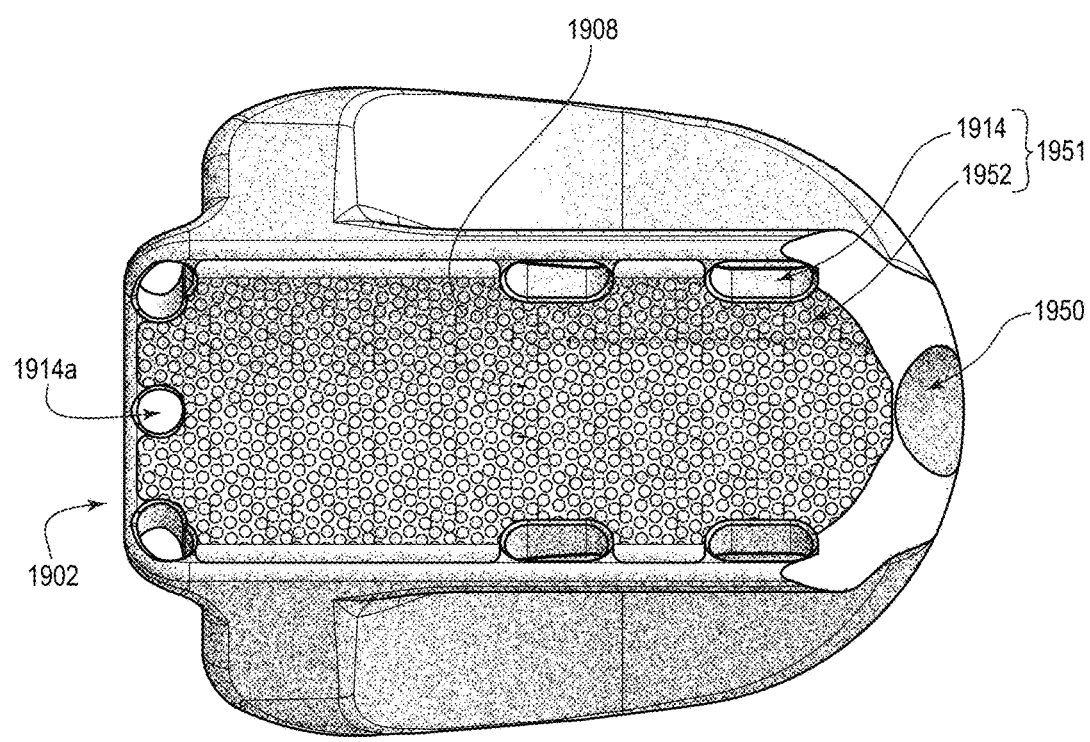
FIG. 31C is a bottom plan view thereof.

FIGS. 31A-31C illustrate another embodiment of a vascular access port 1900, which can resemble the vascular access ports described above in certain respects. The port 1900 can include a guidance passageway 1930, which can include a funnel region 1932 and a channel 1934. The channel 1934 is situated at a front end of the port 1900. As shown in FIG. 31B, the channel 1934 can have a substantially cylindrical outer profile and can define a central axis AX that extends through a center of the cylinder. A distal end of the channel 1934 defines an opening 1950. As shown in FIGS. 31B and 31C, the opening 1950 does not extend to the bottom surface 1908 of the port 1900. Rather, the opening 1950 extends upwardly so as to be spaced from the bottom surface 1908. Ingrowth-inducing features 1951 that are incorporated into a base 1902 of the port 1900 do not encompass the opening 1950. In particular, an ingrowth-inducing covering 1952 that is restricted to the bottom surface 1908 is spaced rearwardly from the opening 1950. It is also noted that no portion of the ingrowth-inducing covering is vertically even with the opening 1950. Similarly, all of the attachment passages 1914 are rearward of the opening 1950. It is also noted that only a portion of a rearward attachment passage 1914a is vertically even with a bottom end of the opening 1950, whereas remaining attachment passages 1914 are fully below the opening 1950.

With reference to FIG. 31B, the base 1902 can define a footprint 1968 that has an outermost perimeter 1969. Both a body 1904 and the base 1902 of the port 1900 can define an outermost periphery 1160 which, when projected vertically, defines a peripheral extent 1966 of the port 1900. The central axis AX can have a region 1986 that is vertically even with the footprint 1968. The entire region 1986 is outside of the outermost perimeter 1969 of the footprint 1968. Moreover, the entire region 1986 is exterior to the peripheral extent 1966 of the port 1900.

Figure 32A:
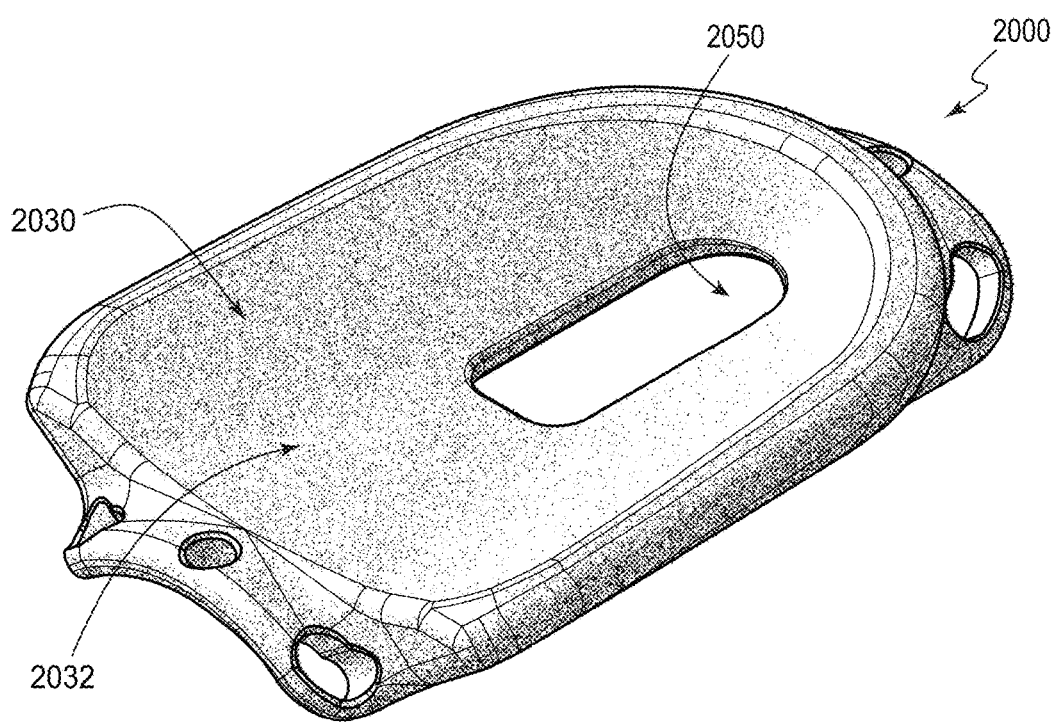
FIG. 32A is a perspective view of another embodiment of a vascular access port.
Figure 32B:
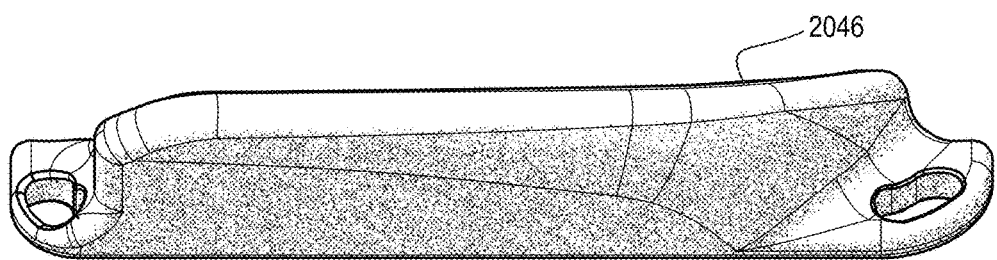
FIG. 32B is a side elevation view thereof.
Figure 32C:
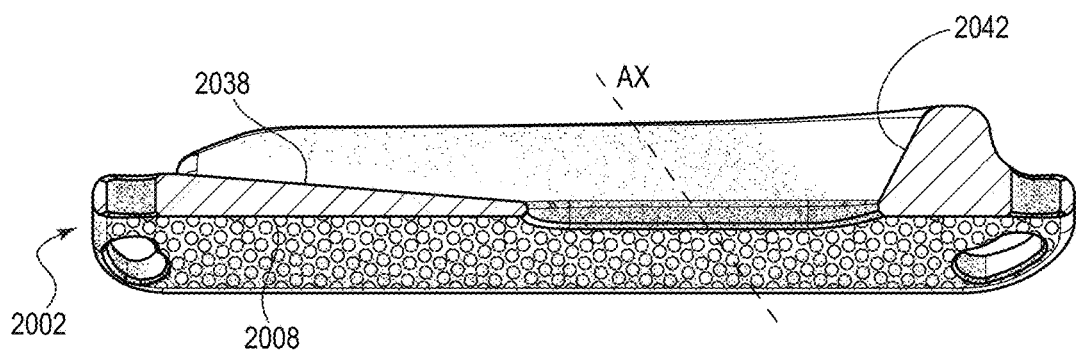
FIG. 32C is a cross-sectional view thereof.

FIGS. 32A-32C illustrate another embodiment of a vascular access port 2000, which can resemble the vascular access ports described above in certain respects. The port 2000 can closely resemble the port 1100 discussed above, but can define a much lower profile. The port 2000 can include a guidance passageway 2030, which can include a funnel region 2032 that narrows toward an opening 2050. As shown in FIG. 32C, a backstop portion 2042 of the funnel region 2032 can be angled forwardly to a greater extent than the backstop portion 1142 of the port 1100, whereas the base surfaces 1138, 2038 of both ports 1100, 2000 can be about the same. Accordingly, a central axis AX of the port 2000 can define a larger acute angle relative to a bottom surface 2008 of a base 2002 of the port 2000, as compared with an angle defined by the central axis AX of the port 1100.

The port 2000 can include a palpation projection 2046 at an upper end of the guidance passageway 2030. As shown in FIG. 32B, the palpation projection 2046 can substantially define a plane. The substantially planar region defined by the palpation projection 2046 is slightly concave in the longitudinal direction at a forward end thereof.

In other embodiments, the backstop portion 1142 may define an even larger angle relative to the bottom surface 2008. In still other embodiments, the funnel region 2032 may be replaced with a substantially planar surface that extends about the opening 2050.

Figure 33A:
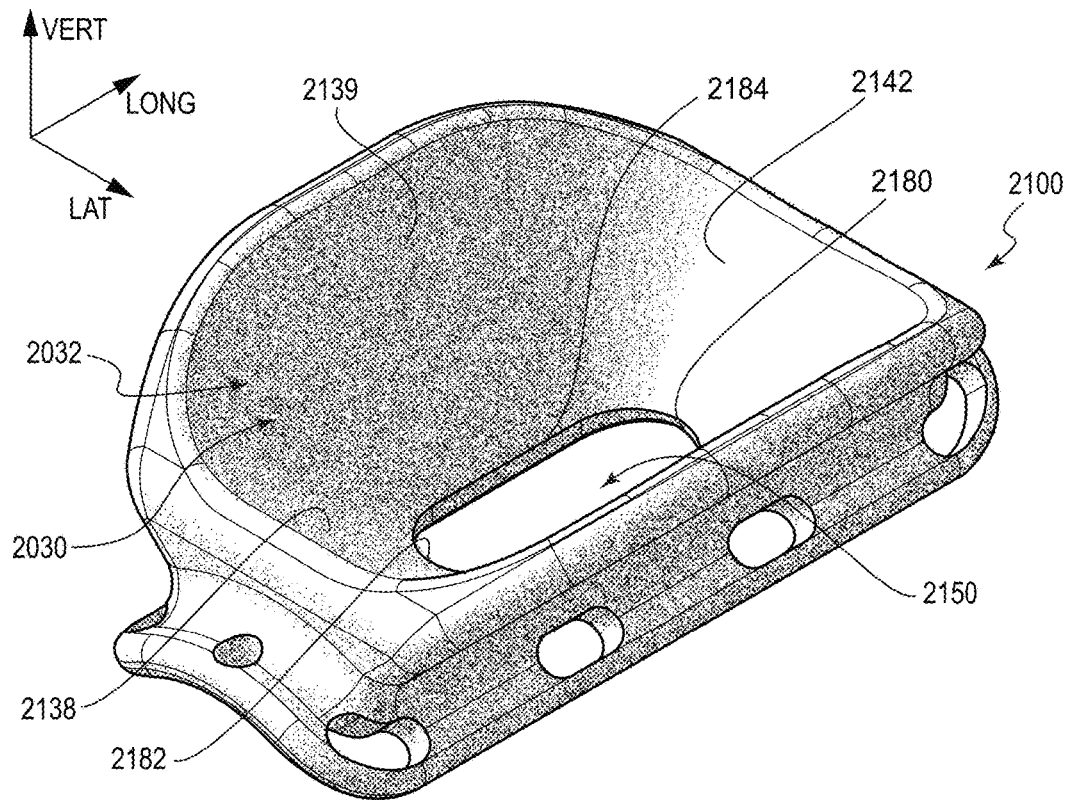
FIG. 33A is a perspective view of another embodiment of a vascular access port.
Figure 33B:
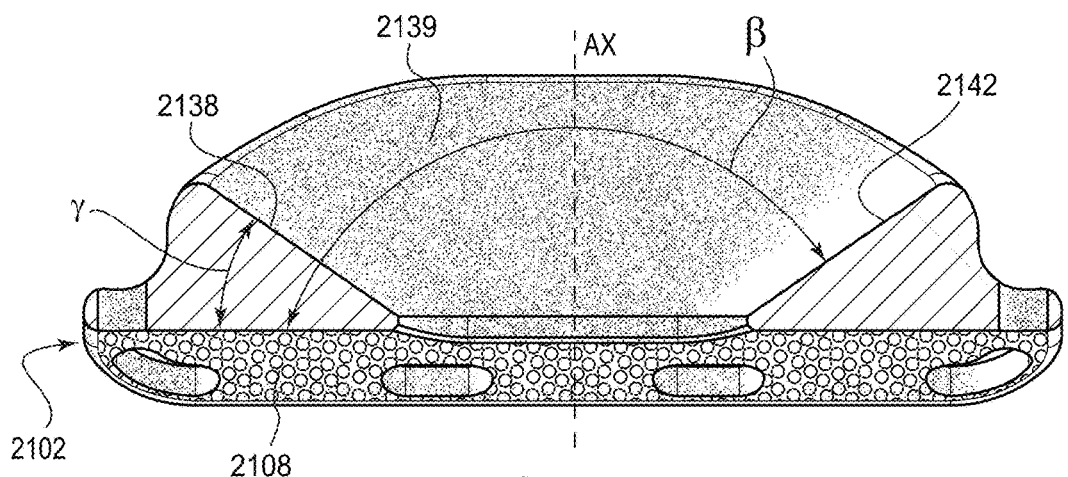
FIG. 33B is a cross-sectional view thereof.

FIGS. 33A-33B illustrate another embodiment of a vascular access port 2100, which can resemble the vascular access ports described above in certain respects. The port 2100 can be particularly well-suited for permitting access to a vessel in either an antegrade or a retrograde direction (e.g., either a forward or a rearward direction). For example, the port 2100 can be used to create a single insertion site 266 in an artery wall that can be accessed either in an antegrade or retrograde direction for uptake in a hemodialysis procedure.

The port 2100 can include a guidance passageway 2130, which can include a funnel region 2132 that narrows toward an opening 2150. The opening 2150 can be at a bottom surface 2108 of a base 2102 of the port 2100. In the illustrated embodiment, a forward portion 2142 of the funnel region 2132 is angled forwardly to a greater extent than the backstop portion 1142 of the port 1100, and a rear portion 2138 of the funnel region 2132 is angled rearwardly so as to define a greater angle than the base surface 1138 of the port 1100. The forward and rearward portions 2142, 2138 rise vertically and outwardly from the opening 2150 to approximately the same height. Accordingly, in the illustrated embodiment, the port 2100 may just as easily direct an access device toward the opening 2150 when the access device is inserted in a forward-to-rearward direction as when the access device is inserted in a rearward-to-forward direction. In the illustrated embodiment, a central axis AX of the port 2100 can define a substantially perpendicular angle relative to the bottom surface 2108 of the base 2108 (e.g., $(\beta+\gamma)/2=90$).

Side portions 2138 of the funnel region 2132 can extend to a greater vertical height than either of the forward and rearward portions 2142, 2138, which may assist in constraining movement of an access device toward the opening 2150. In the illustrated embodiment, the port 2150 is symmetrical about both a lateral-vertical plane through a center thereof as well as a longitudinal-vertical plane through a center thereof.

Other embodiments can have different arrangements. For example, in some embodiments, the port 2100 is asymmetrical about a central lateral-vertical plane. One of the forward and rearward portions 2142, 2138 may, for example, define a different angle relative to the bottom surface 2108 and/or may extend upwardly to a greater height as compared with the other portion. In other or further embodiments, the port 2100 similarly may be asymmetrical about a central longitudinal-vertical plane, as the arrangement of one side portion 2139 may vary relative to an opposing side portion 2139.

The port 2100 can include a palpation projection 2146 at an upper end of the guidance passageway 2130. As shown in FIG. 33B, the palpation projection 2146 can substantially define a plane at a central portion of the port 2100, but may define substantially concavely rounded portions at the forward and rearward ends thereof.

Figure 34A:
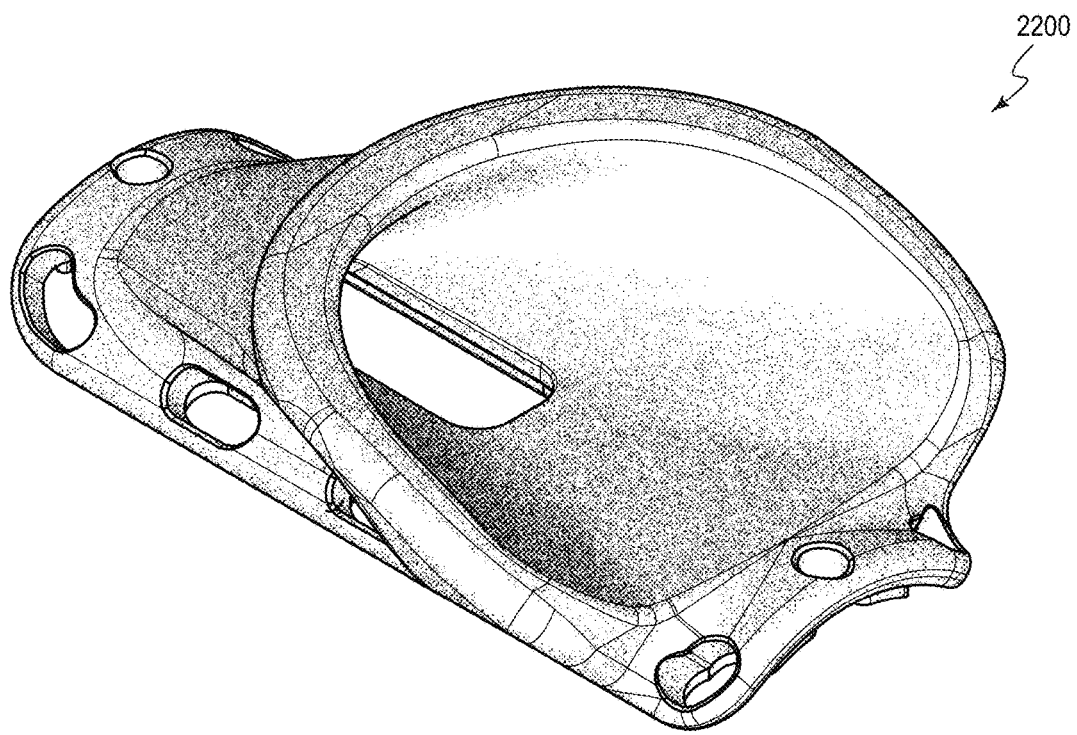
FIG. 34A is a perspective view of another embodiment of a vascular access port.
Figure 34B:
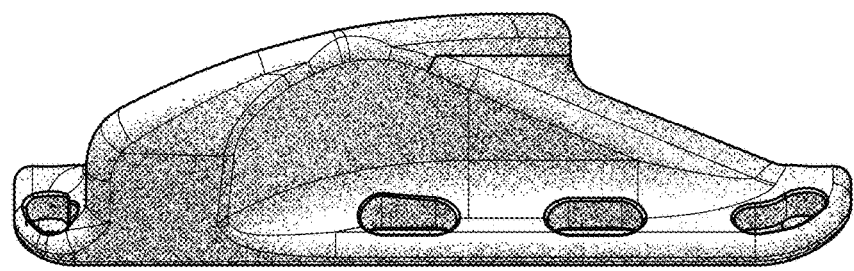
FIG. 34B is a right side elevation view thereof, wherein a left side elevation view thereof is a mirror image of the right side elevation view.
Figure 34C:
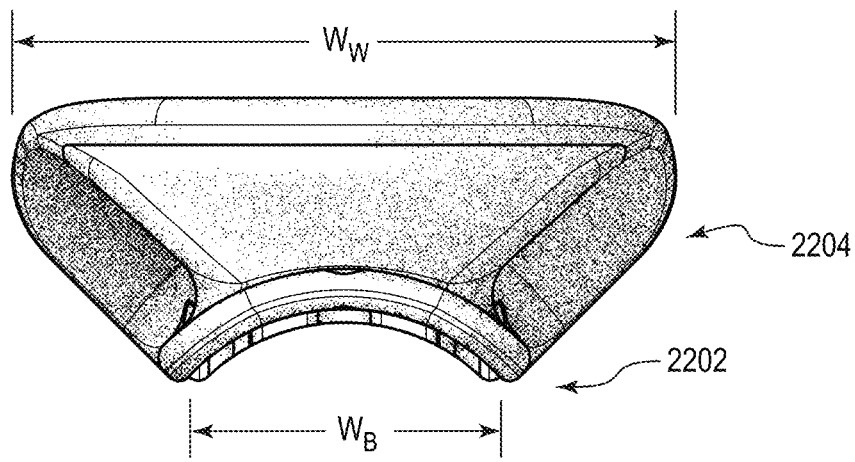
FIG. 34C is a front elevation view thereof.
Figure 34D:
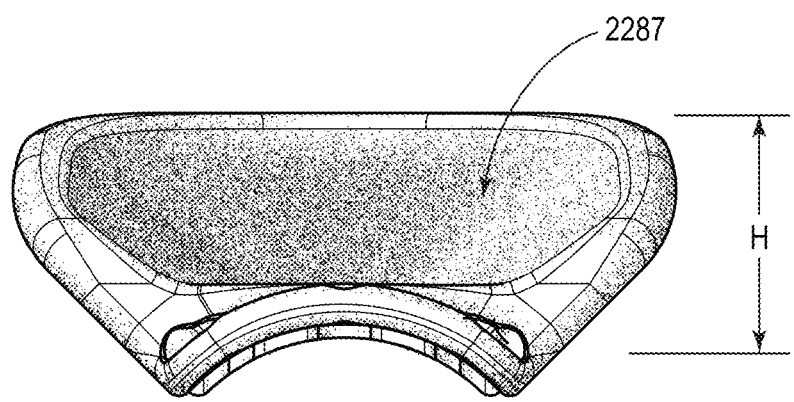
FIG. 34D is a rear elevation view thereof.
Figure 34E:
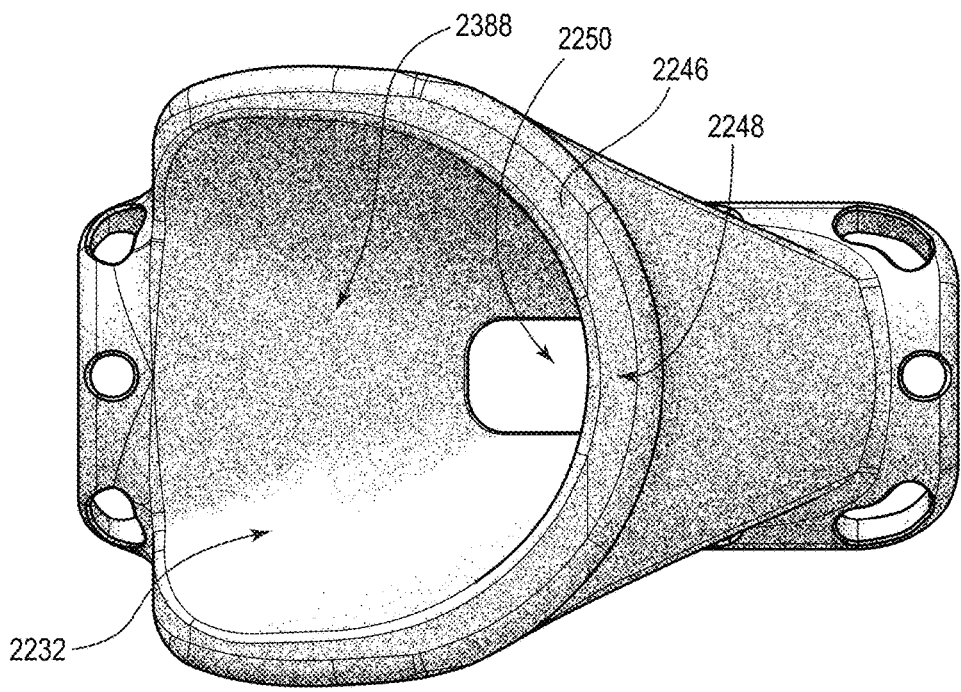
FIG. 34E is a top plan view thereof.
Figure 34F:
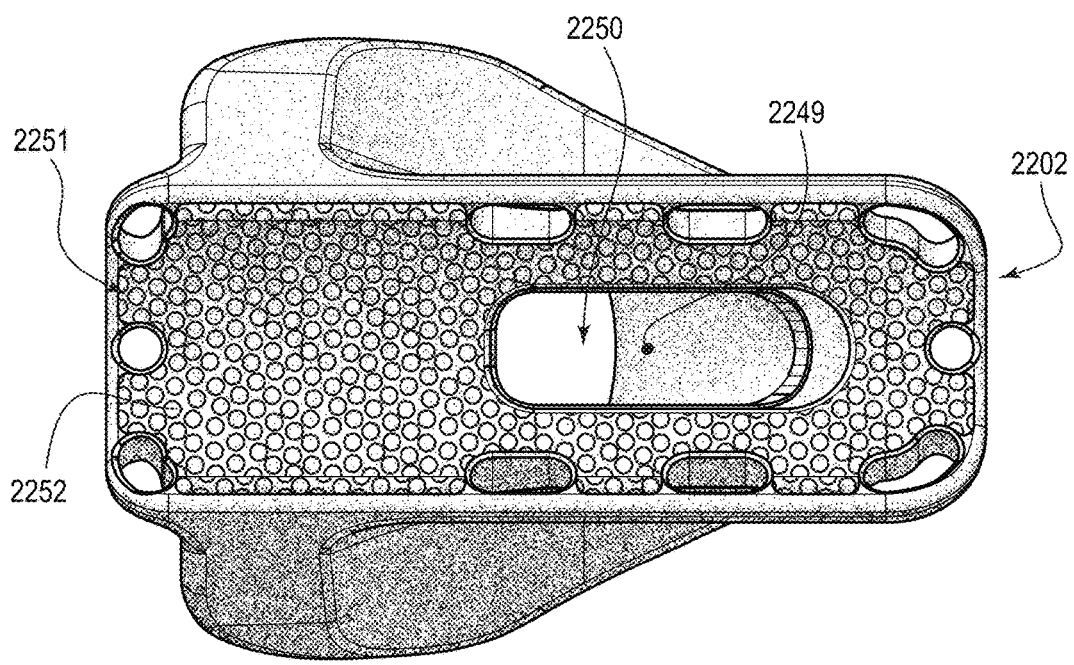
FIG. 34F is a bottom plan view thereof.
Figure 34G:
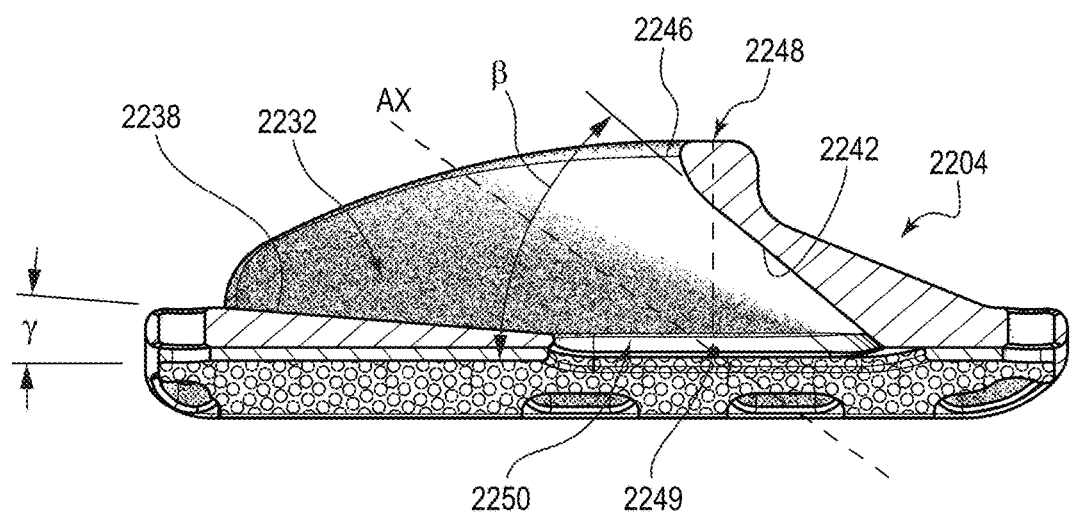
FIG. 34G is a cross-sectional view thereof.
Figure 35A:
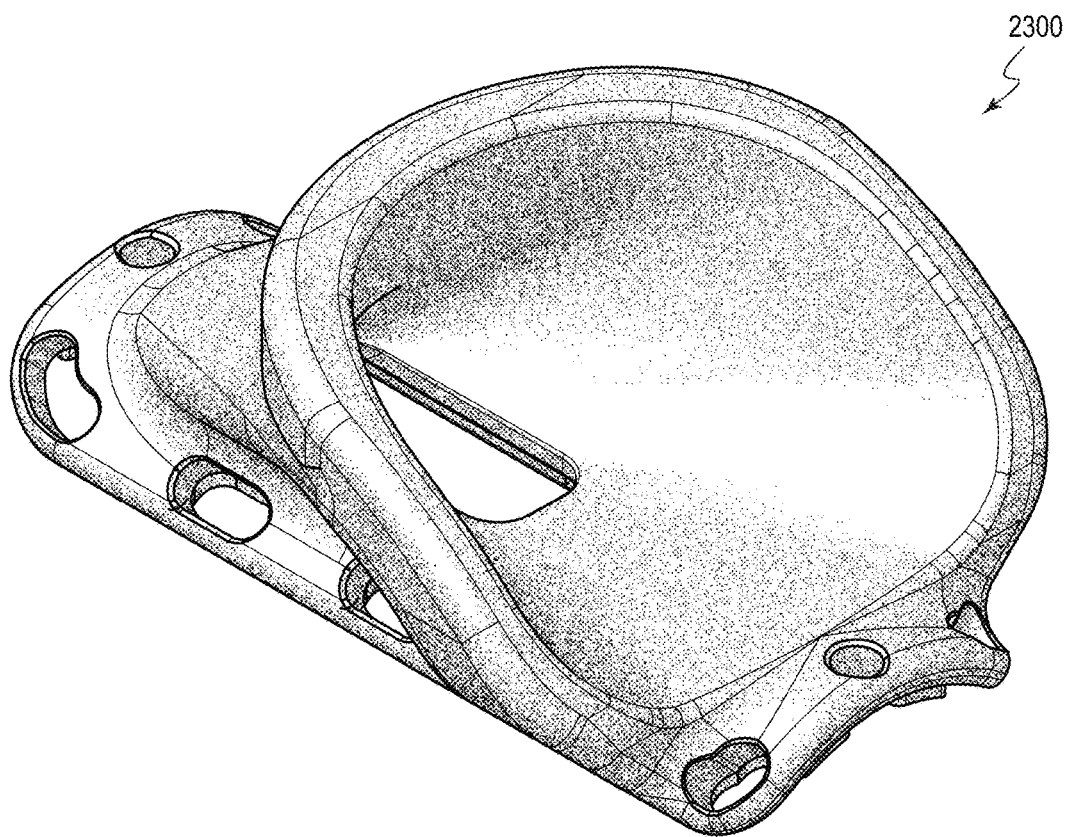
FIG. 35A is a perspective view of another embodiment of a vascular access port.
Figure 35B:
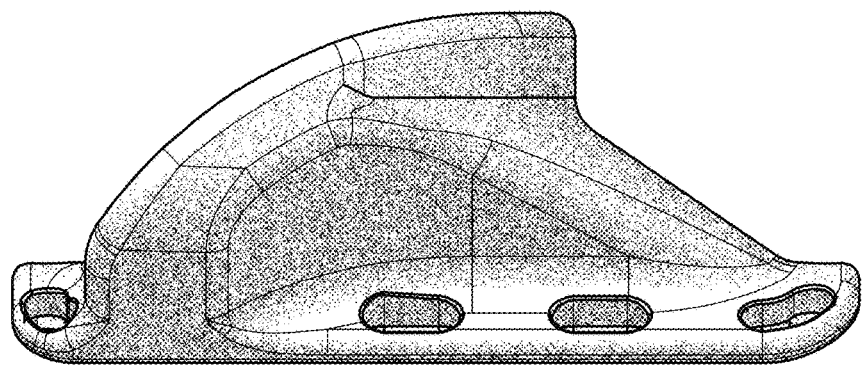
FIG. 35B is a right side elevation view thereof, wherein a left side elevation view thereof is a mirror image of the right side elevation view.
Figure 35C:
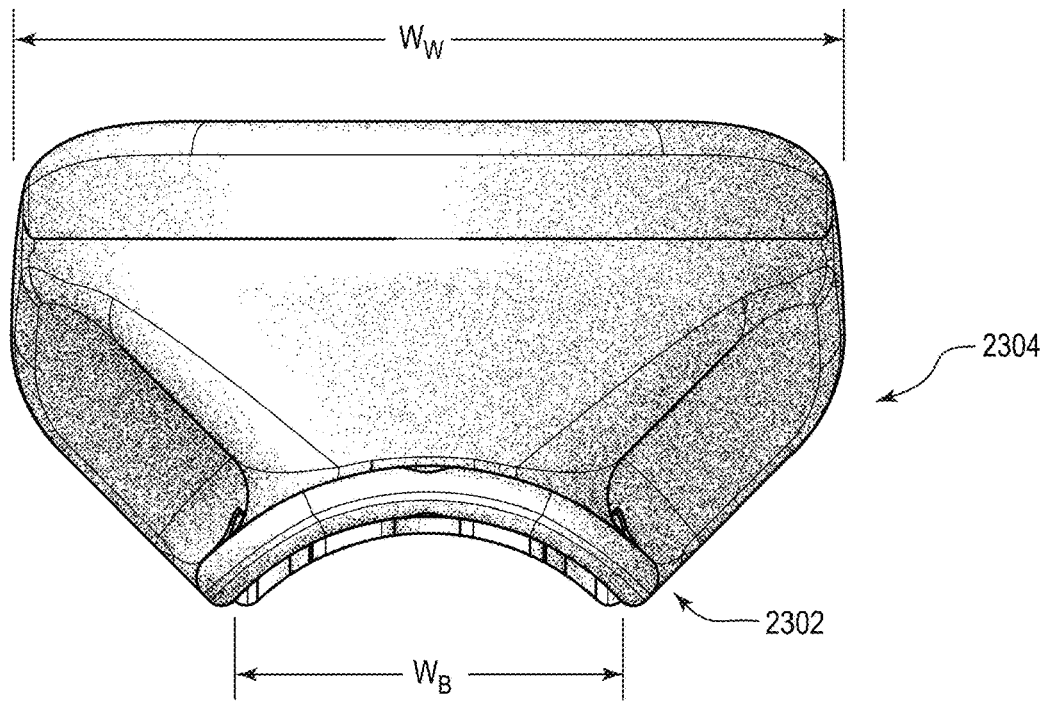
FIG. 35C is a front elevation view thereof.
Figure 35D:
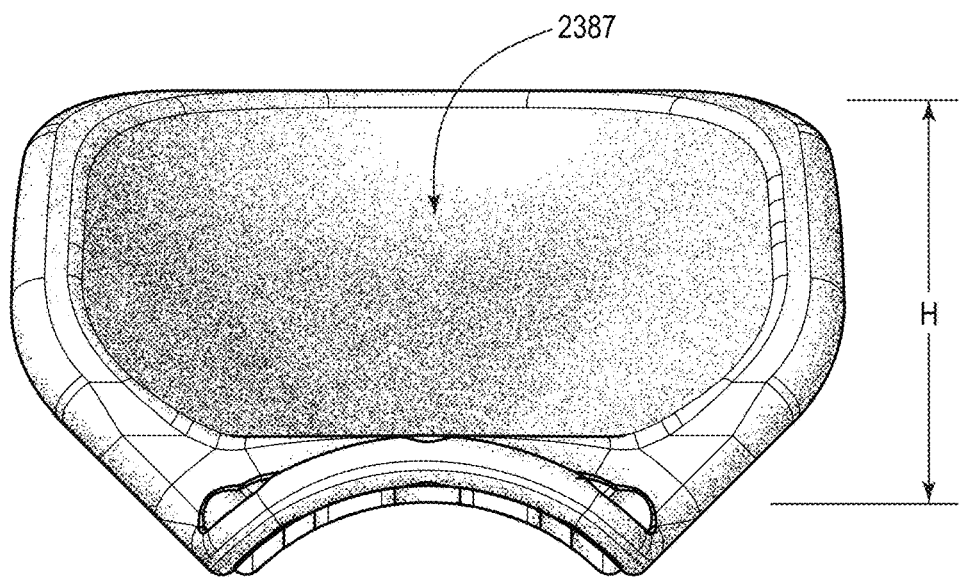
FIG. 35D is a rear elevation view thereof.
Figure 35E:
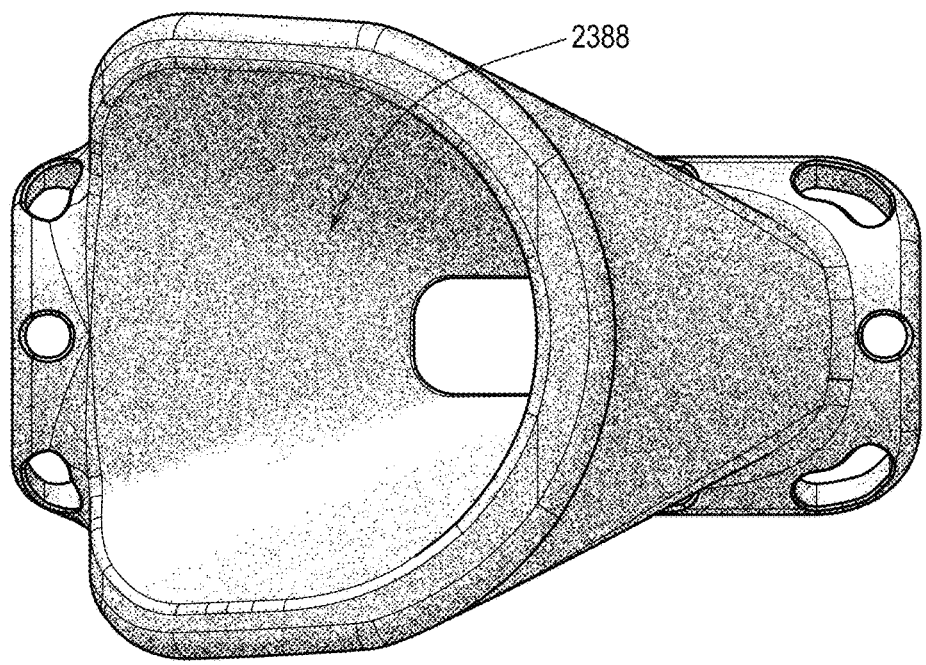
FIG. 35E is a top plan view thereof.
Figure 35F:
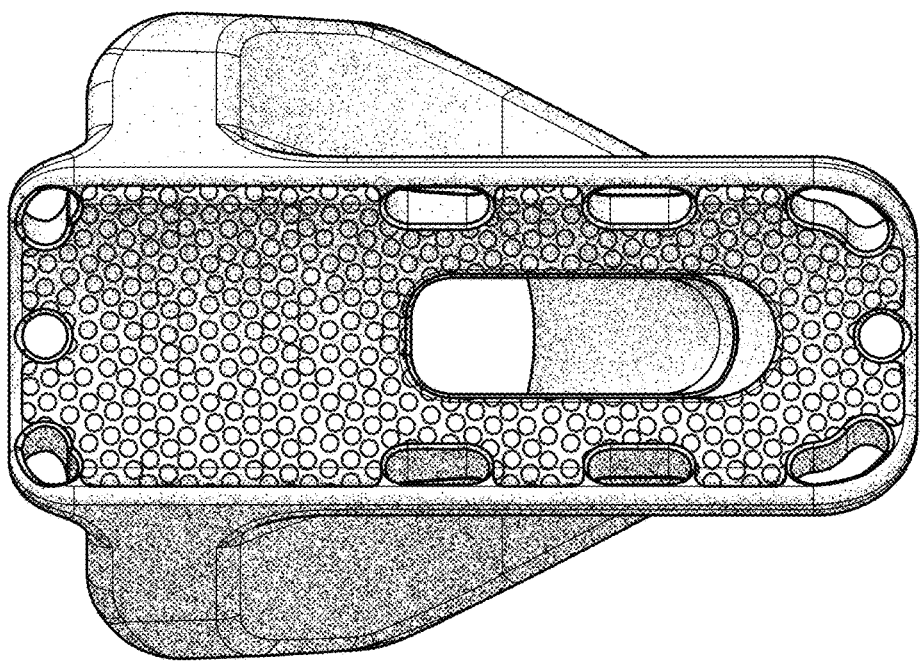
FIG. 35F is a bottom plan view thereof.
Figure 36A:
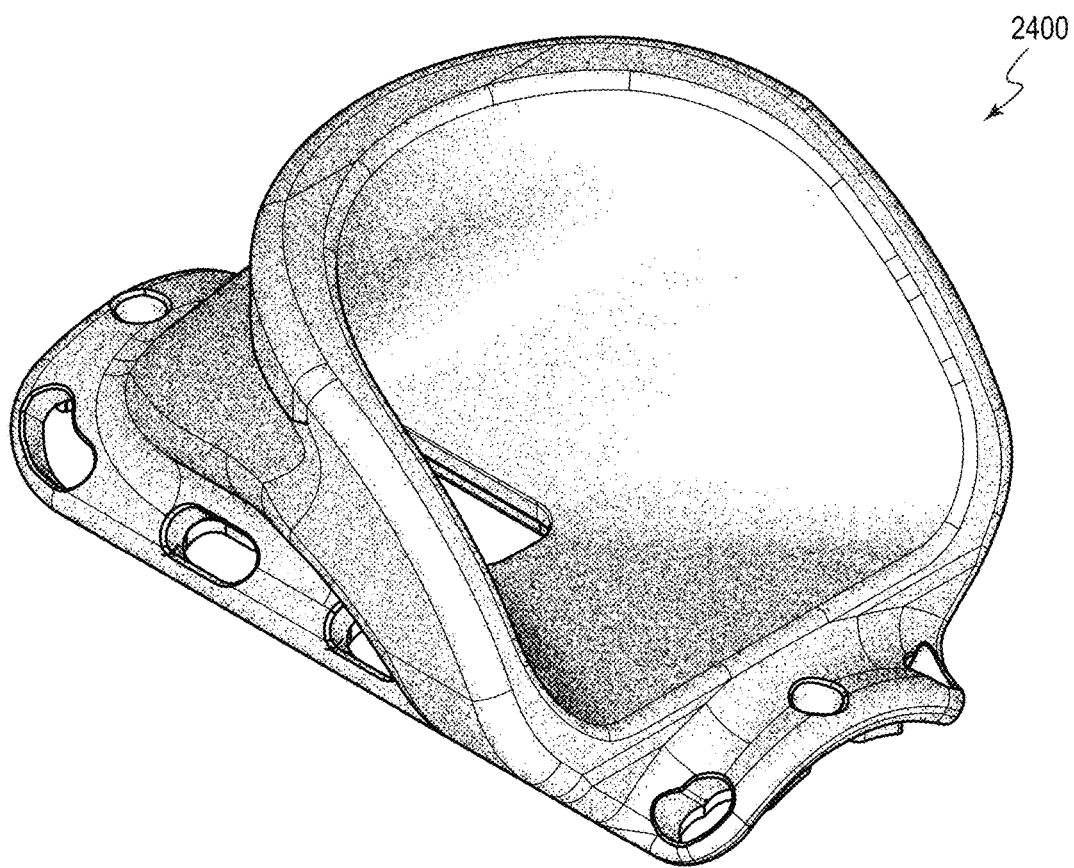
FIG. 36A is a perspective view of another embodiment of a vascular access port.
Figure 36B:
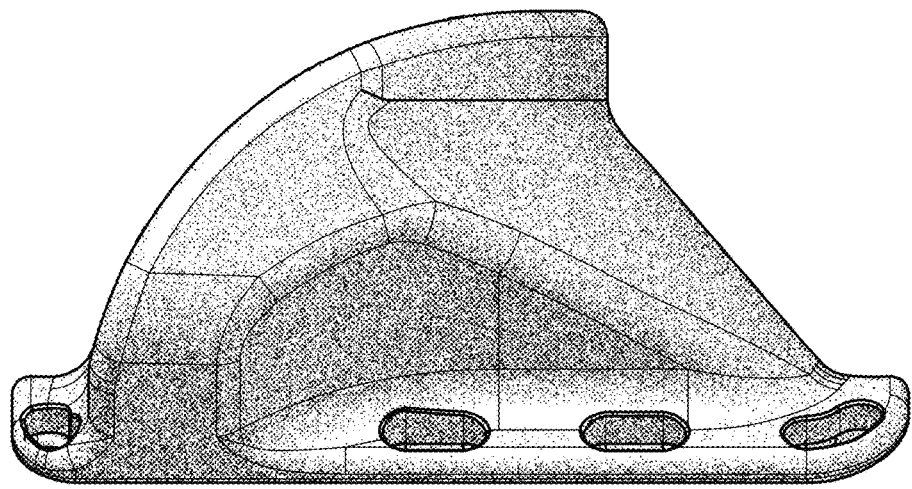
FIG. 36B is a right side elevation view thereof, wherein a left side elevation view thereof is a mirror image of the right side elevation view.
Figure 36C:
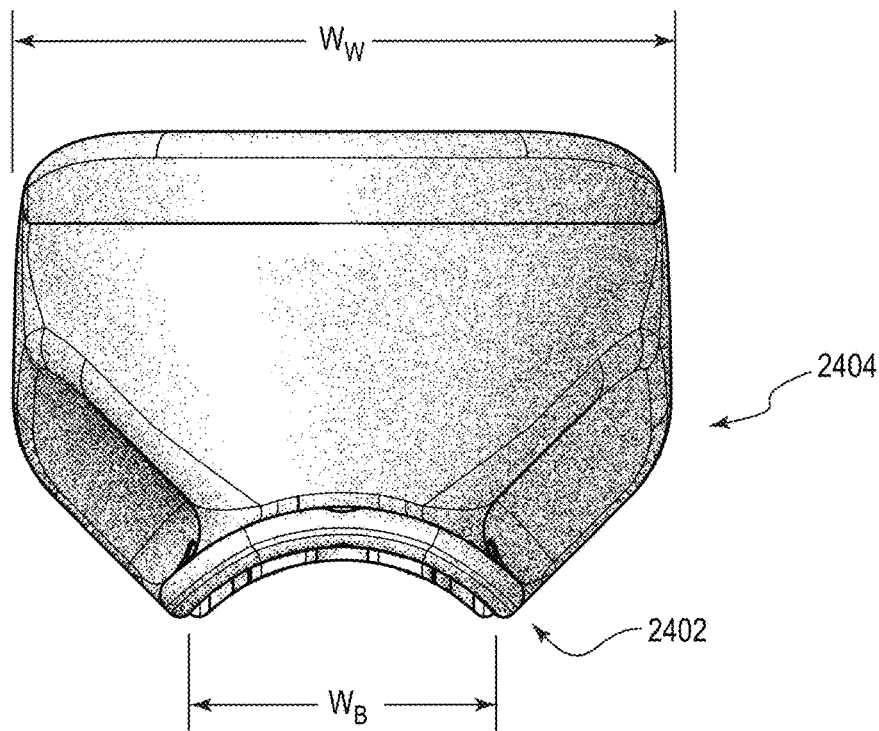
FIG. 36C is a front elevation view thereof.
Figure 36D:
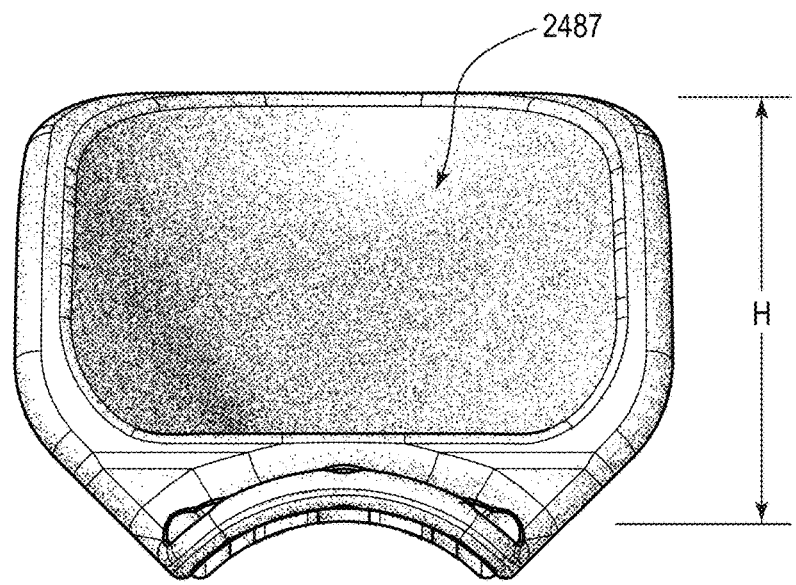
FIG. 36D is a rear elevation view thereof.
Figure 36E:
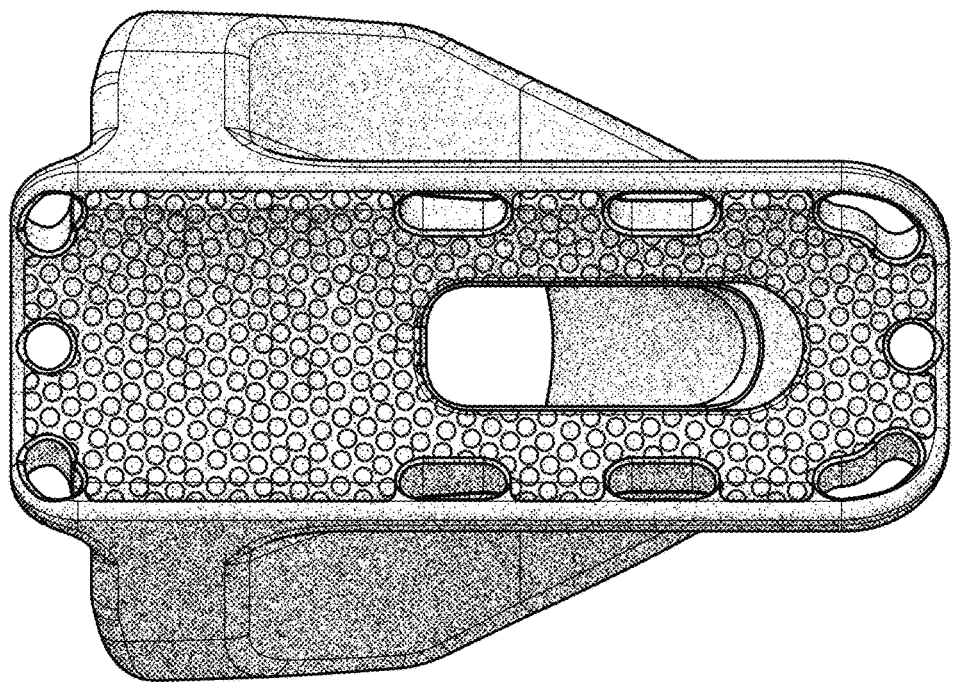
FIG. 36E is a bottom plan view thereof.
Figure 36F:
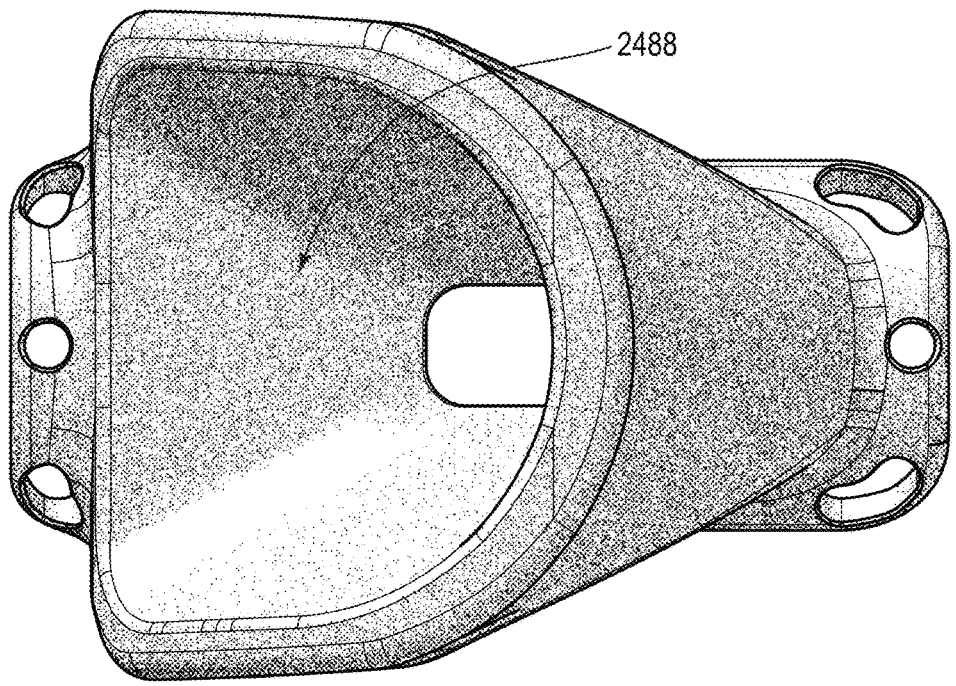
FIG. 36F is a top plan view thereof.
Figure 37A:
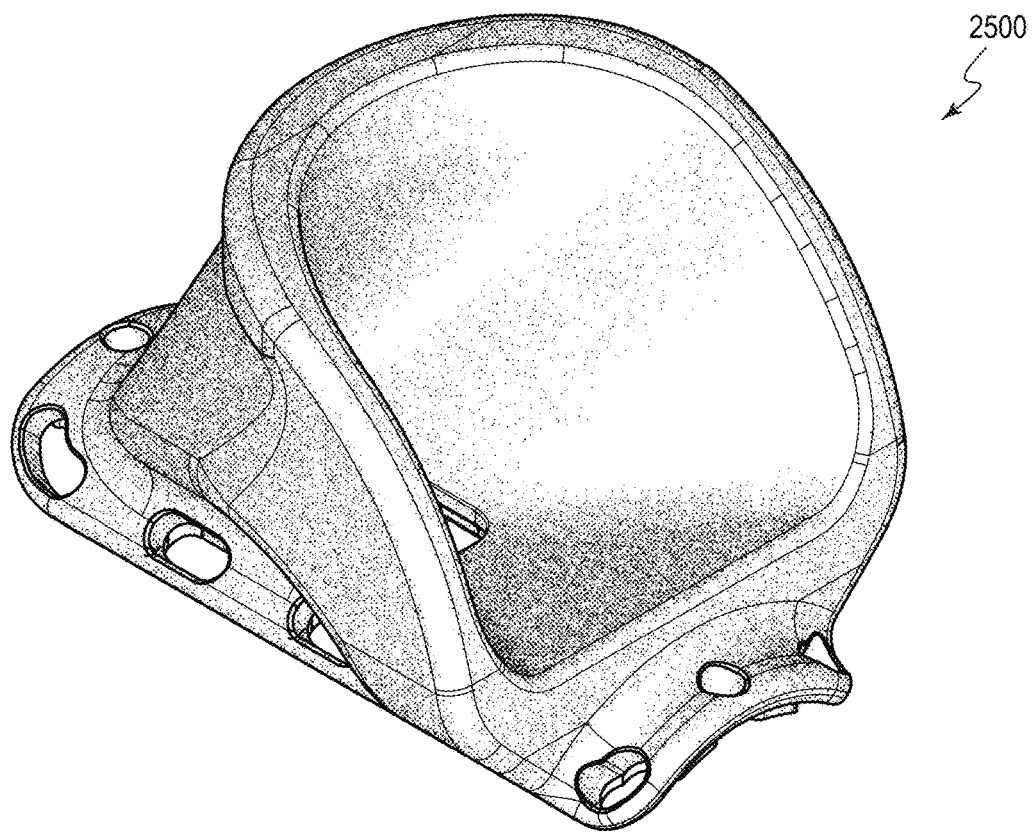
FIG. 37A is a perspective view of another embodiment of a vascular access port.
Figure 37B:
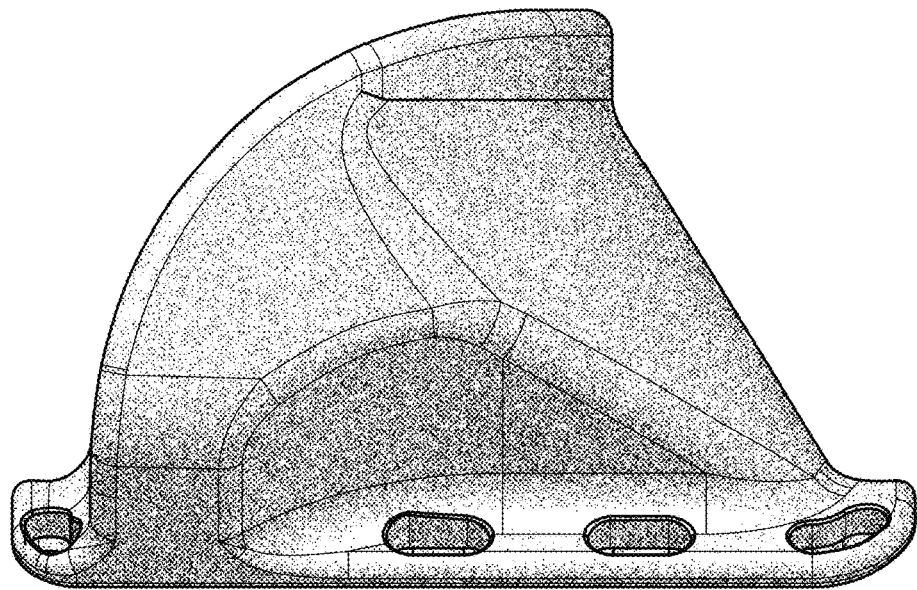
FIG. 37B is a right side elevation view thereof, wherein a left side elevation view thereof is a mirror image of the right side elevation view.
Figure 37C:
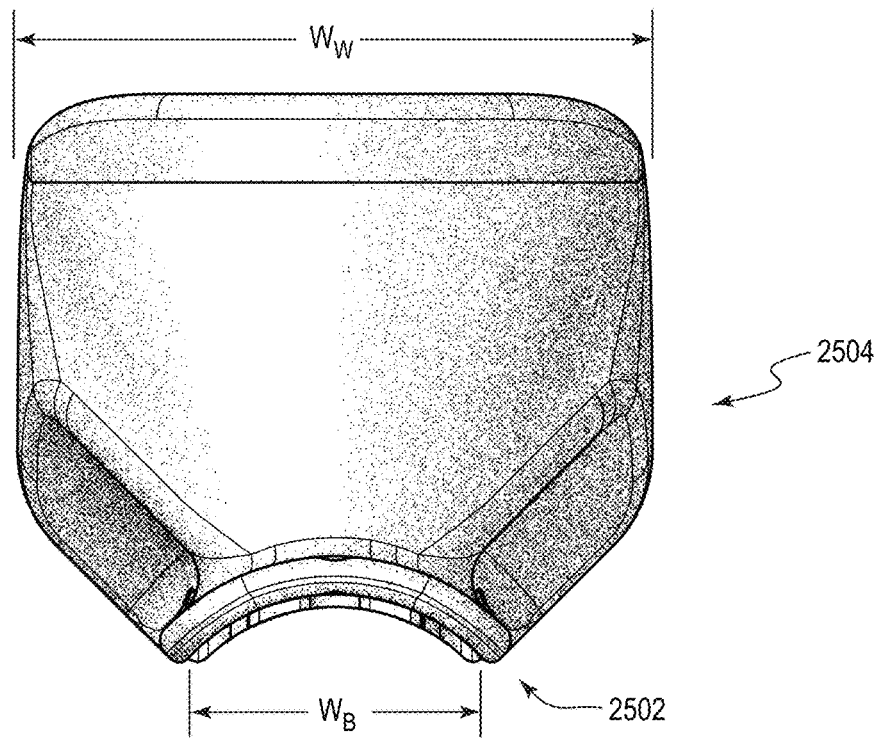
FIG. 37C is a front elevation view thereof.
Figure 37D:
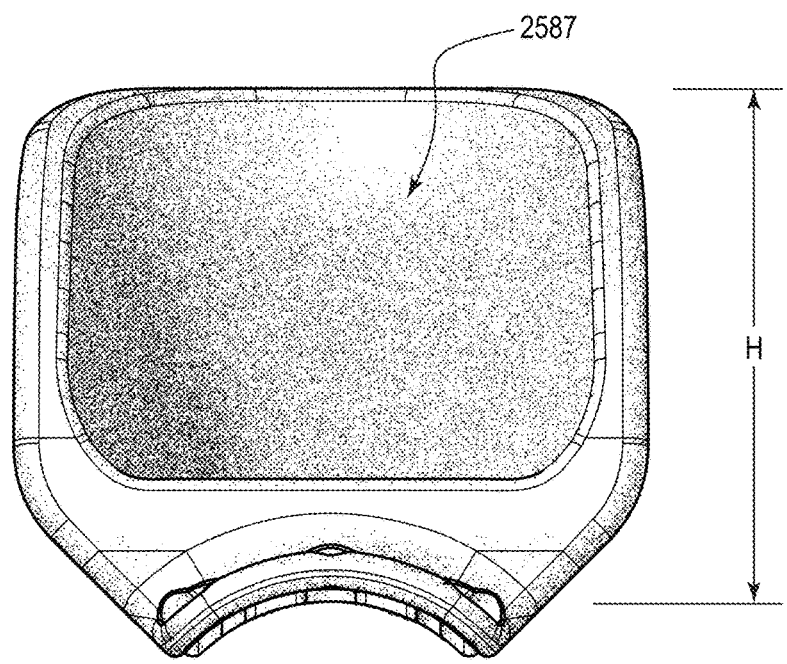
FIG. 37D is a rear elevation view thereof.
Figure 37E:
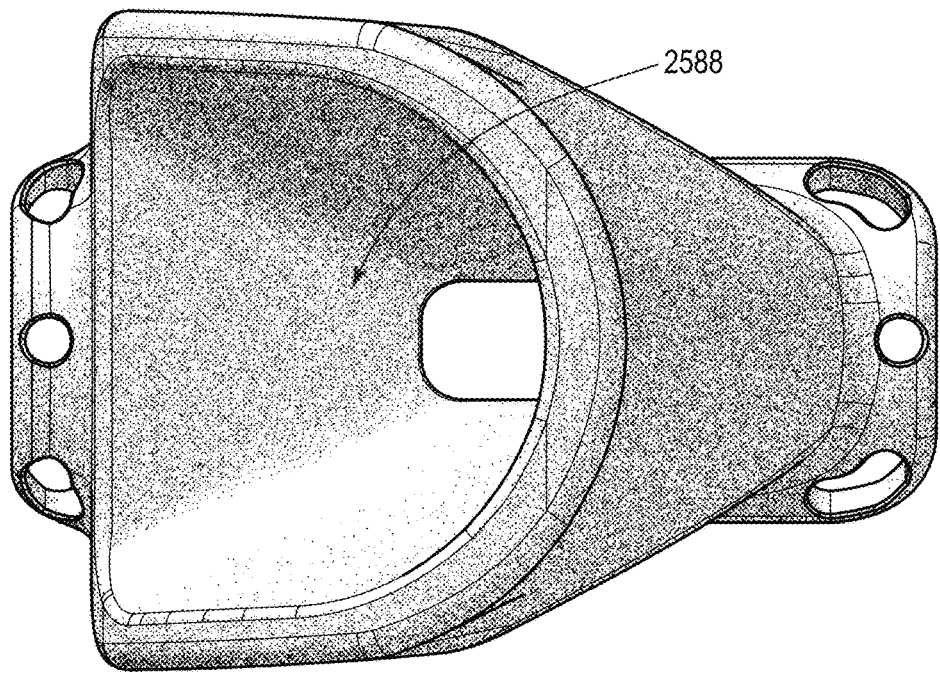
FIG. 37E is a top plan view thereof.
Figure 37F:
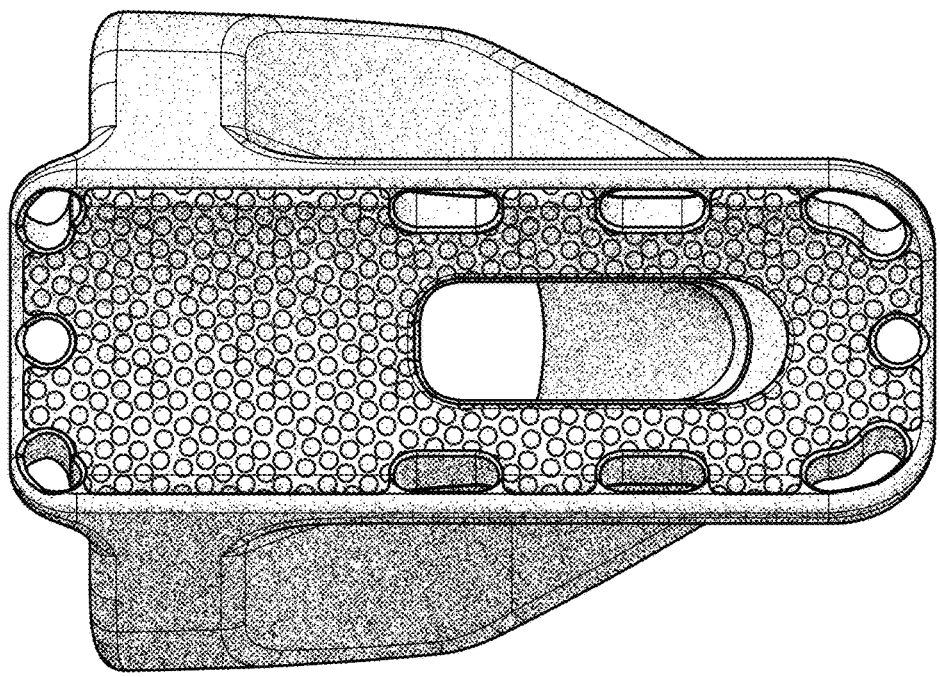
FIG. 37F is a bottom plan view thereof.

FIGS. 34A-34G illustrate another embodiment of a vascular access port 2200, which can resemble the vascular access ports described above in certain respects. The vascular access port 2200 can particularly resemble the access port 1600, and can have a similarly shaped funnel region 2232. As shown in FIG. 34G, the funnel region 2232 can include a base surface 2238 that defines an angle γ relative to a bottom surface of the port 2200, and can include a backstop portion 2242 that defines an angle β relative to the bottom surface of the port 2200. The backstop portion 2242 is angled rearwardly such that the angle β is acute. A central axis AX of the funnel region 2232 thus can be at an angle $(\beta+\gamma)/2$ relative to the bottom surface of the port 2200, which is also acute.

As shown in FIGS. 34E-34G, the port 2200 can comprise a palpation projection 2246 that can include an orientation point or region 2248. The orientation region 2248 can be used by a practitioner in determining a location of a center point 2249 of an opening 2250 defined by a base 2202 of the port 2200. The orientation region 2248 can comprise any suitable arrangement or system that can provide location information to the practitioner. In the illustrated embodiment, the orientation region 2248 comprises a center point of the forward-most portion of the palpation projection 2246. In particular, as seen in FIG. 34E, the palpation projection 2246, as viewed from above, comprises a thin ridge that is substantially C-shaped, with the free ends of the C pointing rearward. The forward, center portion of the ridge comprises the orientation region. Accordingly, a practitioner can palpate the palpation projection 2246 to determine the orientation and location not only of the port 2200, but also of the orientation region 2248.

As shown in FIG. 34G, the orientation region 2248 of the palpation projection 2246 is positioned directly above (e.g., vertically over) the center point 2249 of the opening 2250. Such an arrangement can provide a natural feel or natural procedural adaptation for a practitioner who may be accustomed to accessing a vessel without the assistance of a port. For example, practitioners may generally access a vessel by palpating the vessel with one or more fingers of a first hand and inserting a needle or other access device through the skin of the patient using a second hand such that a tip of the needle enters the vessel at a position directly beneath the fingers of the first hand. In arrangements such as that illustrated in FIG. 34G, a practitioner may palpate the port 2200 at the orientation region 2248, and can insert an access device through the funnel region 2232 and through the center point 2249 of the opening into the vessel of the patient to which the port 2200 is attached. The practitioner may be less prone to contact any surfaces of the funnel 2232 during an initial insertion event, as the practitioner may naturally aim for the point 2249 when palpating the orientation region 2248.

In the illustrated embodiment, the orientation region 2248 is substantially smooth and transitions imperceptibly to other portions of the palpation projection 2246. Stated otherwise, the orientation region 2248 comprises a portion of the palpation projection 2246 that a practitioner can recognize based on the shape of the palpation projection 2246 as a whole (e.g., in the illustrated example, the orientation region 2248 is located at the apex of the palpation projection 2246). In other embodiments, the orientation region 2248 can comprise one or more bumps, projections, or other features that can assist in providing tactile information to a practitioner. In other or further embodiments, the orientation region 2248 may be positioned other than directly above the center point 2249 of the opening 2250.

As can be seen in FIG. 34G, in the illustrated embodiment, a forward end of a body 2204 of the port 2200 slopes forwardly and downwardly from the palpation projection 2246. This portion of the body 2204 can prevent tissue that is directly above it from being pressed downwardly so as to seal the opening 2250. Accordingly, in some instances, it can be desirable to press downwardly on skin that is at or rearward of the orientation region 2248 of the palpation projection 2246 so as to seal the opening 2250 to achieve hemostasis.

As shown in FIGS. 34C and 34D, the body 2204 of the port 2200 can define a maximum width Ww of the port 2200, a maximum width of the base 2202 is depicted at $W_B$, and a height H of the port 2200 is determined as a distance that the port will extend away from a vessel when it is attached to the vessel. As shown in FIGS. 34D and 34E, the port 2200 can also define a rear plan view target area 2287 and a top plan view target area 2288, which resemble the target areas discussed above.

FIGS. 35A-35F, 36A-36F, and 37A-37F illustrate three additional embodiments of vascular access ports 2300, 2400, 2500, respectively, which can resemble the access port 2200. However, the ports 2300, 2400, 2500 can be configured for increasingly deeper implantation within a patient. In some arrangements, the widths Ww and $W_B$ and the longitudinal lengths of each of the ports 2200, 2300, 2400, and 2500 can be substantially the same. However, the heights H of the ports can vary from each other. Accordingly, front elevation view profiles of the ports 2200, 2300, 2400, and 2500 (i.e., the profiles seen in FIGS. 34C, 35C, 36C, 37C, respectively) can vary from each other. In the illustrated embodiments, a lower portion of the front elevation view profiles of each of the ports 2300, 2400, 2500 is substantially the same as the front elevation view profile of the port 2200. However, the bodies 2304, 2404, 2504 of each of the ports 2300, 2400, 2500 extend upwardly from this common profile to respectively greater extents. Similarly, as seen in FIGS. 34D, 35D, 36D, and 37D, the rear plan view target areas of the ports 2200, 2300, 2400, and 2500 can be increasingly larger. Due to similarities between the ports 2200, 2300, 2400, and 2500 in their widths and lengths, however, the top plan view target areas 2288, 2388, 2488, and 2588 defined by these ports each can be approximately the same size.

Similar to the arrangements discussed above with respect to FIG. 26F, forward faces of respective funnel regions of the ports 2200, 2300, 2400, and 2500 can angle upwardly by increasingly greater amounts, whereas rearward faces of the ports can be at approximately the same angle. Central axes defined by the funnel regions thus may define acute angles of increasingly greater size relative to the bases 2202, 2302, 2402, and 2502.

In various embodiments, the base width $W_B$ of the ports 2200, 2300, 2400, 2500 may be approximately 7 millimeters, or may be within a range of from about 6 millimeters to about 8 millimeters. The heights H of the ports 2200, 2300, 2400, 2500 can, in some embodiments, be approximately 4, 6, 8, and 10 millimeters, respectively, or can be within ranges of from about 3 to 5 millimeters, from about 5 to 7 millimeters, from about 7 to 9 millimeters, or from about 9 to 11 millimeters, respectively. Other sizes and dimensions are also possible, including those discussed above with respect to other illustrated embodiments.

Figure 38:
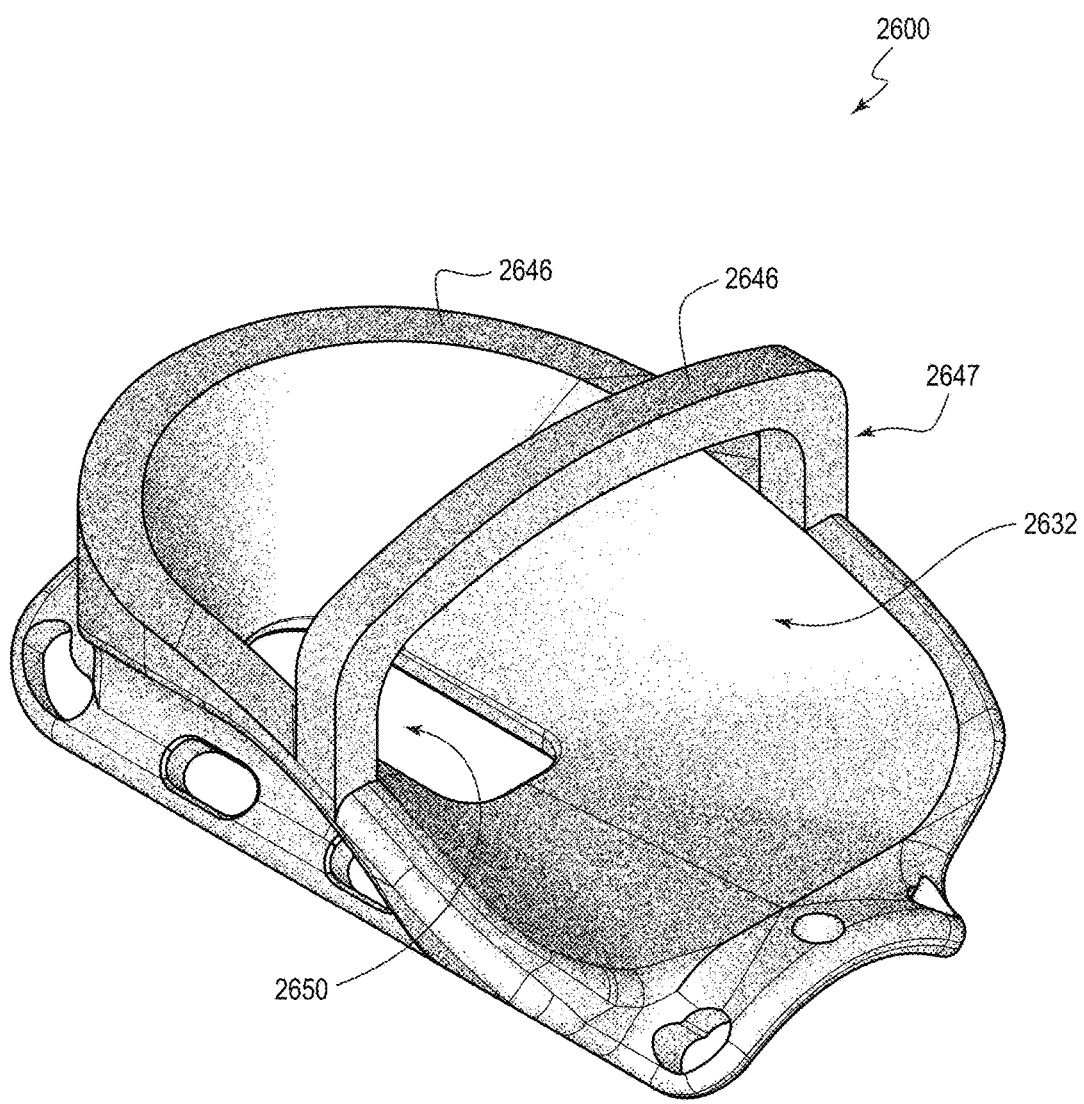
FIG. 38 is a perspective view of another embodiment of a vascular access port.

FIG. 38 illustrates another embodiment of a vascular access port 2600, which can resemble the vascular access ports described above in certain respects. The vascular access port 2600 can particularly resemble the access port 1100, except that a palpation bridge or bar 2647 can extend over a funnel region 2632 defined by the port 2600. The palpation bar 2647 can be configured to provide location and orientation information to a practitioner who palpates the port 2600 when it is implanted. A palpation projection 2646 thus can extend about at least a forward edge and side edges of the funnel region 2632, and can also comprise the palpation bar 2647. The palpation projection 2646 thus can extend over the funnel region 2632.

In the illustrated embodiment, the palpation bar 2646 extends over a rearward end of an opening 2650 defined by the port 2600. In other embodiments, the palpation bar 2646 may pass over a center of the opening 2650, and thus may provide information regarding the position of the center of the opening 2650 that may be used in a natural manner, such as described above with respect to the port 2200. For example, a practitioner can naturally aim for a center of the opening 2650 by palpating the palpation bar 2646 and inserting an access device into a position beneath the palpation bar 2646. In still other embodiments, the palpation bar 2646 may be positioned in other orientations relative to the opening 2650. Although not shown in FIG. 38, a forward portion of the palpation projection 2646 and the palpation bar 2647 can be curved or radiused so as to prevent damage to surrounding tissue.

The port 2600 can permit hemostasis to be achieved by applying downward pressure to skin tissue that is above almost any portion of the port 2600. Stated otherwise, the palpation bar 2647 may provide less of a hindrance to the formation of hemostasis where skin is pressed downward at a forward end of the port 2600, as compared with the illustrated embodiment of the port 2200 as discussed above, although hemostasis can be readily achieved with either port.

As can be appreciated from the foregoing, embodiments of vascular access ports can be sized and dimensioned to reside within a patient and beneath an outer surface of the skin of the patient. For example, the vascular access ports can be sized to fit between a vessel (e.g., any suitable artery or vein, such as, for example, the cephalic, basilic, femoral, jugular, or subclavian vein) and the epidermis of an animal subject.

Moreover, embodiments of one or more vascular access ports can be included in various embodiments of kits. For example, in some embodiments, a kit can comprise a vascular access port such as any of the ports described above. The kit can further include one or more of: one or more sutures or other attachment devices by which the port can be attached to a vessel, one or more synthetic grafts (which may be pre-attached to the port or separate therefrom), one or more pads of ingrowth-inducing material (which may be pre-attached to the port or separate therefrom), and one or more additional vascular access ports of the same configuration and/or of one or more different configurations (e.g., different size, shape, etc.). For example, in some embodiments, the kit can include multiple ports such that a practitioner can select one or more of the ports for implantation. In further embodiments, the kit can include ports of different sizes such that the practitioner can further select an appropriate port (or appropriate ports) based on the particular anatomy of a patient and/or on the target location of the port (or ports).

In various embodiments, a kit can include instructions, which may be contained on a separate sheet or card that may accompany one or more ports within a packet or package. The instructions can include directions for performing any and/or all of the steps or stages of a method for implanting the port, such as any and/or all of the steps or stages of any of the procedures discussed above. In other or further embodiments, the instructions may provide directions for merely accessing such directions. For example, the instructions may list a web address, a mailing address, and/or a telephone number that can be used to locate directions for implanting a port using the contents of the kit.

It is noted that while many of the examples provided herein relate to the use of vascular access ports with blood vessels, this method of disclosure is employed for the sake of convenience and efficiency, but should not be construed as limiting of the types of procedures with which embodiments may be used. Indeed, embodiments of the apparatus, methods, and systems disclosed herein can be used with vessels other than blood vessels, such as, for example, vessels within the gastrointestinal tract. Accordingly, the term "vessel" is a broad term that can include any hollow or walled organ or structure of a living organism, whether natural or synthetic.

It will be understood by those having skill in the art that changes may be made to the details of the above-described embodiments without departing from the underlying principles presented herein. For example, any suitable combination of various embodiments, or the features thereof, is contemplated. For example, any of the access ports can be constructed in a suitable two-component arrangement such as that described with respect to FIG. 20 and/or may comprise one or more resorbable materials.

Additional ports and features thereof are described in U.S. patent application Ser. No. 12/697,190, titled SUBCUTANEOUS VASCULAR ACCESS PORTS AND RELATED SYSTEMS, METHODS, AND IMPLANTATION FEATURES, filed Jan. 29, 2010, which was published as U.S. Patent Application Publication No. 2010/0191191, and issued as U.S. Pat. No. 8,337,465, the entire contents of which are hereby incorporated by reference herein, and are also described in U.S. patent application Ser. No. 12/697, 192, titled SUBCUTANEOUS VASCULAR ACCESS PORTS AND RELATED SYSTEMS AND METHODS, filed Jan. 29, 2010, which was published as U.S. Patent Application Publication No. 2010/0191166, and issued as U.S. Pat. No. 9,072,880, which was incorporated by reference above. Moreover, additional ports and features thereof are described in U.S. patent application Ser. No. 12/697,167, titled VASCULAR ACCESS PORTS AND RELATED METHODS, filed Jan. 29, 2010, which was published as U.S. Patent Application Publication No. 2010/0191179, and issued as U.S. Pat. No. 8,337,464, which was also incorporated by reference above. Such ports include, for example, the ports 400, 500, 800, 900, 1000, 1100, 1200, 1300, 1400, and 1500 in FIGS. 15A-15G, 16A-16G, 19A-19G, 20A-20G, 21A-21G, 22A-22G, 23A-23G, 24A-24G, 25A-25G, and 26A-26G of in U.S. Patent Application Publication No. 2010/0191179. Any suitable combination of such ports and features with those disclosed herein is contemplated.

Although symmetries are present in the illustrated embodiments, some embodiments may be asymmetrical. For example in some embodiments, a guidance passageway of a vascular access port may extend generally at an angle relative to a vertical-longitudinal plane through the port such that a funnel region may more readily receive an access device therein at one lateral side of the port as opposed to an opposite lateral side thereof. Such arrangements may be beneficial in some applications where a port is implanted on a vessel that may more easily be reached from a direction that is not generally aligned with (e.g., nonparallel to) the vessel.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, although it is noted that in various embodiments, the height H of the vascular access port 100 is no greater than about 2, 3, 4, 5, 6, 7, 8, 9, 10, 11, 12, 13, 14, or 15 millimeters, it is understood that in some embodiments, the height H of the vascular access port 100 is no greater than exactly 2, 3, 4, 5, 6, 7, 8, 9, 10, 11, 12, 13, 14, or 15 millimeters. More generally, where qualifiers such as "about," "substantially," and "generally" are used, these terms include within their scope the qualified words in the absence of their qualifiers. For example, where the term "substantially parallel" is recited with respect to a feature, it is understood that in further embodiments, the feature can have a precisely parallel orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on. Similarly, for the second claim set that begins with independent claim 12, claim 14 can depend from either of claims 12 and 13, with these separate dependencies yielding two distinct embodiments; claim 15 can depend from any one of claim 12, 13, or 14, with these separate dependencies yielding three distinct embodiments; claim 16 can depend from any one of claim 12, 13, 14, or 15 with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112 ¶6. Embodiments of the invention in which an exclusive property or privilege is claimed are defined as follows.

The invention claimed is:

1. A vascular access port comprising:
a base configured to be attached to a vessel, the base extending in at least a longitudinal direction and a lateral direction that are orthogonal to each other, wherein at least a portion of the base defines a footprint of the port at which the port is configured to contact the vessel when the base is attached to the vessel;
a body extending away from the base in at least a vertical direction that is orthogonal to each of the longitudinal and lateral directions, wherein a height of the body in the vertical direction is sufficiently small such that the entire port can be implanted subcutaneously in a patient, wherein one or more of the body and the base define an outermost periphery of the port in the longitudinal and lateral directions, and wherein the outermost periphery, when projected vertically, defines a peripheral extent of the port; and
a guidance passageway that is at least partially defined by the body and is configured to direct an access device into the vessel of the patient when the port is attached to the vessel, the guidance passageway comprising a proximal end and a distal end and defining a central axis that is non-vertical such that when the base is attached to the vessel, the central axis is at a non-perpendicular angle relative to a longitudinal axis of the vessel, wherein the guidance passageway is configured to constrain movement of the access device such that when the access device is advanced through the guidance passageway in a proximal-to-distal direction and a distal tip of the access device is at a position that is vertically even with at least a portion of the footprint, the distal tip of the access device is at an interior of the peripheral extent of the port.

2. The port of claim 1, wherein said position that is vertically even with at least a portion of the footprint is outside of an outermost perimeter of the footprint.

3. The port of claim 1, wherein said position that is vertically even with at least a portion of the footprint is interior to an outermost perimeter defined by the footprint.

4. The port of claim 1, wherein the guidance passageway is larger at the proximal end than it is at the distal end.

5. The port of claim 1, wherein the footprint is non-planar.

6. The port of claim 1, wherein a bottom surface of the base further extends in the vertical direction and is bowed so as to be able to receive a portion of the vessel therein.

7. The port of claim 1, wherein the base extends further in the longitudinal direction than it does in the lateral direction.

8. The port of claim 1, wherein the guidance passageway is configured for use with an elongated access device that defines a central axis, and wherein the guidance passageway is configured to constrain movement of the access device along a path in which the central axis of the access device is aligned with the central axis of the guidance passageway.

9. A method of accessing a vessel, the method comprising:
locating a subcutaneously implanted vascular access port that is within a patient, wherein the vascular access port comprises:
a base attached to a vessel, the base extending in at least a longitudinal direction and a lateral direction that are orthogonal to each other, wherein at least a portion of the base defines a footprint of the port at which the port contacts the vessel;
a body extending away from the base in at least a vertical direction that is orthogonal to each of the longitudinal and lateral directions, wherein one or more of the body and the base define an outermost periphery of the port in the longitudinal and lateral directions, and wherein the outermost periphery, when projected vertically, defines a peripheral extent of the port; and
a guidance passageway that is at least partially defined by the body and comprises
a proximal end and a distal end, wherein the guidance passageway defines a central axis
that is non-perpendicular to a longitudinal axis of the vessel;
advancing an access device through the guidance passageway in a proximal-to- distal direction and into the vessel, wherein, when a distal tip of the access device is at a position that is vertically even with at least a portion of the footprint, the distal tip of the access device is at an interior of the peripheral extent of the port.

10. A vascular access port comprising:
a base configured to be attached to a vessel, the base extending in at least a longitudinal direction and a lateral direction that are orthogonal to each other, wherein at least a portion of the base is configured to contact the vessel when the base is attached to the vessel, and wherein a bottom surface of the base is configured to face a wall of the vessel;
a body extending away from the base in at least a vertical direction that is orthogonal to each of the longitudinal and lateral directions, wherein a height of the body in the vertical direction is sufficiently small to permit the entire port to remain beneath an outer surface of skin after the port has been implanted in a patient; and
a guidance passageway that is at least partially defined by the body, the guidance passageway comprising a funnel region that decreases in size from a proximal end of the guidance passageway toward a distal end of the guidance passageway, wherein the distal end of the guidance passageway defines an opening through the bottom surface of the port.

11. The port of claim 10, wherein a maximum length of the opening in the longitudinal direction is greater than a maximum width of the opening in the lateral direction.

12. The port of claim 11, wherein the length is at least two times as great as the width.

13. The port of claim 10, wherein a forward end of the opening is curved and sides of the opening that extend from the forward end define straight lines.

14. The port of claim 10, wherein a forward portion of the funnel region extends vertically upward to a greater extent than does a rearward portion of the funnel region.

15. The port of claim 14, wherein the forward portion of the funnel region is angled forwardly.

16. The port of claim 15, wherein the forward portion of the funnel region defines a backstop portion that is configured to assist in directing an access device toward the opening when the access device is inserted into the port in a rearward-to-forward direction.

17. The port of claim 14, wherein the forward portion of the funnel region is angled rearwardly.

18. The port of claim 14, wherein side portions of the funnel region that extend between the forward and rearward portions are angled outwardly such that a width of the funnel region in the lateral direction decreases toward the opening.

19. The port of claim 10, wherein at least a portion of the opening is defined by the bottom surface of the base.

20. The port of claim 19, wherein the entire opening is defined by the bottom surface of the base and the entire opening is at a surface of a vessel wall when the port is attached to the vessel.

* * * * *